(12) United States Patent
Seidah et al.

(10) Patent No.: US 7,211,424 B1
(45) Date of Patent: May 1, 2007

(54) MAMMALIAN SUBTILISIN/KEXIN ISOZYME SKI-1: A PROPROTEIN CONVERTASE WITH A UNIQUE CLEAVAGE SPECIFICITY

(75) Inventors: Nabil G. Seidah, Ile-des-Soeurs (CA); Michel Chretien, Outremont (CA); Mieczyslaw Marcinkiewicz, Outremont (CA)

(73) Assignee: Institut de Recherches Cliniques de Montreal, Montreal, Quebec (CA)

( * ) Notice: Subject to any disclaimer, the term of this patent is extended or adjusted under 35 U.S.C. 154(b) by 0 days.

(21) Appl. No.: 09/830,837

(22) PCT Filed: Nov. 4, 1999

(86) PCT No.: PCT/CA99/01058

§ 371 (c)(1),
(2), (4) Date: Oct. 18, 2001

(87) PCT Pub. No.: WO00/26348

PCT Pub. Date: May 11, 2000

(30) Foreign Application Priority Data

Nov. 4, 1999 (CA) .................................. 2249648

(51) Int. Cl.
- *C12N 9/64* (2006.01)
- *C12N 15/57* (2006.01)
- *C12N 15/79* (2006.01)
- *C07K 1/00* (2006.01)
- *C07K 16/00* (2006.01)

(52) U.S. Cl. .................. 435/226; 435/68.1; 435/69.1; 435/252.3; 435/320.1; 530/350; 530/326; 530/327; 536/23.1; 536/23.2

(58) Field of Classification Search ............... 435/69.1, 435/226, 23, 252.3, 320.1, 69.6; 530/300; 536/23.2
See application file for complete search history.

(56) References Cited

U.S. PATENT DOCUMENTS 4,777,239 A * 10/1988 Schoolnik et al. .......... 530/326

(Continued)

FOREIGN PATENT DOCUMENTS

EP       0 218 479 A2 * 4/1987

(Continued)

OTHER PUBLICATIONS

Sakai Juro et al: "Molecular identification of the sterol-regulated luminal protease that cleaves SREBPs and controls lipid composition of animal cells." Molecular Cell, vol. 2, No. 4 Oct. 1998, pp. 505-514, XP000867536; ISSN: 1097-2765; see Results section, figures 2, 3, 5, 7.

(Continued)

*Primary Examiner*—Nashaat T. Nashed
*Assistant Examiner*—William W. Moore
(74) *Attorney, Agent, or Firm*—Quarles & Brady LLP

(57) ABSTRACT

Using RT-PCR and degenerate oligonucleotides derived from the active site residues of subtilisin-kexin-like serine proteinases, we have identified a highly conserved and phylogenetically ancestral human, rat and mouse type-I membrane-bound proteinase called subtilisin-kexin-isozyme-1 (SKI-1). Computer data bank searches reveals that human SKI-1 was previously cloned but with no identified function. A SKI-1 processed fragment is secreted in culture media in a soluble form. In vitro studies suggest that SKI-1 is a $Ca^{2+}$-dependent serine proteinase exhibiting a wide pH optimum for cleavage of proBDNF. Peptides mimicking SKI-1 cleavages sites are also disclosed. SKI-1 prosegment has an ex vivo inhibitory effect on SKI-1 activity. The prosegment is also processed and secreted in culture media. One of its fragments is found tightly associated with the SKI-1 soluble form. Therapeutic applications for SKI-1 inhibitors are disclosed.

34 Claims, 33 Drawing Sheets

U.S. PATENT DOCUMENTS

| | | | | |
|---|---|---|---|---|
| 5,415,995 | A * | 5/1995 | Schoolnik et al. | 435/7.1 |
| 5,460,950 | A * | 10/1995 | Barr et al. | 435/69.1 |
| 6,218,165 | B1 * | 4/2001 | Estell et al. | 435/221 |
| 6,322,962 | B1 * | 11/2001 | Brown et al. | 435/4 |
| 6,596,525 | B1 * | 7/2003 | Estell et al. | 435/219 |
| 6,642,011 | B2 * | 11/2003 | Estell | 435/7.24 |
| 6,835,550 | B1 * | 12/2004 | Estell et al. | 435/7.24 |
| 6,838,269 | B1 * | 1/2005 | Estell et al. | 435/183 |
| 2002/0081703 | A1 * | 6/2002 | Estell | 435/220 |

FOREIGN PATENT DOCUMENTS

| | | |
|---|---|---|
| EP | 0 267 629 | 5/1988 |
| WO | WO 93/13127 A1 * | 7/1993 |
| WO | WO 00 09677 | 2/2000 |

OTHER PUBLICATIONS

Database Genembl 'Online' Nov. 23, 1994; Nomura et al.: "Human mRNA for KIAA0091 gene, complete cds." XP002136837; Accession D42053; -&.

Nagase et al.: "Prediction of the coding sequence of unidentified human genes. III. The coding sequence of 40 new genes (KIAA0081-KIAA0-120) deduced by analysis of cDNA clones from human cell line KG-1"; DNA Research, vol. 2, 1995, pp. 37-43; XP00874164; tables 1,2.

Siezen R.J. et al: "Subtilases: The Superfamily of Subtilisin-Like Serine Proteases", Protease Science, GB, Cambridge University Press, vol. 6, No. 3, Mar. 1997, pp. 501-523, XP000856203; ISSN: 0961-8368; cited in the application; figure 2; table I.

Konda Yoshitaka et al: "Proprotein-processing endoprotease furin controls the growth and differential of gastric surface mucous cells." Journal of Clinical Investigation 1997, vol. 99, No. 8, 1997, pp. 1842-1851, XP002136832, ISNN: 0021-9738; figures 11.14; pp. 1847, right-hand column, last paragraph—p. 1849, right-hand column, paragraph 1.

Anderson Eric D. et al.: "Activation of the furin endoprotease is a multiple-step process: Requirements for acidification and internal propeptide cleavage." EMBO (European Molecular Biology Organization) Journal 1997, vol. 16, No. 7, 1997, pp. 1508-1518, XP002136833; ISSN: 0261-4189; p. 1509, right-hand column, last paragraph—p. 1510, right-hand column, paragraph 1, figure 6.

Zhong Wenyan et al: "Development of an internally quenched flourescent substrate for *Escherichia coli* leader peptidase." Analytical Biochemistry, vol. 255, No. 12, Jan 1, 1998; pp. 66-73; XP000929725, ISSN: 0003-2697; the whole document.

Seidah Nabil G. et al.: "Mammalian subtilisin/kexin isozyme SKI-1: widely expressed proprotein convertase with a unique cleavage specifity and cellular localization." Proceedings of The National Academy of Science of The United States of America; Feb. 16, 1999; vol. 96, No. 4, Feb. 16, 1999, pp. 1321-1326; XP002136834; ISSN: 0027-8424; the whole document.

Espenshade Peter J. et al: "Autocatalytic processing of Site-1 protease removes propeptide and permits cleavage of sterol regulatory element0binding proteins." Journal of Biological Chemistry, Aug. 6, 1999; vol. 274, No. 32, Aug. 6, 1999; pp. 22795-22804; XP002136835; ISSN: 0021-9258; the whole document.

Toure B et al: "Biosynthesis and enzymatic characterization of human SKI-1/S1P and the processing of its inhibitory prosegment." Journal of Biological Chemistry, (Jan 28, 2000) 275 (4) 2349-58.; XP00906874.

Abrami, L. et al. (1998). "The Pore-forming Toxin Proaerolysin Is Activated by Furin". The Journal of Biological Chemistry, 273: 32656-32661.

Anderson, E.D. et al. (1993). "Inhibition of HIV-1 gp160-dependent Membrane Fusion by a Furin-directed α1-Antitrypsin Variant", The Journal of Biological Chemistry, 268:24887-24891.

Basak, A. et al. (1995). "Application of the Multiple Antigenic Peptides (MAP) Strategy to the Production of Prohormone Convertases Antibodies: Synthesis Characterization and use of 8-Branched Immunogenic Peptides". Journal of Peptide Science, 1: 385-395.

Basak, A. et al. (1997). "Histidine-rich human salivary peptides are inhibitors of proprotein convertases furin and PC7 but act as substrates for PC1". J. Peptide Res., 49: 596-603.

Bellosta, S. et al. (1998). "Direct vascular effects of HMG-CoA reductase inhibitors". Atherosclerosis 137 Suppl. (1998): S101-S109.

Benjannet, S. et al., (1997). "α1-Antitrypsin Portland Inhibits Processing of Precursors Mediated by proprotein Convertases Primarily within the Constitutive Secretory Pathway". The Journal of Biological Chemistry, 272: 26210-26218.

Benjannet, S. et al. (1998). "Residues unique to the pro-hormone convertase PC2 modulate its autoactivation, binding to 7B2 and enzymatic activity". FEBS Letters, 428: 37-42.

Bourdreault, A. et al. (1998). "Proprotein Convertase PC1/3-related Peptides Are Potent Slow Tight-binding Inhibitors of Murine PC1/3 and Hfurine". The Journal of Biological Chemistry, vol. 273, No. 47: 31574-31580.

Brown, M.S. et al. (1997). "The SREBP Pathway: Regulation of Cholesterol Metabolism by Proteoylsis of a Membrane-Bound Transcription Factor". Cell, 89:331-340.

Brown, M.S. et al. (1999). "A proteolytic pathway that controls the cholesterol content of membranes, cells, and blood". Proc. Natl. acad. Sci. USA, 96: 11041-11048.

Burbach, J.P.H. et al. (1986). "Isolation and primary Structure of neurointermediate pituitary peptides derived from the C-terminal of the rat vasopressin-neurophysin precursor (propressophysin)". Eur. J. Biochem, 156: 137-142.

Checlerc, Frédéric (1995). "Short Review: Processing of the *B*-Amyloid Precursor Protein and Its Regulation in Alzheimer's Disease". Journal of Neurochemistry, vol. 65, No. 4: 1431-1444.

Cheng, D. et al. (1999). "Secreted Site-1 Protease Cleves Peptides Corresponding to Luminal loop of Sterol Regulatory Element-binding Proteins". The Journal of Biological Chemistry, 274: 22805-22812.

Chiron, M.F. et al. (1994). "Cleavage of Pseudomonas Exotoxin and Diphtheria Toxin by a Furin-like Enzyme Prepared from Liver". The Journal of Biological Chemistry, vol. 269, No. 27: 18167-18176.

Chrétien, M. et al. (1995). "Proprotein Convertases and the Pathophysiology of Human Diseases: Prospective Considerations". Proceedings of the Association of American Physicians, 107: 47-66.

De Bie, I. et al. (1996). "The Isoforms of Proprotein Convertases PC5 Are Sorted Subcellular Compartments". Journal of Cell. Biology, 135: 1261-1275.

Declory, E. et al. (1997). "Comparative functional role of PC7 and furin in the processing of the HIV envelope glycoprotein gp160". FEBS Letters, 405: 68-72.

Duncan, E.A. et al.(1997). "Cleavage Site for Sterol-regulated Protease Localized to a Leu-Ser Bond in the Lumenal Loop of Sterol Regulatory Element-binding Protein-2". The Journal of Biological Chemistry, 272:12778-12785.

Edwards, J.B.D.M. et al. (1991). Oligodeoxryibonucleotide ligation to single-stranded cDNAs: a new tool for cloning 5' ends of mRNAs and for constructing cDNA libraries by *in vitro* amplification. Nucleic Acid Research, 19: 5227-5232.

Edwards, P.A. et al. (1999). "Sterols and Isoprenoids: Signaling Molecules Derived from the Cholesterol Biosynthetic Pathway". Annu. Rev. Biochem., 68:157-185.

Endres, M. et al. (1998). "Stroke protection by 3-hydroxy-3-methylglutaryl (HMG)-CoA reductase inhibitos mediated by endothelial nitric oxide synthase". Proc. Natl. Acad. Sci. USA, 95: 8880-8885.

Gallagher, T. et al. (1995). "The prosegment-subtillsin BPN' complex: crystal structure of a specific 'foldase'". Structure, 3: 907-914.

Glasson, M.J. et al. (1998). "Development of mini-gel technology in two-dimensional electrophesis for mass-screening of samples: Application to tears". Electrophoresis, , 19: 852-855.

Gram, Hermann et al. (1994). "A novel Approach for High Level Production of a Recombinant Human Parathyroid Hormone Fragment in *Escherichia coli*". Bio/Technology, 12: 1017-1023.

Grus, F.H. et al. (1999). "Analysis of tear protein patterns by a neural network as a diagnostical tool for the detection of dry eyes". Electrophoresis, 20: 875-880.

Guijarro, C. et al.(1998). "3-Hydroxy-3-Methylglutaryl Coenzyme A Reductase and Isoprenylation Initors Induce Apoptise of Vascular Smooth Muscle Cells in Culture". Circ Res., 83: 490-500.

Gupta, S.K. et al. (1995). "A potent inhibitor or endothelial cell proliferation is generated by proteolytic cleavage of the chemokine platelet factor 4". Proc. Natl. Acad. Sci. USA, 92: 7799-7803.

Hallenberger, S. et al. (1992). "Inhibition of furin-mediated cleavage activation of HIV-1 glycoprotein gp160", Nature, 360: 358-361.

Hallenberger, S. et al. (1997). "The Role of Eukaryotic Subtilisin-Like Endoproteases for the Activation of Human Immunodeficiency Virus Glycoproteins in Natural Host Cells". Journal of Virology, 71: 1036-1045.

Hooper, N.M. et al. (1997). "Membrane protein secretases", Biochem J.321:265-279.

Howland, D.S. et al. (1998). "Modulation of Secreted $B$-Amyloid Precursor Protein and Amyloid $B$-Peptide in Brain by Cholesterol", The Journal of Biological Chemistry, 273: 16576-16582.

Hua, X. et al. (1993). "SREBP-2, a second basic -helix-loop-helix-leucine zipper protrein that simulates transcription by binding to a sterol regulatory element". Proc. Natl. Acad. Sci. USA, 90: 11603-11607.

Hudson, P. et al. (1981). "Molecular cloning and characterization of cDNA sequences coding for rat relaxin". Nature, 291: 127-131.

Inouye, Masayori (1991)/ "Intramolecular Chaperone: The Role of the Pro-Peptide in Protein Folding". Enzyme, 45: 314-321.

Iskeleli, G. et al. "Comparison of Tear Lactate Dehydrognenase Activities of Different Types of Contact Lens Wearers and Normal Control Group". CLAO Journal, 25: 101-104.

Jean, F. et al. (1995). "Flourescent Peptidyl Substrates as an Aid in Studying the Subtrate Specificity of Human Prohormone Convertase PCI and Human Furin and Designing a Potent Irreverible Inhibitor". The Journal of Biological Chemistry, vol. 270, No. 33: 19225-19231.

Kendall, J.M. et al. (1994). "Changes in Free Calcium in the Endoplasmic Reticulum of Living Cells Detected Using Targeted Aequorin". Analytical Biochemistry, 221: 173-181.

Khan, A.R. et al. (1998). "Molecular mechanisms for the conversion of zymogens to active proteolytic enzymes". Protein Science, 7: 815-836.

Kim, J.B. et al. (1996). "ADD1/SREBO1 promotes adipocyte differentiation and gene expression linked to fatty acid metabolism". Genes & Development, 10: 1096-1107.

Kim, J.B. et al. (1998). "ADD1/SREBP1 activates PPARy through the production of endogenous ligand"Proc. Natl. Acad.Sci. USA, 95: 4333-4337.

Kim, J.B. et al. (1998). "Nutritional and Insulin Regulation of Fatty Acid Synthetase and Leptin Gene Expression through ADD1/SREBP1"J. Clin Invest., 101:1-9.

Kim, J.H. et al. (1998). "Noninvasive measurement of the pH of the endoplasmic reticulum at rest and during calcium release". Proc. Natl. Acad. Sci. USA, 95: 2997-3002.

Laufs, U. et al. (1998). "Upregulation of Endothelial Nitric Oxide Synthase by HMG CoA Reductase Inhibitors". Circulation, 97: 1129-1135.

Laufs, U. et al. (1997). "Inhibittion of 3-Hydroxy-3-methylglutaryl (HMG)-CoA Reductase Blocks Hypoxia-mediated Down-regulation of Endothelial Nitric Oxide Synthase". The Joiurnal of Biological Chemistry, 272: 31725-31729.

Laufs, U. and Liao, J.K. (1998). "Post-transcriptional Regulation of Endothelial Nitric Oxide Synthase mRNA Stability by Rho GTPase". The Journal of Biological Chemistry, 273: 24266-24271.

Lei, Y. et al.(1999). "Identification of Mouse CPX-1, a Novel Member of the Metallocarboxypeptidase Gene Family with Highest Similarity to CPX-2". DNA and Cell Biology, 175-185.

Ling, N. et al. (1976). "Isolation, primary structure, and synthesis of α-endorphin and γ-endorphin, two peptides of hypothalamic-hypophysical origin with morphinomimetic activity". Proc. Natl. Acad. Sci. USA, 73: 3942-3946.

Lippincott-Schwartz, J. et al.(1991) "Rapid Redistribution of Golgi Proteins into the ER in Cells Treated with Brefeldin A: Evidence for Membrane Cycling from Golgi to ER". Cell, 56: 801-813.

Lippincott-Schwartz, J. et al. (1991). "Brefeldin A's Effects on Endosomes, Lysosomes, and the TGN Suggest a General Mechanism for Regulating Organelle Structure and Membrane Traffic". Cell, 67: 601-616.

Llopis, Juan et al. (1998). "Measurement of cytosolic, mitochondrial, and Golgi pH in single living cells with green fluorescent proteins". Proc. Natal. Acad. Sci. USA, 95: 6803-6808.

Lusson, J. et al. (1993). "cDNA structure of the mouse and rat subtilisin/kexin-like PC5: A candidate propotein convertase expressed in endocrine and nonendocrine cells". Proc. Natl. Acad. Sci. USA, 90: 6691-6695.

Maisonpierre, P.C. et al., (1991). "Human and Rat Brain-Derived Neurotrophic Factor and Neurotrophin-3: Gene Structures, Distributions, and Chromosomal Localizations". Genomics, 10: 558-568.

Mallde, D. et al. (1995). "Electron Microscopic Immunocytochemical Evidence for the involvement of the Convertase PC1 and PC2 in the Processings of Proinsulin in Pancreatic $B$-Cells". The Journal of Histochemistry and Cytochemistry, 43: 11-19.

Marcinkiewicz, M. et al. (1998). "The pro-protein convertase PC1 is induced in the transected sciatic nerve and is present in cultured Schwann cells: comparison with PC5, furin and PC7, implication in pro-BDNF processing". Molecular Brain Research, 59: 229-246.

McNamara, M.J. et al. (1998). "Immunohistorical and in situ analysis of amyloid precursor-like protein-1 and amyloid precursor-like protein-2 expression in Alzheimer disease and aged conrtol brains". Brain Research, 804: 45-51.

Mizuno, K. et al. (1989). "Characterization of KEX2-Encoded Endopeptidase From Yeast Saccharmyces Cerevisase". Biochemical and Biophyscal Research Communications, 159: 305-311.

Molloy, M.P. et al. (1997). "Establishment of the human reflex tear-dimensional polyacrylamide gel reference map: New protiens of potential diagnostic value". Electrophoresis, 18: 2811-2815.

Muller, L. et al. (1997). "Mechanism of the Facillitation of PC2 Maturation by 7B2: Involvement in ProPC2 Transport and activation but Not Folding". The Journal of Cell Biology, 139: 625-638.

Munzer, J.S. et al. (1997). "*In Vitro* Characterization of the Novel Proprotein Convertase PC7". The Journal of Biological Chemistry, 272: 19672-19681.

Mutoh, T. et al. (1999). "Involvement of tyrosine phosphorylation in HMG-CoA reductase inhibitor-induced cell death in L6 myoblasts". FEBS Letters, 444: 85-89.

Mutoh, T. et al. (1999). "Role of tyrosine phosphorylation of phospholipase C γl in the signaling pathway of HMG-CoA reductase inhibitor-induced cell death of L6 myoblast". FEBS Letters, 446: 91-94.

Nohturfft, Axel et al. (1998). "Sterols regulate processing of carbohydrate chains of wild-type SREBP cleavage-activating protein (SCAP), but not Sterol-resistant mutants Y298C or D443N". Proc. Natl. Acad. Sci. USA, 95: 12848-12853.

Nohturfft, Axel et al. (1999). "Sterols regulate cycling of SREBP cleavage-activating protein (SCAP) between endoplasmic reticulum and Golgi". Proc. Natl. Acad. Sci. USA, 96: 11235-11240.

O'Reilly, M.S. et al. (1994). "Angiostatin: A Novel Angiogensis Inhibitor That Mediates the Suppression of Metastases by a Lewis Lung Carcinoma". Cell, 79: 315-328.

Paquet, L. et al. (1994). "The Neuroendocrine Precursor 7B2 Is a Sulfated Protein Proteolytically Proceesed by a Ubiquitous Furin-like Convertase". The Journal of Biological Chemistry, 269: 19279-19285.

Power, S.D. et al. (1986). "Secretion and autoproteolytic maturation of subtilisin". Proc. Natl. Acad. Sci. USA, 83: 3096-3100.

Raiteri, M. et al. (1997). "Pharmacological Control of the Mevalonate Pathway: Effect on Arterial Smooth Muscle Cell Proliferation". The Journal of Pharmacology and Experimental Therapuetics, 281: 1144-1153.

Rassoulzadegan, M. et al. (1998). "APLP2, a member of the Alzheimer precursor protein family, is required for correct genomic segregation in dividing mouse cells". The EMBO Journal, 17: 4647-4656.

Rawson, R.B. et al. (1997). "Complementation Cloning of *S2P*, a Gene Encoding a Putative Metalloprotease Required for Intramembrane Cleavage of SREBPs". Molecular Cell, 1: 47-57.

Reeves. J.P. et al. (1981). "Intracellular disruption of rat heart lysosomes by leucine methyl ester: Effects on protein degradation". Proc. Natl. Acad. Sci. USA, 78: 4426-4429.

Rittenhouse, J. and Marcus, F. (1984). "Peptide Mapping by Polyacrylamide Gel Electrophoresis after Cleavage at Aspartyl-Prolyl Peptide Bonds in Sodium Dodecyl Sulfate-Containing Buffers". Analytical Biochemistry, 138: 442-448.

Rosendahl. M.S. et al. (1997). "Identification and Characterization of a Pro-tumor Necrosis Factor-α-processing Enzyme from the Adam Family of Zinc Metalloproteases". The Journal of Biological Chemistry, vol. 272, No. 39: 24588-24593.

Rovére, C. et al. (1999). "The RGD Motif and the C-terminal Segment of Proprotein Convertase 1 Are Critical for Its Cellular Trafficking but Not for Its Intracellular Binding to Integrin α5B1". The Journal of Biological Chemistry, 274: 12461-12467.

Sakai, J. et al. (1996). "Sterol-Regulated Release of SREBP-2 from Cell Membranes Requires Two Sequential Cleavages, One Within a Transmembrane Segment". Cell, 85: 1037-1046.

Sambrook, J.F. (1990). "The Involvement of Calcium in Transport of Secretory Proteins from the Endoplasmic Reticulum". Cell, 61: 197-199.

Scheek, S. et al. (1997). "Sphingomyelin depletion in cultured cells blocks proteolysis of sterol regulatory element binding proteins at site 1". Proc. Natl. Acad. Sci. USA, 94: 11179-11183.

Seidah, N.G. et al. (1994). "The family of subtilisin/kexin like pro-protein and pro-hormone convertases: Divergent or shared functions". Biochimie, 76: 197-209.

Seidah, Nabil G. (1995). "Molecular Strategies for Identifying Processing Enzymes". Methods in Neurosciences, 23: 3-15.

Seidah, N.G. et al. (1996). "cDNA structure, tissue distribution, and chromosomal localization of rat PC7, a novel mammalian proprotein convertase closest to yeast kexin-like proteinases". Proc. Natl. Acad. Sci. USA, 93: 3388-3393.

Seidah, N.G. et al. (1996). "Cellular processing of the neurotrophin precursors of NT3 and BDNF by the mammalian proprotein convertases". FEBS Letters 379: 247-250.

Seidah, N.G. et al. (1998). "Precursor Convertases: An Evolutionary Ancient, Cell-Specific, Combinatorial Mechanism Yielding Diverse Bioactive Peptides and Proteins". Ann, NY Acad Sci., 839: 9-24.

Seidah, N.G. et al (1998). "The Mammalian Precursor Convertases: Paralogs of the Substilin/Kexin Family of Calcium-Dependent Serine Proteinases", In: Hook, V.Y.H. (Ed.), Proteolytic and Cellular Mechanisms in Prohormone and Proprotein Processing, R.G. Landes Company, Georgetown, TX, USA, chapter 3: 49-76.

Shimomura, I et al. (1998). "Insulin resistance and diabetes mellitus in transgenic mice expressing nuclear SREBP-1c in adipose tisue: model for congenital generalized lipodystrophy". Genes & Developement, 12: 3182-3194.

Shimomura, I. et al. (1999). "Leptin reverses insulin resistance and diabetes mellitus in mice with congenital lipodystrophy". nature, 401: 73-76.

Sihmomura, I. et al. (1999). "Increased Levels of Nuclear SREBP-1c Associated with Fatty Livers in Two Mouse Models of Diabetes Mellitus". The Journal of Biological Chemistry, 274: 30028-30032.

Soma, M.R. et al. ((1992). "Cholesterol and mevalonic acid modulation in cell metabolism and multiplication". Toxicology Letters, 64/65: 1-15.

Spence, M.W. and Callahan, J.W. (1989). "Sphingomyelin-Cholesterol Lipidoses: The Niemann-Pick Group of Diseases". *In The Metabolic Basis of Inherited Disease* (Scriver, C.R. et al., editors). McGraw-Hill Publ. Co., 6th edition, chapter 66: 1655-1676.

Steiner, Donald F. (1998). "The Proprotein convertases". Curr. Opin. Chem. Biol., 2: 31-39.

Sviridov, D. (1999). "Intracellular cholesterol trafficking". Histology & Histopathology, 14: 305-319.

Volchkov, Viktor E. et al. (1998). "Processing of the Ebola virus glycoprotein converatse furin". Proc. Natl. Acad. Sci. USA, 95: 5762-5767.

Wang, X. et al. (1994). "SREBP-1, a Membrane-Bound Transcription Factor Released by Sterol-Regulated Proeolysis". Cell, 77: 53-62.

Yan, Q. et al. (1997). "Expression of Brain-Derived Neutrophic Factor Protein in the Adult Rat Central Nervous System". Neuroscience, 78: 431-448.

Zhong, Mei et al. (1999). "The Prosegments of Furin and PC7 as Potent Inhibitors of Proprotein Convertases". The Journal of Biological Chemistry, vol. 274, No. 48: 33913-33920.

* cited by examiner

```
Rat    MKLVNIWLLLLVVLLCGKKHLGDRLGKKAFEKAPCPSCSHLTLKVEFSSTVVEYEYIVAFNGYFTAKARNSFISS    75
Mouse     ST   V       R        TR L
Human                           E   S          G Rat    ALKSSEVDNWRIIPRNNPSSDYPSDFEVIQIKEKQKAGLLTLEDHPNIKRVTPQRKVFRSLKFAESDPIVPCNET   150
Mouse       E                                                                N
Human                                                                      Y    T Rat    RWSQKWQSSRPLKRASLSLGSGFWHATGRHSSRRLLRAIPRQVAQTLQADVLWQMGYTGANVRVAVEDTGLSEKH   225
Mouse
Human            R Rat    PHFKNVKERTNWTNERTLDDGLGHGTFVAGVIASMRECQGFAPDAELHIFRVFTNNQVSYTSWFLDAFNYAILKK   300
Mouse
Human Rat    MDVLNLSIGGPDFMDHPFVDKVWELTANNVIMVSAIGNDGPLYGTLNNPADQMDVIGVGGIDFEDNIARFSSRGM   375
Mouse
Human     I Rat    TTWELPGGYGRVKPDIVTYGAGVRGSGVKGGCRALSGTSVASPVVAGAVTLLVSTVQKRELVNPASVKQALIASA   450
Mouse
Human               M                                           M Rat    RRLPGVNMFEQGHGKLDLLRAYQILSSYKPQASLSPSYIDLTECPYMWPYCSQPIYYGGMPTIVNVTILNGMGVT   525
Mouse
Human                  N                                    V
```

FIG. 1A

```
Rat    GRIVDKPEWRPYLPQNGDNIEVAFSYSSVLWPWSGYLAISISVTKKAASWEGIAQGHIMITVASPAETELKNGAE  600
Mouse                                                                       HS
Human      D Q                                              V              S Rat    HTSTVKLPIKVKIIPTPPRSKRVLWDQYHNLRYPPGYFPRDNLRMKNDPLDWNGDHVHTNFRDMYQHLRSMGYFV  675
Mouse
Human      Q                                                      I Rat    EVLGAPFTCFDATQYGTLLMVDSEEEYFPEEIAKLRRDVDNGLSLVVFSDWYNTSVMRKVKFYDENTRQWWMPDT  750
Mouse                      L                           I
Human               S                                  I Rat    GGANVPALNELLSVWNMGFSDGLYEGEFALANHDMYYASGCSIARFPEDGVVITQTFKDQGLEVLKQETAVVDNV  825
Mouse      I                V          K                                    E
Human      I                V          K                                    E ▼
Rat    PILGLYQIPAEGGGRIVLYGDSNCLDDSHRQKDCFWLLDALLQYTSYGVTPPSLSHSGNRQRPPSGAGLAPPERM  900
Mouse             S
Human                                                                   SVT ▼
Rat    EGNHLHRYSKVLEAHLGDPKPRPLPACPHLSWAKPQPLNETAPSNLWKHQKLLSIDLDKVVLPNFRSNRPQVRPL  975
Mouse
Human                           R Rat    SPGESGAWDIPGGIMPGRYNQEVGQTIPVFAFLGAMVALAFFVVQISKAKSRPKRRRPRAKRPQLAQQAHPARTPSV  1052
Mouse
Human                       V   N      K  V   M V  PK
```

FIG. 1B

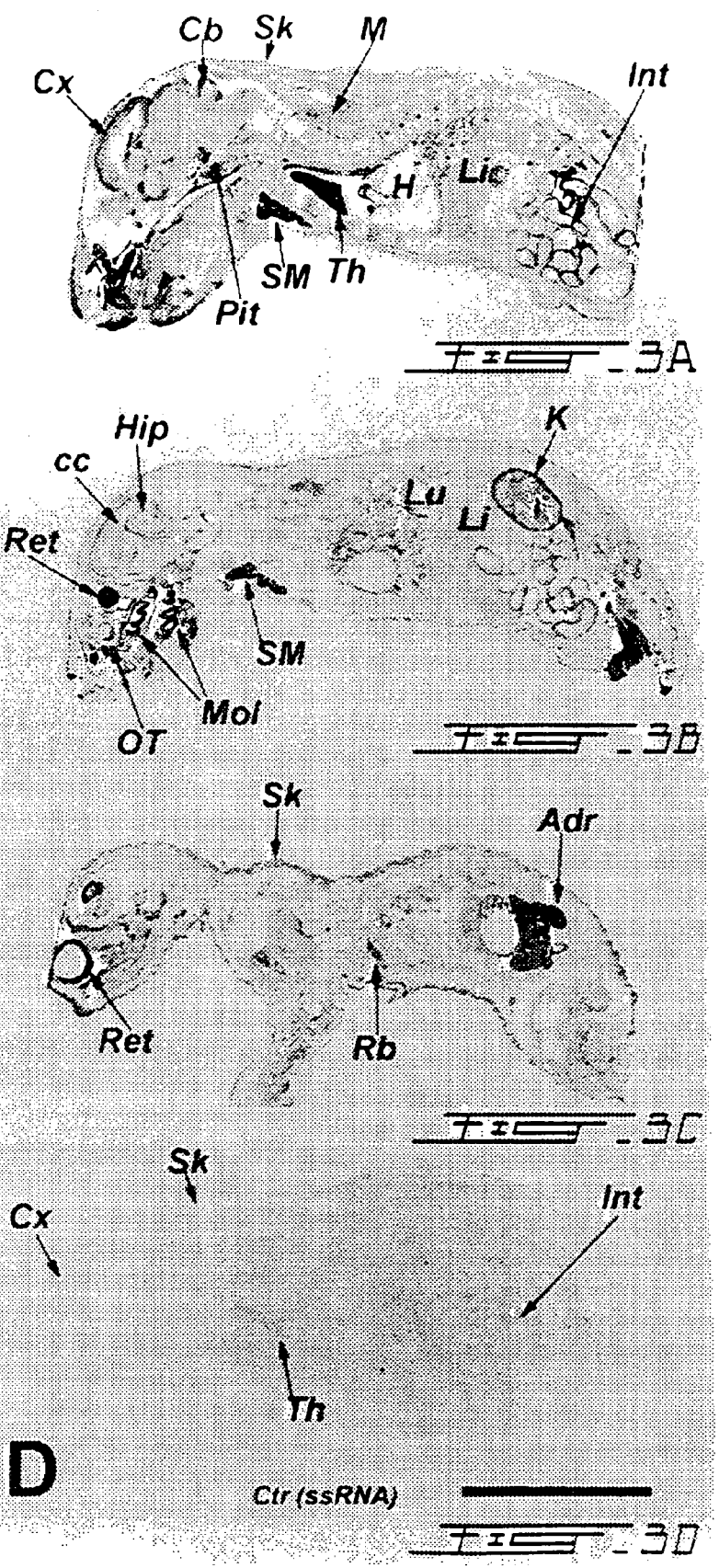

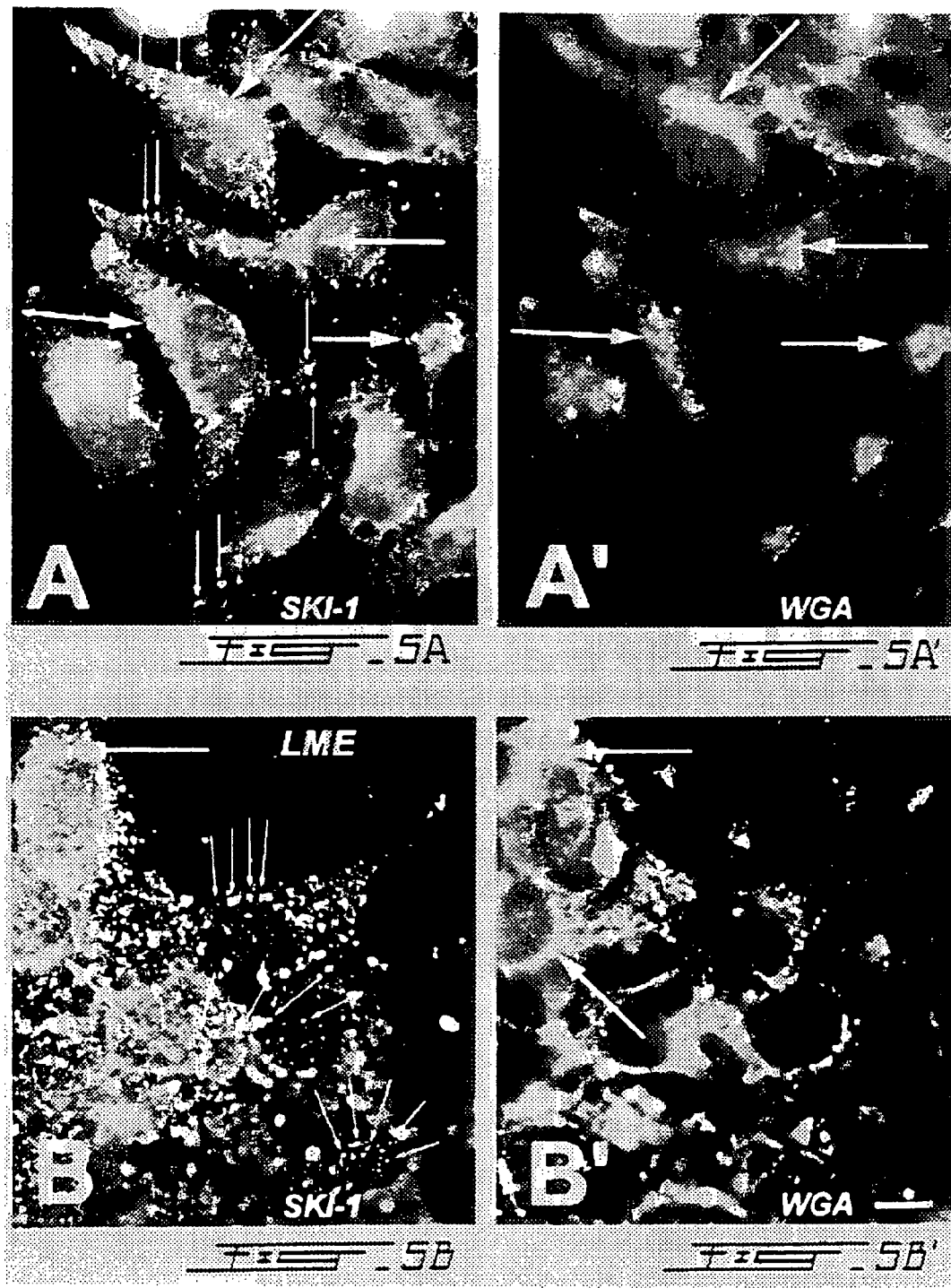

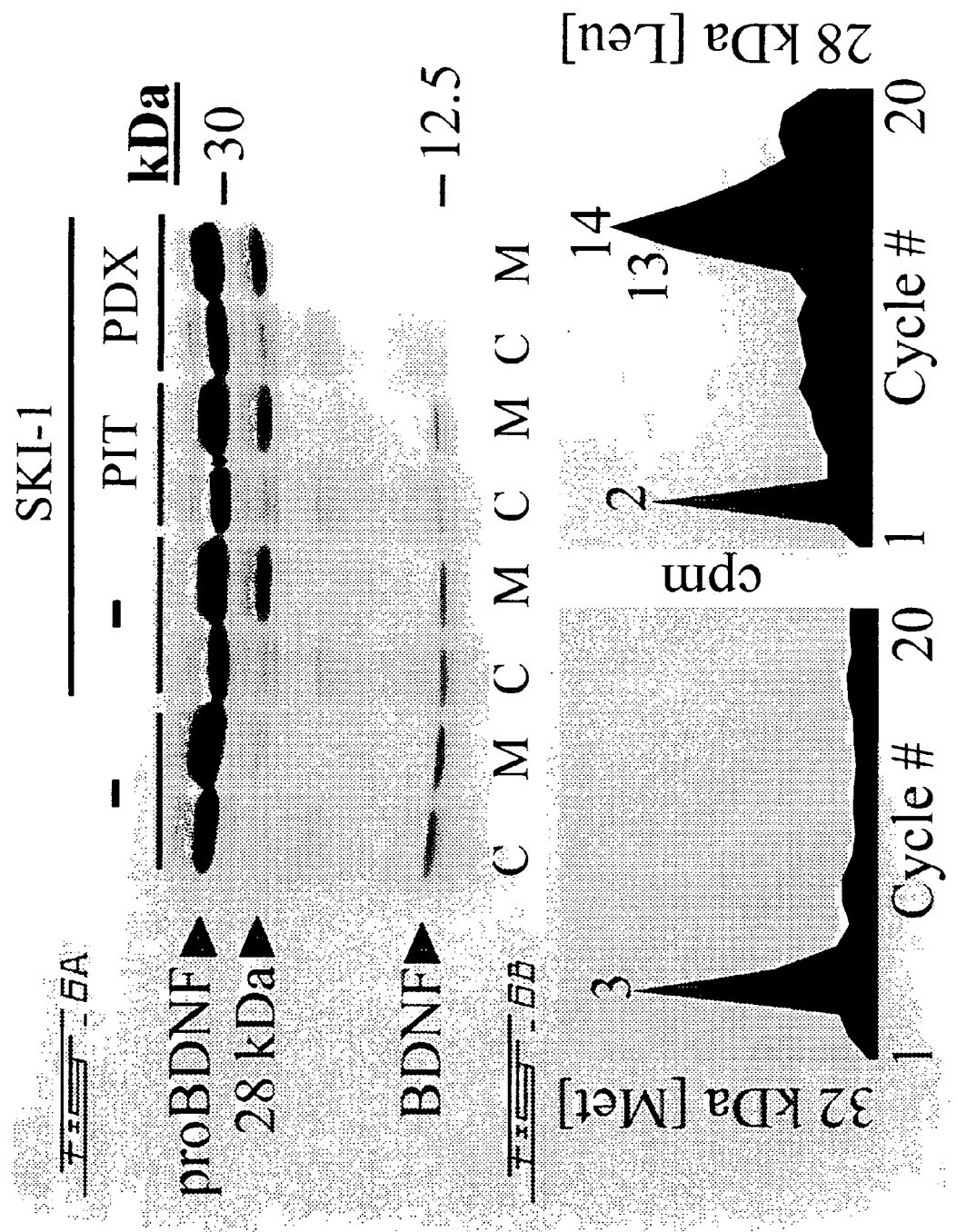

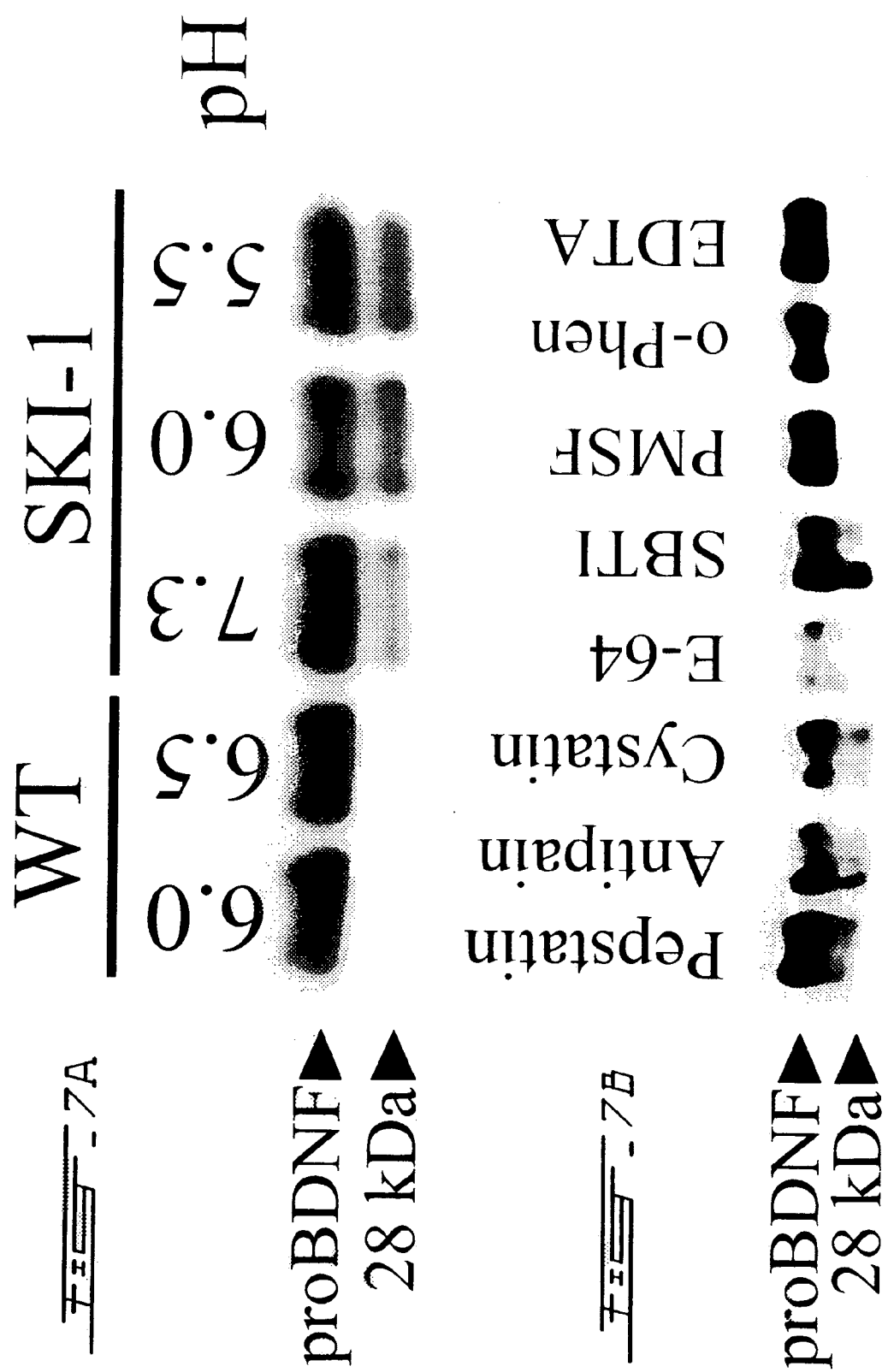

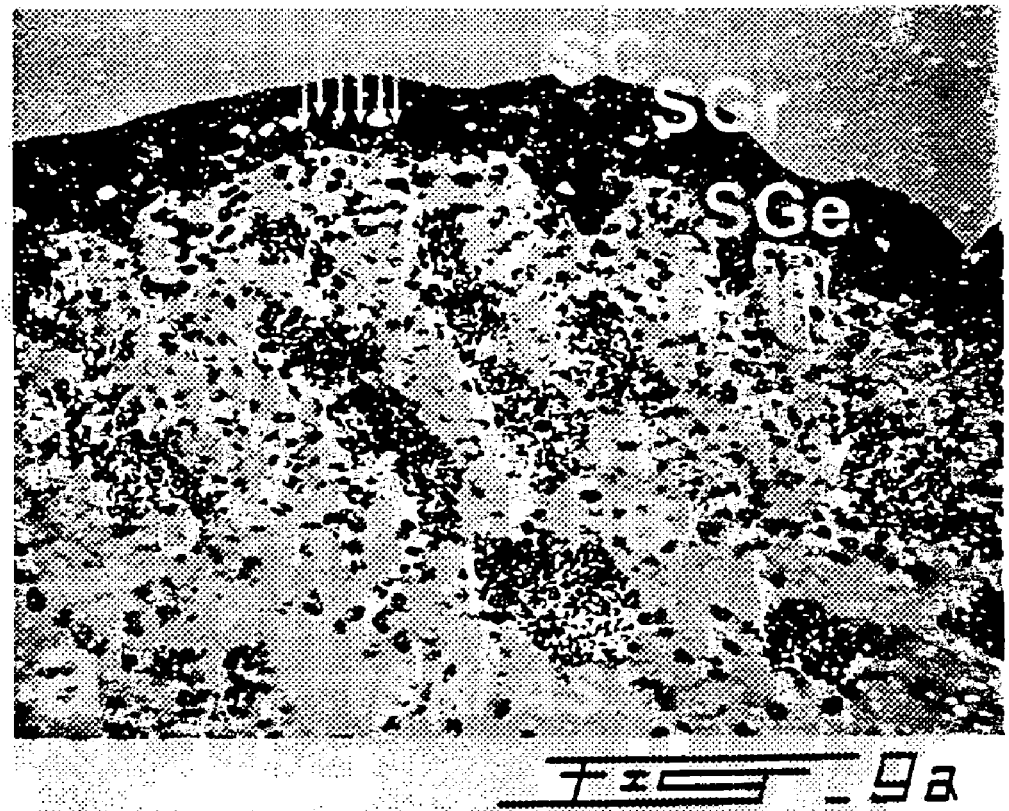
FIG_9a
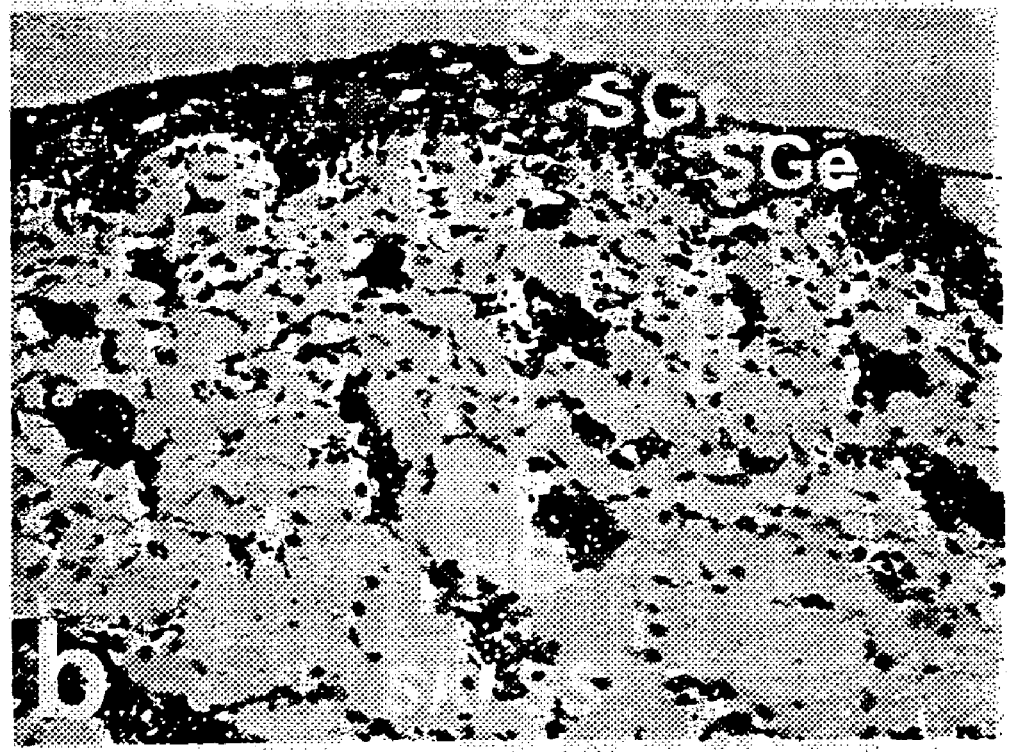
FIG_9b

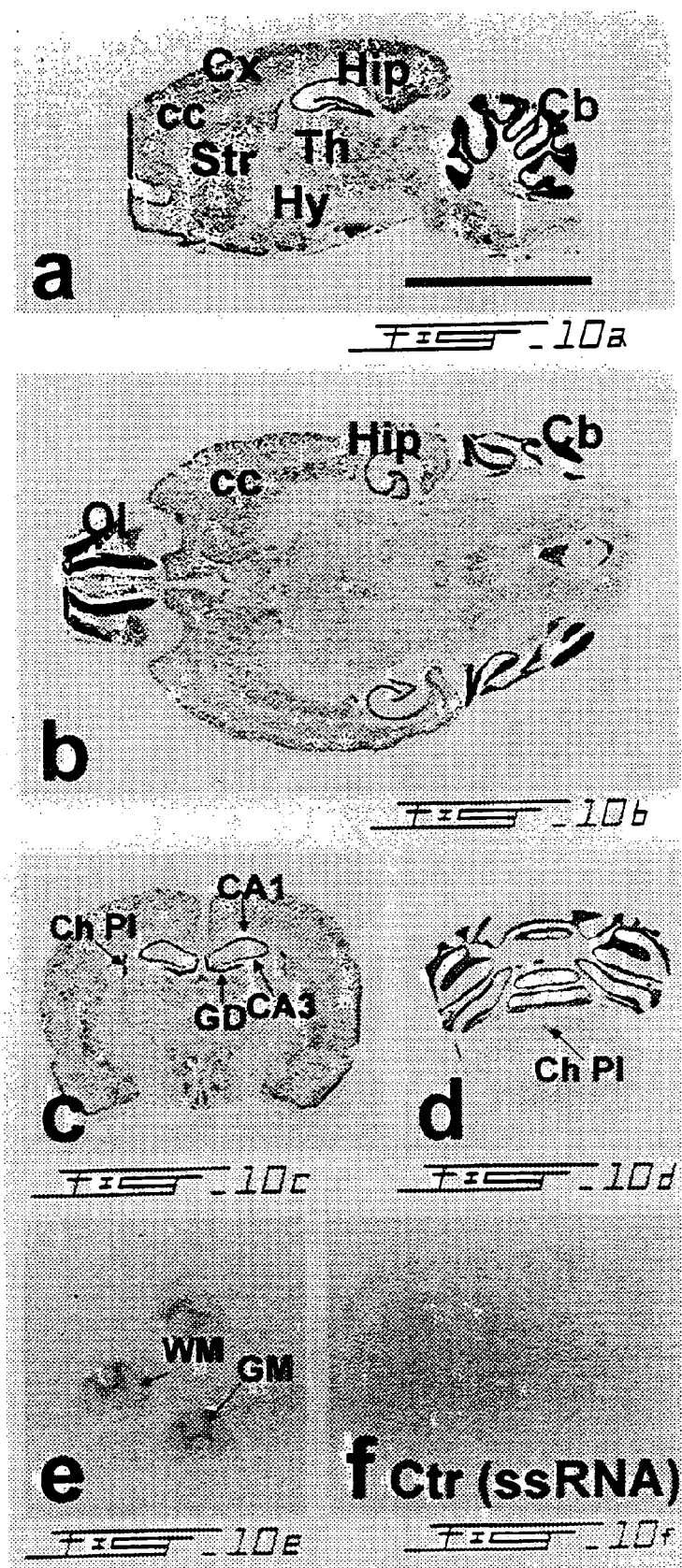

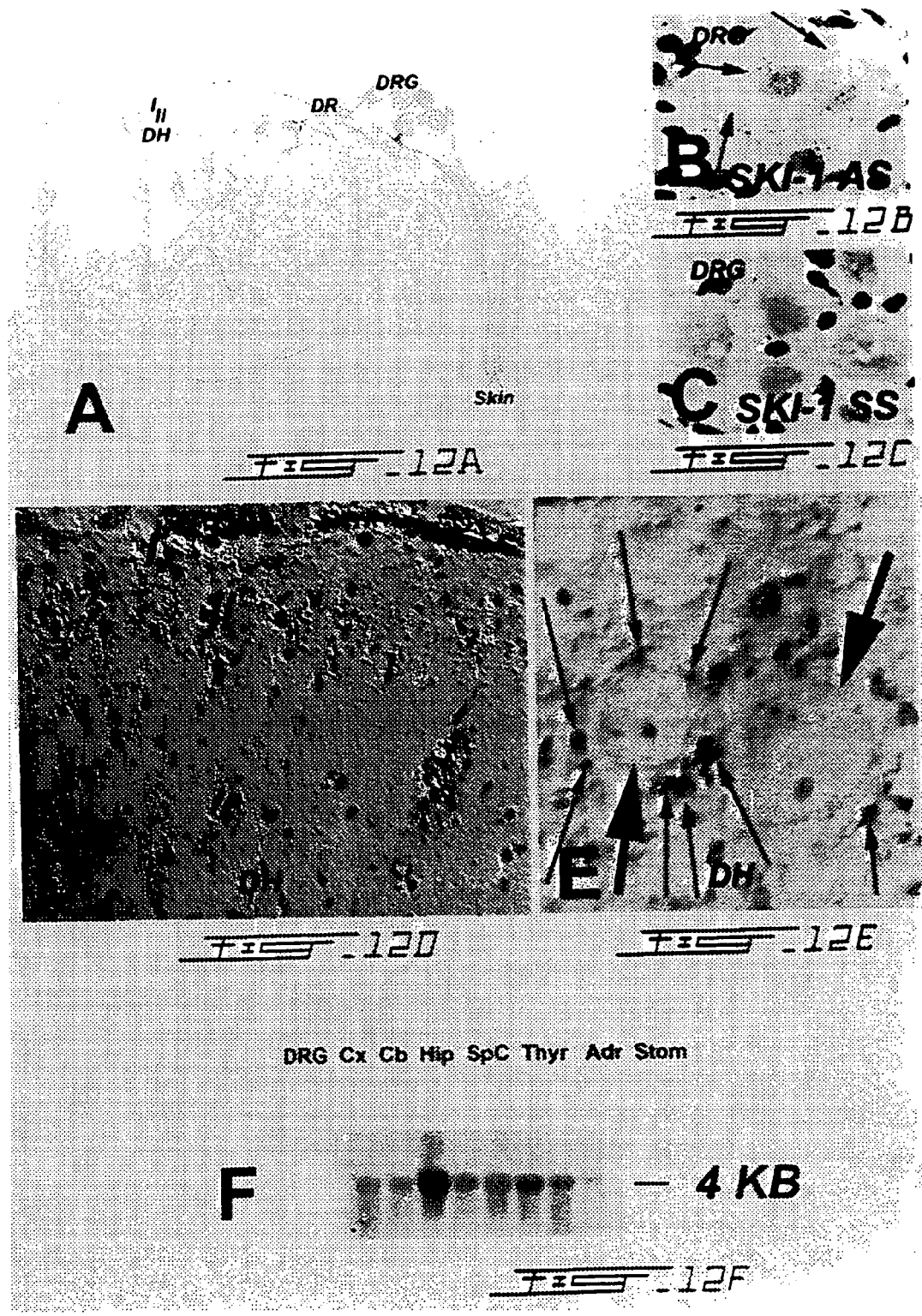

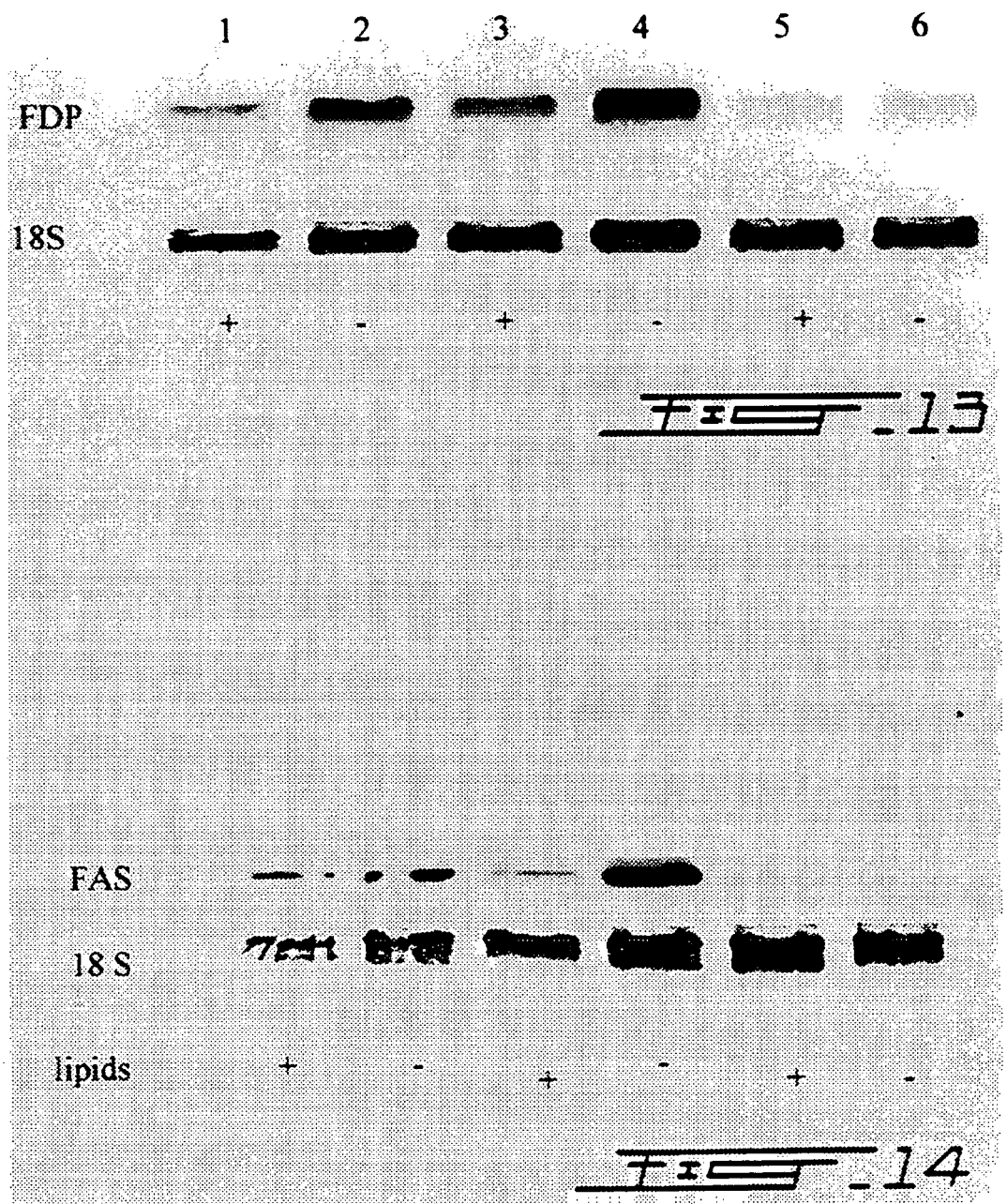

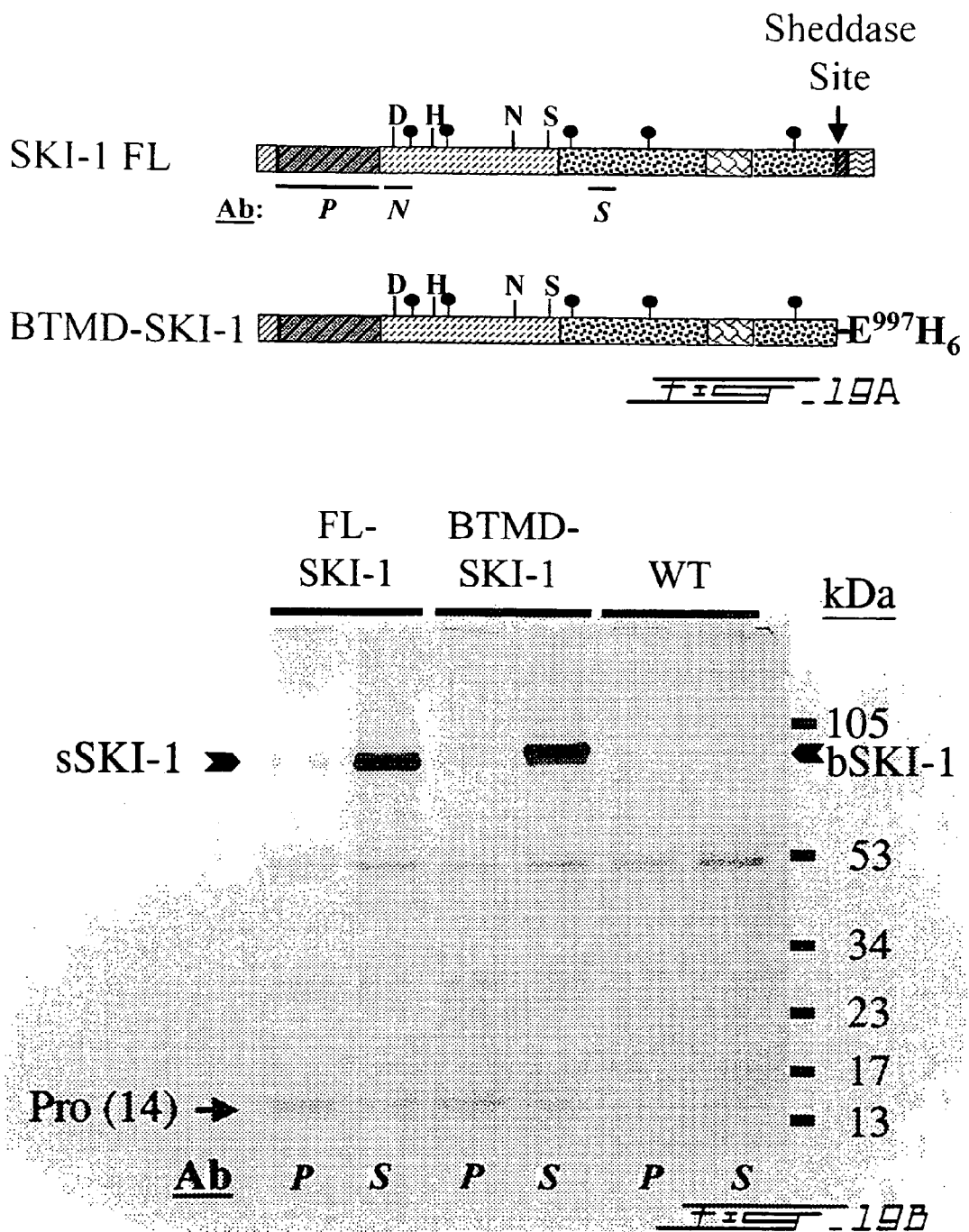

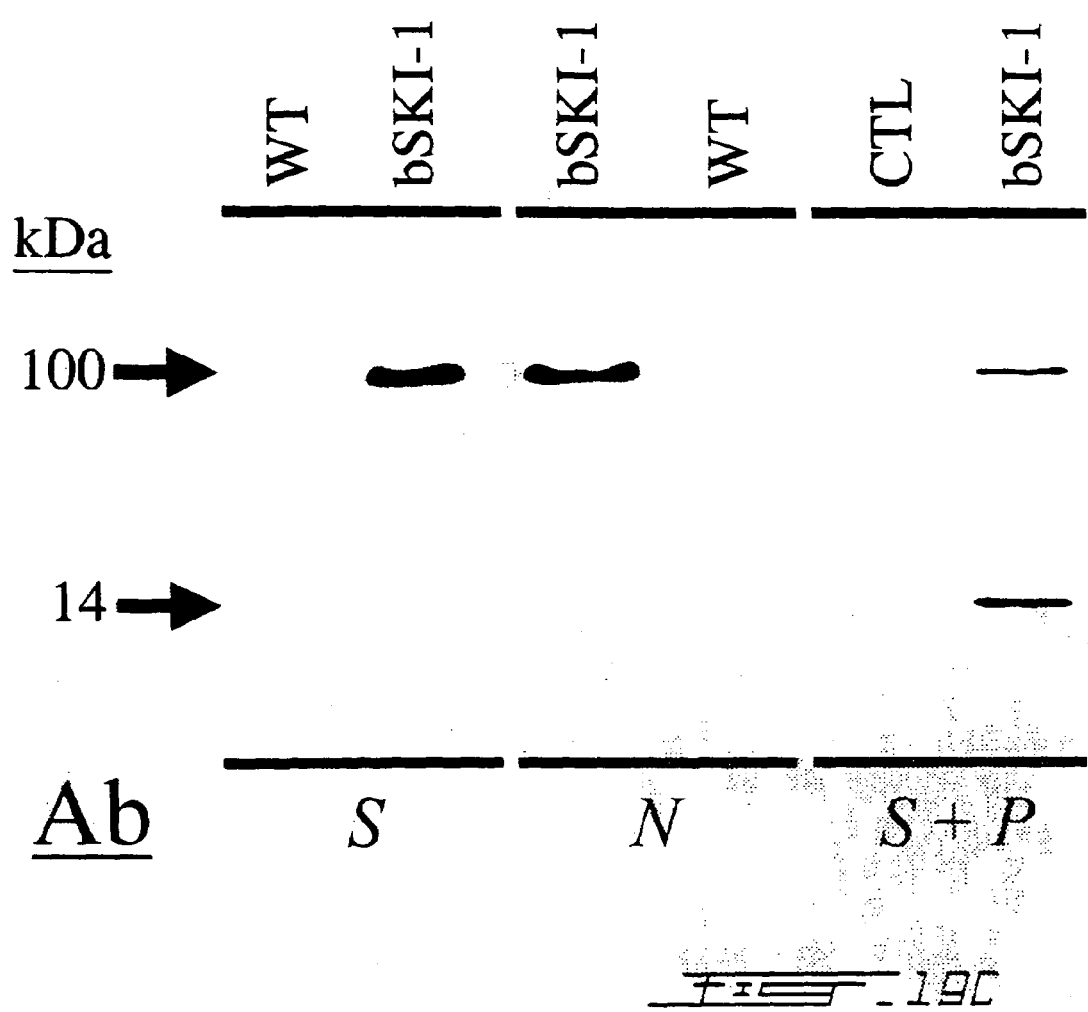

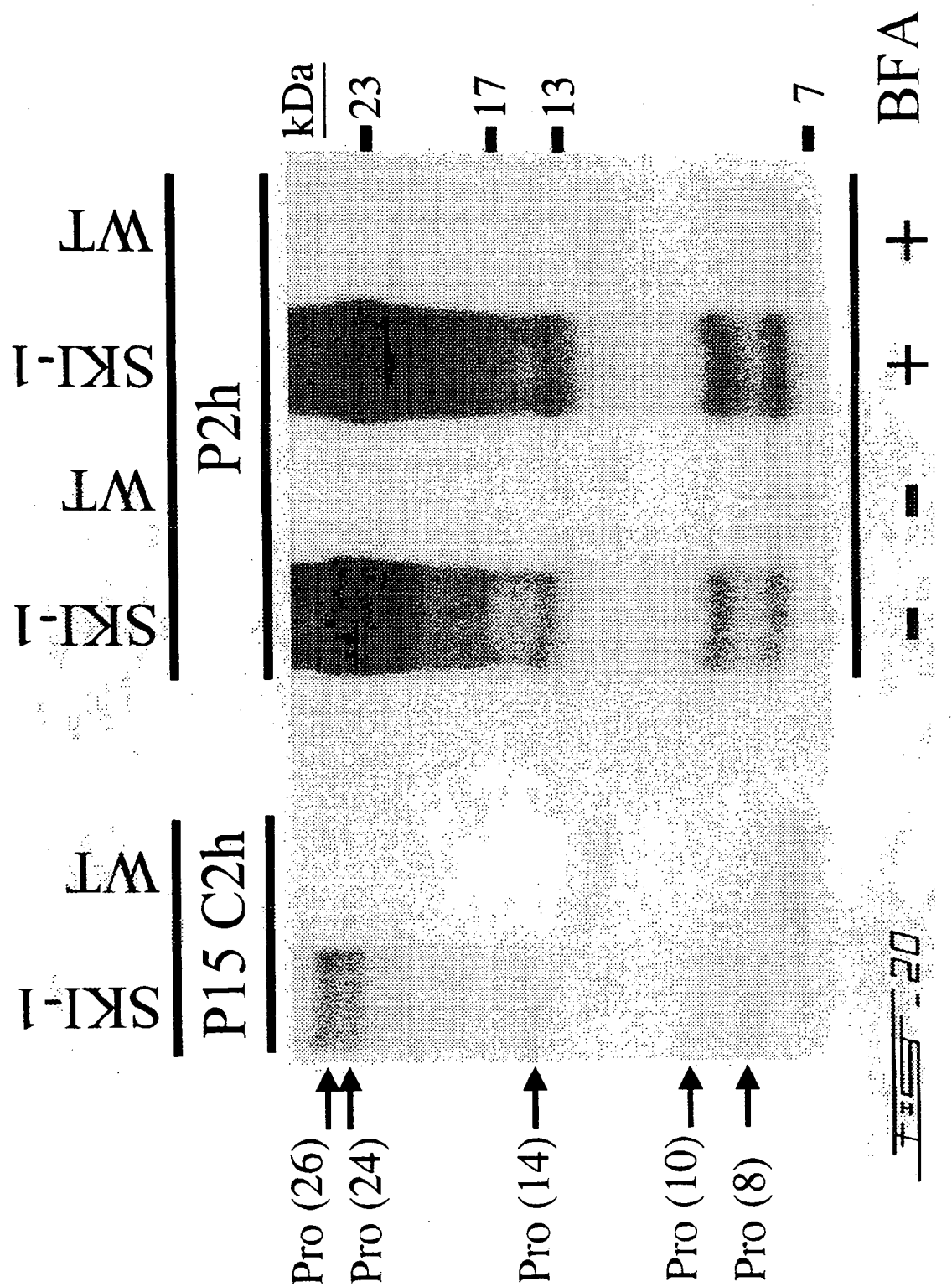

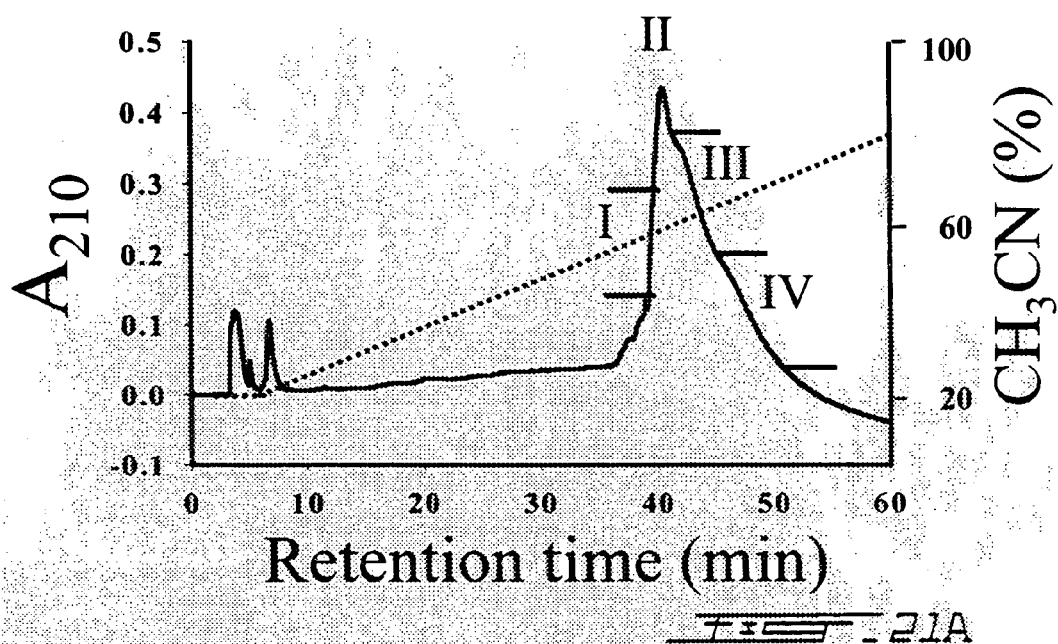
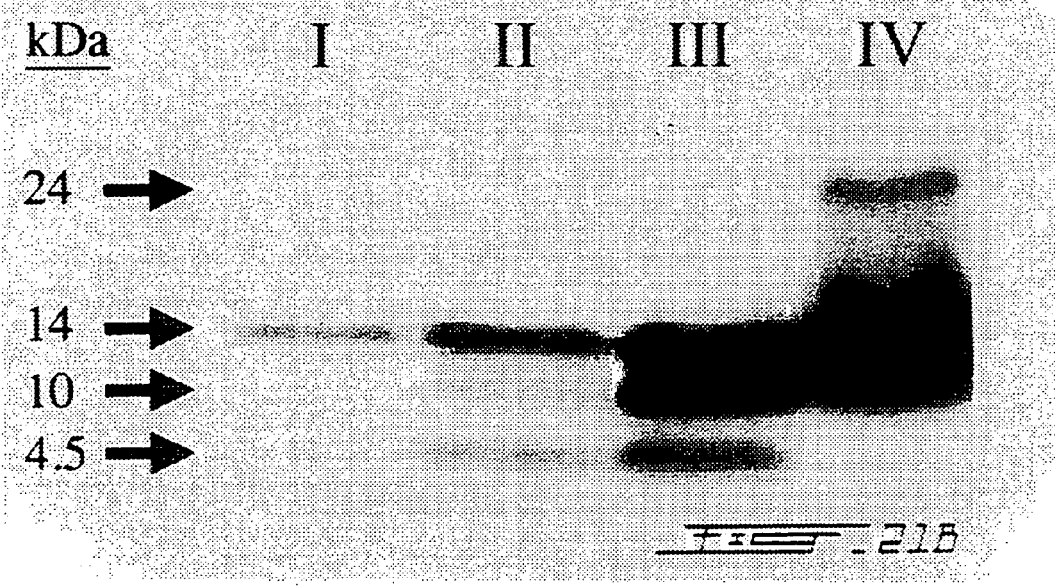

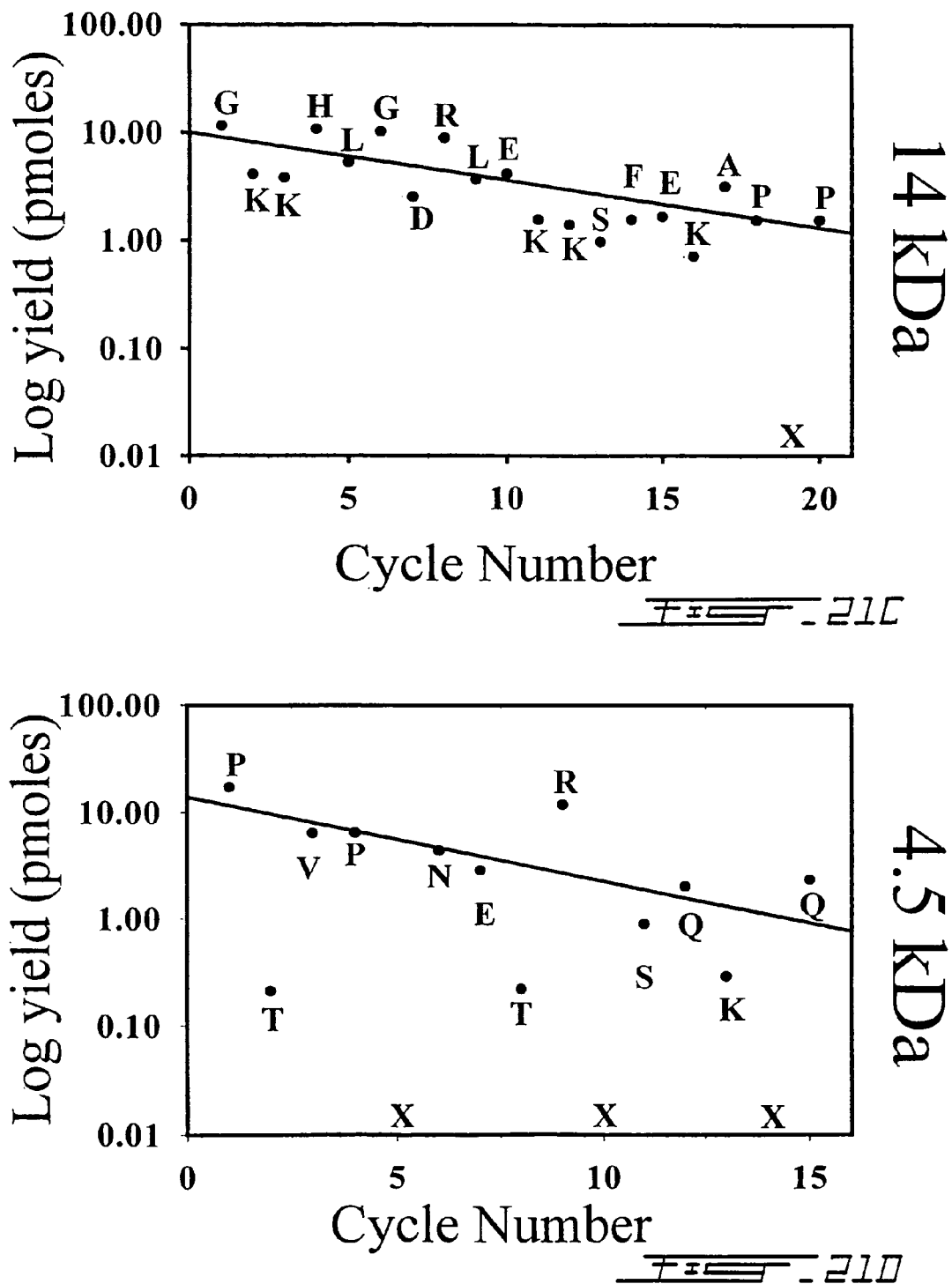

DPKK—RASL$^{167}$SLEH$_6$...RRLL$^{186}$RALEH$_6$...RQVA$^{194}$QTLEH$_6$

FIG. 24A kDa    PS1    PS2    PS3    PS1    PS2    PS3

21→

Ab    P
Western        Coomassie

FIG. 24B

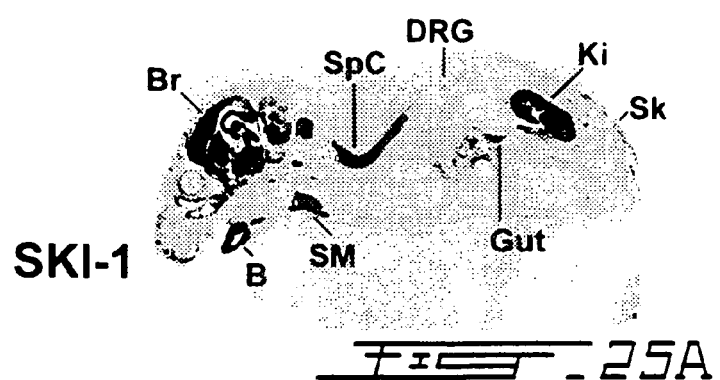
FIG. 25A
FIG. 25B
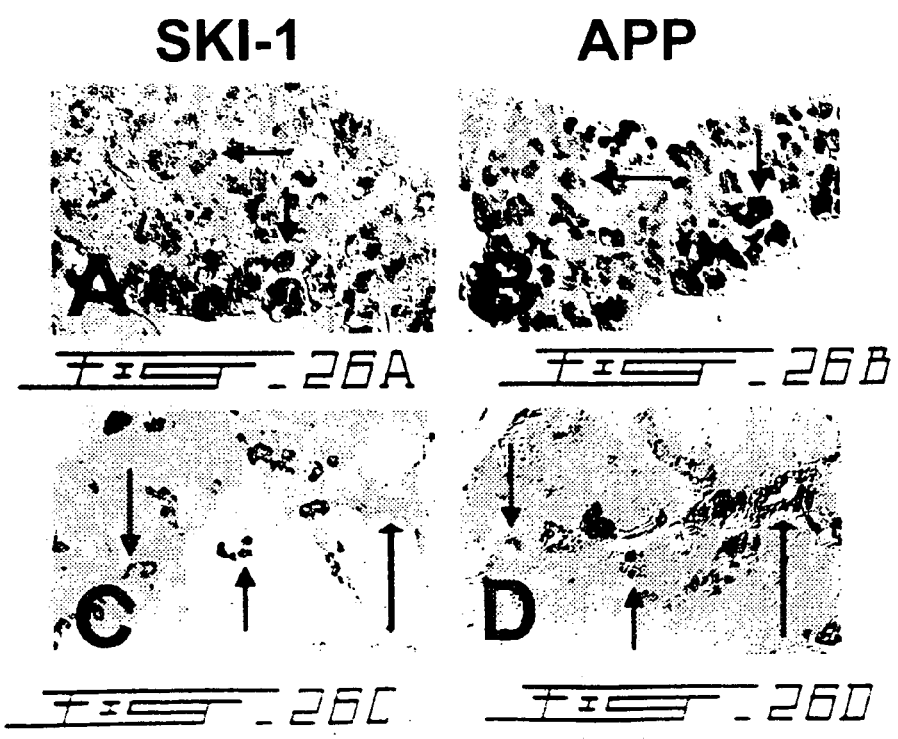
FIG. 26A  FIG. 26B
FIG. 26C  FIG. 26D

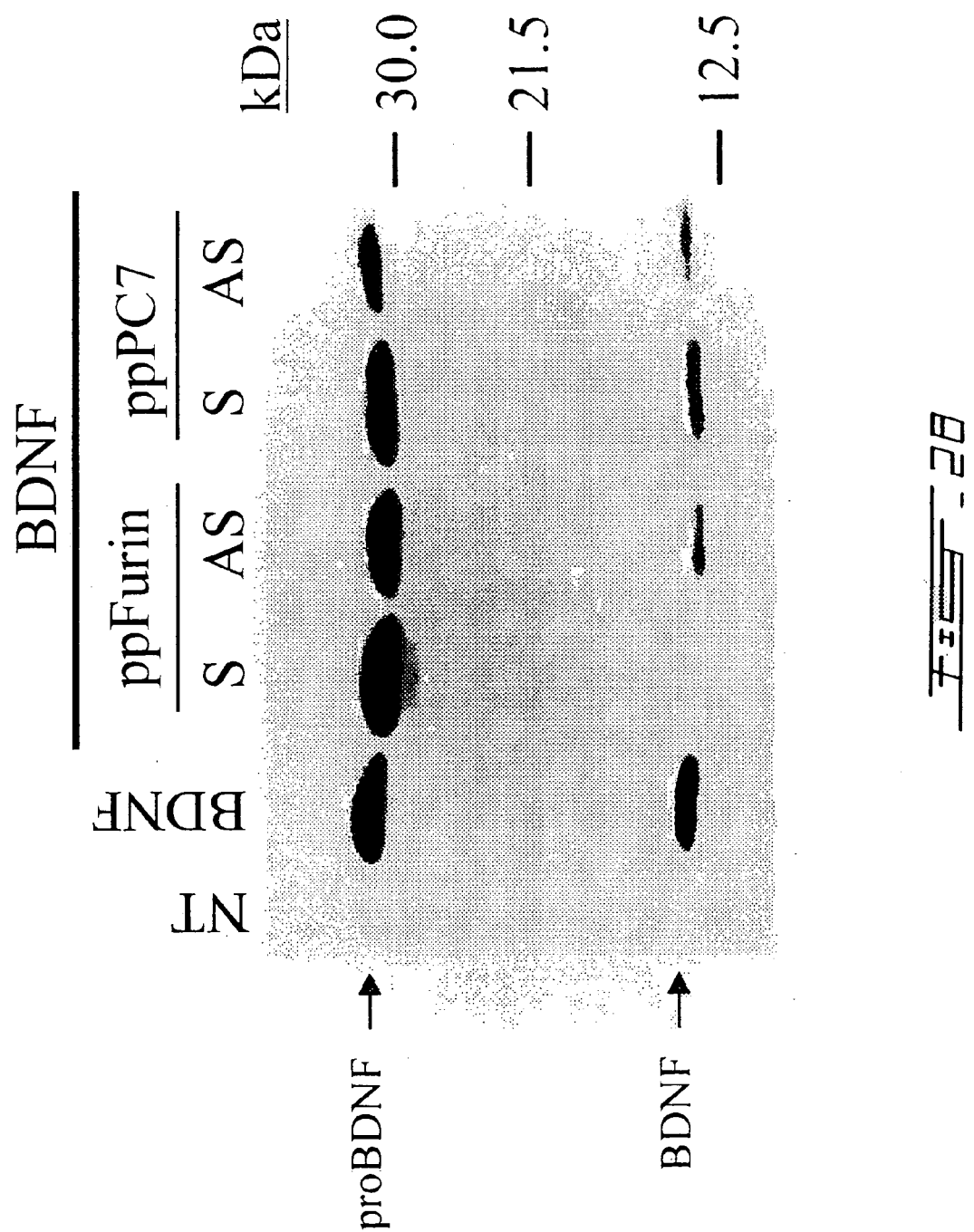

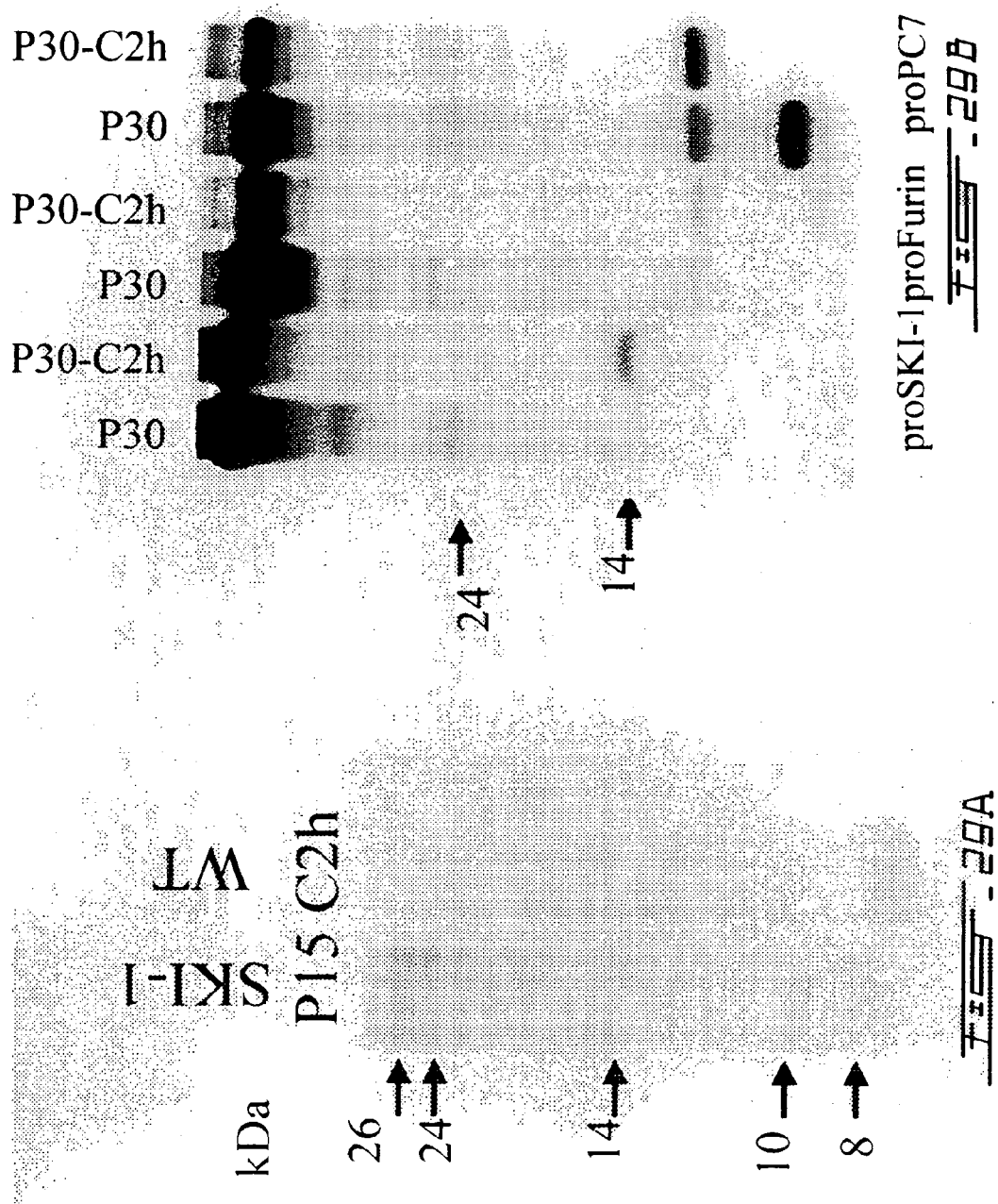

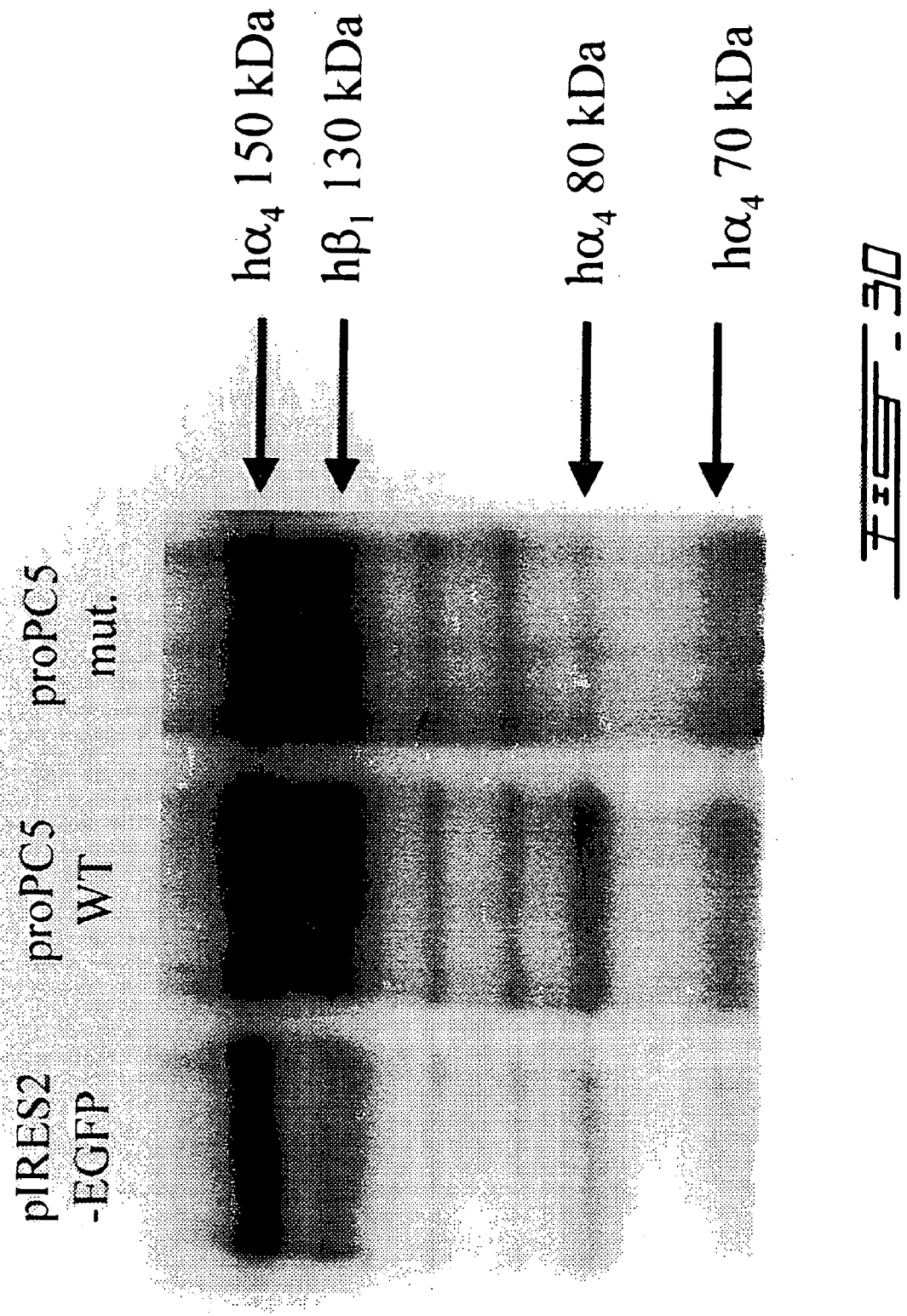

MAMMALIAN SUBTILISIN/KEXIN ISOZYME SKI-1: A PROPROTEIN CONVERTASE WITH A UNIQUE CLEAVAGE SPECIFICITY

FIELD OF THE INVENTION

This invention relates to a serine proteinase capable of converting proteic precursors into mature proteins; particularly a serine proteinase capable of cleaving at non-basic amino acid residues.

BACKGROUND OF THE INVENTION

Limited proteolysis of inactive precursors to produce active peptides and proteins is an ancient mechanism to generate biologically diverse products from a finite set of genes. Most often, such processing occurs at either single or dibasic residues, as a result of cleavage by a family of mammalian serine proteinases related to bacterial subtilisin and yeast kexin(1, 2). These enzymes, known as pro-protein convertases (PCs), participate in the tissue-specific intracellular processing of precursors at the consensus $(R/K)-(X)_n-R\downarrow$ sequence, where X is any amino acid except Cys and n=0, 2, 4 or 6 (1–3). PCs have been implicated in the production of various bioactive polypeptide hormones, neuropeptides, enzymes, growth factors, adhesion molecules, cell surface receptors and surface glycoproteins of infectious agents such as viruses and bacteria (1–3).

Less commonly, bioactive products can also be produced by limited proteolysis at amino acids such as Leu, Val, Met, Ala, Thr, Ser and combinations thereof (3). This type of cellular processing has been implicated in the generation of bioactive peptides such as α-and γ-endorphin (4), the C-terminal glycopeptide fragment 1–19 of pro-vasopressin (5), anti-angiogenic polypeptides such as platelet factor 4 (6) and angiostatin (7), the metalloprotease ADAM-10 (8), site 1 cleavage of the sterol receptor element binding proteins (9), as well as in the production of the Alzheimer's amyloidogenic peptides Aβ40, 42 and 43 (10). Processing of this type occurs in the endoplasmic reticulum (ER) (9), or late along the secretory pathway, within secretory granules (4, 5), at the cell surface, or in endosomes (6–8, 10). So far, the proteinases responsible for these cleavages have not been unambiguously identified.

Since mammalian convertases process precursors at either single or pairs of basic residues, we hypothesised that a distinct, but related, enzyme(s) may generate polypeptides by cleavage at non-basic residues. To test that idea, we employed an RT-PCR strategy similar to the one used to identify the PCs (11), except that we used degenerate oligonucleotides closer to bacterial subtilisin than to yeast kexin. This approach resulted in the isolation of a cDNA fragment encoding a putative subtilisin-like enzyme from human cell lines. This partial sequence was identical to a segment of a human myeloid cells-derived cDNA reported by Nagase et al. (12). A role for this putative subtilase remained undefined up to the present invention.

It was further discovered by Cheng, D. et al. (1999) J. Biol. Chem. 274.22805-22812 that an enzyme call S1p, is capable of cleaving sterol-regulatory element-binding proteins (SREBPs), which function to control lipid biosynthesis and uptake in animal cells. Upon cleavage, SREBPs are released from cell membranes for translocation to the nucleus, where they activate transcription of genes involved in the biosynthesis and uptake of cholesterol and fatty acids. S1p and the present enzyme or the same. Therefore, for diseases involving overexpression of these genes as well as any other disease involving SKI-i activity, it is contemplated that any inhibitor of SKI-1 would be useful in their treatment

SUMMARY OF INVENTION

We show that the sequences of the rat, mouse and human orthologues of this putative type-I membrane-bound subtilisin-kexin-isoenzyme, which we called SKI-1, exhibit a high degree of sequence conservation. Tissue distribution analysis by both Northern blots and in situ hybridization (ISH) revealed that SKI-1 mRNA is widely expressed. A stable transfectant of human SKI-1 in HK293 cells allowed the analysis of its biosynthesis and intracellular localization. We present data demonstrating that SKI-1 cleaves at a specific Thr$\downarrow$ residue within the N-terminal segment of human pro-brain-derived neurotrophic factor (proBDNF). SKI-1 is the first identified secretory mammalian subtilisin/kexin-like enzyme capable of cleaving a proprotein at non-basic residues.

Therefore in accordance with the present invention, there is provided a soluble proteic fragment of a subtilisin-kexin isoenzyme named SKI-1 which has the amino acid sequence defined by amino acids 187 to 996 of any one SEQ ID NOs: 2, 4 and 6, a variant thereof, or an enzymatically active part thereof.

It is further an object of this invention to provide a proteic fragment of SKI-1 enzyme, which has the amino acid sequence defined by amino acids 18 to 137 of any one of SEQ ID NOs: 2, 4 and 6, a variant thereof, or a part thereof, which is a pro-segment capable of binding with amino acids 18 to 1052 of SKI-1 in whole or in part.

A part of this pro-segment has a molecular weight of about 14 KDa and forms a tight complex with the soluble fragment of SKI-1.

The pro-segment is an inhibitor of SKI-1 activity.

To improve its inhibitory activity, the pro-segment sequence is modified to prevent further enzymatic processing in a cell expressing said proteic fragment.

The modification includes amino acid substitution, deletion or rearrangement. Nucleic acids encoding any of the above SKI-1 forms are also objects of this invention.

Recombinant vectors and hosts comprising these nucleic acids are also objects of this invention.

The recombinant vectors are preferably expression vectors.

The recombinant vectors comprise a promoter expressible in a target cell wherein expression of said nucleic acid is desirable, be it for a therapeutic or manufacturing purposes.

The recombinant vectors may also comprise an inducible promoter.

It is further an object of this invention to provide a method of producing a proteic fragment of SKI-1 enzyme, which comprises the steps of:

culturing a recombinant host cell expressing a SKI-1 nucleic acid in a cell growth and expression-supportive culture medium; and recovering the proteic fragment of SKI-1 in the culture medium.

There is also provided a method for cleaving a proteic precursor which is an enzymatic substrate for SKI-1 enzyme, which comprises the step of:

a) contacting the proteic precursor with a SKI-1 enzyme which as an amino acid sequence defined by amino acids 18 to 1052 of SEQ ID Nos: 2, 4 or 6, or a variant thereof, or the soluble form, for a time sufficient and in condition adequate for such cleavage to occur.

The cleavage may be provoked in vivo or in vitro, e.g. serving a therapeutic purpose or an industrial protein manufacturing use.

For the purpose of producing a protein or a peptide from a proteic precursor which is an enzymatic substrate for a SKI-1 enzyme, the method would further comprise the step of:

b) recovering and purifying the protein or peptide.

The method may be performed in cell-free assays, or may take place in a cell or in the presence of a cellular population, and wherein step a) comprises the step of transfecting a cell with a nucleic acid expressing a SKI-1 protein.

The cell may express said proteic precursor or may be transfected with a nucleic acid expressing the proteic precursor.

A method of silencing the expression or the activity of SKI-1 enzyme on a proteic precursor, which comprises the steps of:

contacting the enzyme or a nucleic acid encoding the enzyme with a ligand molecule which binds to the enzyme or to the nucleic acid, thereby interfering with the binding of the enzyme to the proteic precursor or with the expression of the nucleic acid encoding the enzyme, is also an object of this invention.

The ligand molecule may comprise an antisense nucleic acid to the nucleic acid encoding SKI-1, a pro-segment of a precursor protein encoding SKI-1, a SKI-inhibitor, a peptide mimicking a proteic precursor SKI-1 binding site, or an antibody molecule directed against SKI-1, or one which generates an inactive SKI-1 mutant form.

The pro-segment is a polypeptide extending from amino acids 17 to 137 of SEQ ID NOs: 2, 4, 6, or a variant thereof or an inhibitory part thereof.

We also provide a peptide of at least 7 amino acids capable of binding to and of being cleaved by SKI-1 catalytic active site, comprising the following general formula:

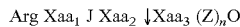

wherein Xaa$_{1, 2, 3}$ and Z are any amino acid

J is an alkyl or aromatic hydrophobic amino acid n is 1, 2 or 3

O is an acidic amino acid.

Preferably Xaa$_2$ is Lys, Leu, Phe or Thr.

A preferred peptide has the structure:

H2N-Val-Phe-Arg-Ser-Leu-Lys-Tyr-Ala-Glu-Ser-Asp-COOH (SEQ. ID. NO. 13).

The peptide may be labelled, a fluorogenic label being one of our preferred embodiments.

A fluorogenic peptide which has the following sequence:

Abz-Val-Phe-Arg-Ser-Leu-Tyr-Ala-Glu-Ser-Asp-Tyr (NO$_2$) (SEQ. ID. NO. 14) has been synthesized.

These peptides can be used for monitoring SKI-1 activity, for screening inhibitors of SKI-1 activity or for screening enhancers of SKI-1 activity.

An inhibitor of SKI-1 activity used in the making of a medication for treating a disease involving an overexpression of a SKI-1 or a SK1-1 substrate, is also a further object of this invention, namely the pro-segment modified or not.

The disease may be associated with any one of hypercholesterolemia, high levels of fatty acids, lipids or farnesyl pyrophosphate, liver steatosis, Ras-dependent cancer, restenosis and amyloid protein formation.

We also provide a method for detecting SKI-1 activity in a sample, which comprises the steps of contacting the sample with a ligand molecule to SKI-1 protein or nucleic acid, and detecting the formation of a complex between said ligand and SKI-protein or nucleic acid as an indication of the presence of SKI-1 in said sample. The ligand includes molecules such as anti-SKI-1-antibodies or a nucleic acid probes or primers.

Finally is provided a new use for SKI-1 enzyme in whole or in part which is for cleaving substrates not cleaved by other members of the subtilisin-kexin family. Variants of SKI-1 are under the scope of this invention, such variants are encoded by nucleic acids sharing at least 70% homology with the sequences defined in SEQ ID NOs: 1, 3, 5.

DESCRIPTION OF THE INVENTION

During our search for new members of the subtilisin-kexin family, we obtained two closely related sequences from mouse and rat tissues. When questioning gene data banks to find a match with other known sequences, we found that the human counterpart has been previously cloned and sequenced. However, no specific function for this enzyme was known. We named our new enzyme subtilisin-kexin isoenzyme 1 (SKI-1).

We characterized this enzyme and found that SKI-1 has a unique cleavage site in cognate substrates. One of these substrates is pro-BDNF. Sakai et al. have found that another substrate, SREBP-2, which is a sterol-responsive transcription element, was cleaved at a first enzyme processing site by an enzyme which they called site 1 protease (S1p). S1p and SKI-1 appeared to be the same enzyme.

Since SKI-1 is autocatalytically cleaved, this brings to three the number of substrates that are known to be recognized and cleaved by SKI-1. One object of this invention is therefore the use of SKI-1 as a protein processing enzyme.

SKI-1 is ubiquitously distributed and appears to be very well conserved amongst mammalian species. Therefore, variants of SKI-1 are within the scope of this invention. We have indeed identified two species variants of the human enzyme disclosed in gene data banks, and per se this is a proof that variants to screen SKI-1 activity exist.

SKI-1 is first located in the endoplasmic reticulum (ER) membrane. Upon processing the pro-segment of pro-SKI-1 is removed and SKI-1 is thus activated. SKI-1 is further processed to remove the transmembrane domain that keeps it integrated in the ER membrane, which generates a SKI-1 soluble form that is directed into the secretory pathway and which remains active. The soluble active form is indeed retrievable in culture media as well as the pro-segment. The pro-segment is itself also processed into shorter fragments. One of these fragments has an apparent molecular weight of about 14 KDa and forms a tight complex with the soluble SKI-1 form. The formation of this complex does not hinder the activity of the enzyme. It is known that the pro-segment of pro-protein convertases is inhibitory in vitro to the activity of the convertases. We demonstrate for the first time hereinbelow that such a behaviour occurs in an ex vivo model. SKI-1 pro-segment also has such an inhibitory activity. We predict that a SKI-1 pro-segment that would be modified to prevent the pro-segment processing will be an even better SKI-1 inhibitor. Such a modification is made by converting an enzyme recognition and cleavage site into a non-cleavable sequence. Such modification is intended to cover amino acid substitutions, deletions or re-arrangements to provide a SKI-1 pro-fragment that has an improved inhibitory activity.

The nucleic acids encoding all the above SKI-1 forms (soluble, pro-segment and sub-fragments, modified or not) are under the scope of this invention. Recombinant vectors and hosts comprising these nucleic acids are also objects of this invention. More particularly, expression vectors capable of producing the different SKI-1 forms are preferred. The expression vectors comprise promoter sequences which govern the expression of the nucleic acids. The promoter may be compatible with the cell wherein the expression of the nucleic acid is sought, be it for a therapeutic purpose or for the industrial production of SKI-1. The promoter may also be an inducible promoter which needs an exogenous inducing agent to activate the expression. For the production of any SKI-1 form, a recombinant host cell may be used and is cultured in a culture medium which supports cell proliferation and the expression of the nucleic acids. Under suitable conditions, the SKI-1 form of interest is expressed and may be conveniently recovered from the culture medium.

A general method for cleaving a proteic precursor is also an object of this invention. SKI-1 whole active enzyme or its soluble form or catalytically active fragments or variants are added to a proteic precursor which is a SKI-1 substrate, in conditions adequate for enzymatic precursor processing (cleavage) to occur. This method may be performed in vivo for curing a SKI-1 deficiency or in vitro for the industrial preparation of active proteins. In the latter case, the processing may be performed in a cell-free assay, using purified proteic precursors and SKI-1 whole enzyme or derived forms. Alternatively, it may be performed using transfected cells expressing SKI-1 whole enzyme and derived forms. The transfected cells may endogenously express the protein precursor or may be co-transfected to express the same. The transformed cells therefore become a manufacture of mature proteins and/or or SKI-1.

Modification of the SKI-1 activity is further an object of this invention. We have succeeded in inhibiting SKI-1 activity using the SKI-1 pro-segment. Alternative ways to achieve the same results include antisense nucleic acids or oligonucleotides, SKI-1 inhibitors, peptides mimicking a precursor SKI-1 binding site (cleavable or not), which would compete for the binding of SKI-1 to its cognate protein precursor site, and antibodies directed against SKI-1 or its cognate proteic precursor binding site. Another alternative is a genic therapy replacing the active SKI-1 by an inactive mutant form. On the opposite, overexpressing SKI-1 may cure a SKI-1 deficiency. Due to the ubiquitous distribution of SKI-1, it may be useful, even necessary, to target the cell wherein SKI-1 activity is to be modified for such a therapeutic purpose. Such targeting may include conjugating or combining molecules capable of modifying or modulating SKI-1 activity to a ligand capable of targeting the cell of interest. Immunoliposomes are examples of targeting vehicles as well as conjugated ligands-oligonucleotides. Even viral vectors may be made targeting if they express such a targeting ligand at the membrane surface. A targetting ligand serves a selection purpose, leaving substantially intact the non-targetted cells.

Peptides of less than 100 amino acids, more preferably of less than 30 amino acids, mimicking a cognate SKI-1 cleaving site in a proteic precursor have been synthesized and are also objects of this invention. Therefore, a peptide of at least 7 amino acids comprising the following preferred structure is capable of binding to and of being cleaved by SKI-1 enzyme catalytic site:

$$ArgXaa_1JXaa_2\downarrow Xaa_3(Z)_nO$$

wherein $Xaa_{1, 2, 3}$ and Z are any amino acid

J is an alkyl or aromatic hydrophobic amino acid
n is 1, 2 or 3
O is an acidic amino acid.
Preferably $Xaa_2$ is Lys, Leu, Phe or Thr.
The preferred peptide has the following sequence:
H2N-Val-Phe-Arg-Ser-Leu-Lys-Tyr-Ala-Glu-Ser-Asp-COOH (SEQ. ID. NO. 13).

These peptides may be labelled in such a way that labelled fragments produced upon cleavage are easily detected and identified. Such labelling include any type of suitable detectable markers. We have developed a fluorogenic peptide which shows a very good affinity for SKI-1. The above preferred peptide has been labelled at its N- and C-terminal ends with an orthoaminobenzoic acid and 3-nitrotyrosine groups, respectively.

These peptides as well as cell lines expressing SKI-1 will be especially useful for monitoring SKI-1 activity and for screening inhibitors or substrates and enhancers of SKI-1 activity.

Inhibitors of SKI-1, namely the SKI-1 pro-segment, will be used in the making of a medication for treating a diseasing involving overexpression of SKI-1 or of its substrate.

Conversely, substrates of SKI-1 will be used in the research field to discover physiological systems involving SKI-1.

Diagnostic methods and kits comprising a ligand to SKI-1 protein or nucleic acid, which is to be contacted with a sample suspected to express SKI-1, is also an object of this invention. Detection of the formation of a ligand-SKI-1 complex or of a hybridization complex is an indication of the presence or amount of SKI-1 in the sample.

Since we were the first to discover the function of SKI-1 enzyme, the use thereof for cleaving proteic precursors that are not substrates for the other members of the subtilisin-kexin family is an object of this invention. SKI-1 is intended in this broad use to cover the whole enzyme, a catalytic part thereof and its functional variants. Variants are encoded by anyone of the nucleic acids depicted in SEQ ID Nos: 1, 3 or 5, and any other sequences sharing at least 70% homology therewith, preferably more than 85% homology, under stringent conditions of hybridization.

Having now defined the general teachings of the present invention, reference will be made hereinbelow to specific examples and embodiments as well to the following appended figures, which purpose is to illustrate the invention rather than to limit its scope.

BRIEF DESCRIPTION OF FIGURES

FIG. 1 shows the comparative protein sequences of SKI-1 deduced from rat, mouse and human cDNAs (SEQ. ID. Nos. 2, 4, and 6 encoded by nucleic acids SEQ. ID. Nos: 1, 3 and 5 respectively). The position of the predicted end of the 17aa signal peptide is shown by an arrow. The active sites Asp 218, His249 and Ser414, as well as the oxyanion hole Asn 338 are in bold, shaded and underlined characters. The positions of the 6 potential N-glycosylation sites are emphasized in bold. The conserved shaded CLDDSHRQKDCFW (SEQ. ID. NO. 77) sequence fits in the consensus signature for growth factors and cytokine receptors family. Each of the two boxed sequences was absent in a number of rat clones. The predicted transmembrane segment is in bold and underlined

FIG. 3 shows in situ hybridization (1SH) of rSKI-1 mRNA in a 2 day old rat. ISH is shown at anatomical resolution on X-ray film using an [$^{35}$S]-labeled antisense riboprobe [A–C] and sense control riboprobe [D]. Abbreviations: Adr—adrenal gland; Cb—cerebellum; cc—corpus callosum; Cx—cerebral cortex; H—heart; nt—intestine; K—kidney; Li—liver; Lu—lungs; M—muscles; Mol—molars; OT—olfactory turbinates; Pit—pituitary gland; Rb—ribs; Ret—retina; Sk—skin, SM—submaxillary gland; Th—thymus. Magnification×4; scale bar (in D)=1 cm.

FIG. 5 shows hSKI-1 immunoreactivity in stably transfected HK293 cells. Representation of the comparative double fluorescence staining using a SKI-1 antiserum (directed against aa 634–651) [A] and [B] and FITC-labeled WGA [A'] and [B'] in control [A, A'] and LME-treated [B, B'] cells is shown. Thin arrows emphasize the observed punctate staining which is enhanced in the presence of LME. Large arrows point to the coincident staining of SKI-1 and WGA. Magnification×900; bar (in B')=10 μm.

FIG. 6 shows the processing of proBDNF by SKI-1. [A] COS-7 cells were infected with vv:BDNF and either w:VWT (–) or vv:SKI-1 in the presence of vv: PIT or vv:PDX. The cells were metabolically labeled with [$^{35}$S] Cys-Met for 4h and the media (M) and cell lysates (C) were immunoprecipitated with a BDNF antiserum, prior to SDS-PAGE analysis. The autoradiogram shows the migration positions of proBDNF (32 kDa), the 28 kDa BDNF produced by SKI-1 and the 14 kDa BDNF. [B] Microsequence analysis of the [$^{35}$S]Met-labeled 32 kDa proBDNF (maximal scale 1000 cpm) and [$^{31}$H]Leu-labeled 28 kDa BDNF (maximal scale 250 cpm), revealing a Met at sequence position 3 and Leu at positions 2, 13 and 14, respectively.

FIG. 7 shows the in vitro processing profile of proBDNF by SKI-1. [A] pH dependence of the processing of proBDNF by SKI-1. The SKI-1 enzyme preparation was compared to that obtained from the media of Schwann cells infected with the wild type virus (WT) as control. [B] Inhibitor profile of the processing of proBDNF to the 28 kDa BDNF by the same SKI-1 preparation as in [A]. The reaction was performed overnight at 37° C., pH 6.0. Notice that only PMSF (0.5 mM PMSF+50 μM pAPMSF), o-phenanthroline (5 mM), and EDTA (10 mM) effectively inhibited SKI-1 cleavage of proBDNF.

FIG. 9 shows the in situ hybridization translating the presence of SKI-1 mRNA sites in the skin of a newborn two days old (p2) rat using antisense (SKI AS) and control sense (SKI SS) riboprobes. The hybridization signal was detected in the stratum germinativum (small vertical arrows in SGe), in both outer and inner hair sheath (medium arrows) and in some cells within the dermis (D). Other abbreviations: HB—hair bulb, SC—stratum corneum, SGr—stratum granulosum. Magnification×80.

FIG. 10 shows the in situ hybridization (ISH) distribution of SKI-1 mRNA in the rat central nervous system (CNS). ISH distribution pattern in the CNS of adult rat demonstrates a higher concentration of SKI-1 mRNA within a grey matter (GM and all structures indicated with capital letters) vs the white matter (WM) including corpus callosum (cc). Representative brain structures are shown in sagittal (a); horizontal (b) and coronal plane (c–f) after hybridization with antisense SKI-1 riboprobe (a–e) and control sense riboprobe (ssRNA in f). As shown at anatomical level this type of mRNA distribution is highly reminiscent to a type of pan-neuronal gene distribution pattern. As complementary to this figure a Table 1 demonstrates at cellular level the predominance of neuronal SKI-1 mRNA expression over glial SKI-1 mRNA expression. Magnification×4; bar (in a)=1 cm. Abbreviations: CA1—area 1 of cornus Ammonis; CA3—area 3 of cornus Ammonis; Cb—cerebellum; cc—corpus callosum; Ch Pl—choroid plexus; Cx—cerebral cortex; GD—gyrus dentatus; GM—grey matter; Hip—hippocamp; Hy—hypothalamus; Ol—olfactory bulb; Str—striatum; WM—white matter.

FIG. 12 shows the distribution of SKI-1, mRNA and/or protein, in the region of spinal cord (SpC) and in the related dorsal root ganglion (DRG) and dorsal root (DR). Demonstrated are the region of neuronal cell bodies in the DRG (SKI-1 mRNA) and the region of nerve terminals in the dorsal horn of the spinal cord (layer I and II) characterized by a especial density of SKI-1 protein.

A) Schematic drawing depicting the position of layer I and ii in the dorsal horn as well as that of the related DRG and DR.

B) SKI-1 mRNA revealed by in situ hybridization labeling (thin arrows) in the DRG using antisense riboprobes (SKI-1 AS).

C) Control hybridization in the DRG using sense riboprobes (SKI-1 SS).

D) Immunocytochemical localization of SKI-1 (brown staining) within layer I and II of the dorsal horn and in the dorsal root (DR) suggesting the sensory afferents arriving from DRG. Neuronal and glial nuclei are stained on blue.

Magnification×300.

E) Immunoreactivity of SKI-1 (thin arrows) detected around neuronal somata (large arrows) within layer II of the dorsal horn at high magnification (×1,500). Pattern of immunoreactive spots is reminiscent to that of axo-somatic or axo-dendritic nerve terminals.

F) Northern blot revealing the concentrations of 4kb SKI-1 mRNA in different tissues including dorsal root ganglia (DRG) and spinal cord (SpC). Abbreviations: I—layer I of the dorsal horn; II—layer II of the dorsal horn; Adr—adrenal gland; Cb—cerebellum; Cx—cerebral cortex; Hip—hippocamp; DH—dorsal horn; DR—dorsal root; DRG—dorsal root ganglion; SpC—spinal cord; Stom—stomach and Thyr—thyroid gland.

FIG. 13 shows the farnesyl diphosphatase mRNA levels in HK 293 cells treated with (+)lipids (cholesterol and 25-hydroxycholesterol) or without lipids (−). 1–2=wild type cells, 3–4=SREBP-1 overexpressors, 5–6=a pool of 3 different clones overexpressing SREBP-1 and Pro-SKI-1; clones 4,6,9.

FIG. 14 shows the fatty acid synthase mRNA levels in HK 293 cells treated with (+) lipids (cholesterol and 25-hydroxycholesterol) or without lipids (−). 1–2=wildtype cells, 3–4=SREBP-1 overexpressors, 5–6=a pool of 3 different clones overexpressing SREBP-1 and Pro-SKI-1; clones 4,6, 9.

Figures 15A, 15B:
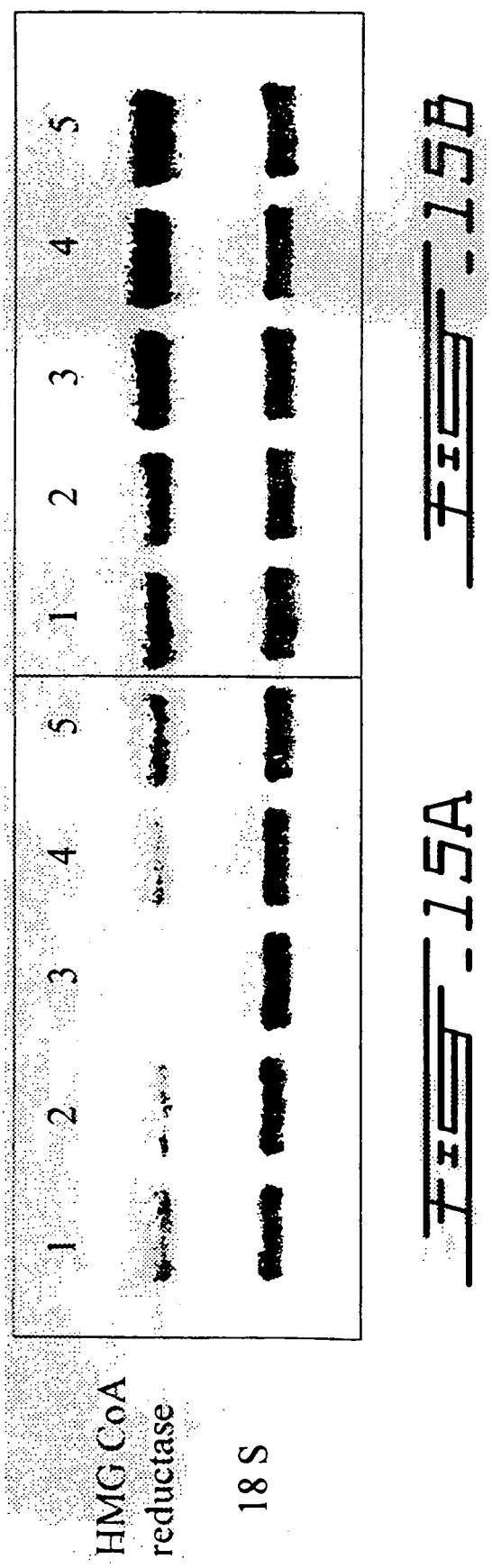

FIG. 15 shows the HMG CoA reductase mRNA levels in HK 293 cells treated with lipids (box A) or without lipids (box B). 1=wild type cells, 2=vector only cells, 3=SREBP-1 overexpressor cells, 4=SREBP-1 and ProSKI-1 overexpressor cells (high SREBP expression, clone 6), 5=SREBP-1 and ProSKI-1 overexpressor cells (low SREBP expression, clone 9).

Figure 16:

FIG. 16 shows the HMG CoA reductase and farnesyl diphosphatase mRNA levels in Hk 293 cells in different clones overexpressing SREBP-1 (1–5) or SREBP-1 and ProSki-1 (clone 4, clone 6, clone 9). Cells were treated with fetal calf serum.

Figure 17:
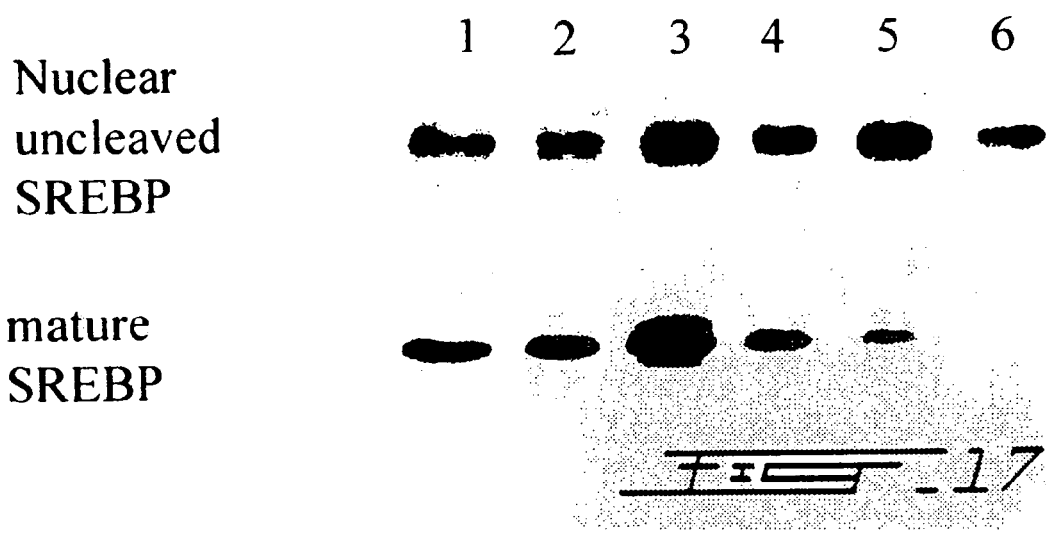

FIG. 17 shows the nuclear SREBP-1 in HK 293 cells in absence of lipids. Mature SREBP is processed in the ER and translocated into the nucleus. 1=wild type cells, 2=vector only cells, 3=SREBP-1 overexpressors, 4=SKI-1 antisense cells, 5=ProSki+SREBP-1 overexpressors clone 6, 6=ProSKI+SREBP-1 overexpressors clone 9.

Figure 18:
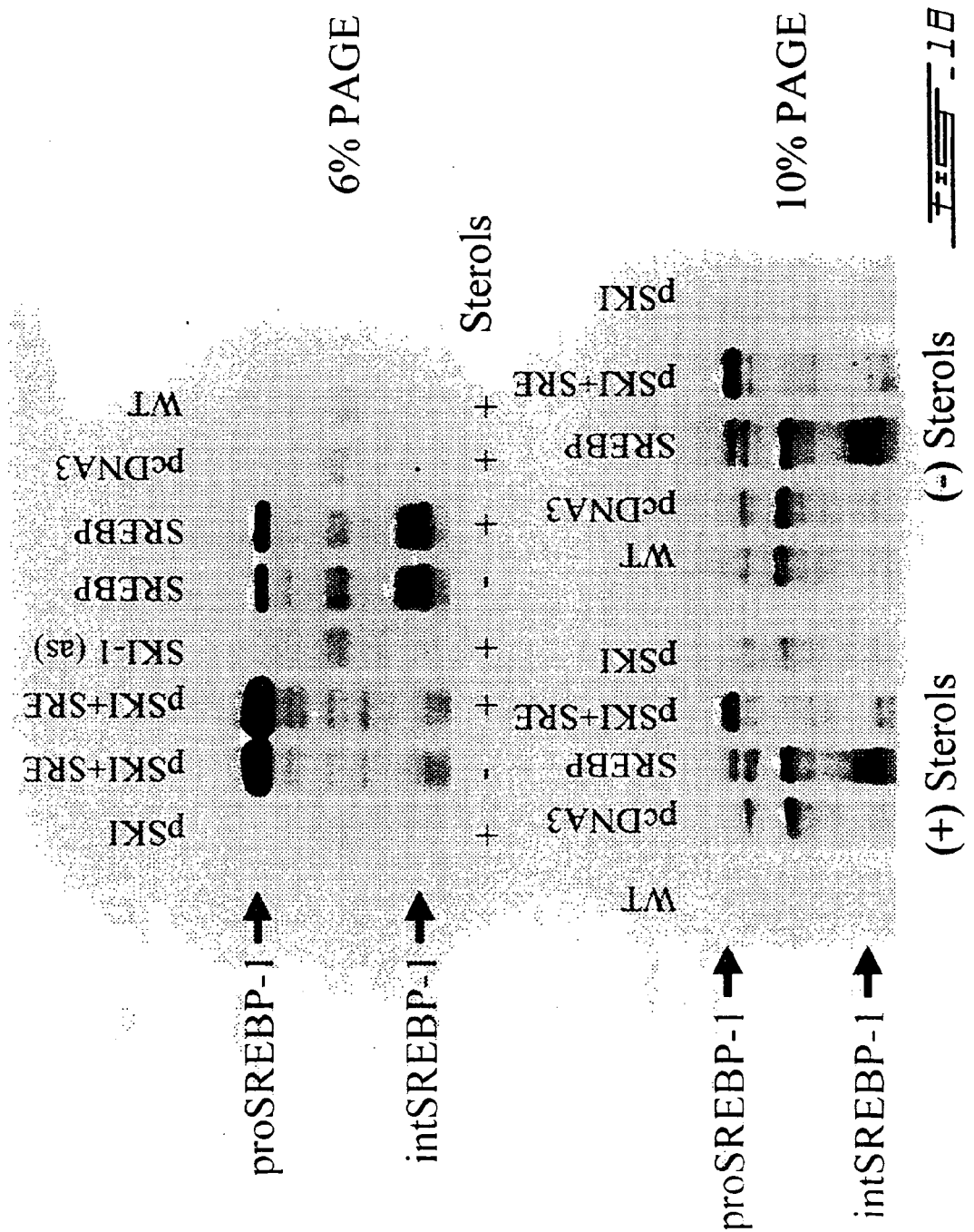

FIG. 18 shows the processing of cytoplasmic SREBP-1 in HK 293 cells. 50 pg of protein per lane was separated in 6% (above) and 10% (below) SDS-PAGE gels. Uncut SREBP-1 (proSREBP-1) and intermediate SREBP-1 (intSREBP-1) cleaved by SKI-1 are indicated with arrows. Cell lines express ProSKI-1 (pSKI), SKI-1 anti-sense (SKI-1 as), SREBP-1, or ProSKI-1 and SREBP-1 (pSKI+SRE), or control vector (pcDNA3), as indicated. Analysis was performed in the presence (+sterols) or absence of sterols (−sterols).

FIG. 19 [A] is a schematic representation of the structure of FL-SKI-1 and its truncation mutant BTMD-SKI-1. The various SKI-1 domains depicted are, respectively, the signal peptide, pro-segment, catalytic domain, and the C-terminal region comprising a cytokine receptor/growth factor motif, a transmembrane domain and a cytosolic tail. The positions of polypeptides used to produce SKI-1-specific antisera (Ab: P, N and S) are also displayed. FIG. 19 [B] shows the biosynthetic analysis of SKI-1. VV:FL-SKI-1, BTMD-SKI-1 (bSKI-1) or control VV:WT infected LoVo cells were pulse-labeled with [$^{35}$S]Cys for 3h. Media were immunoprecipitated with either Ab:S or Ab:P and then resolved by SDS-PAGE on an 8% gel followed by autoradiography. Arrows point to the migration positions of the 100 kDa BTMD-SKI-1 (bSKI-1), the 98 kDa shed form (sSKI-1) as well as the 14 kDa prosegment product. FIG. 19 [C] shows a Western blot analysis of the overexpressed BTMD-SKI-1. Samples from VV:WT or BTMD-SKI-1 infected BSC 40 cells (left and middle panel) were processed as described in "Experimental Procedures" and run on an 8% SDS-PAGE reducing gel. Following electrotransfer to PVDF membranes, protein bands were visualized via ECL detection using primary rabbit antisera Ab:S or Ab:N. Purified BTMD-SKI-1 (right panel, *) was obtained from a Ni$^{2+}$ affinity resin as described in "Experimental Procedures", then processed as described above. A mixture of Ab:S and Ab:P were used as primary antisera. Elution buffer was used as a control (CTL).

FIG. 20 shows the biosynthetic analysis of the rate of zymogen processing and the fate of the prosegment of SKI-1. LoVo cells overexpressing VV:FL-SKI-1 were pulse-labeled with [$^{3}$H]Leu for 15 min and then chased for 2h (P15C2h), or pulsed for 2h in the presence or absence of BFA (P2h). Cell lysates were immunoprecipitated with Ab:P, resolved by SDS-PAGE on a 14% gel and autoradiographed. The migration positions of the major ~26, 24, 14, 10 and 8 kDa prosegments are emphasized.

FIG. 21 illustrates the purification and identification of secreted recombinant pro-SKI-1. [A] Media obtained from HK293 cells stably expressing FL-SKI-1 were concentrated and sequentially applied to C4 semi-preparative column (not shown) followed by a C4 analytical RP-HPLC columns, and then eluted by the indicated linear CH3CN gradient. [B] The fractions labeled I-IV were collected and analyzed by Western blotting using the primary antiserum Ab:P. [C,D] Proteins contained in fraction IV were separated on a 10% SDS-PAGE reducing gel. Following electrotransfer, the proteins were stained with Ponceau Red. The immunoreactive 14 kDa and non-immunoreactive but colored ~4.5 kDa [D] polypeptides were excised and submitted to N-terminal sequencing (X represents an undefined residue). [E] Mass spectrometric analysis by MALDI-TOF spectrometry of fraction IV. The C-terminal residues sites believed to corresponding to the three ~14 kDa polypeptides are underlined, whereas the expected (potential) cleavage sites are indicated by dashed arrows (SEQ. ID. NO. 108.

Figure 22A:
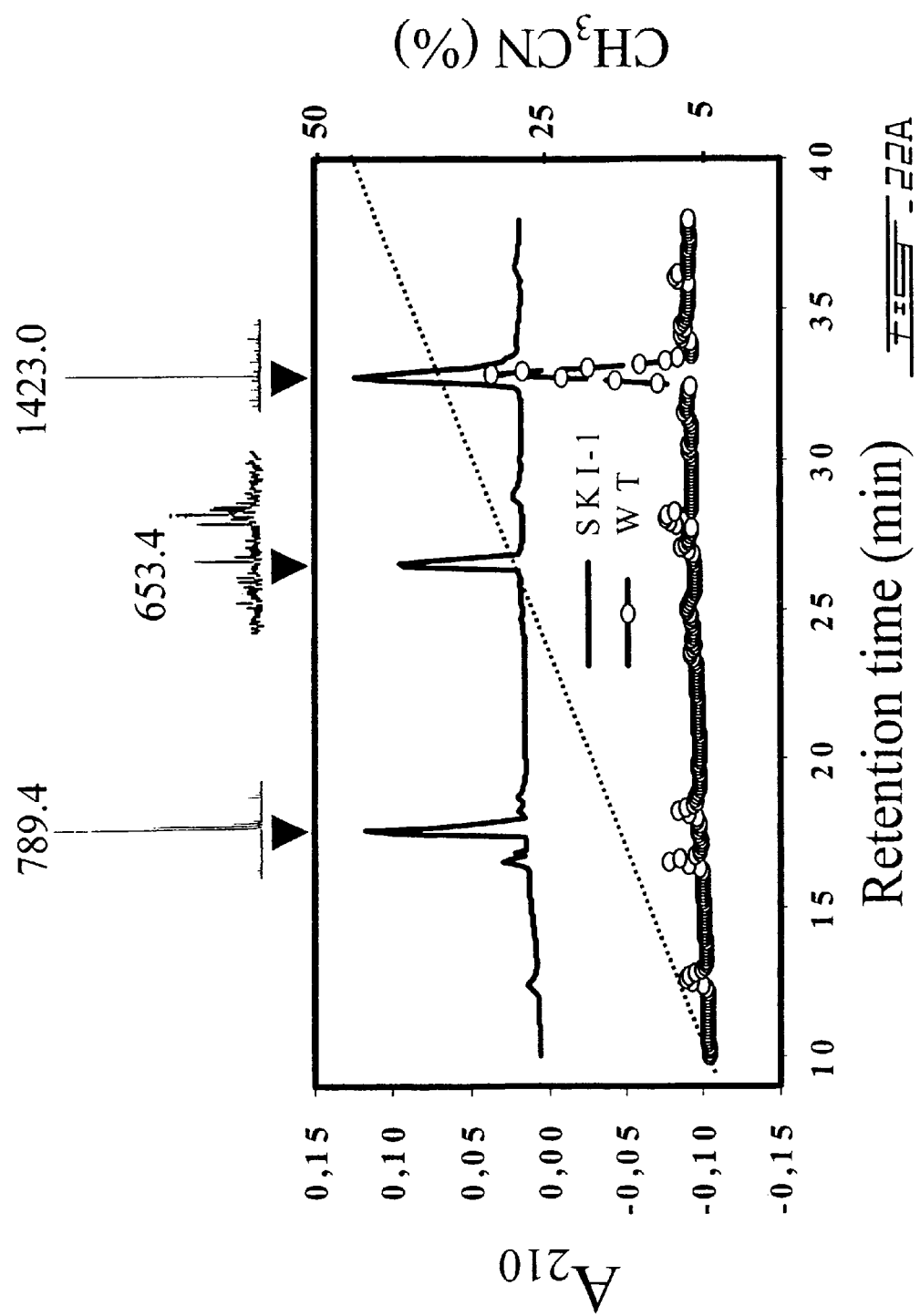
Figure 22B:
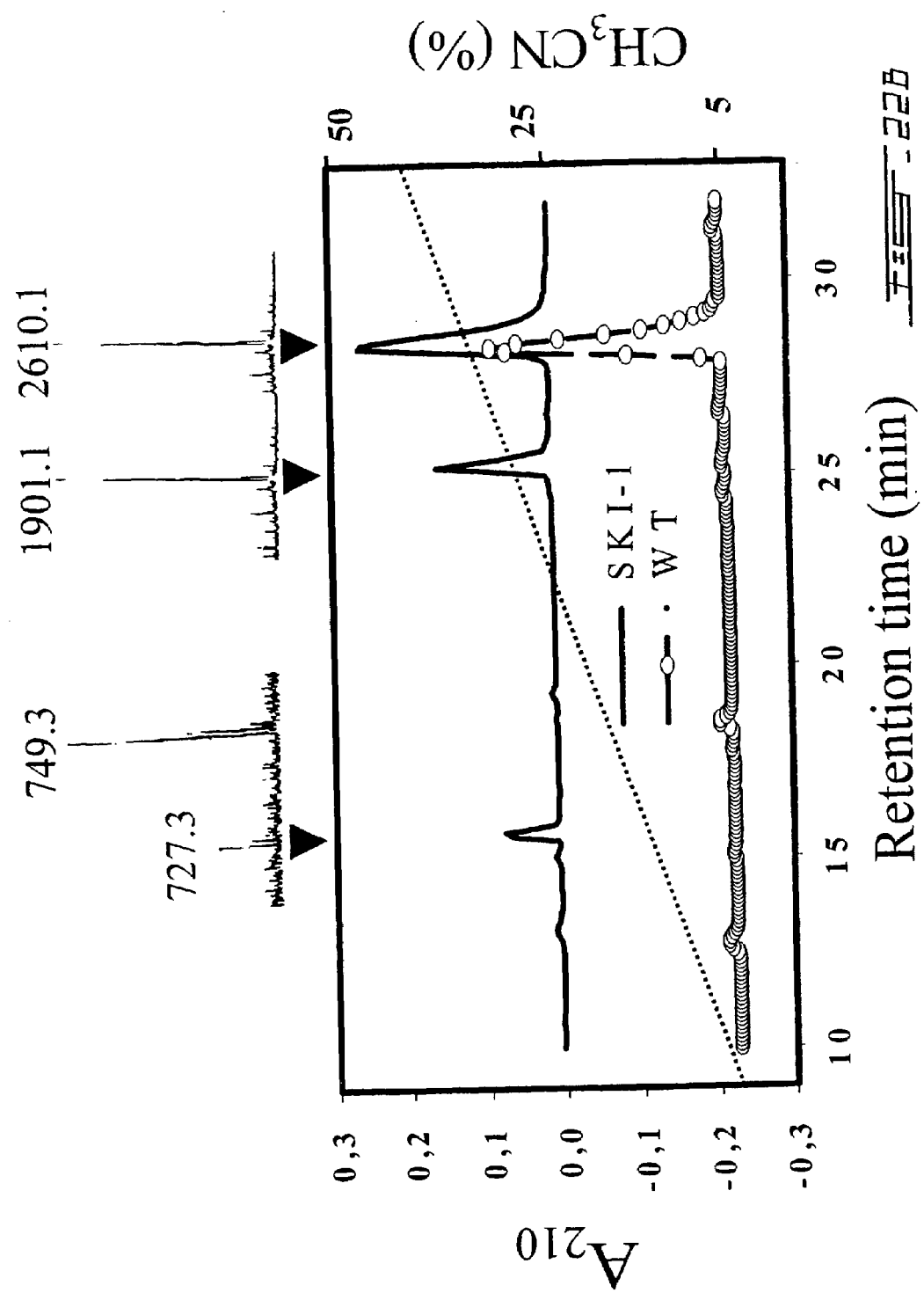

FIG. 22 shows the processing of proSKI-1 autocatalytic prosegement candidate sequences by purified, shed SKI-1. The proposed prosegment C-terminal mutant 17 aa peptide IV [A] and 15 aa peptide IX [B] were digested for 18 h with metal chelation chromatography-purified BTMD-SKI-1. The cleavage products were separated by RP-HPLC using a 5 μm analytical Ultrasphere C18 column (Beckman) as described under "Experimental Procedures". The peptides contained in all but two peaks were identified by mass spectrometry. The unidentified peaks are attributable to contaminating activities seen in WT/empty vector controls.

Figure 23A:
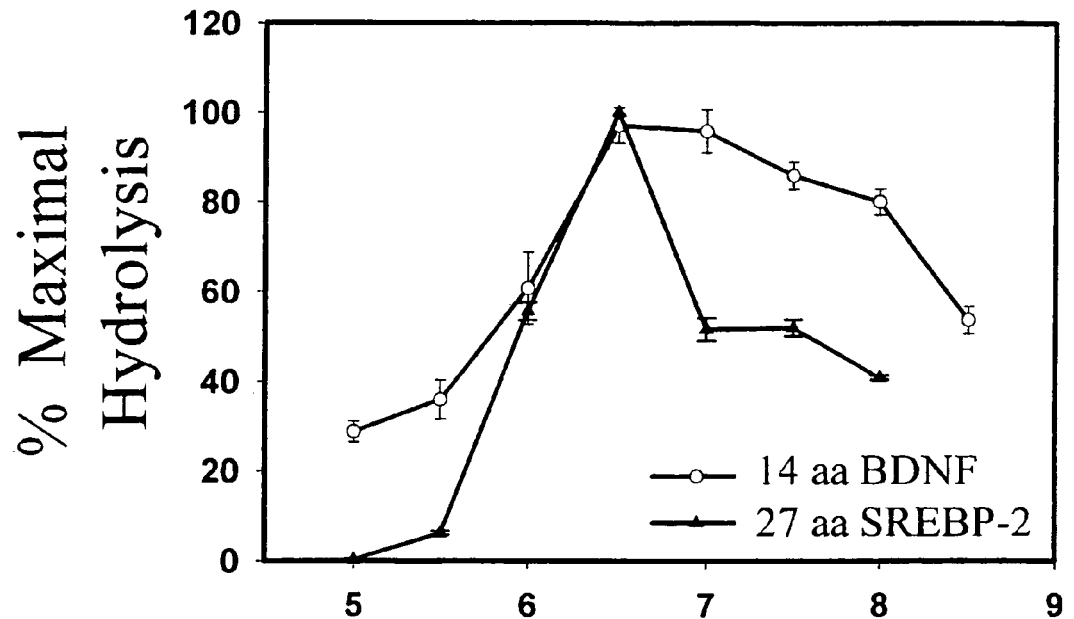
Figure 23B:
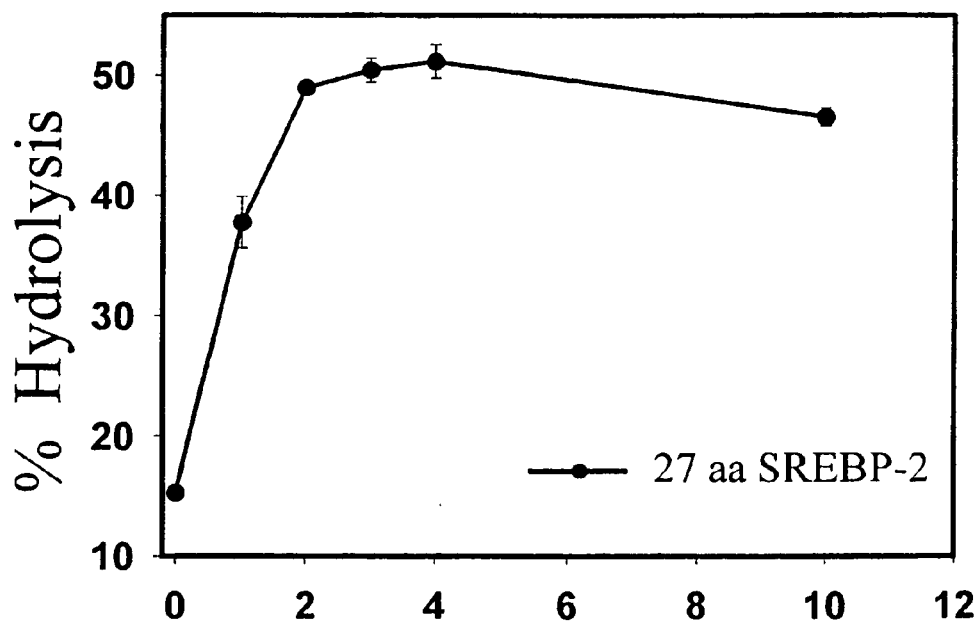

FIG. 23 shows the processing of proBDNF and SREBP-2 peptides by BTMD-SKI-1. The 14 aa peptide I [A] and 27 aa peptide II [B] were digested with BTMD-SKI-1 for 150 and 60 min, respectively. The cleavage products were separated by RP-HPLC using a 5 μm analytical Ultrasphere C18 column (Beckman) as described under "Experimental Procedures". The peptides contained in the major peaks were identified by mass spectrometry and amino acid analysis (not shown).

FIG. 24 shows the pH and Ca$^{2+}$ activation profile of BTMD-SKI-1. BTMD-SKI-1 from VV-infected BSC40 cells was assayed as described under "Experimental Procedures" using a binary buffer system consisting of MES and HEPES, along with peptides I or II for the pH profile [A], and peptide II for the Ca$^{2+}$ profile [B]. The results represent the average ± SD (indicated as error bars) of three separate determinations.

FIG. 25 is a X-ray film autoradiography showing in situ hybridization pattern for SKI-1 mRNA (A) and APP mRNA (B) at the anatomical plane in sagital section from a 4-day mouse. Note similarity of distribution of SKI-1 and APP. A significant concentration of both SKI-1 and APP mRNA is revealed in the brain (Br), apinal cord (SpC), dorsal root ganglia (DRG), kidney (Ki), skin (Sk) submaxillary gland (SM) and bone tissue (B).

FIG. 26 shows the comparative distribution of SKI-1 and APP in different regions of lacrimal gland of adult male mouse shown by immunocytochemistry. Peripherally located lobes display immunoreaction for both SKI-1 (A) and APP (B) in acinar cells. In the centrally located lobes the immunoreaction for SKI-1 (C) and APP (D) is confined to single cells distributed through the acini (medium arrows) and to intralobular ducts (long arrows).

Figure 27:
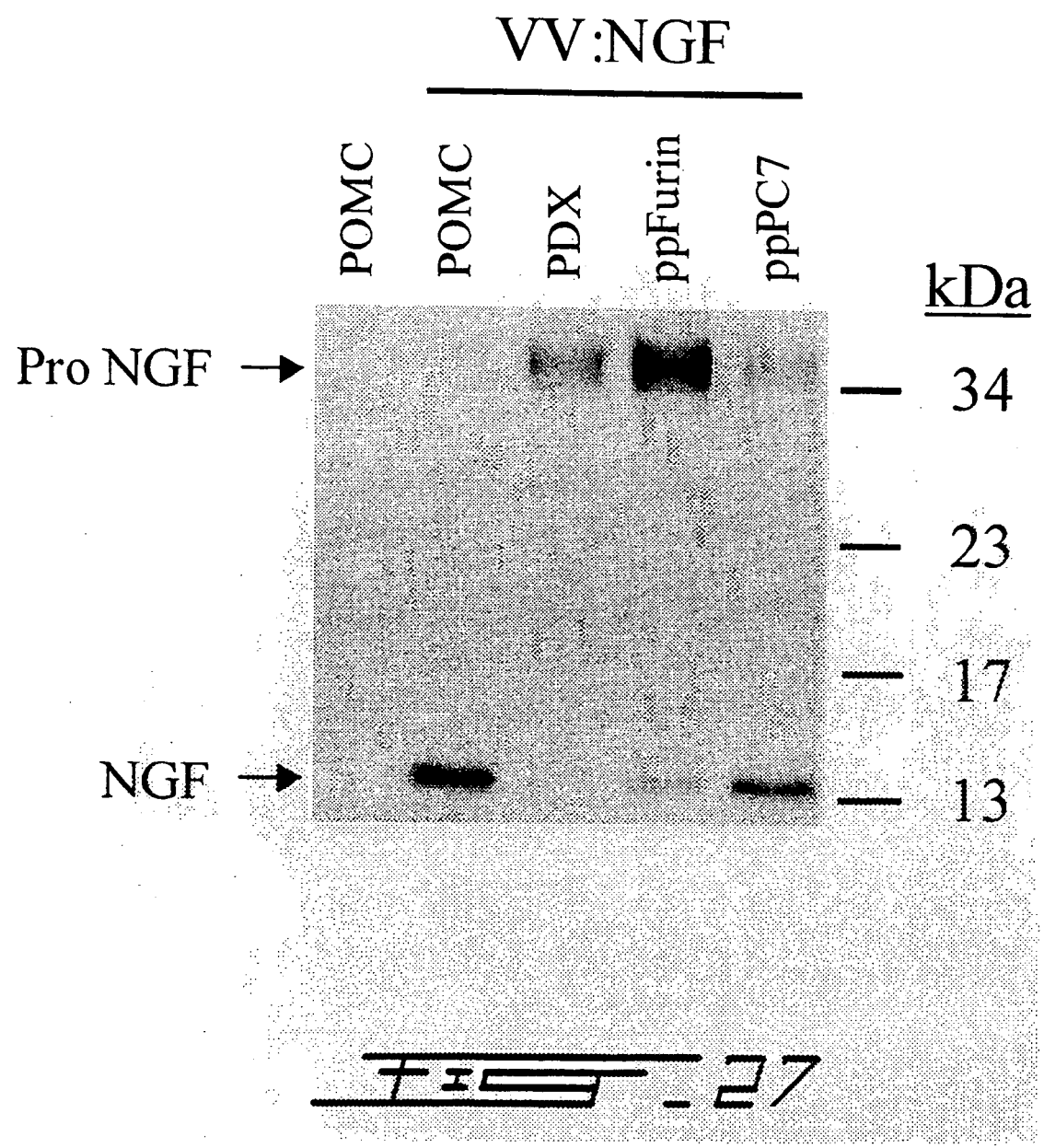

FIG. 27 illustrates the inhibition of proNGF processing. Rat Schwann cells were infected with either W:POMC (antigen control), or co-infected with W:NGF and either VV:POMC (control), W:PDX, W:ppFurin or W:ppPC7. The cells were then pulse-labeled with [$^{35}$S]Met for 4h and the media immunoprecipitated with an NGF antiserum. The migration positions of the 35 kDa proNGF and the 13.5 kDa NGF are shown.

FIG. 28 illustrates the inhibition of proBDNF processing by furin. Western blot analysis of non-transfected (NT) COS-1 or cells transfected with pcDNA3 recombinants of proBDNF as control (BDNF) or together with recombinants expressing sense (S) or antisense (AS) ppPC7 or ppFurin. The secreted products resolved by SDS-PAGE were analyzed with a BDNF-specific antiserum [Santa Cruz].

FIG. 29 shows the biosynthetic analysis of the fate of the prosegment of SKI-1.

(A) Zymogen processing of [$^3$H] Leu SKI-1 in LoVo cells. LoVo cells overexpressing vaccinia virus full length SKI-1 were pulse-labeled for 15 min with [$^3$H] Leu and then chased for 2h (P15C2h). Cell lysates were immunoprecipitated with antibody to the prosegment, resolved by SDS-PAGE on a 14% gel and the dried gel autoradiographed. The migration positions of the major 26, 24, 14, 10 and 8 kDa prosegments are emphasized.

(B) Zymogen processing of [$^3$H] Leu SKI-1 in BSC40 cells. BSC40 cells overexpressing vaccinia virus SKI-1 prosegment were pulse-labeled for 30 min with [$^3$H] Leu and then chased for 2h (P30C2h). Cell lysates were immunoprecipitated with antibody to the prosegment, resolved by SDS-PAGE on a 14% gel and the dried gel autoradiographed. The migration positions of the 24 and 14 kDa prosegments are emphasized.

FIG. 30 shows the inhibition of h$\alpha_4$ processing in stable transfectants of Jurkat T cells expressing the mPC5 pro-domain mutated at Arg$^{84}$ to Ala. The cell surface proteins of $25 \times 10^6$ cells were biotinylated and immunoprecipitated with monoclonal ha$_4$ antibody (HP 2/1). Following SDS gel electrophoresis under reducing conditions and blotting to nitrocellulose the 80 kDa cleavage product was revealed by the chemiluminescence detection of anti-biotin streptavidin horse radish peroxidase.

EXAMPLE 1

Materials and Methods

Polymerase Chain Reaction and Sequencing. Most reverse transcriptase polymerase chain reactions (RT-PCR) were performed using a Titan One Tube RT-PCR system (Boehringer Mannheim) on 1 μg of total RNA isolated from either a human neuronal cell line (IMR-32), mouse corticotrophic cells (AtT20), or rat adrenal glands using a TRIzol reagent kit (Life Technologies). The active site degenerate primers were: His (sense) 5' GICA(C,T)GGIACI(C,T)(A,T)(C,T)(G,T)(T,G)IGCIGG-3'(SEQ. ID. NO. 15) and Ser (antisense) 5'-CCIG(C,T)IACI(T,A)(G,C)IGGI(G,C)(T,A)IG-CIACI(G,C)(A,T)GTICC-3'(SEQ. ID. NO. 16) based on the sequences GHGT(H,F)(V,C)AG (SEQ. ID. NO. 17) and GTS(V,M)A(T,S)P(H,V)V(A,T)G (SEQ. ID. NO. 18) respectively. The amplified 525 bp products were sequenced on an ALF DNA sequencer (Pharmacia). To obtain the full length of rat and mouse SKI-1, we used PCR primers based on the human (12) and mouse sequences, in addition to 5' (13) and 3' (14) RACE amplifications. To avoid errors, at least three clones of the amplified cDNAs were fully sequenced. The GenBank accession numbers of the 3788 bp mouse mSKI-1 cDNA and 3895 bp rat rSKI-1 are AF094820 and AF094821, respectively.

Transfection and Metabolic Labeling. Human SKI-1 (nt 1–4338) (12) in Bluescript (a generous gift from Dr. N. Nomura, Kazusa DNA Research Institute, Chiba, Japan; gene name KIM0091, accession No. D42053) was digested with Sacil (nt 122–4338) and inserted into the vector PMJ602. The construct was digested with 5' Kpnl/3' Nhel, cloned into the Kpnl/Xbal sites of pcDNA3 (Invitrogen), and the cDNA transfected into HK293 cells with a DOSPER liposomal transfection reagent (Boehringer Mannheim). A number of stable transfectants resistant to G418 and positive on western blots using a SKI-1 antiserum (see below) were isolated, and one of them (clone 9), was further investigated. Cells were pulsed for 4h with [$^{35}$S]Met and the media and cell lysates immunoprecipitated with SKI-1 antisera directed against either amino acids (aa) 634–651, or aa 217–233, or a pro-SKI-1 antiserum directed against the pro-segment comprising aa 18–188 (FIG. 1). Immune complexes were resolved by SDS-PAGE on a 6% polyacrylamide/Tricine gel (15).

Northern Blots, in situ Hybridizations and Immunocytochemistry. Northern blot analyses (16) were done on total RNA from adult male rat tissues using either a TRIzol reagent kit (Life Technologies) or a Quick Prep RNA-kit (Pharmacia) and on polyA+ RNA of (male+female) rat adult tissues (Bio/Can Scientific). The blots were hybridized overnight at 68° C. in the presence of [$^{32}$P]UTP SKI-1 cRNA probes, consisting of the antisense of nucleotides 655–1249 of rat SKI-1 (accession No. AF094821). For ISH, the same rat sense and antisense cRNA probes were doubly labeled with uridine and cytosine 5'-{λ-[$^{35}$S]thio}triphosphate (16). The distribution of SKI-1 mRNA in different tissues of adult and newborn rat (P1) after emulsion autoradiography was investigated. Relative densities of specific SKI-1 mRNA labeling per cell in selected organs have been measured upon counting of silver grains produced by antisense SKI-1 riboprobes and subtraction of non-specific background produced with sense SKI-1 riboprobes. Countings were made under 1000-fold microscopical magnification in the similar regions of adjacent sections stained with hematoxylin and eosin. Results are the mean (S.E.D. of 10–16 readings/cell type. Newborn rats were frozen at −35° C. in isopentane and then cut into 14-μm sagital cryostat sections (1, 16). After hybridization, all tissue slides were exposed for 4 or 30 days to X-Ray film or emulsion autoradiography, respectively. For immunofluorescence staining we used a rabbit anti-SKI-1 antiserum at a 1:100 dilution and rhodamine-labeled goat anti-rabbit IgGs diluted 1:20 (16). Red SKI-1 immunostaining was compared with green staining patterns of both fluorescein-labeled concavalin A (ConA; Molecular Probes, OR), an ER marker, or fluorescein-conjugated wheat germ agglutinin (WGA; Molecular Probes, OR), a Golgi marker (17).

Ex vivo and in vitro proBDNF Processing. A vaccinia virus recombinant of human SKI-1 (vv:SKI-1) was isolated as previously described for human proBDNF (vv:BDNF) (15). The vaccinia virus recombinants of the serpins α1-antitrypsin Pittsburgh (α1-PIT; w:PIT) and α1-antitrypsin Portland (α1-PDX; vv:PDX) (18) were generous gifts from Dr. G. Thomas (Vollum Institute, Portland, Oreg.). For analysis of the cleavage specificity of hSKI-1, $4 \times 10^6$ COS-7 cells were co-infected with 1 pfu/cell of vv:BDNF and either the wild type virus (vv:WT) alone at 2 pfu/cell or with 1 pfu/cell of each virus in the combinations: [vv:SKI-1+vv:WT], [vv:SKI-1+vv:PIT] and [vv:SKI-1+vv:PDX]. At 10h post infection, cells were pulse labeled for 4h with 0.2 mCi [$^{35}$S]Cys-Met (Dupont). Media and cell extracts were immunoprecipitated with a BDNF antiserum (19; kindly provided by Amgen) at a concentration of 0.5 μg/ml. The precipitates were resolved on polyacrylamide gradient gels (13–22%) and the autoradiograms obtained as described (15). Microsequencing analysis was performed on the [$^{35}$S]Met-labeled 32 kDa proBDNF and [$^{31}$H]Leu-labeled 28 kDa BDNF, as described (20). For in vitro analysis, the 32 kDa proBDNF obtained from the media of LoVo cells infected with vv:BDNF was incubated overnight with the shed form of SKI-1 obtained from rat Schwann cells (16) co-infected with vv:SKI-1 and vv:PDX, either at different pHs or at pH 6.0 in the presence of selected inhibitors: pepstatin (1 μM), antipain (50 μM), cystatin (5 μM), E64 (5 μM), soya bean trypsin inhibitor (SBTI, 5 μM), 0.5 M phenylmethylsulfonyl fluoride (PMSF)+50 μM para-aminophenylmethylsulfonyl fluoride (pAPMSF), o-phenanthroline (5 mM) and EDTA (10 mM). The products were resolved by SDS-PAGE on a 15% polyacrylamide gel, transferred to a PVDF membrane and then probed with a BDNF antiserum (Santa Cruz) at a dilution of 1:1000.

Results

Protein Sequence Analysis of SKI-1. We first aligned the protein sequences within the catalytic domain of PC7 (21), yeast subtilases and bacterial subtilisins together with that of a novel subtilisin-like enzyme from *Plasmodium falciparum* (J-C. Barale et al., submitted). This led to the following choice of conserved amino acids around the active sites His and Ser: GHGT(H/F)(V/C)AG (SEQ. ID. NO. 17) and GTS(M/V)A(T/S)P(H/V)V(A/T)G(SEQ. ID. NO. 18) respectively. Thus, using degenerate oligonucleotides coding for the sense His and antisense Ser consensus sequences we initiated a series of RT-PCR reactions on total RNA (see Materials and Methods) and isolated a 525 bpcDNA fragment from the human neuronal cell line IMR-32. This sequence was found to be 100% identical to that reported for a human cDNA called KIAA0091 (Accession No. D42053) obtained from a myeloid KG-1 cell line (12) and 88% identical to that of a 324 bp EST sequence (Accession No. H31838) from rat PC12 cells. We next completed the rat and mouse cDNA sequences following RT-PCR amplifications of total RNA isolated from rat adrenal glands and PC12 cells, and from mouse AtT20 cells. Starting from the equivalent rat and mouse 525 bp fragments, the complete sequences were determined using a series of RT-PCR reactions with human-based oligonucleotides in addition to 5' (13) and 3' (14) RACE protocols. As shown in FIG. 1, alignment of the protein sequence deduced from the cDNAs of rat, mouse and human SKI-1 revealed a high degree of conservation. Rat and mouse SKI-1 share 98% sequence identity and a 96% identity to human SKI-1. Interestingly, within the catalytic domain (Asp$^{218}$ to Ser$^{414}$) the sequence similarity between the three species is 100%. Analysis of the predicted amino acid sequence suggests a 17 aa signal peptide, followed by a putative pro-segment beginning at Lys$_{18}$ and extending for some 160–180 amino acids. The proposed catalytic domain encompasses the typical active sites Asp$^{218}$, His$^{249}$ and Ser$^{414}$ and the oxyanion hole Asn$^{338}$. This domain is followed by an extended C-terminal sequence characterized by the presence of a conserved growth factor/cytokine receptor family motif C$_{849}$LDDSHRQKDCFW$^{861}$ (SEQ. ID. NO. 77). This sequence is then followed by a potential 24 aa hydrophobic transmembrane segment and a less conserved 31 aa cytosolic tail that remarkably consists of 35% basic residues. Some of the clones isolated from rat adrenal glands suggested the existence of alternatively spliced rSKI-1 mRNAs in which the segments coding for aa 430483 or 858–901 are absent. Finally, the phylogenetic tree derived from the alignment of the catalytic domain of SKI-1 with subtilases (22) suggests that it is an ancestral protein that is closer to plant and bacterial subtilases than to either yeast or mammalian homologues (not shown).

Figure 2A:
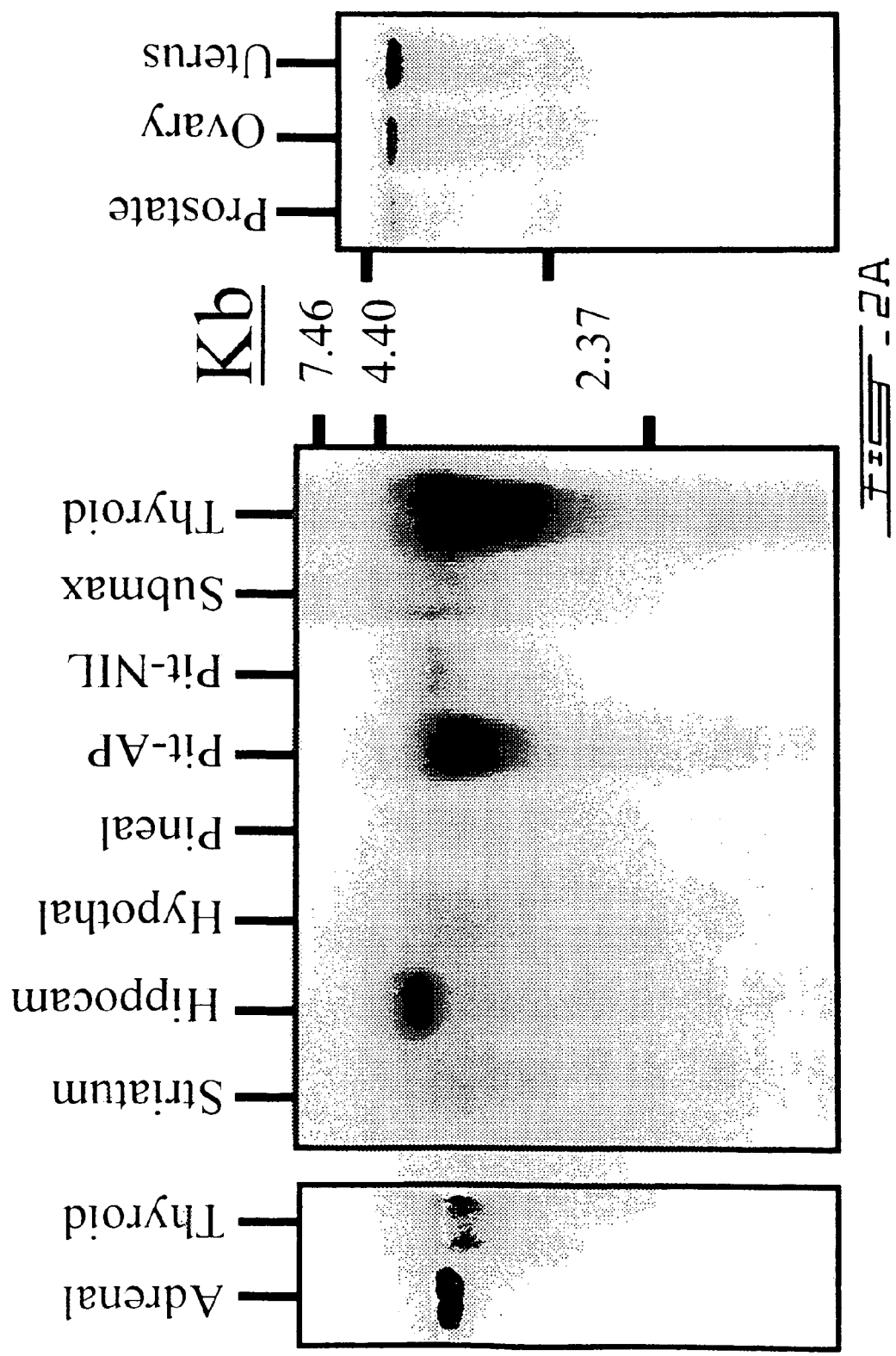
FIG. 2 shows a Northern blot analysis of the expression of SKI-1 in adult rat tissues. [A] 5 μg of male rat total RNA were loaded in each lane. Molecular sizes are based on the migration of an RNA ladder. The tissues include: adrenal, thyroid, striatum, hippocampus, hypothalamus, pineal gland, anterior (AP) and neurointermediate (NIL) lobes of the pituitary, submaxillary gland, prostate, ovary and uterus. Notice the high level of SKI-1 mRNA in adrenal glands. [B] 2 μg of poly-A+ of (male+female) Sprague Dawley rat adult tissues (Bio/Can Scientific) were loaded, which includes: liver, thymus, spleen, kidney, heart and brain. The estimated size of rat SKI-1 mRNA is about 3.9 kb.
Figure 2B:
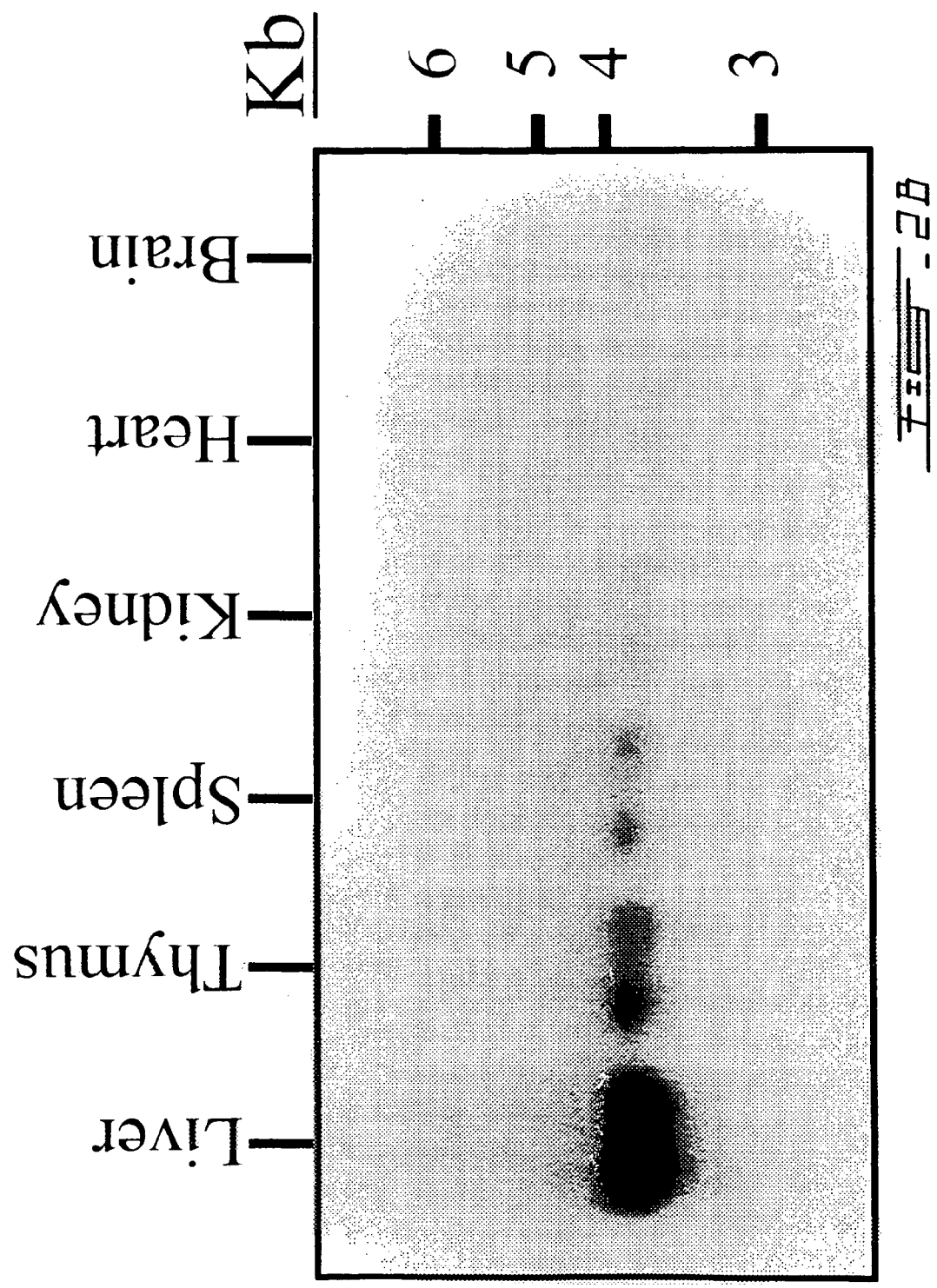
Figure 8A:
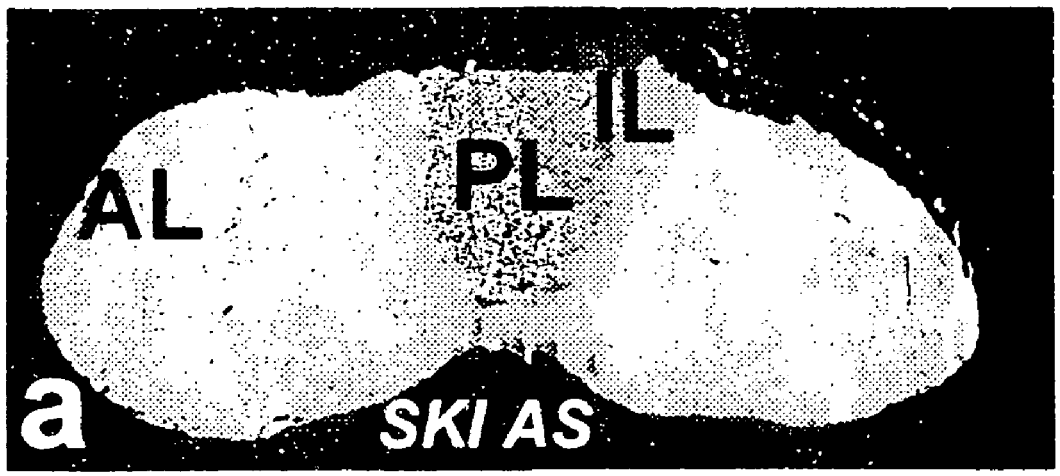
FIG. 8 shows the in situ hybridization translating SKI-1 mRNA expression in the pituitary gland of an adult rat using specific [$^{35}$S]radiolabeled antisense (SKI AS) and control sense (SKI SS) riboprobes. The hybridization signal was detected in the anterior (AL), intermediate (IL) and posterior pituitary lobe (PL). Most of the labeling was confined to endocrine cells in AL and IL and to some pituicytes in the PL. Magnification×5; bar (in b)=1 mm.
Figure 8B:
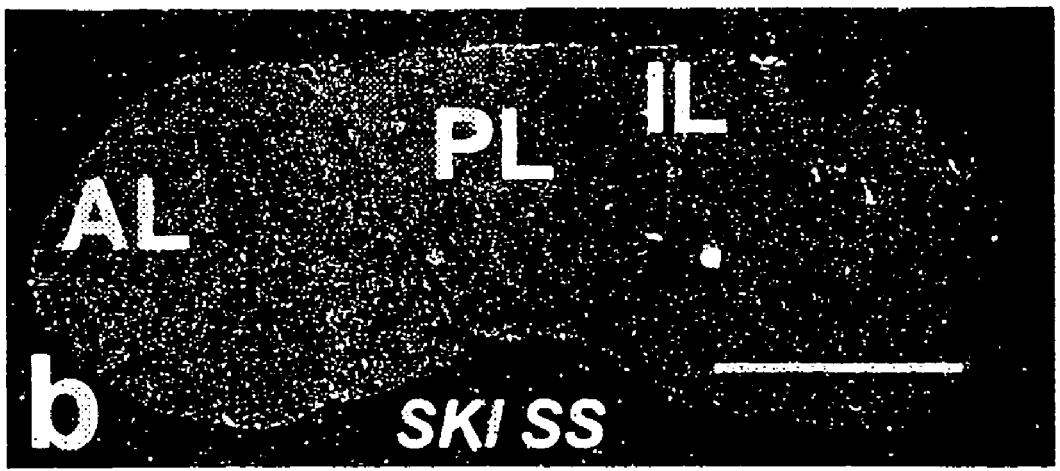

Tissue Distribution of SKI-1 mRNA. Northern blot analyses of SKI-1 mRNA in adult male rat tissues reveal that rSKI-1 mRNA is widely expressed and is particularly rich in anterior pituitary, thyroid and adrenal glands (FIGS. 2A and 8). A Northern blot of polyA+ RNA obtained from mixed adult male and female rat tissues also showed a wide distribution and a particular enrichment in liver (FIG. 2B). Similarly, analysis of 24 different cell lines (23) revealed a ubiquitous expression of SKI-1 mRNA (not shown).

Figures 11A, 11B:
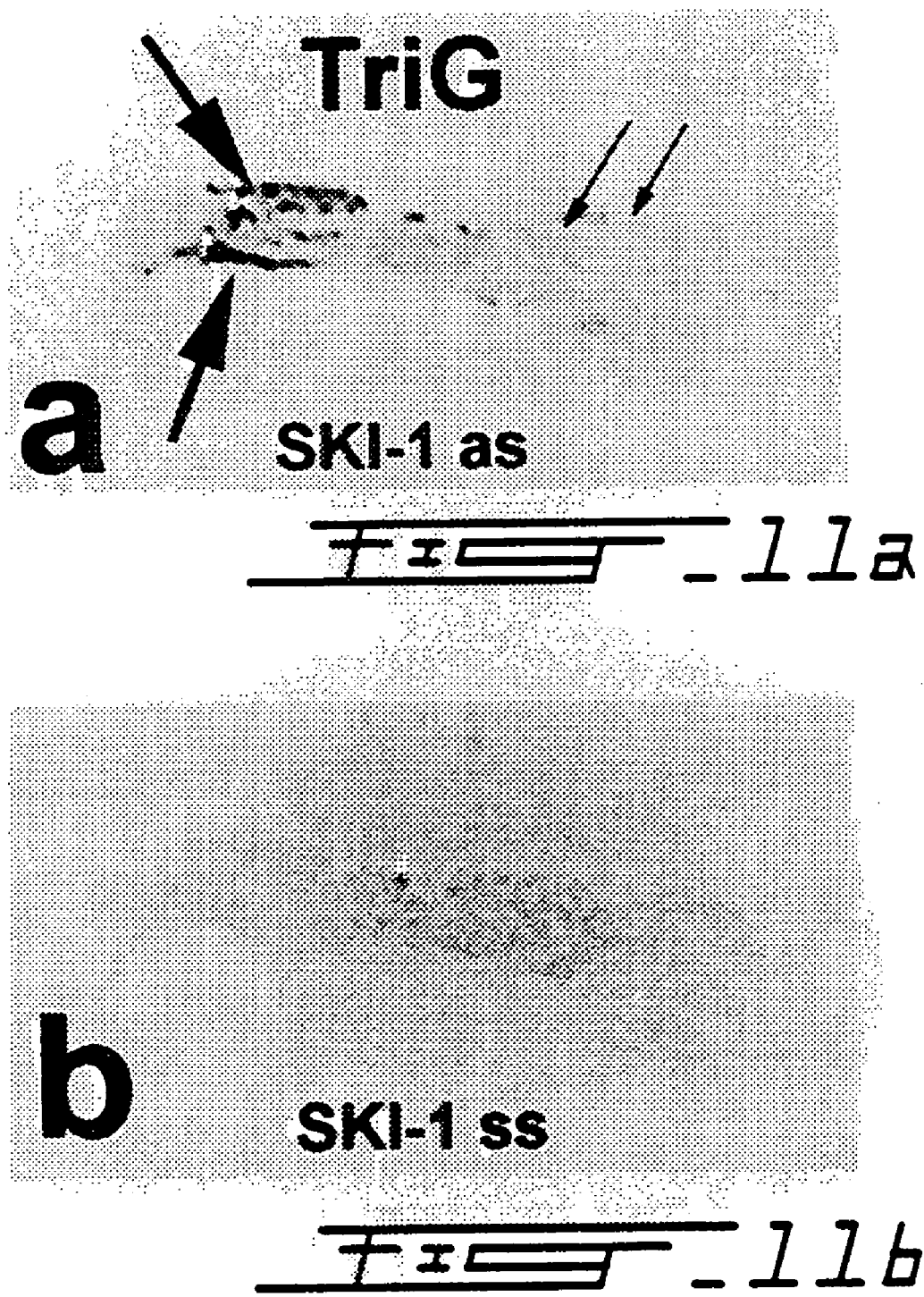
FIG. 11 shows the in situ hybridization (ISH) distribution of SKI-1 mRNA in the rat peripheral nervous system (PNS) trigeminal ganglion (TriG). ISH distribution pattern in the CNS of adult rat demonstrates a higher concentration of SKI-1 mRNA within a region of cell bodies (large arrows) over the region of supportive Schwann cells (small arrows). ISH was performed using antisense (SKI-1 as in a) and sense (SKI-1 ss) riboprobes. Magnification×12.

In situ hybridization data obtained in a day 2 postnatal rat also provided evidence of a widespread, if not ubiquitous distribution of rSKI-1 mRNA. FIG. 3 shows at the anatomical level the presence of SKI-1 mRNA in developing skin (see also FIG. 9), striated muscles, cardiac muscles, bones and teeth as well as brain and many internal organs. Strong hybridization signals were detectable in the retina, cerebellum, pituitary, submaxillary, thyroid and adrenal glands, molars, thymus, kidney and intestine. Evidence for the cellular expression of rSKI-1 mRNA was obtained from analysis of the relative labeling densities per cell in selected tissues, based on a semiquantitative analysis of emulsion autoradiographies (not shown). In the central nervous system (CNS),SKI-1 mRNA labeling was mostly confined to neurons, whereas ependymal cells, supportive glial cells, such as presumed astrocytes, oligodendrocytes, and microglia, exhibited 5–30 fold less labeling/cell (see Table 1 and FIG. 10). In addition, within the peripheral nervous system (PNS) trigeminal ganglia reveal a 5–10 fold greater expression in neurons as compared to presumptive Schwann cells (FIGS. 11 and 12 and Table 1). Labeling was observed in most of the glandular cells in the anterior and intermediate lobes of the pituitary as well as in the pituicytes of the pars nervosa. A semiquantitative comparison in the adult and newborn rat pituitary gland, submaxillary gland, thymus and kidney demonstrated an overall 2-fold decreased labeling of rSKI-1 mRNA with age (not shown).

Figure 4:
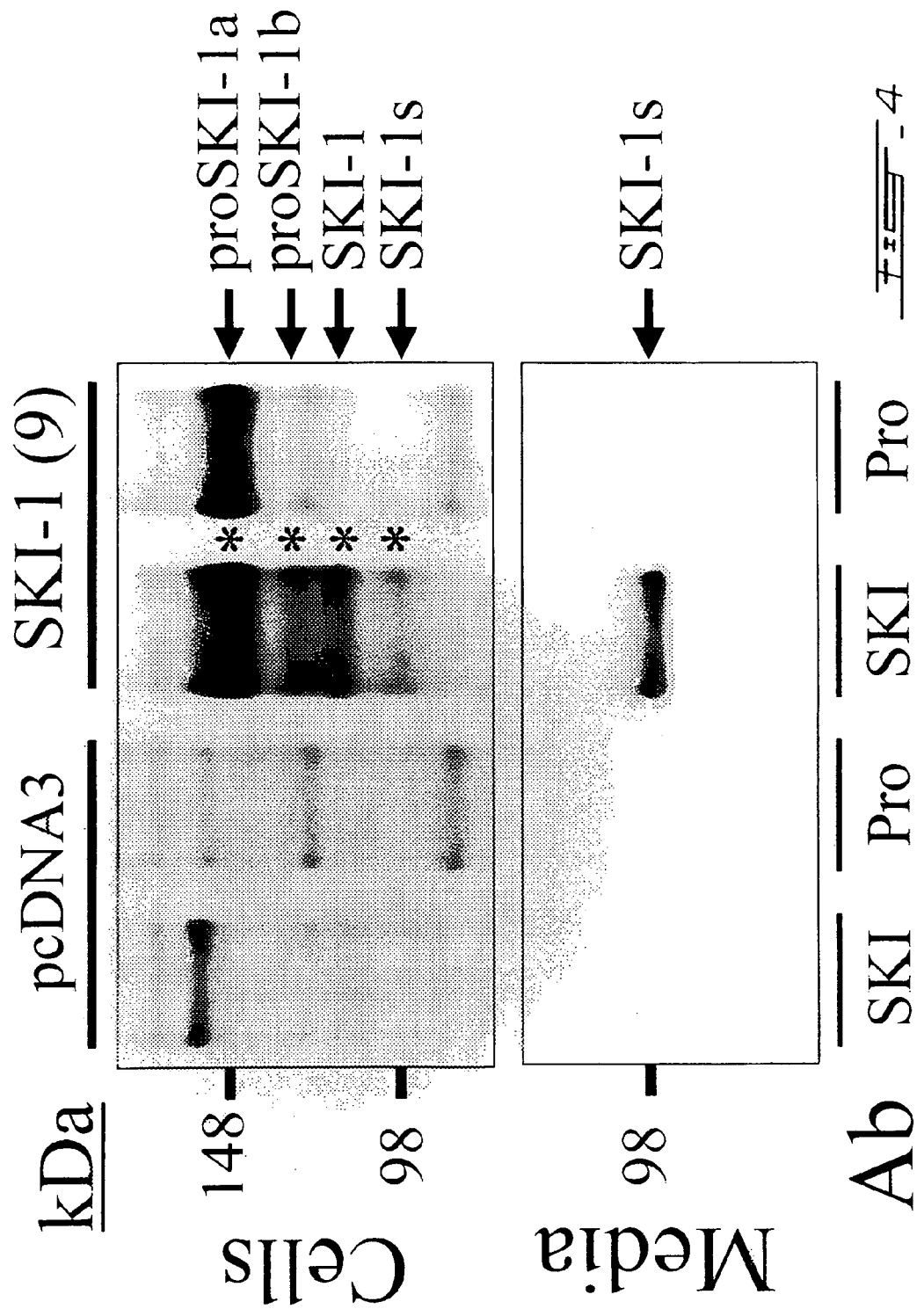
FIG. 4 illustrates the biosynthetic analysis of SKI-1 in HK293 cells. Stable transfectants expressing either the pcDNA3 vector alone or one that expresses SKI-1 (clone 9) were pulse-labeled for 4h with [$^{35}$S]Met. Media and cell lysates were immunoprecipitated with either a SKI-1 antiserum (Ab: SKI; against aa 634–651) or a pro-SKI-1 antiserum (Pro). The stars represent the 4 specific intracellular proteins (Mr 148, 120, 106 and 98 kDa) immunoprecipitated with the SKI-1 antiserum. In these transfected cells, only the 148 kDa band is recognized by the Pro-antiserum. A 98 kDa immunoreactive SKI-1s protein is also detectable in the medium.

Biosynthesis of hSKI-1. To define the molecular forms of human SKI-1 and their biosynthesis, we generated both a vaccinia virus recombinant (vv:SKI-1) and a stable transfectant in HK293 cells. Three antisera were produced against aa 18–188 (prosegment), 217–233 and 634–651 of SKI-1. Expression of vv:SKI-1 in 4 different cell lines revealed that the enzyme is synthesized as a 148 kDa proSKI-1a zymogen which is processed into 120, 106 and 98 kDa proteins. In this system, both the 148 and 120 kDa forms are recognized by the Pro-domain antiserum, whereas all 4 forms react with the other two antisera. Processing of the 148 kDa proSKI-1a into the 120 and 106 kDa forms occurs in the ER based on the presence of these proteins in cells pre-incubated with the fungal metabolite brefeldin A (see 24 for refs., not shown). The same SKI-1-related forms are also observed in stably transfected HK293 cells following a 4h pulse labeling with [$^{35}$S]Met (FIG. 4). The results reveal the intracellular formation of a secretable 98 kDa form (SKI-1s) recognized by both of the SKI antisera but not by the Pro antiserum. These data demonstrate that the 148 kDa proSKI-1a is N-terminally cleaved into an intermediate 120 kDa form containing part of the prosegment (proSKI-1b) which is then further excised to form a non secretable 106 kDa SKI-1. This suggests that two cleavages occur within the prosegment prior to the formation of the presumably membrane-bound 106 kDa form which is later shed into the medium as a 98 kDa soluble SKI-1s.

Intracellular localization of SKI-1. Double staining immunofluorescence was used to compare the intracellular localization of the stably transfected human SKI-1 in HK293 cells and that of either the ER or Golgi markers ConA and WGA (17), respectively. The data show that SKI-1 exhibits: (i) peripheral nuclear staining, colocalizing with ConA fluorescence, presumably corresponding to the ER (not shown); (ii) paranuclear staining colocalizing with WGA fluorescence, suggesting the presence of SKI-1 in the Golgi (FIGS. 5A,B) and (iii) punctate staining observed in the cytoplasm and within extensions of a few cells (FIG. 5A). Some, but not all of the punctate immunostaining matched that observed with WGA. This suggests that SKI-1 localizes in the Golgi but may sort to other organelles, including lysosomal and/or endosomal compartments. Since in HK293 cells we observed scant immunoreaction to either cathepsin B or cathepsin D (not shown), we could not directly assess the presence of SKI-1 within lysosomes. An indication of lysosomal/endosomal localization was provided by the analysis of SKI-1 immunofluorescence within cells pre-incubated for 4h with 10 mM leucine-methyl ester (LME), a specific lysosomal/endosomal protease inhibitor (25). The results showed a net increase in the proportion of cells exhibiting punctate staining (FIG. 5C) as compared to control cells. Thus, SKI-1 immunoreactivity is enhanced upon LME inhibition of lysosomal/endosomal hydrolases.

Enzymatic Activity and Cleavage Specificity of SKI-1. To prove that SKI-1 is a proteolytic enzyme we examined its ability to cleave five different potential precursor substrates. Our choice was based on the tissue expression pattern of SKI-1 (FIGS. 2, 3), which led us to select pro-opiomelanocortin (pituitary), pro-atrial natriuretic factor (heart), HIV gp160 (T-lymphocytes) and based on its neuronal expression, pro-nerve growth factor and pro-brain-derived neurotrophic factor (proBDNF). Cellular co-expression of vv:SKI-1 with the vaccinia virus recombinants of each of the above precursors revealed that only proBDNF could be cleaved intracellularly by SKI-1. Thus, upon expression of vv:BDNF alone in COS-7 cells we observed a partial processing of proBDNF (32 kDa) into the known major 14 kDa BDNF product (15), and the minor production of a previously observed (16; Mowla, S. J. et al., submitted) but still undefined 28 kDa product (FIG. 6A). Upon co-expression of proBDNF and SKI-1, a net increase in the level of the secreted 28 kDa BDNF is evident, without significant alteration in the amount of 14 kDa BDNF (FIG. 6A). To examine whether the 28 kDa product results from cleavage at a basic residue or at an alternative site, we first co-expressed proBDNF, SKI-1 and either α1-PIT or α1-PDX which are inhibitors of thrombin and PC cleavages, respectively (18, 26). The results show that different from α1-PIT, the serpin α1-PDX selectively blocks the production of the 14 kDa BDNF and that neither α1-PIT nor α1-PDX affect the level of the 28 kDa product. This demonstrates that α1-PDX effectively inhibits the endogenous furin-like enzyme(s) responsible for the production of the 14 kDa BDNF (15), but does not inhibit the ability of SKI-1 to generate the 28 kDa product. Thus, it is likely that the generation of the 28 kDa BDNF takes place via an alternate cleavage. Incubation of the cells with the $Ca^{2+}$ ionophore A23187 abolished the production of both the 14 and 28 kDa products (not shown), supporting the notion that similar to the PCs (1–3, 24), SKI-1 is a $Ca^{2+}$-dependent enzyme.

In FIG. 6B, we present the N-terminal microsequence analysis of [$^{35}$S]Met-labeled 32 32 kDa proBDNF and [$^3$H] Leu-labeled 28 kDa BDNF. The sequence of the 32 kDa form revealed the presence of an [$^{35}$S] Met at position 3 (FIG. 6B), which is in agreement with the proposed sequence of human proBDNF (27) resulting from the removal of an 18 aa signal peptide cleaved at GMCLA18↓APMK (SEQ. ID. NO. 78) site. The N-terminal sequence of the 28 kDa product revealed a [$^3$H] Leu at positions 2, 13 and 14 (FIG. 6B). This result demonstrates the 28 kDa BDNF is generated by a unique cleavage at Thr$^{57}$ in the sequence: RGLT$^{57}$ ↓SLADTFEHVIEELL (27) (SEQ. ID. NO.79).

To prove that SKI-1 is directly responsible for the production of the 28 kDa BDNF at the novel Thr-directed cleavage, we performed in vitro studies. Thus, proBDNF was incubated at various pHs with concentrated media of vv:SKI-1-infected Schwann cells. A similar preparation obtained from wild type vaccinia virus-infected cells served as control. The data show that SKI-1 exhibits a wide pH dependence profile revealing activity at both acidic and neutral pHs between pH 5.5 up to 7.3 (FIG. 7A) but also at pH 4.5 and 8 (not shown). Analysis of the inhibitory profile of this reaction revealed that metal chelators such as EDTA and o-phenanthroline, or a mixture of the serine proteinase inhibitors PMSF+pAPMSF effectively inhibit the processing of proBDNF by SKI-1. The inhibition by EDTA is expected since like all PCs, SKI-1 is a $Ca^{2+}$-dependent enzyme. The unexpected inhibition by 5 mM o-phenanthroline may be due to excess reagent since at 1 mM only 25% inhibition is observed (not shown). All other class-specific proteinase inhibitors (aspartyl-, cysteinyl-, and serine proteases—of the trypsin-type) proved to be inactive.

TABLE 1

| Tissue | Adult Silver grains/ Cell ± SED | Newborn (PI) Silver Grains/Cell ± SED |
|---|---|---|
| C.N.S. | | |
| Cerebal Cortex | | |
| Neurons, large | 19.7 ± 5.8 | ND* |
| Neurons, medium & small | 5.7 ± 2.3 | |
| Astrocytes, presumptive | 0.6 ± 0.5 | |

TABLE 1-continued

| Tissue | Adult Silver grains/ Cell ± SED | Newborn (PI) Silver Grains/Cell ± SED |
|---|---|---|
| Hippocampus | | ND |
| Neurons, pyramidal | 15.3 ± 3.9 | |
| Neurons, granules | 23.7 ± 5.3 | |
| Corpus callosum | | ND |
| Oligodendrocytes, presumpt. | 0.6 ± 0.6 | |
| Spinal cord | | ND |
| Motorneurons | 27.8 ± 7.1 | |
| Circumventricular organs | | ND |
| Plexus choroideux | 9.6 ± 1.9 | |
| Ependyma (III ventr.) | 2.9 ± 0.8 | |
| P.N.S. | | ND |
| Trigeminal ganglion | | |
| Neurons, large | 14.6 ± 4 | |
| Satellite cells | 3.8 ± 22 | |
| Schwann cells, presumpt. | 1.3 ± 1.9 | |
| Pituitary gland | | |
| Anterior lobe cells | 4.9 ± 3.6 | 9.3 ± 2.1 |
| Intermediate lobe cells | 4.1 ± 0.9 | 7.2 ± 1.4 |
| Posterior lobe pituicytes | 3.6 ± 3.9 | 6.7 ± 4.2 |
| Thymus | | |
| Cortical lymphocytes | 4.1 ± 0.7 | 7.1 ± 1.0 |
| Medullary reticular cells | 2.7 ± 1.0 | 4.4 ± 0.9 |
| Adipocytes | 0.3 ± 0.6 | ND |
| Fibroblats | 0.2 ± 0.1 | ND |
| Submaxillary gland | | |
| Epithelial cells | 2.1 ± 1.0 | 3.9 ± 1.7 |
| Acinar cells | 2.4 ± 1.2 | 4.5 ± 1.7 |
| Kidney | | |
| Glomerular cells | 2.8 ± 0.9 | 4.2 ± 0.9 |
| Convoluted tubules | 4.1 ± 2.7 | 9.8 ± 1.4 |

*ND = not determined

Discussion

This work provides the first evidence for the existence of a mammalian secretory $Ca^{2+}$—dependent serine proteinase of the subtilisin-kexin type that selectively cleaves at non-basic residues. Thus, SKI-1 processes the 32 kDa human proBDNF at a KAGSRGLT↓SL (SEQ. ID. NO. 80) sequence generating a 28 kDa form, which may have its own biological activity (Mowla, S. J. et al., submitted). Such a cleavage site is close to the consensus site deduced from a large body of work. Done with the PCs, whereby and $(R/K)-(X)_n-R\downarrow X-(L/I/V)$, [where n=0, 2, 4 or 6] motif is favored by most Pcs (1–3, 28). Note that in the SKI-1 site, P1 Arg is replaced by Thr and an aliphatic Leu is present at P2', an amino acid also favored by PCs (1–3, 28). Several proteins are known to be cleaved following Thr. These include human anti-angiogenic platelet factor 4 (6; QCLCVKTT↓SQ (SEQ. ID. NO. 81) and angiostatin (7; KGPWCFTT↓DP (SEQ. ID. NO. 82)), the neuroendocrine α-endorphin (4; KSQTPLVT↓LF (SEQ. ID. NO. 83)), the ADAM-10 metalloprotease (8; LLRKKRTT↓SA (SEQ. ID. NO. 84)), as well as the amyloidogenic peptide Aβ43 (10; VGGVVIAT↓VI (SEQ. ID. NO. 85)).

Interestingly, comparison of the phylogenetically highly conserved sequence of proBDNF revealed an insertion of hydroxylated amino acids (Thr and Ser) just after the identified SKI-1 cleavage site of human proBDNF. Thus, in rat and mouse proBDNF, two threonines are inserted (RGLTTT-SL (SEQ. ID. NO. 86)) and in porcine proBDNF five serines added (RGLTSSSSS-SL (SEQ. ID. NO. 87)) (27). These observations raised a number of questions: (i) do these insertions affect the kinetics of proBDNF cleavage by SKI-1? (ii) does SKI-1 recognize both single and pairs of Thr and Ser and combinations thereof? (iii) is the presence of a basic residue at P4, P6 or P8 important for cleavage? and (iv) similar to enzymes cleaving at basic residues (29), does the possible phosphorylation at specific Thr or Ser residues affect substrate cleavability by SKI-1? Answers to these questions are provided hereinbelow.

Biosynthetic analysis of the zymogen processing of proSKI-1 demonstrated a two-step ER-associated removal of the pro-segment (FIG. 4). Furthermore, analysis of the $[^{35}SO_4]$-labeled SKI-1 demonstrated only the presence of sulfated 106 and 98 kDa forms but not that of either the 148 or 120 kDa forms recognized by the Pro-segment antiserum (not shown). Since sulfation occurs in the trans Golgi network, this confirms that the removal of the pro-segment occurs in the ER. Like furin and PC5-B (1–3, 24) the membrane bound 106 kDa SKI-1 is transformed into a soluble 98 kDa form that is released into the medium by an as yet unknown mechanism. The secreted 98 kDa SKI-1s is enzymatically active since it processes proBDNF in vitro (FIG. 7). Numerous attempts to sequence the SDS-PAGE purified [³H]Leu and Val-labeled 148 kDa and 98 kDa forms, resulted in ambiguous results, suggesting that SKI-1 is refractory to N-terminal Edman degradation. Presently, we cannot define the two zymogen cleavage sites leading to the sequential formation of the 120 kDa proSKI-1b and 106 kDa SKI-1 deduced by pulse (FIG. 4) and pulse-chase studies (not shown). Examination of the pro-segment sequence (FIG. 1), the species-specific proBDNF motif potentially recognized by SKI-1 (see above), and the alignment of SKI-1 with other subtilases (22), suggests two possible conserved sites: $RNNPSS^{95}\downarrow DYPS$ (SEQ. ID. NO. 88) and $RHSS^{182}\downarrow RRLL$ (SEQ. ID. NO. 89). Both sites predict a cleavage after pairs of Ser with either a P6 or a P4 Arg, respectively.

Phylogenetic structural analysis of the predicted amino acid sequence of SKI-1 reveals that this serine proteinase is closer to plant and bacterial subtilases than it is to yeast and mammalian PCs. The 100% conservation of the catalytic domain sequence, although striking and suggestive of an important function, is not far from the 98% similarity between human and rat PC7 (3, 21). The sequence C-terminal to the catalytic domain of SKI-1 is very different from that of any of the known PCs. In fact, although PCs have a typical P-domain critical for the folding of these enzymes (for reviews see 1–3), we did not find the hallmark sequences (3, 30) of the P-domain within the SKI-1 structure. Instead different from the PCs, we find a conserved growth factor/cytokine receptor motif of which functional importance will need to be addressed, especially since this motif is partly missing in alternatively spliced forms (FIG. 1). Finally, the highly basic nature of the cytosolic tail of SKI-1 (FIG. 1) may be critical for its probable cellular localization within endosomai/lysosomal compartments (FIG. 5), similar to the importance of basic residues for the accumulation of the α-amidation enzyme PAM in endosomal compartments (Milgram, S. L., personal communication).

The wide tissue distribution of SKI-1 mRNA transcripts suggests that this enzyme processes numerous precursors in various tissues. Furthermore, the observed developmental down-regulation of the level of its transcripts also suggests a functional importance during embryonic development.

The fact that SKI-1 can cleave C-terminal to Thr and possibly Ser residues suggests that, like the combination of PCs and carboxypeptidases E and D (31), a specific carboxypeptidase may also be required to trim out the newly exposed C-terminal hydroxylated residues. Such a hypothesis may find credence in a report suggesting that the amyloidogenic Aβ43 (ending at Thr) may be transformed in vitro into Aβ42 and Aβ40 by a brain-specific carboxypeptidase(s) (32).

A recent report demonstrated the existence of a soluble subtilisin-like enzyme exhibiting a 29% sequence identity to SKI-1 in *Plasmodium falciparum* merozoites (PfSUB-1). This enzyme localizes to granular-like compartments and presumably cleaves at a Leu↓Asn bond (33). In that context, SKI-1 may represent the first member of an as yet undiscovered mammalian family of proteinases implicated in the limited proteolysis of proproteins at sites other than basic amino acids that may differ by their intracellular localization and cleavage specificity.

EXAMPLE 2

Genetic and biochemical evidence indicates that SKI-1/S1p is the protease that cleaves sterol-regulatory element-binding proteins (SREBPs) which functions to control lipid biosynthesis and uptake in animal cells {Sakai, J. et al. (1998) Molecular Cell 2, 505–514; Cheng, D. et al. (1999) J. Biol. Chem. 274, 22805–22812; Toure, A. et al. (1999) In: Peptides for the Now Millennium: Proceedings of the 16$^{th}$ American Peptide symposium}. SKI-1 and SREBPs play critical roles in the feedback pathways by which cholesterol suppresses transcription of genes encoding HMG CoA reductase and other enzymes of cholesterol biosynthesis as well as the low density lipoprotein (LDL) receptor. A SKI-1 inhibitor would be of use under clinical conditions in which there is not sufficient down regulation of SREBP dependent transcription by sterols. For example, in the Nieman-Pick group of diseases a high sphingomylin content of cells leads to an increase in proteolysis of SREBP-2 and a subsequent increase in cholesterol biosyntheses {Scheek, S. et al. (1997) Proc. Natl. Acad. Sci. USA 94, 11179–11183; Spence, M. W., and Callahan, J. W. (1989) Spingomyelin-cholesterol lipidoses: The Nieman-Pick Group of Diseases. *In The Metabolic Basis of Inherited Disease*) Scriver, C. R., Beaudet, A. L., Sly, W. S., and Valle, D., editors), McGraw-Hill Publ. Co., 6$^{th}$ edition, chapter 66, 1655–1676; Sviridov, D. (1999) Histology & Histopathology 14 (1): 305–319}. Perhaps of greater significance, nuclear SREBP-1c protein levels were significantly elevated in mouse models for non-insulin dependent diabetes, ob/ob and aP2 SREBP-1c mice, which was associated with elevated mRNA levels for known SREBP target genes involved in the biosynthesis of fatty acids (Schimomura, I. et al. J. Biol. Chem. 1999; 274:30028–30032).

In addition, the inhibition of the SREBP-dependent transcription of farnesyl diphosphate synthase, like HMG-CoA reductase and farnesyl-protein transferase inhibitors, by inhibition of farnesyl pyrophosphate biosynthesis could potentially be useful to treat a number of diseases such as Ras-dependant cancers and restenosis (Reference—U.S. Pat. No. 5,925,651). With regard to a potential treatment for restenosis, HMG-CA reductase inhibitors decrease smooth muscle (SMC) cell migration and proliferation, and induce SMC apoptosis {Bellosta, S. et al. (1998) Atherosclerosis 137, S101–S109; Guijarro, C. et al. (1998) Circulation Research 83, 490–500}.

As mentioned above, inhibition of PC activity seems to offer new therapeutical targets. Unfortunately, previous attempts using inhibitory peptides have failed either due to cytotoxicity of used agents or poor targeting[17;18], We have focused on the inhibitory properties of PC prosegments in order to find a safe and effective way for enzyme silencing.

To study the effect of the SKI-1 prosegment (ProSki-1) on the SREBP processing and mediated transcriptional activity we isolated a cDNA fragment covering the 188 amino acids that make up the signal peptide and the prosegment of SKI-1 including the predicted cleavage site RRLL$^{176}$ (SEQ. ID. NO. 90). This autocatalytic cleavage site was confirmed by mass spectral analysis and amino acid sequencing by other investigators 19. We isolated stable cell lines overexpressing SREBP-1 (neo resistance) and ProSki-1 plasmid (zeo resistance). A background SREBP-1 overexpression was used in order to improve detection of nuclear NH$_2$-terminal segment of SREBP in immunoblot experiments.

The effect of ProSki-1 on target gene mRNA: mRNA expression in HK293 cells was studied by Northern blotting as described in the methods section. In wild type (wt), vector only, and SREBP overexpressor cells in presence of lipids the mRNA levels were low for all studied genes: LDL-receptor, HMG-CoA reductase, farnesyl diphosphate (FDP) (FIG. 13), and fatty acid synthase (FAS) (FIG. 14). However, when these cells were treated with media containing no cholesterol a clear increase was observed in mRNA expression for all these genes, as demonstrated in earlier studies. Interestingly, corresponding mRNA levels were greatly reduced in both conditions in cells overexpressing ProSKI-1 and SREBP-1 suggesting that SREBP mediated transcription can be blocked efficiently by the prodomain mediated inhibition of the SKI-1 protease (FIGS. 13 and 14). The effect was observed in early passages of previously frozen cell lines. However, when the same clones were kept in culture for future passages, in contrast to earlier findings the target gene mRNA levels were now normal or even higher than in control cells. (FIG. 15). This finding suggests that cells can adapt to new conditions and maintain their lipid homeostasis even without SREBP mediated regulation and synthesis. This finding was supported in another experiment with several cell lines overexpressing SREBP-1 or SREBP-1 and ProSki-1 (FIG. 16). While HMG CoA reductase and farnesyl diphosphatase varied markedly between different cell lines containing only SREBP-1 (FIG. 16, lanes 1–5), mRNA levels measured from cells overexpressing ProSki-1 and SREBP-1 (FIG. 16, lanes cl4, cl6, and cl9) showed no variation and were higher than in SREBP-1 cells.

The ff ct of ProSki-1 on nuclear SREBPs: Western blot experiments were performed to illustrate the effect of ProSKI-1 on SREBP-1 processing in these cells. After staining with an antibody against the NH$_2$-terminal end of SREBP-1 a band around 60 kDa appeared on blots of nuclear extracts (FIG. 17), as demonstrated earlier by other investigators[2,3]. As expected, only a weak signal was detected in presence of sterols. In absence of sterols a significant increase was observed, especially in SREBP-1 cells. Only minute amounts of nuclear SREBPs were detected when ProSKi-1 was present suggesting that sterol mediated proteolysis of SREBPs is efficiently blocked in these cells in presence of ProSki-1 (FIG. 17 shows the data from clones 6 {lane 5} and 9 {lane 6}).

The inhibitory effect of ProSKI-1 was further demonstrated by studying the processing of cytoplasmic full length SREBP-1 (proSREBP-1) (FIG. 18). The processing of proSREBP-1 by SKI-1/S1P into intermediate (intSREBP-1)

forms shown previously by other investigators[19], was clearly demonstrated in clones overexpressing SREBP-1. Significantly, in cell lines overexpressing SREBP-1 together with the inhibitory prodomain of SKI-1 (pSKI+SRE) accumulation of the proSREBP-1 was observed and formation of the intermediate form(s) of SREBP-1 was abolished. These results, along with the observed reduction in nuclear SREBP (FIG. 17), indicate that ProSKI-1 efficiently inhibits SKI-1 protease activity and blocks SREBP processing in mammalian cells. In addition, the specificity of ProSKI-1 inhibition was studied by using a substrate not processed by SKI-1 (neurotrophin-3; NT-3). Both the level and furin-derived processing of NT-3 were unaffected by the presence of ProSKI-1 (not shown). These results suggest that ProSKI-1 is SREBP—and pro-BDNF—specific and that it does not affect other secretory proteins which are not substrates for SKI-1.

In these experiments a pro-domain was successfully used for the first time as a subtilase inhibitor in vivo. ProSki-1 seems to be a promising therapeutical tool for SREBP-mediated pathologies, which may or may not be directly related to cholesterol or fatty acid homeostasis. For instance SREBP-dependent isoprenoids, such as farnesol and geranylgeraniol, have been shown to associate e.g. with endothelial nitric oxide synthetase (eNOS)[20-23], vascular smooth muscle proliferation and migration as well as ras-protein mediated cell proliferation[24-28]. Furthermore, links to PPAR-γ mediated signaling system including adipocyte differentiation and insulin resistance have already been reported[29-33]. This novel prosegment approach to inhibit enzyme activity will certainly also inspire other investigators in different fields, since it may be possible to specifically inhibit other enzymes with this prosegment technology leading to new treatments for a variety of diseases. On the other hand, these results provide new data supporting the existence of an SREBP-independent, but lipid dependent (FIG. 3) control of the lipid homeostasis in human cells, although the alternative sensor of lipids under these conditions is currently unknown.

Materials and Methods

Materials:

Cell Culture: HK293 cells were maintained as monolayers in Dulbecco's modified Eagle's medium containing 100 units/ml penicillin and 100 μg/ml streptomycin sulfate (medium A) supplemented with 10% fetal calf serum. 24 hours before RNA and protein extractions medium A was supplemented with 5% lipoprotein deficient serum, 50 μM mevalonate (Sigma), 50 μM compactin (Sigma) and with no sterols or 1 μg/ml of 25-hydroxy-cholesterol and 10 μg/ml of cholesterol. 4 hours before protein extraction 25 μg/ml N-acetyl-leucinyl—leucinyl norleucinal was added. Total RNA was isolated with Trizol (Gibco BRL) reagent according to the instructions of the manufacturer. In order to extract proteins cells were washed and collected in PBS with protease inhibitors ( ). After addition of buffer A (Triton×100 1%, 50 mM tris maleate, 2 mM $CaCl_2$, inhibitor coctail ( ), and ALLN) cells were mixed with pipette and allowed to swell on ice for 20 minutes Then the solution was centrifuged for 5 minutes at 15,000 rpm and supernatants representing membrane proteins were collected and stored until analyzed at −70° C. Remaining pellets were resuspended in Buffer B (20 mM Tris pH 7.9, 400 mM NaCl, 1 mM EDTA, 1 mM EGTA, and protease inhibitors). Samples were shaken at 4 C for 1 hour and centrifuged and the supernatant was frozen in aliquots at −70° C.

Plasmid constructions: SKI-1 prosegment containing aa 1–188 was isolated by PCR using following oligonucleotides: [5' GGA TCC GAA GAA ACA TCT GGG CGA CAGA 3' (SEQ. ID. NO. 19)] and [5'CTC GAG GGC TCT CAG CCG TGT GCT 3'(SEQ. ID. NO. 20)] and cloned into PCR 2.1 TA cloning vector for sequencing. After that it was subcloned into the pcDNA$_{3zeocin}$ vector (Invitrogen) (BamHI/HindIII sites) for transfections.

SREBP-1 in bluescript IISK (ATCC 79810) subcloned into SaII/BamHI sites of the pcDNA$_{3geneticin}$.

Transfections: HK293 cells were plated at a density of $5×10^5$/60 mm dish in medium A with 10% fetal calf serum and were cultured until they were 40–60% confluent. The cells were then transfected with 10 μg plasmid DNA (pcDNA$_{3neo}$, pcDNA$_{3neo}$-SREBP-1, pcDNA$_{3neo}$-SREBP-1 and pcDNA$_{3zeo}$-proSKI-1) using Lipofectin reagent (Life Technologies, city, state) according to manufactures instructions. On day two medium containing appropriate selection agents (800 μg/ml Geneticin for pcDNA$_{3neo}$, x00 μg/ml Zeocin for pcDNA$_{3zeo}$) were added. The medium was changed every two days until defined colonies were evident. Colonies were isolated and formed stable cell lines were analyzed by immunoblotting with ProSKI-1 and SREBP-1 antibodies.

Northern blotting: 20 μg of total RNA was electroforetically separated in an 1.0% agarose gel, and transferred to Hybond N$^+$ filters (Amersham, city, state) by capillary blotting. After transfer filters were crosslinked by UV irradiation in a Stratalinker (Stratagene). Filters were prehydridized at 42° C. for 1 hour and hybridized with random labeled $^{32}P$ cDNA probes for 16–20 hours. Ultrahyb™ buffer (Ambion) was used. After hybridization filters were washed and exposed to film for indicated time and bands were quantified by densitometry. Primer pairs were used to clone cDNA probes: HMG CoA reductase [5' GAG GAA GAG ACA GGG ATA AAC 3' (SEQ ID NO: 21)] [5' GGG ATA TGC TTA GCA TTG AC 3' (SEQ ID NO: 22)], farnesyl diphosphate [5' AGC CCT ATT ACC TGA ACC TG 3' (SEQ ID NO: 23)], [5' GAA TCT GAA AGA ACT CCC CC 3' (SEQ ID NO: 24)], Fatty acid synthase [5' TTC CGA GAT TCC ATC CTA CG 3' (SEQ ID NO: 25)], [5' TGC AGC TCA GCA GGT CTA TG 3' (SEQ ID NO: 26)], Acetyl CoA carboxylase [5' TCT CCT CCA ACC TCA ACC AC 3' (SEQ ID NO: 27)], [5' CCA GCC TGT CAT CCT CAA TAT C$_3$ (SEQ ID NO: 28)], SREBP-1 [5' GGA GCC ATG GAT TGC ACT TTC 3' (SEQ ID NO: 29)], [5' AGG AGC TCA ATG TGG CAG GA 3' (SEQ ID NO: 30)]. Amplification products were cloned into pGEM (Promega) and sequenced. 18S cDNA was purchased from Ambion.

Immunoblot analysis: 50 μg of nuclear extract and membrane fractions were separated in an SDS-PAGE gel. After electrophoresis proteins were transferred to a nitrocellulose membrane. Membranes were stained with appropriate primary SREBP-1 (Santa Cruz), ProSki-1 and secondary antibodies. After washing chemiluminescent substrate (Santa Cruz) was added, and membranes were exposed to x-ray film for 1–30 min. Gels were calibrated with prestained molecular weight markers (New England Biolabs).

EXAMPLE 3

The soluble SKI-1 isoform, collected from cell media, was used to study the in vitro cleavage properties of this enzyme on a number of synthetic substrates. In addition, we present data on the in vitro inhibitory character of three prosegment constructs of SKI-1, which we obtained as bacterial recombinant proteins. Moreover, we examined the processing of hSKI-1 in LoVo cells infected with a VV recombinant as well as in a stable transfectant of HK293 cells (10).

Experimental Procedures

Vaccinia Virus Recombinant of BTMD-SKI-1—The preparation of a soluble form of hSKI-1 involved the initial amplification by polymerase chain reaction (PCR) of a 1250 base pair (bp) product encompassing nucleotides (nts) 491–1740 of the hSKI-1 cDNA (12), which includes the initiator methionine. The sense (s) and antisense (as) oligonucleotides were 5' GTGACCATG-AAGCTTGTCAA-CATCTGG 3' (SEQ. ID. NO.31) and 5' ACACTGGTCCCT-GAGAGGGCCCGGCA 3' (SEQ. ID. NO. 32) respectively. This completely sequenced fragment, which had been inserted into the PCR2.1 TA cloning vector (Invitrogen), was first digested with NotI and AccI. It was then ligated with the similarly digested full-length hSKI-1 cDNA 3.5kb product, resulting in a product called 5' hSKI-1-FL. In order to obtain a soluble form of hSKI-1 with a hexa-His sequence just before the stop codon, PCR amplification was carried out using the sense and antisense oligonucleotides: 5'ATTGAC-CTGGACAAGGTGGTG3' (SEQ. ID. NO. 33) and 5'GGATCCTCTAGATCAGTGGTGGTGGTGG-TGGTG-GTGCTCCTGGTTGTAGCGGCCAGG 3' (SEQ. ID. NO. 34). This resulted in a 165 bp fragment encoding the C-terminal sequence PGRYNQE$^{997}$-(H$_6$)* (SEQ. ID. NO. 91) (10). Following digestion with 5' EcoNI and 3' XbaI, the product was ligated to the aforementioned and similarly digested 5' hSKI-1-FL. This cDNA, coding for BTMD-SKI-1 ending with a hexa-His sequence, was then transferred to the BamH1/XbaI site of the (VV) transfer vector PMJ601. A recombinant was then isolated as previously reported (13). The VV recombinant of full-length hSKI-1 has been described (10).

Biosynthetic Analyses—Seventeen hours following infection with 2 pfu each of VV:SKI-1 and VV:BTMD-SKI-1 recombinants, human LoVo cells (3×10$^6$) were radiolabeled with 500 μCi of [$^3$H]Leu for 2h or pulsed for 15 min followed by a chase of 2h, in the presence or absence of 5 μg/ml of the fungal metabolite brefeldin A (BFA) as described (10,14). Media and cell lysates were immunoprecipitated with SKI-1 antiserum directed against either aa 634–651, or the prosegment comprising aa 18–188 (10). Immune complexes were resolved by SDS-PAGE on an 8% or 14% polyacrylamide/Tricine gel (10) and the dried gels autoradiographed (10,14). All biosynthesis experiments were performed at least twice.

Isolation and Purification of Recombinant hSKI-1 Prosegments—Three N-terminal fragments of hSKI-1 were isolated by PCR using a common (s) oligonucleotide [5' GGATCCGAAGAAACATCTGGGCGACAGA 3' (SEQ. ID. NO. 19)] and one of three (as) oligonucleotides [5'CTC-GAGGGAGAGGCTGGCTCTTCG 3' (SEQ. ID. NO. 35)], [5' CTCGAGGGCTCTCAGCCGTGTGCT 3' 3' (SEQ. ID. NO. 20)], or [5' CTCGAGTGTCTGGGCAACCTG-GCGCGGG 3' (SEQ. ID. NO. 36)]. These prosegment fragments, ending at aa 169, 188, and 196 (10), were cloned in the PCR 2.1 TA cloning vector for sequencing. Then they were transferred into the BamHI/XhoI sites of the bacterial expression vector pET 24b (Novagen). These recombinants were transformed into the E. Coli strain BL21. Protein expression was induced with 1 mM isopropyl β-D-thiogalactoside and the cultures were grown for 3h at 37° C. The cell pellets were sonicated on ice in a binding buffer containing 6M guanidine-HCl (Novagen) until a clear solution was obtained. The clarified and filtered solution was then applied to a nickel affinity column (Novagen) and eluted with 500 mM imidazole. The eluates were dialyzed overnight at 4° C. against 50 mM sodium acetate (pH 7). The protein precipitate was solubilized with glacial acetic acid, filtered through a 0.45 μm disk and further purified on a 5 μm C4 column (0.94×25 cm; Chromatographic Sciences Company Inc; CSC) by reverse-phase high performance liquid chromatography (RP-HPLC). The purity was assessed by Coomassie staining and the identity of the products verified by mass spectrometry on a Matrix Assisted Laser Desorption Time of Flight (MALDI-TOF) Voyageur DE-Pro instrument (PE PerSeptive Biosystems). The amounts of prosegments were determined by quantitative amino acid analysis (13).

Expression and Purification of Recombinant BTMD-SKI-1—Following infection of BSC40 cells (75×10$^6$ cells) with 2 pfu/cell of recombinant Vv:BTMD-SKI-1, the cells were washed and incubated at 37° C. for 18h in a serum-free minimal essential medium (MEM; Life Technologies). Media (45 ml) were then dialyzed, concentrated 20-fold to 2.2 ml on Centriprep-30's (Amicon) and stored at −20° C. in 40% glycerol. For purification[2], the concentrated media were applied to a Ni$^{2+}$ affinity resin (Novagen) or a Co$^{2+}$ affinity resin (Clontech Laboratories) as described by the manufacturer. After two washes with 5 mM imidazole, the protein was eluted with 200 mM imidazole and tested for enzymatic activity and immunoreactivity by Western blot (see below).

Western Blot Analyses—Aliquots of partially purified BTMD-SKI-1 were separated by 8 or 12% SDS-PAGE followed by electro-transfer of the proteins onto polyvinylidene fluoride (PVDF) membranes (Schleicher and Schuell). These membranes were probed with an antiserum directed against either SKI-1 [aa 217–233 (Ab:N) or aa 634–651 (Ab:S)] or pro-SKI-1 [(aa 18–188 (Ab:P)]. Protein bands were visualized by enhanced chemiluminescence (ECL) (Boehringer Mannheim).

Purification, N-terminal Sequencing and Mass Spectrometric Analysis of the Secreted Recombinant Prosegment(s) of hSKI-1—Concentrated media obtained from either VV:BTMD-SKI-1 infected BSC40 cells or from a stable transfectant of full-length hSKI-1 in HK293 cells (10) were loaded onto an RP-HPLC 5 μm C4 column (0.94×25 cm) (Vydac). Proteins were eluted at 2 ml/min using a 1%/min linear gradient (15–70%) of 0.1% aqueous trifluoroacetic acid (TFA)/CH$_3$CN with monitoring at 210 nm. The products were analyzed by Western blotting, after which the immunoreactive fractions were further purified on a CSC 5 μm C4 column (0.2×25 cm). Mass values were obtained by MALDI-TOF spectrometry using the [1] matrix 3,5 dimethoxy-4-hydroxycinnamic acid (Aldrich Chemical Co). For N-terminal sequencing, fraction IV proteins (FIG. 21A) were separated by SDS-PAGE, transferred to Immobilon-P membranes, and stained with Ponceau Red. The 14 and 5 kDa bands were excised and sequenced using an Applied Biosystems Model 477 sequenator operating in the gas-phase mode (15).

Synthesis of Peptide Substrates—All Fmoc amino acid derivatives (L-form), the coupling reagents, and the solvents for peptide synthesis were purchased from PE Biosystems Inc. (Framingham, Mass, USA), Calbiochem (San Diego, Calif., USA), or Richelieu Biotechnologies (Montréal, QC, Canada). The various linear synthetic peptides and internally quenched fluorogenic (Q-) substrates reported in this article are: (I) hproBDNF(50–63): KAGSRGLTSLADTF (SEQ. ID. NO. 37), (II) hSREBP-2(504–530): GGAHDSDQHPH-SGSGRSVLSFESGSGG (SEQ. ID. NO. 38), III) hSKI-1

(174–191): WHATGRHSSRRLLRAIPR (SEQ. ID. NO. 39), (IV) hSKI-1 (174–188+LE): WHATGRHSSRRLL-RALE (SEQ. ID. NO. 40), (V) hSKI-1 (182–188+LE): SRRLLRALE (SEQ. ID. NO: 41), (VI) hSKI-1 (156–172): WQSSRPLRRASLSLGSG (SEQ. ID. NO. 42), (VII) hSKI-1 (187–201): RAIPRQVAQTLQADV (SEQ. ID. NO. 43), (VIII) hSKI-1 (128–136): PQRKVFRSL (SEQ. ID. NO. 44), (IX) hSKI-1 (128–142): PQRKVFRSLKYAESD (SEQ. ID. NO. 45), (X) Q-hSKI-1 (132–142): Abz-VFRSLKYAESD-Y($NO_2$)-A (SEQ. ID. NO. 46), (XI) Q-hSKI-1 (134–142): Abz-RSLKYAESD-Y($NO_2$)-A (SEQ. ID. NO. 47). Except for the first two peptides, which were purchased from the Sheldon Biotechnology Institute (McGill University, QC, Canada), all other peptides were synthesized with the carboxy-terminus in the amide form. Peptides III–XI were prepared on a solid phase peptide synthesizer (Pioneer model, PE Biosystems) using either 2-(1H-benzotriazole-1-yl)-1, 1,3,3-tetramethyluronium hexafluophosphate (HBTU)/N-hydroxybenzotriazole (HOBT) or HATU (O-[7-azabenzotriazol-1-yl]-N,N,N',N'-tetramethyluronium hexafluorophosphate)/diisopropyl ethyl amine (DIEA)-mediated Fmoc chemistry with PAL-PEG unloaded resin and the standard side chain protecting groups (16). For the incorporation of the two unnatural amino acids [Abz and Y($NO_2$)], an extended coupling cycle was used instead of either the standard or fast cycles.

[1] Although we managed to produce limited quantities of partially purified SKI-1 using metal chelating resins, there was insufficient enzyme to carry out full kinetic analyses. However, since the medium of WT virus-(or control vector)-expressing cells produced no significant peptide hydrolysis (with the exception of peptides VII and IX), we mainly used the concentrated media of BSC40 cells infected with W:BTMD-SKI-1. Thus, the metal chelation-purified enzyme served mainly to verify that the enzyme from concentrated media behaved similarly to this form. We therefore confirmed all of the peptide cleavage sites, the SREBP-2 pH optimum, and the $Ca^{2+}$ requirement presented below.

Purification, Analysis, and Digestion of Peptide Substrates—The crude peptides were purified by RP-HPLC using a semi-preparative CSC-Exsil C18 column (2.5×25 cm). Monitoring at 210 nm, the peptides were eluted with a 1%/min linear gradient (5% to 60%) of aqueous 0.1% TFA/$CH_3CN$ at 2 ml/min and. The peptide purity and concentration were determined by quantitative amino acid analysis (16). The identity of each purified peptide was confirmed by MALDI-TOF spectrometry using the matrix α-cyano 4-hydroxycinnamic acid (Aldrich Chemical Co).

For digestions, each peptide was typically reacted at 37° C. with 10 μl of the concentrated enzyme preparation in a buffer consisting of 50 mM HEPES (N-2-Hydroxyethyl piperazine-N'-2 EthaneSulfonic acid) (ICN Biomedicals Inc), 50 mM MES (2-[N-Morpholino] EthaneSulfonic acid) (Sigma Chem Co.), and 3 mM $Ca^{2+}$-acetate (pH 6.5). The digestion products were separated by RP-HPLC on a Beckman 5 μm Ultrasphere C18 column (0.2×25 cm) and eluted with a 1%/min linear gradient of aqueous 0.1% TFA/$CH_3CN$ (545%) at a flow rate of 1 ml/min. The collected peptides were characterized by mass spectrometry and amino acid composition, which was also used to quantitate the amount of various substrates and products. The digestions of the quenched fluorogenic peptides were analyzed by RP-HPLC using a dual UV (210 nm) and fluorescence (excitation and emission wavelengths of 320 and 420 nm, respectively) detector (Rainin).

pH Optimum, Calcium-Dependence and Inhibitor Profile—The protocols used were essentially the same as reported previously (13). Stocks of the buffer described above were adjusted to pH 5.0–8.5 at 0.5 unit increments by addition of either acetic acid or sodium hydroxide. In order to investigate the calcium requirement of SKI-1, increasing concentrations of $Ca^{2+}$-acetate were used ranging from 0 to 10 mM. For inhibition studies, the enzyme in the reaction buffer was preincubated with the desired agents for 30 min prior to addition of peptide II.

$K_{m(app)}$, $V_{max(app)}$ and $K_{i(app)}$ determinations—Following digestion reactions with increasing substrate concentrations, the products were separated by RP-HPLC. The rate of substrate hydrolysis was obtained from the integrated peak areas of the chromatograms. $K_{m(app)}$ and $V_{max(app)}$ values were estimated using nonlinear regression analysis (Enzfitter software; Elsevier Biosoft, Cambridge, UK) of plots of the hydrolysis rate vs the substrate concentration. For apparent inhibitor constant [$K_{i(app)}$] determinations, variable inhibitor concentrations within the range of 15–70% inhibition were used at three concentrations of peptide IV ranging from 0.6 to 3.5 times the $K_{m(app)}$ value. The $K_{i(app)}$ values were estimated from Dixon plots as described (16). For the two quenched peptides, kinetic parameters were determined as described (17).

Results

SKI-1 Overexpression, Purification, Biosynthesis, and Prosegment Processing

We have previously shown that overexpression of full-length SKI-1 (FL-SKI-1) in HK293 cells results in shedding of a 98 kDa form (sSKI-1) of this enzyme into the medium (10). Based on this finding, we engineered a soluble form of SKI-1 (BTMD-SKI-1), ending at residue 997, to which we added a hexa-His sequence at the C-terminus (FIG. 19A). In a comparative biosynthetic analysis, shown in FIG. 19B, LoVo cells were infected with the SKI-1 virus constructs W:FL-SKI-1, W:BTMD-SKI-1, and wild type virus (VV: WT). After labeling the cells for 3h with [$^{35}$S]Cys, proteins in the media were immunoprecipitated with an antiserum directed against either the prosegment of SKI-1 (Ab:P) or an internal SKI-1 sequence (Ab:S). In both cases, a protein of ~14 kDa co-immunoprecipitated with the 98 kDa sSKI-1 or the 100 kDa BTMD-SKI-1 (bSKI-1, FIG. 19B) that was not seen with W:WT infections. Since Ab:P was raised against a recombinant SKI-1 prosegment peptide and has been shown previously to detect the SKI-1 zymogen (10), we concluded that the ~14 kDa peptide is most likely derived from the cleaved prosegment (the full-length prosegment is ~24 kDa—see below). The fact that it co-immunoprecipitated with the enzyme under denaturing conditions suggests a strong interaction between SKI-1 and this region of its prosegment. The actual stoichiometry of enzyme-to-prosegment is not clear from this experiment, since it was carried out using two different antisera and denaturing conditions. We also observed that some of the 100 kDa BTMD-SKI-1 is cleaved into a 98 kDa form similar to that found with FL-SKI-1 (FIG. 19B). This conversion is presumably carried out by endogenous "shedding enzymes" (10,18) that can act on both forms of SKI-1, although C-terminal sequencing would be needed to confirm this hypothesis.

Western blot analyses of media now obtained from BSC40 cells infected with VV:BTMD-SKI-1 also revealed a secreted ~100 kDa immunoreactive band (FIG. 19C). The same band was detected using either an antiserum against the N-terminal region of the SKI-1 catalytic domain (Ab:N) or one against a more C-terminal region (Ab:S). When Ab:P was mixed together with Ab:S and used to probe the metal affinity column-purified SKI-1 preparation (indicated by the * in FIG. 19C), we were able to again detect the ~14 kDa prosegment fragment, further supporting our hypothesis that it forms a strong association with the enzyme. (It should be noted that although a mixture of Ab:S and Ab:P was used in order to detect both proSKI-1 and BTMD-SKI-1 simultaneously, when either Ab:N or Ab:S were used alone, only the 100 kDa or 14 kDa species were observed, respectively (not shown)).

In order to evaluate the rate of zymogen processing and the fate of the prosegment, LoVo cells overexpressing W:FL-SKI-1 were pulse-labeled with [$^3$H]Leu for 15 min and then chased for 2h. FIG. 20 shows an SDS-PAGE analysis of the cell lysates immunoprecipitated with Ab:P (left panel). At least five immunoreactive polypeptides (molecular masses of ~26, 24,14,10 and 8 kDa) which were not present in controls infected with W:WT, were detected. In order to further define in which organelle(s) this processing occured, LoVo cells infected with VV:FL-SKI-1—were pulse-labeled with [$^3$H]Leu for 2h in the presence or absence of BFA (FIG. 20, right panel). In both cases, the same five major, intracellular, immunoreactive prosegment forms could still be detected. Since the fungal metabolite BFA is known to disassemble the Golgi complex and cause the ER to fuse with the cis, medial and trans Golgi (but not the trans Golgi network, TGN) (19), this result strongly implies that the initial zymogen processing of proSKI-1 occurs early along the secretory pathway. Possible locations include the ER or cis Golgi, as was previously reported (10). Moreover, further processing of the prosegment into yet smaller fragments also occurs in these organelles.

To further characterize the prosegment of SKI-1, we took advantage of a stable transfectant of FL-SKI-1 in human HK293 cells that we had made previously (10). This system has the added advantage that the possibility of VV overexpression artifacts influencing the processing of the prosegment is eliminated. Concentrated culture medium from these cells (serum-free) was purified via RP-HPLC using first a semi-preparative C4 column (not shown) followed by an analytical C4 column (FIG. 21A). The eluted fractions were analyzed by Western blot using Ab:P (FIG. 21B). Immunoreactive peptides ranging from ~4.5–24 kDa were apparent. N-temlinal sequencing of the very abundant ~14 kDa protein in fraction IV (FIG. 21C) revealed a major sequence starting at Gly$^{17}$ of pre-proSKI-1 (10,12). This clearly defines the signal peptidase cleavage site as LWLLC$^{16}$↓GKKHLG (SEQ. ID. NO. 92), which is one aa before that predicted by signal peptidase cleavage site algorithms (10,11). The N-terminal sequence of the ~4.5 kDa polypeptide (FIG. 21D) revealed that it starts at Pro$^{143}$, indicating a cleavage at the sequence KYAESD$^{142}$↓PTVPCNETRWSQK (SEQ. ID. NO. 93). This fragment is most likely the product of cleavage between Asp and Pro that may be caused by the acidic conditions encountered in either RP-HPLC, Edman sequencing (20), or sample preparation for SDS-PAGE analysis (21). An unexpected benefit of this cleavage was our finding that phenylthiohydantoin (PTH)-Asn $^{148}$, which occurs in the putative N-glycosylation site AsnGluThr was readily detected in this sequence. Thus, the predicted N-glycosylation site Asn$^{148}$ within the prosegment of SKI-1 is not employed, at least in this expression system. This conclusion was also supported by the prosegment's resistance to endo H and endo F digestion (not shown). Of the two eukaryotic subtilases known to contain a potential N-glycosylation AsnGluThr site, i.e. kexin (22) and SKI-1 (10), it appears that at least the latter's prosegment is not N— glycosylated. Finally, the separation of the above prosegment fragments from mature SKI-1 using RP-HPLC (FIG. 21A,B) and non-reducing SDS-PAGE (not shown), suggests that none of the Cys residues in the prosegment (10) are linked by disulfide bridges to the rest of the enzyme.

Figure 21E:
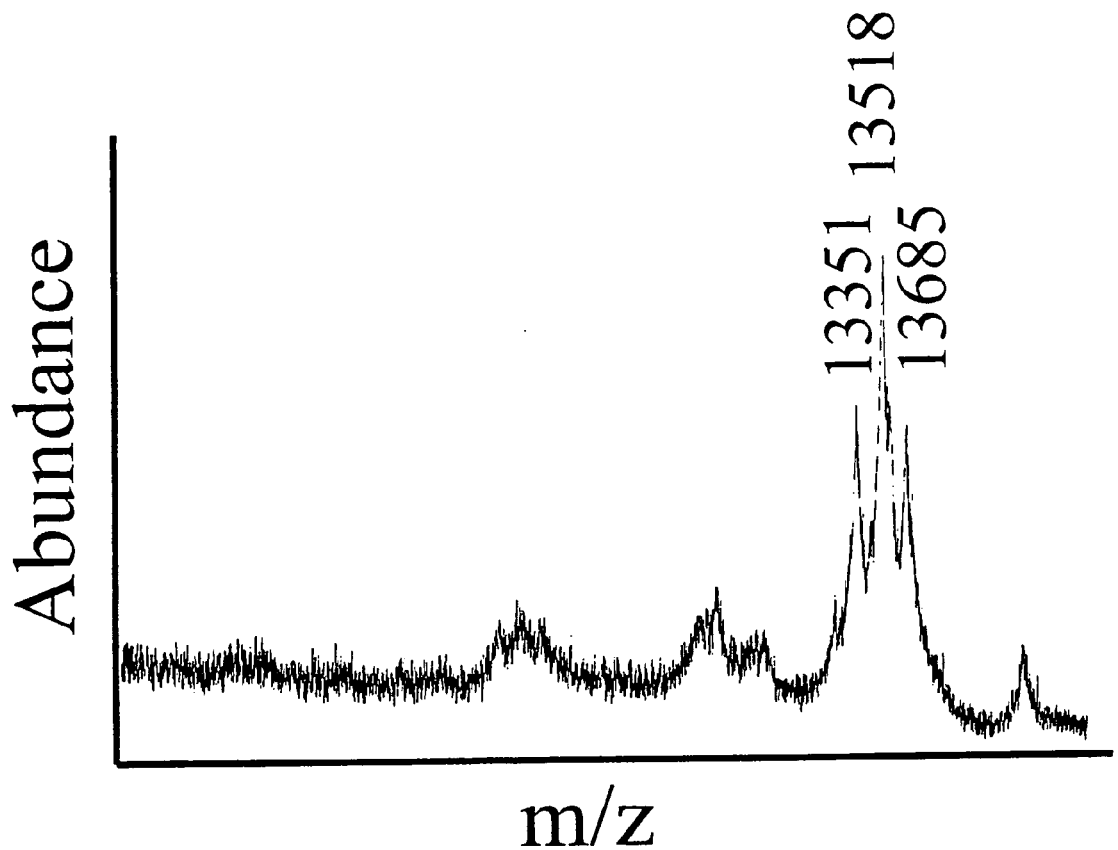

As a preliminary means of characterizing the SKI-1 prosegment fragments, MALDI-TOF analysis (FIG. 21E) of fraction IV from FIG. 21B was carried out. Three major molecular ions of masses 13,351, 13,518, and 13,685 Da were detected, with an expected error of +25 Da for this mass range. Combined with the previous N-terminal sequencing results of the ~14 kDa peptide (FIG. 21C), these mass values indicate that this peptide has heterogeneous C-termini that are derived from cleavages near the sequence RKVFRSLK$^{137}$(SEQ. ID. NO. 94), as indicated in FIG. 21E. In fact this region contains three potential SKI-1 cleavage sites (8) with an R or K at the P4 position and either an F, R or K at the P1 position. Although the calculated molecular masses of 13,339, 13,496 and 13,696 for the polypeptides G$^{17}$KK—-RKVF$^{133}$ (SEQ. ID. NO. 95), G$^{17}$KK—RKVFR$^{134}$(SEQ. ID. NO. 96) and G$^{17}$KK—-RKVFRSL$^{136}$ (SEQ. ID. NO. 97) espectively, match within experimental error (±22 Da) the observed masses in FIG. 21E, these assignments should only be taken as a first indication (see below). Moreover, the predicted G$^{17}$KK—RKVFRSL$^{136}$ (SEQ. ID. NO. 98) Lys$^{137}$ followed by basic carboxypeptidase cleavage of the C-terminal Lys (23). Since we were unable to obtain consistent mass spectra of the ~4.5 kDa polypeptide that was sequenced in FIG. 21D, we could not use this technique to approximate its C-terminus, which presumably corresponds to the C-terminus of the processed SKI-1 pro-segment. We therefore resorted to synthetic peptide cleavage as a tool to accurately define potential prosegment cleavage sites.

Analysis of Synthetic Prosegment-derived Peptide Cleavages-Based on our detection of 26[ ]and 24 kDa SKI-1 prosegment products (FIG. 20), as well as on a mutagenesis study of SREBP-2 cleavage sites (8), we synthesized three SKI-1 prosegment peptides encompassing potential, C-terminal, autocatalytic cleavage sites (10,11). All contain Arg at P4 and either Leu, Lys, Ala or Phe at P1 (peptides III, VI and VII shown in Table II-A). Of these peptides containing only native sequences, the only one with detectable cleavage by SKI-1-containing concentrated medium (from either VV:BTMD-SKI-1-infected BSC40 cells or SKI-1 transfected HK293 cells) was peptide III (WHATGRHSSRRLL$^{186}$↓RAIPR (SEQ. ID. NO. 39) (see Table II-A). No cleavages were observed when VV:WT-infected or empty vector-transfected media were used (not shown). Metal chelation chromatography-purified enzyme further supported that this cleavage is effected by SKI-1 (FIG. 22A; peptide III), and the products were positively identified via mass spectrometry.

Similarly, based on the mass spectrometry data in FIG. 21E, we synthesized two peptides (VIII and IX) encompassing the putative internal processing site(s) of the SKI-1 prosegment. Both were cleaved at multiple locations by SKI-1-containing concentrated medium from HK293 transfectants (not shown). Further analysis revealed that one of these cleavages, corresponding to PQRKVF$^{133}$↓RSL (SEQ. ID. NO. 44), was as prevalent in empty vector-transfected HK293 medium as in SKI-1-transfected medium (see. Table III-A, peptide VIII). In contrast, the PQRKVFRSLK$^{137}$↓YAESD (SEQ. ID. NO. 45) cleavage was only seen in SKI-1-containing medium. This cleavage was also confirmed using metal chelation chromatography-purified enzyme (FIG. 22B; peptide IX) and mass spectrometry to identify the products. However, also clearly visible are the PQRKVF$^{133}$↓RSLKYAESD (SEQ. ID. NO. 45) cleavage products. We acknowledge that there could be residual contaminating proteases in our purified SKI-1 preparations (minor bands were visible on colloidal gold-stained membranes of SKI-1 preparations). Thus, while we are confident that SKI-1 cleaves its prosegment at the C-terminal WHATGRHSSRRLL$^{186}$↓RAIPR (SEQ. ID. NO. 39) site and at the internal PQRKVFRSLK$^{137}$↓ YAESD (SEQ. ID. NO. 45) site, our data do not allow us to rule out SKI-1-mediated cleavage at the PQRKVF$^{133}$↓RSLKYAESD (SEQ. ID. NO. 45) site.

Comparing the simple cleavage rates of the SKI-1 pro-segment internal and C-terminal sites, we observed that the former was vastly superior to the latter (not shown). We also noticed that the peptides best processed by SKI-1 contain an acidic residue at the P3' or P4' substrate site, whereas those that did not appeared to be cleaved poorly or not at all (Table III-A). Moreover, we had previously established that SKI-1 does not cleave the fluorogenic peptides RGLT-MCA, RGLTT-MCA and RSVL-MCA (10), which lack P' residues. Based on these observations, we asked if replacing the Ile and Pro residues at P3' and P4' of the C-terminal prosegment processing site would significantly improve the SKI-1-mediated cleavage of peptide III. Thus, we synthesized two mutants of this peptide (peptides IV and V, the latter truncated by 8 aa at the N-terminus) in which the Ile and Pro residues at P3' and P4' were replaced by Leu and Glu, respectively. As shown in Table II-B, this change significantly improved the processing of these peptides, such that we were able to determine $V_{max(app)}/K_{m(app)}$ values. The approximately two-fold difference in these values for peptides IV and V further suggests that determinants N-terminal to the P4 position may also play a role in substrate specificity. The SKI-1 specificity of these peptide cleavages was also verified using metal chelation chromatography-purified enzyme (when W:WT-infected or empty vector-transfected media were used, no peptide processing was observed).

In Vitro Kinetic Properties of SKI-1: *Comparative Analysis of Synthetic Peptide Cleavages*—In a previous report (10), sSKI-1 was shown, to cleave the 32 kDa proBDNF into a 28 kDa form at the RGLT↓SL (SEQ. ID. NO. 99) sequence in vitro with a pH optimum close to neutrality. Similar to PCs (1–3), we suggested that SKI-1 might be a $Ca^{2+}$-dependent enzyme since the calcium ionophore A23187 inhibited the ex vivo cleavage of proBDNF (10). In order obtain kinetic analyses of defined SKI-1 substrates, we examined a 14 aa peptide spanning the hproBDNF processing site (10), K$^{50}$AGSRGLT↓SLADTF$^{63}$ (SEQ. ID. NO. 37) peptide I) and a 27 aa hSREBP-2-related peptide (8), G$^{504}$GAHDSDQHPHSGSGRSVL↓SFESGSGG$^{530}$ peptide II). Concentrated SKI-1-containing medium (from either VV:BTMD-SKI-1-infected BSC40 cells or SKI-1 transfected HK293 cells) was reacted with these peptides at pH 6.5, followed by MALDI-TOF mass spectrometric analysis of the RP-HPLC-purified products. The expected cleavages were confirmed and did not occur using WT-/empty vector-derived media (FIG. 23). Again, the metal chelation chromatography-purified enzyme generated the same products as the concentrated media (not shown). We then demonstrated that the optimal pH and calcium concentrations for efficient cleavage of the hSREBP-2 peptide (II) are pH 6.5 and 2 mM $Ca^{2+}$, respectively (FIG. 23). Interestingly, the pH optimum observed with the proBDNF peptide (I) is sharper than that obtained with peptide II. In the former case, the enzyme still retains about 30% of its activity at pH 5.0 and 55% of its activity at pH 8.5 (FIG. 24A). Similar results for the pH optimum of peptide II cleavage were obtained with metal chelation-purified BTMD-SKI-1 (not shown). In contrast, however, the pH optimum of peptide IX with the purified enzyme was 8.0, with no activity detectable below pH 5.5.

A summary of the kinetic analyses of the synthetic proBDNF (peptide 1) and SREBP-2 (peptide II) cleavages by SKI-1 is shown in Table II-B. Both peptides are cleaved at comparable kinetic efficiencies with $V_{max(app)}/K_{m(app)}$ values of 0.002 and 0.004 $h^{-1}$, respectively. In comparison, the $V_{max(app)}/K_{m(app)}$ value estimated with peptide IV is 5–10-fold higher than those obtained with peptides I and II (Table II-B). The N-terminal truncation of peptide IV from 17 to 9 aa (peptide V, Table II-A) caused a 4-fold reduction in catalytic efficiency (Table II-B).

Table III shows the inhibitor profile of SKI-1, in which it is clear that this enzyme is quite sensitive to metal chelators such as EDTA and to the calcium chelator EGTA. In addition, the transition metals $Cu^{2+}$ and $Zn^{2+}$, but not $Ni^{2+}$ or $Co^{2+}$, inhibit the enzyme at mM concentrations. As reported using the 32 kDa proBDNF (10), assays with the synthetic SREBP-2 peptide demonstrated that the metal chelator o-phenanthroline becomes inhibitory at concentrations above 1 mM. The other non-chelator inhibitors tested had minimal or no effects on SKI-1 activity.

In order to develop a convenient in vitro assay for SKI-1, we designed a number of internally quenched fluorogenic substrates and tested their cleavage efficacy by SKI-1. The two best peptides encompassed the processing site RSLK↓ within the hSKI-1 prosegment (peptides X and XI, Table II-A). Mass spectrometric analysis confirmed that both peptides were cleaved at the RSLK↓ (SEQ. ID. NO. 100) site by shed SKI-1 derived from HK293 cell transfects, but not by medium obtained from HK293 empty vector transfectants. This processing generated the fluorescent N-terminal peptides Abz-VFRSLK (SEQ. ID. NO. 101), or Abz-RSLK (SEQ. ID. NO. 102), and a non-fluorescent C-terminal peptide YAESDY($NO_2$)-A (SEQ. ID. NO. 103) not shown). Measurements of kinetic parameters demonstrated that peptides X and XI are about 3- and 16-fold better substrates than the C-terminal prosegment peptide IV (Tables I-B and III), suggesting that the shorter peptide XI may be the best SKI-1 substrate tested to date. This cleavage was completely abolished in the presence of 10 mM EDTA, in agreement with the $Ca^{2+}$-dependence of SKI-1 activity (FIG. 24B).

SKI-1 Inhibition by its Prosegment—One important question remaining is whether the SKI-1 prosegment functions as an inhibitor of its enzymatic activity, analogous to the prosegments of other subtilases (3). We thus prepared prosegment constructs, designated ending near the proposed C-terminal processing site RRLL$^{186}$ (SEQ. ID. NO. 90) (FIG. 22A): PS1, extending to Leu$^{169}$; PS2, extending to Ala$^{188}$; and PS3, extending to Leu$^{197}$ To each C-terminus we coupled a hexa-His tag. These prosegment constructs were expressed in bacteria and purified by $Ni^{2+}$-chelation chromatography followed by RP-HPLC (see Experimental Procedures). The purity of these prosegments was confirmed by SDS-PAGE/Coomassie staining and aa analysis (not shown). A summary of the inhibitory potency of each prosegment using peptide IV as a substrate is shown in Table V. Kinetic analysis using Dixon plots (15) indicated a competitive inhibition mechanism (not shown). Although PS2 exhibits the best apparent inhibitory constant ($K_{i(app)}$=97 nM), PS3 ($K_{i(app)}$=127 nM) and PS1($K_{i(app)}$=182 nM) are similarly potent SKI-1 inhibitors. When PS2 was digested with carboxypeptidase B to eliminate the His-tag, its inhibitory potency was not affected (not shown), confirming that this tag is not responsible for the observed inhibition. We also tested the inhibitory activity of the RP-HPLC-fractionated native prosegment (see FIG. 21). Only, the material from fraction IV, which included the full-length ~24 kDa prosegment, was inhibitory, whereas that of the others, including the ~14 kDa peptide alone or in combination with smaller fragments, were not inhibitory (not shown).

DISCUSSION

Limited proteolysis of inactive precursor proteins at sites marked by paired or multiple basic residues is a widespread process (1,2). Less common is the recent finding that bioactive peptides or proteins can also be generated by limited proteolysis after either hydrophobic or small residues (3). SKI-1 represents the first mammalian member of subtilisin-like processing enzymes with such substrate specificity (10,11). It is a widely expressed enzyme (10) that may play a crucial role in cholesterol and fatty acid metabolism (11). Due to its very recent discovery, information regarding its enzymatic properties, substrate specificity, and the function of its proregion have only begun to be addressed.

Many peptidyl hydrolases, including subtilases, possess a prodomain which acts both as an intramolecular chaperone and a highly potent inhibitor of its associated protease (24,25). Activation of the enzyme typically requires release of the prosegment in an organelle-specific manner. For furin (26) the release occurs in the TGN, whereas for PC1 and PC2 (27) it occurs in immature secretory granules. The data presented in this report demonstrate that SKI-1 is unique among the mammalian subtilases, since both the C-terminal and internal cleavages of its prosegment occur in the ER. Hence, this enzyme does not appear to require an acidic environment for activation, assuming, by analogy with other subtilases (3), that prosegment release is the crucial step leading to zymogen activation. We propose the following sequence of events presumably leading to SKI-1 activation: 1) The signal peptide is removed in the ER by a signal peptidase cleavage at LVVLLC$^{17}$↓GKKHLG (SEQ. ID. NO. 92) FIG. 21C). 2) The prosegment is processed into a non-N-glycosylated polypeptide with an apparent molecular mass of ~24–26 kDa (FIG. 20). 3) This prosegment is further processed into 14, 10 and 8 kDa intermediates (FIG. 20). While these multiple cleavages may be catalyzed by SKI-1 itself, the participation of other proteases cannot be excluded. The major cleavages leading to the formation of the ~24 and ~14 kDa products occur within 10 min, and the other secondary ones within 30 min (not shown). Since treatment of cells with BFA did not significantly alter these processing events, they most likely occur in the ER (FIG. 20). It is possible that the generation of prosegment fragments from the ~24–26 kDa pro-form leads to a loss of inhibition in a fashion similar to that of subtilisin E (24,25). Indeed, our results demonstrate that while the full-length prosegment is inhibitory, its ~14 kDa product is not. Surprisingly, some pro-region-derived polypeptides are found associated with SKI-1 in cell culture media. Thus, in contrast to furin (26), the low pH and high $Ca^{2+}$ concentrations prevailing in the TGN do not lead to propeptide dissociation. High ionic concentrations (up to 1 M NaCl) such as those used in immunoprecipitation (FIG. 19B) and metal chelation protein purification (FIG. 19C) also do not disrupt the complex. It is only during RP-HPLC purification (FIG. 21A), in the presence of strong acids and organic solvents, that the prosegment peptides dissociate from SKI-1. These data suggest that hydrophobic interactions may be critical, as is the case for subtilisin (24,25).

To distinguish the SKI-1 prosegment autoprocessing sites (C-terminal and internal) from several closely situated candidate sites, we employed a combination of mass spectrometry and synthetic peptide digestion. In the case of the C-terminal site, only one of three candidate peptides (III) was processed by SKI-1 (Table II-A), indicating that RRLL$^{186}$↓RAIP (SEQ. ID. NO. 104) is the most likely autoprocessing site. For the internal site, preliminary mass spectrometric data suggested three distinct cleavages occurring within the sequence PQRKVFRSLKYAESD$^{142}$ (SEQ. ID. NO. 45) (FIG. 21E). Two of the three possible sites (PQRKVF$^{133}$↓RSLKYAESD (SEQ. ID. NO. 45) and PQRKVFR$^{134}$↓SLKYAESD (SEQ. ID. NO. 45) appeared to satisfy the proposed SKI-1 recognition motif requiring a P4 basic residue (8). The third possibility (PQRKVFRSL$^{136}$↓KYAESD (SEQ. ID. NO. 45) could be considered by assuming the cleavage actually occurred at PQRKVFRSLK$^{137}$↓YAESD (SEQ. ID. NO. 45) followed by endogenous, basic carboxypeptidase removal of the C-terminal Lys residue (23). Assays carried out in vitro with synthetic peptides corresponding to this region of the prosegment (peptides VIII and IX) produced the same cleavage products (not shown), but only the PQRKVFRSLK$^{137}$↓YAESD cleavage was unique to SKI-1. Thus, we propose that the aforementioned site is the most likely internal autoprocessing site, with the qualification that PQRKVF$^{133}$↓RSLKYAESD (SEQ. ID. NO. 45) may occur to a lesser extent (see Results and FIG. 22).

Other information regarding the substrate preferences of SKI-1 was obtained by replacing the P3' and P4' Ile and Pro residues of the C-terminal cleavage site peptide (III) by Leu and Glu (peptides IV and V) to create a very well processed SKI-1 substrate. While it would appear that the presence of an acidic residue at P4' significantly enhances the rate of substrate hydrolysis, it is also possible that the presence of Pro at P4' hinders efficient substrate processing. The presence of similar acidic residues at the P3' or P4' position of the two confirmed substrates of SKI-1 (peptides I and II) as well as in the prosegment internal cleavage site RSLK$^{137}$↓YAES (SEQ. ID. NO. 105) (Table II-A) lends support to the first argument. In addition to these residues, others also appear to play a role in SKI-1 substrate cleavage catalysis. The peptide pairs IV/N and X/XI both point to influences of positions N-terminal to the P4 residue. Interestingly, the efficiency of the truncated C-terminal peptide V is lower than that of peptide IV, whereas that of the truncated internal (quenched) peptide XI is higher. Taken together, these data indicate the importance of aa at both the P and P' positions in SKI-1-mediated substrate hydrolysis.

The data presented in FIG. 24 indicate that SKI-1 functions most efficiently near neutral pH and at 2–3 mM $Ca^{2+}$. This is in general agreement with the conditions that reportedly prevail in the ER (28,29). However, closer examination of the data reveal that the pH optimum of SREBP-2 cleavage (peptide II, FIG. 24A) is actually 6.5, an observation that we confirmed using our purified SKI-1 preparation (not shown). This suggests that the processing of SREBP might occur outside of the ER, perhaps in the Golgi where pH values of ~6.5 have recently been reported (30,31). Indeed, there is now cellular evidence suggesting that SREBP cleavage may occur in the Golgi rather than in the ER (32,33). The pH optimum of SKI-1 appears to be dependent on the substrate employed; proBDNF (10) and its related peptide (I), appear to be well cleaved even at pH 5.5, suggesting that it could cleavethis (and possibly other substrates) in acidic endosome-like compartments where it was previously localized (10). On the other hand, cleavage of the internal, autocatalytic, prosegment processing site PQRKVFRSLK$^{137}$↓YAESD (SEQ. ID. NO. 45) (FIG. 22B) is optimal at pH 8 (not shown), implying that this event, as we concluded from our biosynthesis assays, takes place most effectively in the ER. Overall, the pH and Ca$^{2+}$ profiles of SKI-1 resemble those of the constitutively secreted PCs (1,13). The inhibitor profile of SKI-1 (10, Table III), showing that enzymatic activity is significantly inhibited by EDTA, EGTA and only high concentrations of o-phenanthroline, tend to discount the likelihood that SKI-1 is a transition metal-dependent proteinase. In fact, SKI-1 activity is inhibited by low concentrations of certain transition metals, such as Cu$^{2+}$ and Zn$^{2+}$.

Directed by the observation that peptides containing the primary processing site of the prosegment of PC1 are potent inhibitors of its activity, and that the C-terminal basic residues of furin and PC7 are essential for enzyme inhibition (34,35), we assessed the inhibitory potency of three SKI-1 recombinant propeptides. All of these end at sequences near the RRLL$^{186}$RA (SEQ ID. NO. 106) cleavage site. Interestingly, the three prosegments displayed comparable inhibitory potencies (Table V). Compared to proPC1 (34), profurin and proPC7 (35), the K$_{i(app)}$ values (Table V) are up to 250 fold higher. This suggests that the prosegment of SKI-1, although potentially inhibitory in vivo, may function more as a chaperone, catalyzing the productive folding of SKI-1. Indeed, since SKI-1 may be active in the ER (10,11), whereas the PCs are not (13,26), the lower inhibitory potency of the prosegment of SKI-1 may be adapted to the conditions prevailing in this cellular compartment. In the case of PCs, highly effective inhibition by the prosegment may be needed in order to ensure that these enzymes are activated only when they reach the TGN or secretory granules (1–3). The 14 kDa fragment, which represents the major secreted form of the prosegment, is tightly associated with SKI-1 (FIG. 19C) yet it is not inhibitory (not shown). Accordingly, this segment may serve a chaperonin-like function similar to that reported for the N-terminal 150 aa of 7B2 towards proPC2 (36,37).

Two articles describing the processing, purification and in vitro activity of hamster SKI-1/S1P were published (38,39). On most points, our results are in close agreement with those recently published. Thus, these authors characterized the processing of the SKI-1/S1P prosegment, proposing that the ER is the major site of autocatalytic activation of SKI-1 at the same cleavage sites as we present here. They also went on to purify a soluble form of the enzyme, showing that it correctly processes SREBP-2 derived peptides as well as a 16 residue peptide spanning the internal prosegment cleavage site. In addition, they find that cleavage of fluorogenic RSLK-MCA peptide derived from the same sequence is optimal at ~3 mM Ca$^{2+}$ at slightly alkaline pH. Discrepancies such as the lack of detectable shed SKI-1/S1P, multiple secreted prosegment forms, and a different signal peptidase site can most likely be attributed to the different cell types and species employed in the two studies.

In conclusion, the present work firmly establishes that SKI-1 is a Ca$^{2+}$-dependent subtilase with a reasonably neutral pH optimum, depending on the substrate employed. [ ]We also demonstrate that SKI-1 can cleave substrates C-terminal to Thr, Leu and Lys residues, thus providing direct, in vitro evidence that it is a candidate converting enzyme responsible for the generation of 28 kDa proBDNF (10) and SREBP-2 processing at site 1 (11). For efficient cleavage, it appears that substrates should contain a basic residue at P4 and an aliphatic one at P2 (Table II-A). Furthermore, aa at the P3' and P4' positions seem to exert an important discriminatory effect. The best substrate tested so far is the quenched fluorogenic substrate Abz-RSLK_YAESDY(NO$_2$) (SEQ. ID. NO. 107), thereby providing a convenient and sensitive assay for SKI-1 activity. The present data demonstrate that only the full length SKI-1 prosegment is inhibitory. Thus, overexpression of this prosegment in cell lines may provide a novel method for inhibiting the cellular activity of this enzyme in a fashion similar to the that of over-expressed profurin and proPC7 (35). Finally, it is anticipated that precursor substrates other than the sterol regulating SREBPs (8) and the neurotrophin proBDNF (10) will be identified, thereby extending the spectrum of activity of this unique and versatile enzyme.

TABLE II-A

Synthetic peptide substrates
Peptides were first reacted with approximately equal quantities of BTMD-SKI-1 medium for 2–18 h as described in "Experimental Procedures". When cleavage was not detected, a 10-fold concentrated enzyme preparation was tested. Arrow thickness is a qualitative estimate of the cleavage efficacy.

| Peptide | P16 | P12 | P8 | P4 | P1 | P4' | P8' | |
|---|---|---|---|---|---|---|---|---|
| I | | | K A G S | R G L T | _ S L A D | T F | | (SEQ ID NO:37) |
| II | G G A H | D S D Q H P H S | G S G R | S V L | _ S F E S | G S G G | | (SEQ ID NO:38) |
| III | | | W H A T G R H S | S R R L L | ↓ R A I P R | | | (SEQ ID NO:39) |
| IV | | | W H A T G R H S | S R R L L | _ R A L E | | | (SEQ ID NO:40) |
| V | | | | S R R L L | _ R A L E | | | (SEQ ID NO:41) |
| VI[1] | | | W Q S S R P L R | R A S L | - S L G S G | | | (SEQ ID NO:42) |
| VII[1] | | | | R A I P | R Q V A | - Q T L Q A D V | | (SEQ ID NO:43) |
| VIII[2] | | | | P Q R K V | F - R S L | | | (SEQ ID NO:44) |
| IX[2,3] | | | | P Q R K V | F R S L K | _ Y A E S D | | (SEQ ID NO:45) |

TABLE II-A-continued

Synthetic peptide substrates
Peptides were first reacted with approximately equal quantities of BTMD-SKI-1
medium for 2–18 h as described in "Experimental Procedures". When cleavage was not
detected, a 10-fold concentrated enzyme preparation was tested. Arrow thickness is
a qualitative estimate of the cleavage efficacy.

| Peptide | P16 | P12 | P8 | P4 | P1 | P4' | P8' | | |
|---|---|---|---|---|---|---|---|---|---|
| X | | | Abz-V F R S L K _ Y A E S D Y(NO$_2$)-A | | | | | (SEQ ID NO:46) | |
| XI | | | Abz-R S L K _ Y A E S D Y(NO$_2$)-A | | | | | (SEQ ID NO:47) | |

$^1$No cleavage detected even with a 10-fold excess of enzyme.
$^2$Cleavage detected but not attributable to SKI-1.
$^3$Kinetic determinations of this peptide were not attempted due to the presence of multiple cleavages.

TABLE II-B

Kinetic constants for the hydrolysis of peptide substrates by BTMD-hSKI-1
Increasing concentrations of peptides were reacted with identical quantities of BTMD-SKI-1 medium for times chosen to produce 5–30% substrate hydrolysis. Data analysis was carried out as described in "Experimental Procedures". The values are averages of duplicate assays.

| Peptide | $K_{m(app)}$ (nM*1000) | $V_{max(app)}$ (nmol/h) | $V_{max(app)}/K_{m(app)}$ ($h^{-1}L^{-1}$) |
|---|---|---|---|
| I | 169 | 0.4 | 0.002 |
| II | 124 | 0.5 | 0.004 |
| IV | 17 | 0.4 | 0.023 |
| V | 109 | 1.1 | 0.010 |

TABLE III

Effect of selected protease inhibitors on BTMD-hSKI-1 activity
Digestion reactions using BTMD-SKI-1 medium plus peptide II were carried out as described in "Experimental Procedures". The agents were preincubated with the enzyme for 30 min.

| Inhibitor | Concentration (mM) | Hydrolysis of SREBP-2 peptide (% of control)$^1$ |
|---|---|---|
| Control | — | 100 |
| APMSF | 1.0 | 95 |
| PMSF | 1.0 | 85 |
| TPCK | 1.0 | 71 |
| TLCK | 1.0 | 100 |
| SBTI | 0.5$^2$ | 100 |
| Cystatin | 0.01 | 100 |
| Antipain | 1.0 | 100 |
| Chymostatin | 1.0 | 100 |
| Leupeptin | 1.0 | 100 |
| Pepstatin | 0.1 | 97 |
| E-64 | 0.01 | 100 |
| O-Phenanthroline | 0.05 | 135 |
| | 1.0 | 90 |
| | 5.0 | 0 |
| EDTA | 10.0 | 0 |
| EGTA | 10.0 | 15 |
| Dithiothreitol | 10.0 | 92 |
| CuSO$_4$ | 1.0 | 0 |
| ZnSO$_4$ | 1.0 | 0 |
| NiSO$_4$ | 1.0 | 93 |
| MgCl$_2$ | 1.0 | 100 |
| CoCl$_2$ | 1.0 | 100 |

$^1$Values represent averages of duplicate assays (variation is ± 5%).
$^2$Concentration in mg/ml.

TABLE IV

Kinetic constants for the hydrolysis of quenched fluorogenic substrates by shed-hSKI-1
Assays and data analysis were carried out as described in Table II-A. The values are averages of duplicate assays.

| Peptide | $K_{m(app)}$ (μM) | $V_{max(app)}$ (μmoles/h) | $V_{max(app)}/K_{m(app)}$ ($h^{-1}L^{-1}$) |
|---|---|---|---|
| X | 31.3 | 34.0 | 1.1 |
| XI | 8.7 | 56.9 | 6.5 |

TABLE V

Effect of pro-segment peptide constructs on BTMD-hSKI-1 activity
Digestion reactions using BTMD-SKI-1 medium plus peptide IV were carried out as described in "Experimental Procedures". The prosegment peptides were preincubated with the enzyme for 30 min. Values were deduced from the Dixon plots obtained from three separate experiments.

| Pro-segment construct | $K_{i(app)}$ (nM) |
|---|---|
| PS1 | 182.0 ± 0.5 |
| PS2 | 97.5 ± 4.5 |
| PS3 | 127.3 ± 6.2 |

EXAMPLE 4

Similarity of Anatomical Distribution of SKI-1 mRNA to that of App

β-amyloid precursor protein (β-APP) is a member of a highly conserved gene family, which includes amyloid precursor-like protein-1 and amyloid precursor-like protein-2 {McNamara, M. J. et al. (1998) Brain Research 804,45–51; Rassoulzadegan, M. et al. (1998) The EMBO Journal 17, 4647–4656}. Mammalian subtilases, exemplified by SKI-1, may be responsible for limited cleavage at hydrophobic residues present in biologically important precursor proteins such as β-amyloid precursor protein (β-APP) (TableVI). SKI-1 has recently been identified as the enzyme which cleaves sterol-regulatory element-binding protein (SREBP) in a fashion analogous to the β-secretase cleavage of APP {Sakai, J. et al. (1998) Molecular Cell 2, 505–514} The cleavage of SREBP by SKI-1 (Site 1 protease) at a position 20 residues to the lumenal side of the first membrane-spanning segment is analogous to the β-secretase cleavage of β-APP at a position 28 amino acids from the membrane {Brown, M. S. and Goldstein, J. L. (1997) Cell 89, 331–340}.

Similarity of Anatomical Distribution of SKI-1 mRNA to that of APP Suggests a Functional Link Between both Proteins.

In situ hybridization performed in 4-day-mouse provides evidence of a similar distribution of mRNA coding for the membrane proteins SKI-1 and APP (FIG. 25). Their spatial distribution was observed to be significantly overlapping within different tissues such as brain and spinal cord, cranial and spinal ganglia, submaxillary gland, thymus, kidney, bones, skin and many other. Their mRNA distribution was partially similar to that of two other proteases, namely the convertase furin and the peptidase neprilysin. A much different distribution was observed with convertases PC1, PC2 and PC5. It is clearly established that an increase in cellular cholesterol levels results in the inhibition of activity of SKI-1/S1P {reviewed in Edwards, P. A., and Ericsson, J. (1999) Annu. Rev. Biochem. 68,157–185}. In a similiar fashion, an increase in dietary cholesterol leds to significant reductions in brain levels of secreted APP derivatives, including sAPPα, sAPPβ, Aβ1–40 and Aβ1–42 {Howland, D. S. et al. (1998) J. Biol. Chem. 273,16576–16582}. The nature of the relationships between cholesterol, SKI-1 and APP metabolism are complex.

Cellular association between SKI-1 and APP in lacrimal gland. Potential use of shed SKI-1 in tears as diagnostic tool.

Results of immunocytochemistry performed in mouse lacrimal glands provides evidence for the presence of SKI-1 and APP in the same cells types, including intralobular duct epithelial cells and some acinar cells (FIG. 26). The finding of SKI-1 in the lacrimal gland suggests the possibility of developing a diagnostic assay analyzing tears; perhaps based on two-dimensional polyacrylamide gel electrophoresis for disease diagnosis {Moley, M. P. et al. (1997) Electrophoresis 18, 2811–2815; Glasson, M. J. et al. (1998) Electrophoresis 19, 852–855; Grus, F. H., and Augustin, A. J. (1999) Electrophoresis 20, 875–880; Iskeleli, G. et al. (1999) CLAO Journal, 25:101–104;

TABLE VI

PRECURSOR CLASSIFICATION BASED ON HYDROPHOBIC AND/OR SMALL AMINO ACID CLEAVAGE

| Precursor protein | Cleavage site sequence | | |
|---|---|---|---|
| | P8 P7 P6 P5 P4 P3 P2 P1 | P1' P2' P3 ' P4' P5' P6' P7' P8' | |
| (h)proBDNF | Lys-Ala-Gly-Ser-Arg-Gly-Leu-Thr | ↓ Ser-Leu-Ala-<u>Asp</u>-Thr-Phe-<u>Glu</u>-His | (SEQ ID NO: 48) |
| (r)proBDNF | Lys-Ala-Gly-Ser-Arg-Gly-Leu-Thr | ↓ Thr-Thr-Ser-Leu-Ala-<u>Asp</u>-Thr-Phe | (SEQ ID NO: 49) |
| (h)proSKI-1 | Arg-His-Ser-Ser-Arg-Arg-Leu-Leu | ↓ Arg-Ala-Ile-Pro-Arg-Gln-Val-Ala | (SEQ ID NO: 50) |
| | Arg-Lys-Val-Phe-Arg-Ser-Leu-Lys | ↓ Tyr-Ala-<u>Glu</u>-Ser-<u>Asp</u>-Pro-Thr-Val | (SEQ ID NO: 51) |
| | Thr-Pro-Gln-Arg-Lys-Val-Phe-Arg | ↓ Ser-Leu-Lys-Tyr-Ala-<u>Glu</u>-Ser-<u>Asp</u> | (SEQ ID NO: 52) |
| | Val-Thr-Pro-Gln-Arg-Lys-Val-Phe | ↓ Arg-Ser-Leu-Lys-Lys-Tyr-Ala-<u>Glu</u> | (SEQ ID NO: 53) |
| (h)SREBP-2 | Ser-Gly-Ser-Gly-Arg-Ser-Val-Leu | ↓ Ser-Phe-<u>Glu</u>-Ser-Gly-Ser-Gly-Gly | (SEQ ID NO: 54) |
| (h)SREBP-1a | His-Ser-Pro-Gly-Arg-Asn-Val-Leu | ↓ Gly-Thr-<u>Glu</u>-Ser-Arg-<u>Asp</u>-Gly-Pro | (SEQ ID NO: 55) |
| (r)pro-Relaxin (B-chain) | Ala-Ser-Val-Gly-Arg-Leu-Ala-Leu | ↓ Ser-Gln-<u>Glu</u>-<u>Glu</u>-Pro-Ala-Pro-Leu | (SEQ ID NO: 56) |
| (h)pro-CCK (CCK5) | Arg-Ile-Ser-Asp-Arg-Asp-Tyr-Met | ↓ GIy-Trp-Met-<u>Asp</u>-Phe-Gly-Arg-Arg | (SEQ ID NO: 57) |
| (r)pro-Somatostatin (Antrin) | Asp-Pro-Arg-Leu-Arg-Gln-Phe-Leu | ↓ Gln-Lys-Ser-Leu-Ala-Ala-Ala-Thr | (SEQ ID NO: 58) |
| (b)Chromogranin A (82↓83) | Leu-Leu-Lys-Glu-Leu-Gln-Asp-Leu | ↓ Ala-Leu-Gln-Gly-Ala-Lys-<u>Glu</u>-Arg | (SEQ ID NO: 59) |
| (b)Chromogranin A (309↓310) | Met-Ala-Arg-Ala-Pro-Gln-Val-Leu | ↓ Phe-Arg-Gly-Gly-Lys-Ser-Gly-<u>Glu</u> | (SEQ ID NO: 60) |
| (b)Chromogranin B (629↓630) | Glu-Leu-Glu-Asn-Leu-Ala-Ala-Met | ↓ <u>Asp</u>-Leu-<u>Glu</u>-Leu-Gln-Lys-Ile-Ala | (SEQ ID NO: 61) |
| (b)Chromogranin B (634↓635) | Ala-Ala-Met-Asp-Leu-Glu-Leu-Gln | ↓ Lys-Ile-Ala-<u>Glu</u>-Lys-Phe-Ser-Gly | (SEQ ID NO: 62) |
| (r)pro-Renin | Lys-Ser-Ser-Phe-Thr-Asn-Val- | ↓ Ser-Pro-Val-Val-Leu-Thr-Asn-Tyr | (SEQ ID NO: 63) |
| (r)α-Endorphin | Lys-Ser-Gln-Thr-Pro-Leu-Val-Thr | ↓ Leu-Phe-Lys-Asn-Ala-Ile-Ile-Lys | (SEQ ID NO: 64) |
| (r)γ-Endorphin | Ser-Gln-Thr-Pro-Leu-Val-Thr-Leu | ↓ Phe-Lys-Asn-Ala-Ile-IIe-Lys-Asn | (SEQ ID NO: 65) |
| (r)pro-AVP (CPP) | Gly-Pro-Ala-Arg-<u>Glu</u>-Leu-Leu-Leu | ↓ Arg-Leu-Val-Gln-Leu-Ala-Gly-Thr | (SEQ ID NO: 66) |
| (h)ADAM-10 (kuzbanian) | Leu-Leu-Arg-Lys-Lys-Arg-Thr-Thr | ↓ Ser-Ala-<u>Glu</u>-Lys-Asn-Thr-Cys-Gln | (SEQ ID NO: 67) |
| (h)β-APP β-Secretase site | Glu-Glu-Ile-Ser-<u>Glu</u>-Val-Lys-Met | ↓ <u>Asp</u>-Ala-<u>Glu</u>-Phe-Arg-His-<u>Asp</u>-Ser | (SEQ ID NO: 68) |
| β-Secretase site (Swedish) | Glu-Glu-Ile-Ser-<u>Glu</u>-Val-Asn-Leu | ↓ <u>Asp</u>-Ala-<u>Glu</u>-Phe-Arg-His-<u>Asp</u>-Ser | (SEQ ID NO: 69) |
| βε₁-Secretase site | Ile-Ser-Glu-Val-Lys-Met-Asp-Ala | ↓ <u>Glu</u>-Phe-Arg-His-<u>Asp</u>-Ser-Gly-Tyr | (SEQ ID NO: 70) |
| βε₂-Secretase site | Glu-Phe-Arg-His-Asp-Ser-Gly-Tyr | ↓ <u>Glu</u>-Val-His-His-Gln-Lys-Leu-Val | (SEQ ID NO: 71) |

EXAMPLE 5

Prodomains in general (for example furin and PC7 prodomains) function in trans when expressed in mammalian cells to inhibit their cognate subtilisn-like convertase We have recently shown that the prosegment of furin expressed as an independent domain (preprofurin, ppfurin) can specifically inhibit neurotrophin processing. In these assays, successful inhibition requires not only that the prodomain enter the secretory pathway, but that it remain there long enough to interact with the target PC (most likely furin within the TGN). FIGS. 27 & 28 depict vaccinia virus constructs or transient transfections of prosegments preventing the maturation of the neurotrophins NGF and BDNF in Schwann or COS-1 cells, respectively. The modest inhibition with the prodomain of PC7 (ppPC7) is most likely due to inhibition of furin, since PC7 is a poor effector of proNGF and proBDNF maturation in these cells. The complementary experiment to demonstrate selectivity by the prosegment of PC7 will be carried out once we are able to establish unique in vivo PC7 substrates.

Most proteases from the four major classes (thiol, aspartic, serine, and metallo) are synthesized as inactive precursor molecules with N-terminal extensions (prosegments) that play critical roles in folding, stability and regulation of enzymatic activity {Khan, A. R., and James, M. N. (1998) Protein Sci. 7, 815–836}. The proregions of the PCs have been shown to function as potent inhibitors of their cognate enzymes in vitro. We present data for the first time showing that the expression of a prosegment as an independent domain in a cell-based (ex vivo) assay functions as a PC inhibitor (FIGS. 27 and 28). In these assays, successful inhibition requires not only that the prodomain enter the secretory pathway, but that it remain there long enough to interact with the target PC (most likely furin within the TGN).

We have shown that expression of full length SKI-1 prosegment (22–24 kDa with sequence ending at the secondary cleavage sequence RHSSRRLL (SEQ. ID. NO. 89)) Inhibits SKI-1 activity in stable HK 293 cell lines (Example 2). However, since the prodomain of SKI-1 is processed at an internal primary cleavage site RKVFRSLK (SEQ. ID. NO. 94) to give a 14 kDa N-terminal fragment (FIG. 29A&B) we predict that mutation of this site will generate an even more effective SKI-1 inhibitor. In fact, in the case of the mouse PC5 prodomain we have shown that mutation of the internal prosegment cleavage site does in fact generate a inhibitor of integrin hα4 150 kDa processing to 80 kDa and 70 kDa species (FIG. 15).

EXAMPLE 6

SKI-1 Peptide Substrates for Fluorescence Resonance Energy Transfer (FRET) Based Proteolysis Assays A large number of synthetic peptides based on potential cleavage sites in the hSKI-1 prodomain, proBDNF and the loop region of SREBP-2 were synthesized.

These are:

(i) hSKI-1 (156–172)

Trp-Gln-Ser-Ser-Arg-Pro-Leu-Arg-Arg-Ala-Ser-Leu↓Ser-Leu-Gly-Ser-Gly (SEQ. ID. NO. 42)

(ii) hSKI-1 (174–191)

Trp-His-Ala-Thr-Gly-Arg-His-Ser-Ser-Arg-Arg-Leu-Leu↓Arg-Ala-Ile-Pro-Arg (SEQ. ID. NO. 39)

(iii) hSKI-1 (174–188+Leu+Glu)

Trp-His-Ala-Thr-Gly-Arg-His-Ser-Ser-Arg-Arg-Leu-Leu↓Arg-Ala-Leu-Glu (SEQ. ID. NO. 40)

(iv) hSKI-1 (181–188+Glu)

Ser-Ser-Arg-Arg-Leu-Leu↓Arg-Ala-Ile-Glu(SEQ. ID. NO. 72)

(v) hSKI-1 (187–201)

Arg-Ala-Ile-Pro-Arg-Gln-Val-Ala↓Gln-Thr-Leu-Gln-Ala-Asp-Val (SEQ. ID. NO. 43)

(vi) hSKI-1 (128–136)

Pro-Gln-Arg-Lys-Val-Phe-Arg-Ser-Leu ((SEQ. ID. NO.44)

(vii) hSKI-1 (128–142)

Pro-Gln-Arg-Lys-Val-Phe-Arg-Ser-Leu-Lys↓Tyr-Ala-Glu-Ser-Asp ((SEQ. ID. NO.45)

(viii) hProBDNF (50–63)

Lys-Ala-Gly-Ser-Arg-Gly-Leu-Thr↓Ser-Leu-Ala-Asp-Thr-Phe (SEQ. ID. NO.37)

(ix) SREBP-2 27 mer

Gly-Gly-Ala-His-Asp-Ser-Asp-Gln-His-Pro-His-Ser-Gly-Ser-Gly-Arg-Ser-Val-Leu↓Ser-Phe-Glu-Ser-Gly-Ser-Gly-Gly (SEQ ID NO:38)

(x) SREBP-2 10 mer

Ser-Gly-Ser-Gly-Arg-Ser-Val-Leu↓Ser-Phe-Glu-Ser (SEQ. ID. NO.73).

These peptides were examined as possible substrates of SKI-1. Our data indicate that only the peptides (iii), (iv), (vii), (viii) (ix) and (x) are efficiently cleaved by the recombinant SKI-1.

Novel Fluorogenic Substrate Based Assay of SKI-1 Activity:

Based on the results reported above with various synthetic peptides we designed a number of internally quenched fluorogenic substrates of SKI-1. Our main goal was to develop a rapid and a sensitive method for the assay of SKI-1 enzymatic activity. SKI-1 activity was monitored by following the cleavage of suitable peptide substrates with HPLC that is often extremely slow and cumbersome. The following internally quenched fluorogenic peptides were synthesized and tested as substrates for SKI-1:

(a) QSKI (132–142):

Abz-Val-Phe-Arg-Ser-Leu-Lys↓Tyr-Ala-Glu-Ser-Asp-Tyr(NO$_2$)-Ala (SEQ. ID. NO.46)

(b) QSKI (134–142):

Abz-Arg-Ser-Leu-Lys↓Tyr-Ala-Glu-Ser-Asp-T r(NO$_2$)-Ala (SEQ. ID. NO.47)

(c) QSKI (178–188)

Abz-Arg-His-Ser-Ser-Arg-Arg-Leu-Leu↓Arg-Ala-Ile-Tvr(NO$_2$)-Ala (SEQ. ID. NO.74)

(d) QSKI (181–187+Leu+Glu)

Abz-Ser-Arg-Arg-Leu-Leu↓Arg-Ala-Leu-Glu-Tvr(NO$_2$)-Ala (SEQ. ID. NO.75)

(e) QBDNF (47–58)

Abz-Asn-Gly-Pro-Lys-Ala-Gly-Ser-Arg-Gly-Leu-Thr↓Ser-Tyr(NO$_2$)-Ala (SEQ. ID. NO. 76)

The main feature of these peptides is the incorporation of two special amino acids namely Abz [Ortho amino benzoic acid also known as anthranalic acid] and Tyr(NO$_2$) [3-nitro Tyrosin] at the amino (N—) and carboxy (C—) terminal end of the peptide chain respectively. Abz, an electron donor, is a powerful fluorescent moiety whereas Tyr(NO$_2$), an electron acceptor, acts as a fluorescence quench group. All the above peptides exhibit weak fluorescence background values (at λ$_{ex}$=320 nm and λ$_{em}$=420 nm). It is expected that upon cleavage by the proteolytic action of SKI, these peptides will release two peptide fragments of which the Abz-containing N-terminal part should display a very high degree of fluorescence. The net result will be the increase of fluorescence intensity that can be measured very accurately with a fluorimeter instrument. This technique of measurement of enzymatic activity has been applied to a number of enzymes {F. Jean, A. Boudreault, A. Basak, N. G. Seidah and C. Lazure., J. Biol. Chem., 1995, 270, 19225–19231}

RESULTS

Our data indicates that among the above quenched fluorogenic peptides, peptide (a) is most effective as a substrate for SKI-1. In fact the measurement of kinetic parameters (V$_{max}$/Km) indicted that this peptide is 6-fold more efficient that the nearest candidate quenched peptide (b). HPLC analysis using both UV and fluorescence detector systems clearly revealed a single site of cleavage in peptides (a) and (b) (as indicated above by a vertical arrow ↓), again reenforcing the notion that the preferred sequence motif for SKI-1 is characterized by the presence of an Arg residue at P4, an alkyl hydrophobic residue at P2 and possibly an aromatic hydrophobic residue at P1'. Therefore, peptide (a) is a highly specific fluorogenic substrate for monitoring the activity of SKI-1

This invention has been described in details hereinabove, and it will be readily apparent to the skilled artisan that modifications can be made thereto without departing form the teachings of the present disclosure. These modifications are considered within the scope of the present invention, as defined in the appended claims.

```
                                         Human SKI-1 cagggcacgctgggtcggcggagctgaggctcccagctgtgggcctcgctggcccggtcg
       gtcccgtgcgaccagccgcctcgactccgagggtcgacacccggagcgaccgggccagc
   1   ---------+---------+---------+---------+---------+---------+    60 cccagtctcgcgagagttgggagtaaacagcccgaatggagtgcccaggcgtgttcgcc
       gggtcagagcgctctcaaccctcatttgtcggggcttacctcacgggtccgcacaagcgg
  61   ---------+---------+---------+---------+---------+---------+   120 gcggaggcgccgttatcccgggcccgccggccctgagctcccggcggcgcagattggctc
       cgcctccgcggcaatagggcccgggcggccgggactcgagggccgccgcgtctaaccgag
 121   ---------+---------+---------+---------+---------+---------+   180 acagtggttgattgatcaaccccattggacgttggttctgtggtacaaatggagtacagg
       tgtcaccaactaactagttggggtaacctgcaaccaagacaccatgtttacctcatgtcc
 181   ---------+---------+---------+---------+---------+---------+   240 actcagtcgtcacggcctgagtgagagaagccttatttccaagatggagaagaagcggag
       tgagtcagcagtgccggactcactctcttcggaataaaggttctacctcttcttcgcctc
 241   ---------+---------+---------+---------+---------+---------+   300 aaagaaatgaaagcctctcttcaggctgaaccacaaaaggccatgggatttaacttttat
       tttctttactttcggagagaagtccgacttggtgttttccggtaccctaaattgaaaata
 301   ---------+---------+---------+---------+---------+---------+   360 ttatgttgggcaagactgtaagatggctgatcagtaatgttgcagcttttagctgaaaca
       aatacaacccgttctgacattctaccgactagtcattacaacgtcgaaaatcgactttgt
 361   ---------+---------+---------+---------+---------+---------+   420 aaaattcacttttaatcaagaagaaaaaagtgtgatttgaatatatgcaattttatgatc
       ttttaagtgaaaattagttcttctttttcacactaaacttatatacgttaaaatactag
 421   ---------+---------+---------+---------+---------+---------+   480

1               M   K   L   V   N   I   W   L   L   L   L   V   L   L        15
       atattcgcttgtgaccatgaagcttgtcaacatctggctgcttctgctcgtggttttgct
       tataagcgaacactggtacttcgaacagttgtagaccgacgaagacgagcaccaaaacga
 481   ---------+---------+---------+---------+---------+---------+   540

16   C   G   K   K   H   L   G   D   R   L   E   K   K   S   F   E   K   A   P   C    35
       ctgtgggaagaaacatctgggcgacagactggaaaagaaatcttttgaaaaggcccatg
       gacaccttctttgtagacccgctgtctgacctttctttagaaaacttttccggggtac
 541   ---------+---------+---------+---------+---------+---------+   600

36   P   G   C   S   H   L   T   L   K   V   E   F   S   S   T   V   V   E   Y   E    55
       ccctggctgttcccacctgactttgaaggtggaattctcatcaacagttgtggaatatga
       gggaccgacaagggtggactgaaacttccaccttaagagtagttgtcaacaccttatact
 601   ---------+---------+---------+---------+---------+---------+   660

56   Y   I   V   A   F   N   G   Y   F   T   A   K   A   R   N   S   F   I   S   S    75
       atatattgtggctttcaatggatactttacagccaaagctagaaattcatttatttcaag
       tatataacaccgaaagttacctatgaaatgtcggtttcgatctttaagtaaataaagttc
 661   ---------+---------+---------+---------+---------+---------+   720

76   A   L   K   S   S   E   V   D   N   W   R   I   I   P   R   N   N   P   S   S    95
       tgccctgaagagcagtgaagtagacaattggagaattatacctcgaaacaatccatccag
       acgggacttctcgtcacttcatctgttaacctcttaatatggagcttttgttaggtaggtc
```

-continued

Human SKI-1

```
              96  D   Y   P   S   D   F   E   V   I   Q   I   K   E   K   Q   K   A   G   L   L   115
                  tgactaccctagtgattttgaggtgattcagataaaagaaaaacagaaagcggggctgct
                  actgatgggatcactaaaactccactaagtctattttcttttgtctttcgccccgacga
             781  ---------+---------+---------+---------+---------+---------+   840

116  T   L   E   D   H   P   N   I   K   R   V   T   P   Q   R   K   V   F   R   S   135
                  aacacttgaagatcatccaaacatcaaacgggtcacgccccaacgaaaagtctttcgttc
                  ttgtgaacttctagtaggtttgtagtttgcccagtgcggggttgcttttcagaaagcaag
             841  ---------+---------+---------+---------+---------+---------+   900

136  L   K   Y   A   E   S   D   P   T   V   P   C   N   E   T   R   W   S   Q   K   155
                  cctcaagtatgctgaatctgacccacagtacccctgcaatgaaacccggtggagccagaa
                  ggagttcatacgacttagactggggtgtcatgggacgttactttgggccacctcggtctt
             901  ---------+---------+---------+---------+---------+---------+   960

156  W   Q   S   S   R   P   L   R   R   A   S   L   S   L   G   S   G   F   W   H   175
                  gtggcaatcatcacgtcccctgcgaagagccagcctctccctgggctctggcttctggca
                  caccgttagtagtgcaggggacgcttctcggtcggagagggacccgagaccgaagaccgt
             961  ---------+---------+---------+---------+---------+---------+  1020

176  A   T   G   R   H   S   S   R   R   L   L   R   A   I   P   R   Q   V   A   Q   195
                  tgctacgggaaggcattcgagcagacggctgctgagagccatcccgcgccaggttgccca
                  acgatgccct tccgtaagctcgtctgccgacgactctcggtagggcgcggtccaacgggt
            1021  ---------+---------+---------+---------+---------+---------+  1080

196  T   L   Q   A   D   V   L   W   Q   M   G   Y   T   G   A   N   V   R   V   A   215
                  gacactgcaggcagatgtgctctggcagatgggatatacaggtgctaatgtaagagttgc
                  ctgtgacgtccgtctacacgagaccgtctaccctatatgtccacgattacattctcaacg
            1081  ---------+---------+---------+---------+---------+---------+  1140

216  V   F   D   T   G   L   S   E   K   H   P   H   F   K   N   V   K   E   R   T   235
                  tgttttgacactgggctgagcgagaagcatcccacttcaaaaatgtgaaggagagaac
                  acaaaaactgtgaccgactcgctcttcgtaggggtgaagttttacacttcctctcttg
            1141  ---------+---------+---------+---------+---------+---------+  1200

236  N   W   T   N   E   R   T   L   D   D   G   L   G   H   G   T   F   V   A   G   255
                  caactggaccaacgagcgaacgctggacgatgggttgggccatggcacattcgtggcagg
                  gttgacctggttgctcgcttgcgacctgctacccaacccggtaccgtgtaagcaccgtcc
            1201  ---------+---------+---------+---------+---------+---------+  1260

256  V   I   A   S   M   R   E   C   Q   G   F   A   P   D   A   E   L   H   I   F   275
                  tgtgatagccagcatgagggagtgccaaggatttgctccagatgcagaacttcacatttt
                  acactatcggtcgtactccctcacggttcctaaacgaggtctacgtcttgaagtgtaaaa
            1261  ---------+---------+---------+---------+---------+---------+  1320

276  R   V   F   T   N   N   Q   V   S   Y   T   S   W   F   L   D   A   F   N   Y   295
                  cagggtctttaccaataatcaggtatcttacacatcttggttttggacgccttcaacta
                  gtcccagaaatggttattagtccatagaatgtgtagaaccaaaaacctgcggaagttgat
            1321  ---------+---------+---------+---------+---------+---------+  1380

296  A   I   L   K   K   I   D   V   L   N   L   S   I   G   G   P   D   F   M   D   315
                  tgccattttaaagaagatcgacgtgttaaacctcagcatcggcggcccggacttcatgga
                  acggtaaaatttcttctagctgcacaatttggagtcgtagccgccgggcctgaagtacct
            1381  ---------+---------+---------+---------+---------+---------+  1440

316  H   P   F   V   D   K   V   W   E   L   T   A   N   N   V   I   M   V   S   A   335
                  tcatccgtttgttgacaaggtgtgggaattaacagctaacaatgtaatcatggtttctgc
                  agtaggcaaacaactgttccacaccct taattgtcgattgttacattagtaccaaagacg
            1441  ---------+---------+---------+---------+---------+---------+  1500

336  I   G   N   D   G   P   L   Y   G   T   L   N   N   P   A   D   Q   M   D   V   355
                  tattggcaatgacggacctctttatggcactctgaataaccctgctgatcaaatggatgt
                  ataaccgttactgcctggagaaataccgtgagacttattgggacgactagtttacctaca
            1501  ---------+---------+---------+---------+---------+---------+  1560

356  I   G   V   G   G   I   D   F   E   D   N   I   A   R   F   S   S   R   G   M   375
                  gattggagtaggcggcattgactttgaagataacatcgcccgcttttcttcaagggaat
                  ctaacctcatccgccgtaactgaaacttctattgtagcgggcgaaaagaagttcccctta
            1561  ---------+---------+---------+---------+---------+---------+  1620

376  T   T   W   E   L   P   G   G   Y   G   R   M   K   P   D   I   V   T   Y   G   395
                  gactacctgggagctaccaggaggctacggtcgcatgaaacctgacattgtcacctatgg
                  ctgatggaccctcgatggtcctccgatgccagcgtactttggactgtaacagtggatacc
            1621  ---------+---------+---------+---------+---------+---------+  1680
```

-continued

Human SKI-1

```
 396  A  G  V  R  G  S  G  V  K  G  G  C  R  A  L  S  G  T  S  V   415
      tgctggcgtgcggggttctggcgtgaaagggggtgccgggccctctcagggaccagtgt
      acgaccgcacgcccaagaccgcacttccccccacggcccgggagagtccctggtcaca
1681  ---------+---------+---------+---------+---------+---------+  1740

416  A  S  P  V  V  A  G  A  V  T  L  L  V  S  T  V  Q  K  R  E   435
      tgcttctccagtggttgcaggtgctgtcaccttgttagtgagcacagtccagaagcgtga
      acgaagaggtcaccaacgtccacgacagtggaacaatcactcgtgtcaggtcttcgcact
1741  ---------+---------+---------+---------+---------+---------+  1800

436  L  V  N  P  A  S  M  K  Q  A  L  I  A  S  A  R  R  L  P  G   455
      gctggtgaatcccgccagtatgaagcaggccctgatcgcgtcagcccggaggctccccgg
      cgaccacttagggcggtcatacttcgtccgggactagcgcagtcgggcctccgaggggcc
1801  ---------+---------+---------+---------+---------+---------+  1860

456  V  N  M  F  E  Q  G  H  G  K  L  D  L  L  R  A  Y  Q  I  L   475
      ggtcaacatgtttgagcaaggccacggcaagctcgatctgctcagagcctatcagatcct
      ccagttgtacaaactcgttccggtgccgttcgagctagacgagtctcggatagtctagga
1861  ---------+---------+---------+---------+---------+---------+  1920

476  N  S  Y  K  P  Q  A  S  L  S  P  S  Y  I  D  L  T  E  C  P   495
      caacagctacaagccacaggcaagtttgagccccagctacatagatctgactgagtgtcc
      gttgtcgatgttcggtgtccgttcaaactcggggtcgatgtatctagactgactcacagg
1921  ---------+---------+---------+---------+---------+---------+  1980

496  Y  M  W  P  Y  C  S  Q  P  I  Y  Y  G  G  M  P  T  V  V  N   515
      ctacatgtggccctactgctcccagcccatctactatggaggaatgccgacagttgttaa
      gatgtacaccgggatgacgagggtcgggtagatgataccctccttacggctgtcaacaatt
1981  ---------+---------+---------+---------+---------+---------+  2040

516  V  T  I  L  N  G  M  G  V  T  G  R  I  V  D  K  P  D  W  Q   535
      tgtcaccatcctcaacggcatgggagtcacaggaagaattgtagataagcctgactggca
      acagtggtaggagttgccgtaccctcagtgtccttcttaacatctattcggactgaccgt
2041  ---------+---------+---------+---------+---------+---------+  2100

536  P  Y  L  P  Q  N  G  D  N  I  E  V  A  F  S  Y  S  S  V  L   555
      gccctatttgccacagaacggagacaacattgaagttgccttctcctactcctcggtctt
      cgggataaacggtgtcttgcctctgttgtaacttcaacggaagaggatgaggagccagaa
2101  ---------+---------+---------+---------+---------+---------+  2160

556  W  P  W  S  G  Y  L  A  I  S  I  S  V  T  K  K  A  A  S  W   575
      atggccttggtcgggctacctggccatctccatttctgtgaccaagaaagcggcttcctg
      taccggaaccagcccgatggaccggtagaggtaaagacactggttcttcgccgaaggac
2161  ---------+---------+---------+---------+---------+---------+  2220

576  E  G  I  A  Q  G  H  V  M  I  T  V  A  S  P  A  E  T  E  S   595
      ggaaggcattgctcagggccatgtcatgatcactgtggcttcccagcagagacagagtc
      ccttccgtaacgagtcccggtacagtactagtgacaccgaagggtcgtctctgtctcag
2221  ---------+---------+---------+---------+---------+---------+  2280

596  K  N  G  A  E  Q  T  S  T  V  K  L  P  I  K  V  K  I  I  P   615
      aaaaaatggtgcagaacagacttcaacagtaaagctcccccattaaggtgaagataattcc
      ttttttaccacgtcttgtctgaagttgtcatttcgaggggtaattccacttctattaagg
2281  ---------+---------+---------+---------+---------+---------+  2340

616  T  P  P  R  S  K  R  V  L  W  D  Q  Y  H  N  L  R  Y  P  P   635
      tactccccgcgaagcaagagagttctctgggatcagtaccacaacctccgctatccacc
      atgaggggcgcttcgttctctcaagagaccctagtcatggtgttggaggcgataggtgg
2341  ---------+---------+---------+---------+---------+---------+  2400

636  G  Y  F  P  R  D  N  L  R  M  K  N  D  P  L  D  W  N  G  D   655
      tggctatttccccaggataaatttaaggatgaagaatgaccccttagactggaatggtga
      accgataaaggggtccctattaaattcctacttcttactgggaaatctgaccttaccact
2401  ---------+---------+---------+---------+---------+---------+  2460

656  H  I  H  T  N  F  R  D  M  Y  Q  H  L  R  S  M  G  Y  F  V   675
      tcacatccacaccaatttcagggatatgtaccagcatctgagaagcatgggctactttgt
      agtgtaggtgtggttaaagtccctatacatggtcgtagactcttcgtacccgatgaaaca
2461  ---------+---------+---------+---------+---------+---------+  2520

676  E  V  L  G  A  P  F  T  C  F  D  A  S  Q  Y  G  T  L  L  M   695
      agaggtcctcggggcccccttcacgtgttttgatgccagtcagtatggcactttgctgat
      tctccaggagccccgggggaagtgcacaaaactacggtcagtcataccgtgaaacgacta
2521  ---------+---------+---------+---------+---------+---------+  2580

696  V  D  S  E  E  E  Y  F  P  E  E  I  A  K  L  R  R  D  V  D   715
      ggtggacagtgaggaggagtacttccctgaagagatcgccaagctccggagggacgtgga
```

-continued

Human SKI-1

```
          ccacctgtcactcctcctcatgaagggacttctctagcggttcgaggcctccctgcacct
2581 ---------+---------+---------+---------+---------+---------+ 2640

716   N   G   L   S   L   V   I   F   S   D   W   Y   N   T   S   V   M   R   K   V    735
          caacggcctctcgctcgtcatcttcagtgactggtacaacacttctgttatgagaaagt
          gttgccggagagcgagcagtagaagtcactgaccatgttgtgaagacaatactcttttca
2641 ---------+---------+---------+---------+---------+---------+ 2700

736   K   F   Y   D   E   N   T   R   Q   W   W   M   P   D   T   G   G   A   N   I    755
          gaagttttatgatgaaaacacaaggcagtggtggatgccggataccggaggagctaacat
          cttcaaaatactacttttgtgttccgtcaccacctacggcctatggcctcctcgattgta
2701 ---------+---------+---------+---------+---------+---------+ 2760

756   P   A   L   N   E   L   L   S   V   W   N   M   G   F   S   D   G   L   Y   E    775
          cccagctctgaatgagctgctgtctgtgtggaacatggggttcagcgatggcctgtatga
          gggtcgagacttactcgacgacagacacaccttgtaccccaagtcgctaccggacatact
2761 ---------+---------+---------+---------+---------+---------+ 2820

776   G   E   F   T   L   A   N   H   D   M   Y   Y   A   S   G   C   S   I   A   K    795
          aggggagttcaccctggccaaccatgacatgtattatgcgtcagggtgcagcatcgcgaa
          tcccctcaagtgggaccggttggtactgtacataatacgcagtcccacgtcgtagcgctt
2821 ---------+---------+---------+---------+---------+---------+ 2880

796   F   P   E   D   G   V   V   I   T   Q   T   F   K   D   Q   G   L   E   V   L    815
          gtttccagaagatggcgtcgtgataacacagacttttcaaggaccaaggattggaggtttt
          caaaggtcttctaccgcagcactattgtgtctgaaagttcctggttcctaacctccaaaa
2881 ---------+---------+---------+---------+---------+---------+ 2940

816   K   Q   E   T   A   V   V   E   N   V   P   I   L   G   L   Y   Q   I   P   A    835
          aaagcaggaaacagcagttgttgaaaacgtccccattttgggactttatcagattccagc
          tttcgtcctttgtcgtcaacaactttgcaggggtaaaaccctgaaatagtctaaggtcg
2941 ---------+---------+---------+---------+---------+---------+ 3000

836   E   G   G   G   R   I   V   L   Y   G   D   S   N   C   L   D   D   S   H   R    855
          tgagggtggaggccggattgtactgtatgggactccaattgcttggatgacagtcaccg
          actcccacctccggcctaacatgacatacccctgaggttaacgaacctactgtcagtggc
3001 ---------+---------+---------+---------+---------+---------+ 3060

856   Q   K   D   C   F   W   L   L   D   A   L   L   Q   Y   T   S   Y   G   V   T    875
          acagaaggactgcttttggcttctggatgccctcctccagtacacatcgtatggggtgac
          tgtcttcctgacgaaaaccgaagacctacgggaggaggtcatgtgtagcataccccactg
3061 ---------+---------+---------+---------+---------+---------+ 3120

876   P   P   S   L   S   H   S   G   N   R   Q   R   P   P   S   G   A   G   S   V    895
          accgcctagcctcagtcactctgggaaccgccagcgccctcccagtggagcaggctcagt
          tggcggatcggagtcagtgagacccttggcggtcgcgggagggtcacctcgtccgagtca
3121 ---------+---------+---------+---------+---------+---------+ 3180

896   T   P   E   R   M   E   G   N   H   L   H   R   Y   S   K   V   L   E   A   H    915
          cactccagagaggatggaaggaaaccatcttcatcggtactccaaggttctggaggccca
          gtgaggtctctcctaccttcctttggtagaagtagccatgaggttccaagacctccgggt
3181 ---------+---------+---------+---------+---------+---------+ 3240

916   L   G   D   P   K   P   R   P   L   P   A   C   P   R   L   S   W   A   K   P    935
          tttgggagacccaaaacctcggcctctaccagcctgtccacgcttgtcttgggccaagcc
          aaacccctctggttttggagccggagatggtcggacaggtgcgaacagaaccccggttcgg
3241 ---------+---------+---------+---------+---------+---------+ 3300

936   Q   P   L   N   E   T   A   P   S   N   L   W   K   H   Q   K   L   L   S   I    955
          acagcctttaaacgagacggcgcccagtaacctttggaaacatcagaagctactctccat
          tgtcggaaatttgctctgccgcgggtcattggaaacctttgtagtcttcgatgagagta
3301 ---------+---------+---------+---------+---------+---------+ 3360

956   D   L   D   K   V   V   L   P   N   F   R   S   N   R   P   Q   V   R   P   L    975
          tgacctggacaaggtggtgttaccccaactttcgatcgaatcgccctcaagtgaggcccctt
          actggacctgttccaccacaatgggttgaaagctagcttagcgggagttcactcccgggaa
3361 ---------+---------+---------+---------+---------+---------+ 3420

976   S   P   G   E   S   G   A   W   D   I   P   G   G   I   M   P   G   R   Y   N    995
          gtcccctggagagagcggcgcctgggacattcctggagggatcatgcctggccgctacaa
          cagggggacctctctcgccgcggaccctgtaaggacctccctagtacggaccggcgatgtt
3421 ---------+---------+---------+---------+---------+---------+ 3480

996   Q   E   V   G   Q   T   I   P   V   F   A   F   L   G   A   M   V   V   L   A   1015
          ccaggaggtgggccagaccattcctgtctttgccttcctgggagccatggtggtcctggc
          ggtcctccacccggtctggtaaggacagaaacggaaggaccctcggtaccaccaggaccg
3481 ---------+---------+---------+---------+---------+---------+ 3540
```

-continued

Human SKI-1

```
1016  F   F   V   V   Q   I   N   K   A   K   S   R   P   K   R   R   K   P   R   V   1035
      cttctttgtggtacaaatcaacaaggccaagagcaggccgaagcggaggaagcccaggt
      gaagaaacaccatgtttagttgttccggttctcgtccggcttcgcctccttcgggtccca
3541  ---------+---------+---------+---------+---------+---------+ 3600

1036  K   R   P   Q   L   M   Q   Q   V   H   P   P   K   T   P   S   V   *          1053
      gaagcgcccgcagctcatgcagcaggttcacccgccaaagacccctccggtgtgaccggc
      cttcgcgggcgtcgagtacgtcgtccaagtgggcggtttctgggaagccacactggccg
3601  ---------+---------+---------+---------+---------+---------+ 3660 agcctggctgaccgtgagggccagagagagccttcacggacggcgctggtgggtgagccg
      tcggaccgactggcactcccggtctctctcggaagtgcctgccgcgaccacccactcggc
3661  ---------+---------+---------+---------+---------+---------+ 3720 agctgtggtggcggctggtttaaaagggatccagtttccagctgcaggtttgttagagtc
      tcgacaccaccgccgaccaaattttccctaggtcaaaggtcgacgtccaaacaatctcag
3721  ---------+---------+---------+---------+---------+---------+ 3780 tgttctacatgggcctgccctcctgtgatgggcagaggctcctggtacatcgagaagatt
      acaagatgtacccggacgggaggacactacccgtctccgaggaccatgtagctcttctaa
3781  ---------+---------+---------+---------+---------+---------+ 3840 cctgtggatcccgtcaggagggacttagtggctctgccgccagtgagacttcccgccggc
      ggacacctagggcagtcctccctgaatcaccgagacggcggtcactctgaagggcggccg
3841  ---------+---------+---------+---------+---------+---------+ 3900 agctgtgcgcaccaaagactcgggagaactggaaaggctgtctgggtcttctgactgca
      tcgacacgcgtggtttctgagccctcttgacctttccgacagaccccagaagactgacgt
3901  ---------+---------+---------+---------+---------+---------+ 3960 ggggaaggatgtactttccaaacaaatgatacaaccctgaccaagctaaaagacgcttgt
      cccttcctacatgaaaggtttgtttactatgttgggactggttcgattttctgcgaaca
3961  ---------+---------+---------+---------+---------+---------+ 4020 taaaggctattttctatatttattgttgggaaaagtcactttaaagacttgtgctatttg
      atttccgataaaagatataaataacaaccccttttcagtgaaatttctgaacacgataaac
4021  ---------+---------+---------+---------+---------+---------+ 4080 gaagcaaagctattttttttgtcagtggaatgcagttttttttactattccatcatgagga
      cttcgtttcgataaaaaaaacagtcacctttacgtcaaaaaaatgataaggtagtactcct
4081  ---------+---------+---------+---------+---------+---------+ 4140 acaacatagattccatgatctttttaatgacagtacagactgagatttgaaggaaacatg
      tgttgtatctaaggtactagaaaaattactgtcatgtctgactctaaacttcctttgtac
4141  ---------+---------+---------+---------+---------+---------+ 4200 cacaaatctgtaaaacatagaccttcgctttatttttgtaagtatcacctgccaccatgt
      gtgtttagacattttgtatctggaagcgaaataaaaacattcatagtggacggtggtaca
4201  ---------+---------+---------+---------+---------+---------+ 4260 tttgtaatttgaggtcttgatttcaccattgtcggtgaagaaaattttcaataaatatgt
      aaacattaaactccagaactaaagtggtaacagccacttctttttaaaagttatttataca
4261  ---------+---------+---------+---------+---------+---------+ 4320 attacccgtctgaagctt
      taatgggcagacttcgaa
4321  ---------+-------- 4338
```

Rat SKI-1

```
  1  GCGAGTAAACATCCCCCGAATGGATACCCGAGGCGTGTTCGCGGCGGAGGCCCCGTTTTC   60
     CGCTCATTTGTAGGGGGCTTACCTATGGGCTCCGCACAAGCGCCGCCTCCGGGGCAAAAG

61  CCGGGTCCGCCGATCCCGAGCCTGAGGCGACGCAGATCGGCTCAGAGCGGTGGCTTGGGC  120
     GGCCCAGGCGGCTAGGGCTCGGACTCCGCTGCGTCTAGCCGAGTCTCGCCACCGAACCCG

121  TCCTGCTAGATTTGGGTCTGTGGTACAAATGGAGTTTAGGACTCAGTGGACTCGGCCCTA  180
     AGGACGATCTAAACCCAGACACCATGTTTACCTCAAATCCTGAGTCACCTGAGCCGGGAT

181  ATGAGAGAAGCCCCCTGTCCAAGATGGAGAAGAAGCGGAGAAAGAAATGAAAGCCTCTTT  240
     TACTCTCTTCGGGGGACAGGTTCTACCTCTTCTTCGCCTCTTTCTTTACTTTCGGAGAAA
```

-continued

Rat SKI-1

```
 241 TTGGGCCAAGCTGTGGGTGACCATGGGACTGAGGTTTTCTTTACGTTGGACAAGTCTGTA     300
     AACCCGGTTCGACACCCACTGGTACCCTGACTCCAAAAGAAATGCAACCTGTTCAGACAT

301 GGATGGCTGATCAGTAAGGTTGCAGCTTTTAGCGAAAACAGAAATCCACTTCTGATCAAG     360
     CCTACCGACTAGTCATTCCAACGTCGAAAATCGCTTTTGTCTTTAGGTGAAGACTAGTTC

1
                                                              M      1
 361 GAAGAGCCTAGTGCAATTTGAATTTATGCAATTTTATGACCATATTCACTTAGGACCATG    420
     CTTCTCGGATCACGTTAAACTTAAATACGTTAAAATACTGGTATAAGTGAATCCTGGTAC

2 K  L  V  N  I  W  L  L  L  L  V  V  L  L  C  G  K  K  H  L    21
 421 AAGCTCGTCAACATCTGGCTTCTTCTGCTGGTGGTTTTGCTCTGTGGGAAAAAGCATCTG    480
     TTCGAGCAGTTGTAGACCGAAGAAGACGACCACCAAAACGAGACACCCTTTTTCGTAGAC

22 G  D  R  L  G  K  K  A  F  E  K  A  P  C  P  S  C  S  H  L    41
 481 GGTGACAGGCTGGGGAAGAAAGCTTTTGAAAAGGCCCCATGCCCCAGCTGTTCCCACCTG    540
     CCACTGTCCGACCCCTTCTTTCGAAAACTTTTCCGGGGTACGGGGTCGACAAGGGTGGAC

42 T  L  K  V  E  F  S  S  T  V  V  E  Y  E  Y  I  V  A  F  N    61
 541 ACTTTGAAGGTGGAATTCTCCTCAACTGTAGTGGAATATGAATATATTGTGGCTTTCAAC    600
     TGAAACTTCCACCTTAAGAGGAGTTGACACCACCTTATACTTATATAACACCGAAAGTTG

62 G  Y  F  T  A  K  A  R  N  S  F  I  S  S  A  L  K  S  S  E    81
 601 GGATACTTCACAGCCAAAGCTAGAAACTCATTTATTTCAAGTGCTCTAAAAAGCAGTGAA    660
     CCTATGAAGTGTCGGTTTCGATCTTTGAGTAAATAAAGTTCACGAGATTTTTCGTCACTT

82 V  D  N  W  R  I  I  P  R  N  N  P  S  S  D  Y  P  S  D  F   101
 661 GTGGACAACTGGAGAATAATACCTCGGAACAACCCATCTAGTGACTACCCTAGTGATTTT    720
     CACCTGTTGACCTCTTATTATGGAGCCTTGTTGGGTAGATCACTGATGGGATCACTAAAA

102 E  V  I  Q  I  K  E  K  Q  K  A  G  L  L  T  L  E  D  H  P   121
 721 GAGGTGATTCAGATAAAAGAGAAGCAGAAGGCGGGGCTGCTCACACTTGAAGATCACCCA    780
     CTCCACTAAGTCTATTTTCTCTTCGTCTTCCGCCCCGACGAGTGTGAACTTCTAGTGGGT

122 N  I  K  R  V  T  P  Q  R  K  V  F  R  S  L  K  F  A  E  S   141
 781 AACATCAAGCGGGTGACACCCCAGCGGAAAGTCTTTCGTTCCCTGAAGTTTGCTGAATCC    840
     TTGTAGTTCGCCCACTGTGGGGTCGCCTTTCAGAAAGCAAGGGACTTCAAACGACTTAGG

142 D  P  I  V  P  C  N  E  T  R  W  S  Q  K  W  Q  S  S  R  P   161
 841 GACCCCATTGTGCCCTGTAATGAGACCCGGTGGAGCCAGAAGTGGCAGTCATCACGTCCC    900
     CTGGGGTAACACGGGACATTACTCTGGGCCACCTCGGTCTTCACCGTCAGTAGTGCAGGG

162 L  K  R  A  S  L  S  L  G  S  G  F  W  H  A  T  G  R  H  S   181
 901 CTGAAAAGAGCCAGTCTCTCCCTGGGCTCTGGATTCTGGCATGCAACAGGAAGGCATTCA    960
     GACTTTTCTCGGTCAGAGAGGGACCCGAGACCTAAGACCGTACGTTGTCCTTCCGTAAGT

182 S  R  R  L  L  R  A  I  P  R  Q  V  A  Q  T  L  Q  A  D  V   201
 961 AGTCGACGATTGCTGAGAGCCATTCCTCGCCAGGTTGCCCAGACATTGCAGGCAGATGTG   1020
     TCAGCTGCTAACGACTCTCGGTAAGGAGCGGTCCAACGGGTCTGTAACGTCCGTCTACAC

202 L  W  Q  M  G  Y  T  G  A  N  V  R  V  A  V  F  D  T  G  L   221
1021 CTTTGGCAGATGGGATACACAGGTGCTAATGTCAGGGTTGCCGTTTTTGATACTGGGCTC   1080
     GAAACCGTCTACCCTATGTGTCCACGATTACAGTCCCAACGGCAAAAACTATGACCCGAG

222 S  E  K  H  P  H  F  K  N  V  K  E  R  T  N  W  T  N  E  R   241
1081 AGTGAGAAGCATCCACATTTCAAGAATGTGAAGGAAAGAACCAACTGGACCAATGAGCGG   1140
     TCACTCTTCGTAGGTGTAAAGTTCTTACACTTCCTTTCTTGGTTGACCTGGTTACTCGCC

242 T  L  D  D  G  L  G  H  G  T  F  V  A  G  V  I  A  S  M  R   261
1141 ACCCTGGACGATGGGCTGGGCCATGGCACATTCGTTGCAGGTGTGATTGCCAGCATGAGA   1200
     TGGGACCTGCTACCCGACCCGGTACCGTGTAAGCAACGTCCACACTAACGGTCGTACTCT

262 E  C  Q  G  F  A  P  D  A  E  L  H  I  F  R  V  F  T  N  N   281
1201 GAGTGCCAAGGATTTGCCCCAGATGCAGAGCTGCACATCTTCAGGGTCTTTACCAACAAT   1260
     CTCACGGTTCCTAAACGGGGTCTACGTCTCGACGTGTAGAAGTCCCAGAAATGGTTGTTA

282 Q  V  S  Y  T  S  W  F  L  D  A  F  N  Y  A  I  L  K  K  M   301
1261 CAGGTGTCTTACACGTCTTGGTTTTTGGATGCCTTCAACTATGCCATCCTAAAGAAGATG   1320
     GTCCACAGAATGTGCAGAACCAAAAACCTACGGAAGTTGATACGGTAGGATTTCTTCTAC

302 D  V  L  N  L  S  I  G  G  P  D  F  M  D  H  P  F  V  D  K   321
1321 GACGTTCTGAACCTTAGCATCGGTGGGCCTGACTTCATGGATCACCCCTTTGTTGACAAG   1380
     CTGCAAGACTTGGAATCGTAGCCACCCGGACTGAAGTACCTAGTGGGGAAACAACTGTTC
```

-continued

Rat SKI-1

```
322 V   W   E   L   T   A   N   N   V   I   M   V   S   A   I   G   N   D   G   P   341
1381 GTATGGGAATTAACAGCGAACAATGTAATCATGGTTTCTGCTATTGGCAATGATGGACCT 1440
     CATACCCTTAATTGTCGCTTGTTACATTAGTACCAAAGACGATAACCGTTACTACCTGGA

342 L   Y   G   T   L   N   N   P   A   D   Q   M   D   V   I   G   V   G   G   I   361
1441 CTCTATGGCACTCTGAATAACCCTGCTGATCAGATGGATGTGATTGGAGTGGGTGGCATT 1500
     GAGATACCGTGAGACTTATTGGGACGACTAGTCTACCTACACTAACCTCACCCACCGTAA

362 D   F   E   D   N   I   A   R   F   S   S   R   G   M   T   T   W   E   L   P   381
1501 GACTTTGAAGACAACATCGCCCGCTTCTCTTCCAGGGGAATGACTACCTGGGAACTACCG 1560
     CTGAAACTTCTGTTGTAGCGGGCGAAGAGAAGGTCCCCTTACTGATGGACCCTTGATGGC

382 G   G   Y   G   R   V   K   P   D   I   V   T   Y   G   A   G   V   R   G   S   401
1561 GGAGGCTATGGTCGTGTGAAGCCTGACATTGTCACCTATGGTGCTGGAGTGCGGGGTTCT 1620
     CCTCCGATACCAGCACACTTCGGACTGTAACAGTGGATACCACGACCTCACGCCCCAAGA

402 G   V   K   G   G   C   R   A   L   S   G   T   S   V   A   S   P   V   V   A   421
1621 GGTGTGAAAGGGGGCTGCCGTGCACTCTCAGGGACCAGTGTCGCCTCCCCAGTGGTTGCT 1680
     CCACACTTTCCCCCGACGGCACGTGAGAGTCCCTGGTCACAGCGGAGGGGTCACCAACGA

422 G   A   V   T   L   L   V   S   T   V   Q   K   R   E   L   V   N   P   A   S   441
1681 GGGGCTGTCACCTTGTTAGTAAGCACAGTACAGAAGCGGGAGCTAGTGAATCCTGCCAGT 1740
     CCCCGACAGTGGAACAATCATTCGTGTCATGTCTTCGCCCTCGATCACTTAGGACGGTCA

442 V   K   Q   A   L   I   A   S   A   R   R   L   P   G   V   N   M   F   E   Q   461
1741 GTGAAGCAAGCTTTGATAGCATCAGCCCGGAGACTTCCTGGTGTCAACATGTTTGAGCAA 1800
     CACTTCGTTCGAAACTATCGTAGTCGGGCCTCTGAAGGACCACAGTTGTACAAACTCGTT

462 G   H   G   K   L   D   L   L   R   A   Y   Q   I   L   S   S   Y   K   P   Q   481
1801 GGCCATGGCAAGTTGGATCTACTGCGAGCCTATCAGATCCTCAGCAGCTATAAACCGCAG 1860
     CCGGTACCGTTCAACCTAGATGACGCTCGGATAGTCTAGGAGTCGTCGATATTTGGCGTC

482 A   S   L   S   P   S   Y   I   D   L   T   E   C   P   Y   M   W   P   Y   C   501
1861 GCGAGCCTGAGTCCTAGCTACATCGACCTGACTGAGTGTCCCTACATGTGGCCCTACTGC 1920
     CGCTCGGACTCAGGATCGATGTAGCTGGACTGACTCACAGGGATGTACACCGGGATGACG

502 S   Q   P   I   Y   Y   G   G   M   P   T   I   V   N   V   T   I   L   N   G   521
1921 TCCCAGCCCATCTACTATGGAGGAATGCCAACAATTGTTAATGTCACCATCCTCAATGGC 1980
     AGGGTCGGGTAGATGATACCTCCTTACGGTTGTTAACAATTACAGTGGTAGGAGTTACCG

522 M   G   V   T   G   R   I   V   D   K   P   E   W   R   P   Y   L   P   Q   N   541
1981 ATGGGAGTTACAGGAAGAATTGTGGATAAGCCTGAGTGGCGACCCTATTTACCACAGAAT 2040
     TACCCTCAATGTCCTTCTTAACACCTATTCGGACTCACCGCTGGGATAAATGGTGTCTTA

542 G   D   N   I   E   V   A   F   S   Y   S   S   V   L   W   P   W   S   G   Y   561
2041 GGAGACAACATTGAAGTGGCCTTCTCCTACTCCTCAGTGTTGTGGCCTTGGTCAGGTTAC 2100
     CCTCTGTTGTAACTTCACCGGAAGAGGATGAGGAGTCACAACACCGGAACCAGTCCAATG

562 L   A   I   S   I   S   V   T   K   K   A   A   S   W   E   G   I   A   Q   G   581
2101 CTTGCCATCTCCATTTCTGTGACCAAGAAGGCAGCTTCCTGGGAAGGCATCGCGCAGGGC 2160
     GAACGGTAGAGGTAAAGACACTGGTTCTTCCGTCGAAGGACCCTTCCGTAGCGCGTCCCG

582 H   I   M   I   T   V   A   S   P   A   E   T   E   L   K   N   G   A   E   H   601
2161 CACATCATGATCACAGTGGCTTCCCCAGCAGAGACGGAATTAAAAAATGGTGCCGAGCAT 2220
     GTGTAGTACTAGTGTCACCGAAGGGGTCGTCTCTGCCTTAATTTTTTACCACGGCTCGTA

602 T   S   T   V   K   L   P   I   K   V   K   I   I   P   T   P   P   R   S   K   621
2221 ACTTCCACAGTGAAGCTGCCCATCAAGGTGAAGATCATTCCCACCCCTCCTCGGAGCAAG 2280
     TGAAGGTGTCACTTCGACGGGTAGTTCCACTTCTAGTAAGGGTGGGAGGAGCCTCGTTC

622 R   V   L   W   D   Q   Y   H   N   L   R   Y   P   P   G   Y   F   P   R   D   641
2281 AGAGTCCTCTGGGACCAGTACCACAACCTCCGCTACCCACCCGGCTACTTCCCCAGGGAC 2340
     TCTCAGGAGACCCTGGTCATGGTGTTGGAGGCGATGGGTGGGCCGATGAAGGGGTCCCTG

642 N   L   R   M   K   N   D   P   L   D   W   N   G   D   H   V   H   T   N   F   661
2341 AACTTGCGGATGAAGAATGATCCTTTAGACTGGAATGGCGACCACGTCCACACCAACTTC 2400
     TTGAACGCCTACTTCTTACTAGGAAATCTGACCTTACCGCTGGTGCAGGTGTGGTTGAAG

662 R   D   M   Y   Q   H   L   R   S   M   G   Y   F   V   E   V   L   G   A   P   681
2401 AGGGACATGTACCAGCATCTGCGCAGCATGGGCTACTTTGTGGAGGTGCTTGGTGCCCCA 2460
     TCCCTGTACATGGTCGTAGACGCGTCGTACCCGATGAAACACCTCCACGAACCACGGGGT

682 F   T   C   F   D   A   T   Q   Y   G   T   L   L   M   V   D   S   E   E   E   701
2461 TTCACATGCTTTGACGCCACGCAGTACGGCACTCTGCTTATGGTGGACAGTGAGGAAGAG 2520
     AAGTGTACGAAACTGCGGTGCGTCATGCCGTGAGACGAATACCACCTGTCACTCCTTCTC
```

-continued

Rat SKI-1

```
 702 Y  F  P  E  E  I  A  K  L  R  R  D  V  D  N  G  L  S  L  V       721
2521 TACTTCCCTGAGGAGATTGCTAAGCTGAGGAGGGACGTGGACAATGGCCTTTCCCTTGTC     2580
     ATGAAGGGACTCCTCTAACGATTCGACTCCTCCCTGCACCTGTTACCGGAAAGGGAACAG

722 V  F  S  D  W  Y  N  T  S  V  M  R  K  V  K  F  Y  D  E  N       741
2581 GTCTTCAGTGACTGGTACAACACTTCTGTTATGAGAAAAGTGAAGTTTTACGATGAAAAC     2640
     CAGAAGTCACTGACCATGTTGTGAAGACAATACTCTTTTCACTTCAAAATGCTACTTTTG

742 T  R  Q  W  W  M  P  D  T  G  G  A  N  V  P  A  L  N  E  L       761
2641 ACAAGGCAGTGGTGGATGCCAGATACTGGAGGAGCCAACGTCCCAGCTCTAAACGAGCTG     2700
     TGTTCCGTCACCACCTACGGTCTATGACCTCCTCGGTTGCAGGGTCGAGATTTGCTCGAC

762 L  S  V  W  N  M  G  F  S  D  G  L  Y  E  G  E  F  A  L  A       781
2701 CTGTCTGTGTGGAACATGGGGTTCAGTGACGGCCTGTATGAAGGGGAGTTTGCCCTGGCA     2760
     GACAGACACACCTTGTACCCCAAGTCACTGCCGGACATACTTCCCCTCAAACGGGACCGT

782 N  H  D  M  Y  Y  A  S  G  C  S  I  A  R  F  P  E  D  G  V       801
2761 AACCACGACATGTACTATGCATCGGGGTGCAGCATTGCCAGGTTTCCAGAAGATGGTGTG     2820
     TTGGTGCTGTACATGATACGTAGCCCCACGTCGTAACGGTCCAAAGGTCTTCTACCACAC

802 V  I  T  Q  T  F  K  D  Q  G  L  E  V  L  K  Q  E  T  A  V       821
2821 GTGATCACACAGACTTTCAAGGACCAAGGATTGGAAGTCTTAAAACAAGAGACAGCAGTT     2880
     CACTAGTGTGTCTGAAAGTTCCTGGTTCCTAACCTTCAGAATTTTGTTCTCTGTCGTCAA

822 V  D  N  V  P  I  L  G  L  Y  Q  I  P  A  E  G  G  G  R  I       841
2881 GTCGACAATGTCCCCATTCTGGGGCTATATCAGATTCCAGCTGAAGGTGGAGGCCGGATT     2940
     CAGCTGTTACAGGGGTAAGACCCCGATATAGTCTAAGGTCGACTTCCACCTCCGGCCTAA

842 V  L  Y  G  D  S  N  C  L  D  D  S  H  R  Q  K  D  C  F  W       861
2941 GTGCTGTATGGAGACTCCAACTGCTTGGATGACAGTCACAGACAGAAGGACTGCTTTTGG     3000
     CACGACATACCTCTGAGGTTGACGAACCTACTGTCAGTGTCTGTCTTCCTGACGAAAACC

862 L  L  D  A  L  L  Q  Y  T  S  Y  G  V  T  P  P  S  L  S  H       881
3001 CTTCTGGATGCACTCCTTCAGTACACATCCTATGGTGTGACCCCTCCCAGCCTCAGCCAT     3060
     GAAGACCTACGTGAGGAAGTCATGTGTAGGATACCACACTGGGGAGGGTCGGAGTCGGTA

882 S  G  N  R  Q  R  P  P  S  G  A  G  L  A  P  P  E  R  M  E       901
3061 TCAGGGAACCGGCAGCGCCCACCCAGCGGGGCTGGCTTGGCCCCTCCTGAAAGGATGGAA     3120
     AGTCCCTTGGCCGTCGCGGGTGGGTCGCCCCGACCGAACCGGGGAGGACTTTCCTACCTT

902 G  N  H  L  H  R  Y  S  K  V  L  E  A  H  L  G  D  P  K  P       921
3121 GGAAACCACCTTCATCGCTACTCCAAAGTTCTTGAGGCCCACTTGGGAGACCCGAAACCT     3180
     CCTTTGGTGGAAGTAGCGATGAGGTTTCAAGAACTCCGGGTGAACCCTCTGGGCTTTGGA

922 R  P  L  P  A  C  P  H  L  S  W  A  K  P  Q  P  L  N  E  T       941
3181 CGGCCCCTTCCAGCCTGTCCACACTTGTCGTGGGCCAAGCCACAGCCTTTGAATGAGACG     3240
     GCCGGGGAAGGTCGGACAGGTGTGAACAGCACCCGGTTCGGTGTCGGAAACTTACTCTGC

942 A  P  S  N  L  W  K  H  Q  K  L  L  S  I  D  L  D  K  V  V       961
3241 GCACCCAGTAATCTTTGGAAACACCAGAAGCTGCTCTCCATTGACCTGGACAAAGTAGTG     3300
     CGTGGGTCATTAGAAACCTTTGTGGTCTTCGACGAGAGGTAACTGGACCTGTTTCATCAC

962 L  P  N  F  R  S  N  R  P  Q  V  R  P  L  S  P  G  E  S  G       981
3301 TTACCCAACTTTCGCTCAAATCGCCCTCAAGTGAGACCTTTGTCCCCTGGAGAAAGTGGT     3360
     AATGGGTTGAAAGCGAGTTTAGCGGGAGTTCACTCTGGAAACAGGGGACCTCTTTCACCA

982 A  W  D  I  P  G  G  I  M  P  G  R  Y  N  Q  E  V  G  Q  T      1001
3361 GCCTGGGACATTCCTGGAGGGATCATGCCTGGCCGCTACAACCAGGAAGTAGGCCAGACC     3420
     CGGACCCTGTAAGGACCTCCCTAGTACGGACCGGCGATGTTGGTCCTTCATCCGGTCTGG

1002 I  P  V  F  A  F  L  G  A  M  V  A  L  A  F  F  V  V  Q  I      1021
3421 ATCCCTGTTTTTGCCTTCCTTGGAGCCATGGTGGCCCTGGCCTTCTTCGTGGTACAGATC     3480
     TAGGGACAAAAACGGAAGGAACCTCGGTACCACCGGGACCGGAAGAAGCACCATGTCTAG

1022 S  K  A  K  S  R  P  K  R  R  R  P  R  A  K  R  P  Q  L  A      1041
3481 AGTAAGGCCAAGAGCCGGCCGAAGCGGAGGAGGCCCAGGGCAAAGCGTCCACAACTTGCA     3540
     TCATTCCGGTTCTCGGCCGGCTTCGCCTCCTCCGGGTCCCGTTTCGCAGGTGTTGAACGT

1042 Q  Q  A  H  P  A  R  T  P  S  V                                 1052
3541 CAGCAGGCCCACCCTGCAAGGACCCCGTCAGTGTGATCATCACAGTGGCCAGACACGAA      3600
     GTCGTCCGGGTGGGACGTTCCTGGGGCAGTCACACTAGTAGTGTCACCGGTCTGTGTCTT

3601 GCTGACAAGCTTTGAACCCCTCTGGTGGCCACACAGCATCAGAGAGCATCCTGGGAAGTG     3660
     CGACTGTTCGAAACTTGGGGAGACCACCGGTGTGTCGTAGTCTCTCGTAGGACCCTTCAC

3661 CCTGTTTCCAAGGAGCCCTATCTCTGGATTGTGGCTGGCTTAGTGTGTTCTGCCCAGACG     3720
     GGACAAAGGTTCCTCGGGATAGAGACCTAACACCGACCGAATCACACAAGACGGGTCTGC
```

Rat SKI-1

```
3721 TCTATGAGGTACATCCTGCAGTCCTCACTGTGTTTGGCTCTGGCCGAAGGTGCCCAGTA 3780
     AGATACTCCATGTAGGACGTCACGGAGTGACACAAACCGAGACCGGCTTCCACGGGTCAT

3781 GCTCAGCCTCCGGTGGCATCAGGCCCAGTGACAGTGCACCAAAGACACAGAGCCTGGAAG 3840
     CGAGTCGGAGGCCACCGTAGTCCGGGTCACTGTCACGTGGTTTCTGTGTCTCGGACCTTC

3841 GGCTGTCGGGACATACTTTCTACATAATGCTACAACCCTGACCAAGCGAAGACAT     3895
     CCGACAGCCCTGTATGAAAGATGTATTACGATGTTGGGACTGGTTCGCTTCTGTA
```

Mouse SKI-1

```
  1       M  K  L  V  S  T  W  L  L  V  L  V  V  L  L  C  G  K       18
          GCATTCCATGAAGCTCGTCAGCACCTGGCTTCTTGTGCTGGTGGTTTTGCTCTGTGGGAA
  1       CGTAAGGTACTTCGAGCAGTCGTGGACCGAAGAACACGACCACCAAAACGAGACACCCTT    60

19       R  H  L  G  D  R  L  G  T  R  A  L  E  K  A  P  C  P  S  C  38
          ACGGCACCTGGGCGACAGGCTGGGGACGAGAGCTTTGGAAAAGGCCCCGTGCCCCAGCTG
 61       TGCCGTGGACCCGCTGTCCGACCCCTGCTCTCGAAACCTTTTCCGGGGCACGGGGTCGAC  120

39       S  H  L  T  L  K  V  E  F  S  S  T  V  V  E  Y  E  Y  I  V   58
          CTCCCACCTGACTTTGAAGGTGGAATTCTCTTCAACTGTGGTGGAGTACGAATATATTGT
121       GAGGGTGGACTGAAACTTCCACCTTAAGAGAAGTTGACACCACCTCATGCTTATATAACA  180

59       A  F  N  G  Y  F  T  A  K  A  R  N  S  F  I  S  S  A  L  K   78
          GGCTTTCAACGGATACTTCACAGCCAAAGCTAGAAACTCATTTATTTCAAGTGCGCTGAA
181       CCGAAAGTTGCCTATGAAGTGTCGGTTTCGATCTTTGAGTAAATAAAGTTCACGCGACTT  240

79       S  S  E  V  N  W  R  I  I  P  R  N  N  P  S  S  D  Y  P      98
          AAGCAGTGAAGTGGAAAACTGGAGAATAATACCTCGGAACAACCCATCCAGTGACTACCC
241       TTCGTCACTTCACCTTTTGACCTCTTATTATGGAGCCTTGTTGGGTAGGTCACTGATGGG  300

99       S  D  F  E  V  I  Q  I  K  E  K  Q  K  A  G  L  L  T  L  E   118
          TAGTGATTTTGAGGTGATTCAGATAAAAGAGAAGCAGAAGGCGGGGCTGCTCACACTTGA
301       ATCACTAAAACTCCACTAAGTCTATTTTCTCTTCGTCTTCCGCCCCGACGAGTGTGAACT  360

119       D  H  P  N  I  K  R  V  T  P  Q  R  K  V  F  R  S  L  K  F   138
          AGATCACCCCAACATCAAGCGGGTGACACCCCAGCGGAAAGTCTTTCGTTCCCTCAAGTT
361       TCTAGTGGGGTTGTAGTTCGCCCACTGTGGGGTCGCCTTTCAGAAAGCAAGGGAGTTCAA  420

139       A  E  S  N  P  I  V  P  C  N  E  T  R  W  S  Q  K  W  Q  S   158
          TGCTGAATCCAACCCCATCGTGCCCTGTAATGAAACCCGGTGGAGCCAGAAGTGGCAGTC
421       ACGACTTAGGTTGGGGTAGCACGGGACATTACTTTGGGCCACCTCGGTCTTCACCGTCAG  480

159       S  R  P  L  K  R  A  S  L  S  L  G  S  G  F  W  H  A  T  G   178
          ATCACGTCCCCTGAAAAGAGCCAGTCTCTCCCTGGGCTCTGGATTCTGGCATGCAACAGG
481       TAGTGCAGGGGACTTTTCTCGGTCAGAGAGGGACCCGAGACCTAAGACCGTACGTTGTCC  540

179       R  H  S  S  R  R  L  L  R  A  I  P  R  Q  V  A  Q  T  L  Q   198
          AAGACATTCAAGTCGGCGATTGCTGAGAGCCATTCCTCGCCAGGTCGCCCAGACACTGCA
541       TTCTGTAAGTTCAGCCGCTAACGACTCTCGGTAAGGAGCGGTCCAGCGGGTCTGTGACGT  600

199       A  D  V  L  W  Q  M  G  Y  T  G  A  N  V  R  V  A  V  F  D   218
          GGCAGATGTGCTGTGGCAGATGGGATACACAGGTGCTAATGTCAGAGTTGCTGTTTTTGA
601       CCGTCTACACGACACCGTCTACCCTATGTGTCCACGATTACAGTCTCAACGACAAAAACT  660

219       T  G  L  S  E  K  H  P  H  F  K  N  V  K  E  R  T  N  W  T   238
          TACTGGGCTCAGTGAGAAGCATCCGCATTTTAAGAATGTGAAGGAGAGAACCAACTGGAC
661       ATGACCCGAGTCACTCTTCGTAGGCGTAAAATTCTTACACTTCCTCTCTTGGTTGACCTG  720

239       N  E  R  T  L  D  D  G  L  G  H  G  T  F  V  A  G  V  I  A   258
          CAATGAGCGGACCCTGGATGATGGGCTAGGCCATGGCACATTCGTTGCAGGTGTGATTGC
721       GTTACTCGCCTGGGACCTACTACCCGATCCGGTACCGTGTAAGCAACGTCCACACTAACG  780

259       S  M  R  E  C  Q  G  F  A  P  D  A  E  L  H  I  F  R  V  F   278
          CAGCATGAGGGAGTGCCAAGGATTTGCTCCAGATGCAGAGCTGCACATCTTCAGGGTCTT
781       GTCGTACTCCCTCACGGTTCCTAAACGAGGTCTACGTCTCGACGTGTAGAAGTCCCAGAA  840

279       T  N  N  Q  V  S  Y  T  S  W  F  L  D  A  F  N  Y  A  I  L   298
          TACCAACAATCAGGTGTCTTACACATCTTGGTTTCTGGATGCCTTCAACTATGCCATCCT
841       ATGGTTGTTAGTCCACAGAATGTGTAGAACCAAAGACCTACGGAAGTTGATACGGTAGGA  900
```

-continued

Mouse SKI-1

```
 299  K   K   M   D   V   L   N   L   S   I   G   G   P   D   F   M   D   H   P   F    318
      AAAGAAGATGGACGTTCTCAACCTTAGCATCGGTGGGCCCGACTTCATGGATCATCCGTT
 901  TTTCTTCTACCTGCAAGAGTTGGAATCGTAGCCACCCGGGCTGAAGTACCTAGTAGGCAA    960

319  V   D   K   V   W   E   L   T   A   N   N   V   I   M   V   S   A   I   G   N    338
      TGTTGACAAGGTGTGGGAATTAACAGCTAACAATGTAATTATGGTTTCTGCTATTGGCAA
 961  ACAACTGTTCCACACCCTTAATTGTCGATTGTTACATTAATACCAAAGACGATAACCGTT   1020

339  D   G   P   L   Y   G   T   L   N   N   P   A   D   Q   M   D   V   I   G   V    358
      TGATGGACCTCTCTATGGCACTCTGAATAACCCTGCTGATCAGATGGATGTGATTGGAGT
1021  ACTACCTGGAGAGATACCGTGAGACTTATTGGGACGACTAGTCTACCTACACTAACCTCA   1080

359  G   G   I   D   F   E   D   N   I   A   R   F   S   S   R   G   M   T   T   W    378
      GGGTGGCATTGACTTTGAAGATAACATCGCTCGCTTTTCTTCCAGGGGAATGACTACCTG
1081  CCCACCGTAACTGAAACTTCTATTGTAGCGAGCGAAAAGAAGGTCCCCTTACTGATGGAC   1140

379  E   L   P   G   G   Y   G   R   V   K   P   D   I   V   T   Y   G   A   G   V    398
      GGAATTACCAGGAGGCTATGGTCGTGTGAAGCCTGACATTGTCACCTATGGTGCTGGAGT
1141  CCTTAATGGTCCTCCGATACCAGCACACTTCGGACTGTAACAGTGGATACCACGACCTCA   1200

399  R   G   S   G   V   K   G   G   C   R   A   L   S   G   T   S   V   A   S   P    418
      GCGGGGTTCCGGTGTGAAAGGGGGCTGCCGTGCACTCTCAGGGACCAGTGTCGCTTCCCC
1201  CGCCCCAAGGCCACACTTTCCCCCGACGGCACGTGAGAGTCCCTGGTCACAGCGAAGGGG   1260

419  V   V   A   G   A   V   T   L   L   V   S   T   V   Q   K   R   E   L   V   N    438
      AGTGGTCGCTGGGGCCGTCACCTTGTTAGTAAGCACAGTACAGAAGCGGGAGCTGGTGAA
1261  TCACCAGCGACCCCGGCAGTGGAACAATCATTCGTGTCATGTCTTCGCCCTCGACCACTT   1320

439  P   A   S   V   K   Q   A   L   I   A   S   R   R   L   P   G   V   N   M        458
      TCCTGCCAGTGTGAAGCAAGCTTTGATAGCGTCAGCCCGGAGACTTCCTGGGGTCAACAT
1321  AGGACGGTCACACTTCGTTCGAAACTATCGCAGTCGGGCCTCTGAAGGACCCCAGTTGTA   1380

459  F   E   Q   G   H   G   K   L   D   L   L   R   A   Y   Q   I   L   S   S   Y    478
      GTTCGAGCAAGGTCATGGCAAGTTGGATCTGCTGCGAGCTTATCAGATCCTCAGCAGCTA
1381  CAAGCTCGTTCCAGTACCGTTCAACCTAGACGACGCTCGAATAGTCTAGGAGTCGTCGAT   1440

479  K   P   Q   A   S   L   S   P   S   Y   I   D   L   T   E   C   P   Y   M   W    498
      TAAACCGCAGGCAAGCCTGAGTCCTAGCTACATCGACCTGACTGAGTGTCCCTACATGTG
1441  ATTTGGCGTCCGTTCGGACTCAGGATCGATGTAGCTGGACTGACTCACAGGGATGTACAC   1500

499  P   Y   C   S   Q   P   I   Y   Y   G   G   M   P   T   I   V   N   V   T   I    518
      GCCCTACTGCTCCCAGCCTATCTACTATGGAGGAATGCCAACAATCGTTAATGTCACCAT
1501  CGGGATGACGAGGGTCGGATAGATGATACCTCCTTACGGTTGTTAGCAATTACAGTGGTA   1560

519  L   N   G   M   G   V   T   G   R   I   V   D   K   P   E   W   R   P   Y   L    538
      CCTCAATGGCATGGGCGTCACAGGAAGAATTGTGGATAAGCCTGAGTGGCGACCCTATTT
1561  GGAGTTACCGTACCCGCAGTGTCCTTCTTAACACCTATTCGGACTCACCGCTGGGATAAA   1620

539  P   Q   N   G   D   N   I   E   V   A   F   S   Y   S   S   V   L   W   P   W    558
      ACCACAGAATGGAGACAACATTGAAGTGGCCTTCTCCTACTCCTCAGTGTTGTGGCCCTG
1621  TGGTGTCTTACCTCTGTTGTAACTTCACCGGAAGAGGATGAGGAGTCACAACACCGGGAC   1680

559  S   G   Y   L   A   I   S   I   S   V   T   K   K   A   A   S   W   E   G   I    578
      GTCAGGTTACCTTGCCATCTCCATTTCTGTGACCAAGAAGGCAGCTTCCTGGGAAGGCAT
1681  CAGTCCAATGGAACGGTAGAGGTAAAGACACTGGTTCTTCCGTCGAAGGACCCTTCCGTA   1740

579  A   Q   G   H   I   M   I   T   V   A   S   P   A   E   T   E   L   H   S   G    598
      CGCTCAGGGCCACATCATGATCACAGTGGCGTCCCAGCAGAGACAGAGTTACACAGTGG
1741  GCGAGTCCCGGTGTAGTACTAGTGTCACCGCAGGGGTCGTCTCTGTCTCAATGTGTCACC   1800

599  A   E   H   T   S   T   V   K   L   P   I   K   V   K   I   I   P   T   P   P    618
      TGCGGAGCACACTTCCACCGTGAAGCTGCCCATCAAGGTGAAGATCATTCCCACCCCTCC
1801  ACGCCTCGTGTGAAGGTGGCACTTCGACGGGTAGTTCCACTTCTAGTAAGGGTGGGGAGG   1860

619  R   S   K   R   V   L   W   D   Q   Y   H   N   L   R   Y   P   P   G   Y   F    638
      TCGGAGCAAGAGAGTCCTCTGGGACCAGTACCACAACCTCCGCTACCCACCTGGCTACTT
1861  AGCCTCGTTCTCTCAGGAGACCCTGGTCATGGTGTTGGAGGCGATGGGTGGACCGATGAA   1920

639  P   R   D   N   L   R   M   K   N   D   P   L   D   W   N   G   D   H   V   H    658
      CCCCAGGGACAACTTGCGGATGAAGAATGACCCTTTAGACTGGAATGGCGACCACGTCCA
1921  GGGGTCCCTGTTGAACGCCTACTTCTTACTGGGAAATCTGACCTTACCGCTGGTGCAGGT   1980

659  T   N   F   R   D   M   Y   Q   H   L   R   S   M   G   Y   F   V   E   V   L    678
      CACCAACTTCAGGGACATGTACCAGCATCTGCGCAGCATGGGCTACTTCGTGGAGGTGCT
1981  GTGGTTGAAGTCCCTGTACATGGTCGTAGACGCGTCGTACCCGATGAAGCACCTCCACGA   2040
```

Mouse SKI-1

```
 679  G  A  P  F  T  C  F  D  A  T  Q  Y  G  T  L  L  L  V  D  S   698
      CGGCGCCCCATTCACATGTTTTGACGCCACACAGTATGGCACTTTGCTGCTGGTGGACAG
2041  GCCGCGGGGTAAGTGTACAAAACTGCGGTGTGTCATACCGTGAAACGACGACCACCTGTC  2100

699  E  E  E  Y  F  P  E  E  I  A  K  L  R  R  D  V  D  N  G  L   718
      TGAGGAAGAGTACTTCCCTGAGGAGATTGCTAAGCTGAGGAGGGATGTGGACAATGGCCT
2101  ACTCCTTCTCATGAAGGGACTCCTCTAACGATTCGACTCCTCCCTACACCTGTTACCGGA  2160

719  S  L  V  I  F  S  D  W  Y  N  T  S  V     R  K  V  K  F  Y   738
      TTCCCTCGTCATCTTCAGTGACTGGTACAACACTTCTGTTATGAGAAAAGTGAAGTTTTA
2161  AAGGGAGCAGTAGAAGTCACTGACCATGTTGTGAAGACAATACTCTTTTCACTTCAAAAT  2220

739  D  E  N  T  R  Q  W  W  H  P  D  T  G  G  A  N  I  P  A  L   758
      TGATGAAAACACCAGGCAGTGGTGGATGCCAGACACCGGAGGAGCGAACATCCCAGCTCT
2221  ACTACTTTTGTGGTCCGTCACCACCTACGGTCTGTGGCCTCCTCGCTTGTAGGGTGGAGA  2280

759  N  E  L  L  S  V  W  N  M  G  F  S  D  G  L  Y  E  G  E  F   778
      GAATGAGCTGCTGTCTGTGTGGAACATGGGGTTCAGTGACGGCCTATATGAAGGGGAGTT
2281  CTTACTCGACGACAGACACACCTTGTACCCCAAGTCACTGCCGGATATACTTCCCCTCAA  2340

779  V  L  A  N  H  D  M  Y  Y  A  S  G  C  S  I  A  K  F  P  E   798
      TGTCCTGGCAAACCATGACATGTACTATGCGTCGGGGTGCAGCATCGCCAAGTTTCCAGA
2341  ACAGGACCGTTTGGTACTGTACATGATACGCAGCCCCACGTCGTAGCGGTTCAAAGGTCT  2400

799  D  G  V  V  I  T  Q  T  F  K  D  Q  G  L  E  V  L  K  Q  E   818
      AGATGGCGTCGTGATCACACAGACTTTCAAGGACCAAGGATTGGAGGTCTTAAAACAAGA
2401  TCTACCGCAGCACTAGTGTGTCTGAAAGTTCCTGGTTCCTAACCTCCAGAATTTTGTTCT  2460

819  T  A  V  V  E  N  V  P  I  L  G  L  Y  Q  I  P  S  E  G  G   838
      GACAGCAGTTGTGGAAAATGTTCCCATTTTGGGGCTTTATCAGATTCCATCTGAAGGTGG
2461  CTGTCGTCAACACCTTTTACAAGGGTAAAACCCCGAAATAGTCTAAGGTAGACTTCCACC  2520

839  G  R  I  V  L  Y  G  D  S  N  C  L  D  D  S  H  R  Q  K  D   858
      AGGCCGGATCGTGCTGTATGGAGACTCCAACTGCTTGGATGACAGTCACAGACAGAAGGA
2521  TCCGGCCTAGCACGACATACCTCTGAGGTTGACGAACCTACTGTCAGTGTCTGTCTTCCT  2580

859  C  F  W  L  L  D  A  L  L  Q  Y  T  S  Y  G  V  T  P  P  S   878
      CTGCTTTTGGCTTCTGGATGCGCTCCTTCAGTACACATCCTATGGCGTGACCCCTCCCAG
2581  GACGAAAACCGAAGACCTACGCGAGGAAGTCATGTGTAGGATACCGCACTGGGGAGGGTC  2640

879  L  S  H  S  G  N  R  Q  R  P  P  S  G  A  G  L  A  P  P  E   898
      CCTCAGCCATTCAGGGAACCGGCAGCGCCCACCTAGCGGAGCCGGCTTGGCCCCTCCTGA
2641  GGAGTCGGTAAGTCCCTTGGCCGTCGCGGGTGGATCGCCTCGGCCGAACCGGGGAGGACT  2700

899  R  M  E  G  N  H  L  H  R  Y  S  K  V  L  E  A  H  L  G  D   918
      AAGGATGGAAGGAAACCACCTCCATCGGTACTCCAAAGTTCTTGAAGCCCACTTGGGAGA
2701  TTCCTACCTTCCTTTGGTGGAGGTAGCCATGAGGTTTCAAGAACTTCGGGTGAACCCTCT  2760

919  P  K  P  R  P  L  P  A  C  P  H  L  S  W  A  K  P  Q  P  L   938
      CCCGAAACCTCGGCCCCTGCCAGCCTGTCCACATTTGTCATGGGCCAAGCCACAGCCTTT
2761  GGGCTTTGGAGCCGGGGACGGTCGGACAGGTGTAAACAGTACCCGGTTCGGTGTCGGAAA  2820

939  N  E  T  A  P  S  N  L  W  K  H  Q  K  L  L  S  I  D  L  D   958
      GAATGAGACGGCACCCAGTAATCTTTGGAAACATCAGAAGCTGCTCTCCATTGACCTGGA
2821  CTTACTCTGCCGTGGGTCATTAGAAACCTTTGTAGTCTTCGACGAGAGGTAACTGGACCT  2880

959  K  V  V  L  P  N  F  R  S  N  R  P  Q  V  R  P  L  S  P  G   978
      CAAAGTAGTGTTACCCAACTTTCGATCCAATCGCCCTCAAGTGAGACCTTTGTCCCCTGG
2881  GTTTCATCACAATGGGTTGAAAGCTAGGTTAGCGGGAGTTCACTCTGGAAACAGGGGACC  2940

979  E  S  G  A  W  D  I  P  G  G  I  M  P  G  R  Y  N  Q  E  V   998
      AGAGAGTGGTGCCTGGGACATTCCTGGAGGGATCATGCCTGGCCGCTACAACCAGGAGGT
2941  TCTCTCACCACGGACCCTGTAAGGACCTCCCTAGTACGGACCGGCGATGTTGGTCCTCCA  3000

999  G  Q  T  I  P  V  F  A  F  L  G  A  M  V  A  L  A  F  F  V  1018
      GGGACAGACCATCCCCGTCTTCGCCTTCCTCGGAGCCATGGTGGCCCTGGCCTTCTTTGT
3001  CCCTGTCTGGTAGGGGCAGAAGCGGAAGGAGCCTCGGTACCACCGGGACCGGAAGAAACA  3060

1019  V  Q  I  S  K  A  K  S  R  P  K  R  R  R  P  R  A  K  R  P  1038
      GGTACAGATCAGCAAGGCCAAGAGCCGGCCAAAGCGGAGGAGGCCCAGGGCAAAGCGTCC
3061  CCATGTCTAGTCGTTCCGGTTCTCGGCCGGCTTCGCCTCCTCCGGGTCCCGTTTCGCAGG  3120
```

-continued

Mouse SKI-1

```
1039  Q  L  A  Q  Q  A  H  P  A  R  T  P  S  V                    1052
      ACAACTTGCACAGCAGGCCCACCCTGCAAGGACCCCATCAGTGTGAGCATCGCAGTAGCC
3121  TGTTGAACGTGTCGTCCGGGTGGGACGTTCCTGGGGTAGTCACACTCGTAGCGTCATCGG  3180

AGCCACAGAAGCTAACAAGCCTTGAACCACTCTGGTGGCCACACAGCGCCTCAGAGAGCA
3181  TCGGTGTCTTCGATTGTTCGGAACTTGGTGAGACCACCGGTGTGTCGCGGAGTCTCTCGT  3240

TTCTGGGAAGTGCCTGTTTCCGAGGACCCTGTCTCCAGCTTGTGGCTATCTTACTGTGTT
3241  AAGACCCTTCACGGACAAAGGCTCCTGGGACAGAGGTCGAACACCGATAGAATGACACAA  3300

CTGCCCAGGCACCTGATGAGGTACATCCTGCAGTGCCTCTCTGTGCTTGGCTCTGGCAGA
3301  GACGGGTCCGTGGACTACTCCATGTAGGACGTCACGGAGAGACACGAACCGAGACCGTCT  3360

AGGCACCCAGTGACATCAGGCATCAGGCCCAGTGACAGTGCACCAAAGACACAGAGCCTG
3361  TCCGTGGGTCACTGTAGTCCGTAGTCCGGGTCACTGTCACGTGGTTTCTGTGTCTCGGAC  3420

GAAGGGCTGTCGGGACATACTTTCTACATAACGCTACAACCCTGACCAAGCAAAGACATG
3421  CTTCCCGACAGCCCTGTATGAAAGATGTATTGCGATGTTGGGACTGGTTCGTTTCTGTAC  3480

CTTGTTACAGGCTATTTTCTATATTTATTGTGGGAGAGTCACTTTAAAGACTGTGCTAGT
3481  GAACAATGTCCGATAAAAGATATAAATAACACCCTCTCAGTGAAATTTCTGACACGATCA  3540

TGGAAACAGAGCTGTTGCTGTTGTCAGTCGAGTGCAGTTTTCTGCAGCGATGTCATAAGG
3541  ACCTTTGTCTCGACAACGACAACAGTCAGCTCACGTCAAAAGACGTCGCTACAGTATTCC  3600

AGTCAGATTCCGTGACCTCCTCTTTGATGGAGGACACACTGAACTGAAGGGGACTTGCGC
3601  TCAGTCTAAGGCACTGGAGGAGAAACTACCTCCTGTGTGACTTGACTTCCCCTGAACGCG  3660

GGATGTGGGAGATGCAAGCCTTCGCTTTATTTTTTTATAACTATCAACTGCCATCATGTT
3661  CCTACACCCTCTACGTTCGGAAGCGAAATAAAAAAATATTGATAGTTGACGGTAGTACAA  3720

TTGTAATTTGGGGATCTTGATTTCACCGTTGTTGGTGAAGGAAATTTTCAATAAATATGC
3721  AACATTAAACCCCTAGAACTAAAGTGGCAACAACCACTTCCTTTAAAAGTTATTTATACG  3780

ATAACCTT
3781  TATTGGAA                                                      3788
```

REFERENCES

Example 1

1. Seidah, N. G., Day, R., Marcinkiewicz, M., & Chrétien, M. (1998) *Ann. N.Y. Acad. Sci.* 839, 9–24.
2. Steiner, D. F. (1998) *Curr. Opin. Chem. Biol.* 2, 31–39.
3. Seidah, N. G., Mbikay, M., Marcinkiewicz, M., & Chrétien, M. (1998) in *Proteolytic and Cellular Mechanisms in Prohormone and Proprotein Processing*, ed. Hook, V. Y. H. (R.G. Landes Company, Georgetown, Tex.), pp. 49–76.
4. Ling, N., Burgus, R., & Guillemin, R. (1976) *Proc. Natl. Acad. Sci. USA* 73, 3942–3946.
5. Burbach, J. P. H., Seidah, N. G., & Chrétien, M. (1986) *Eur. J. Biochem.* 156, 137–142.
6. Gupta, S. K., Hassel, T., & Singh, J. P. (1995) *Proc. Nat. Acad. Sci. USA* 92, 7799–7803.
7. O'Reilly, M. S., Holmgren, L., Shing, Y., Chen, C., Rosenthal, R. A., Moses, M., Lane, W. S., Cao, Y., Sage, E. H., & Folkman, J. (1994) *Cell* 79, 315–328.
8. Rosendahl, M. S., Christine Ko, S., Long, D. L., Brewer, M. T., Rosenzweig, B., Hedl, E., Anderson, L., Pyle, S. M., Moreland, J., Meyers, M. A., Kohno, T., Lyons, D., & Lichenstein, H. S. (1997) *J. Biol. Chem.* 272, 24588–24593.
9. Duncan, E. A., Brown, M. S., Goldstein, J. L., & Sakai, J. (1997) *J. Biol. Chem.* 272, 12778–12785.
10. Checler, F. (1995) *J. Neurochem.* 65, 1431–1444.
11. Seidah, N. G. (1995) *Methods Neurosci.* 23, 3–15.
12. Nagase, T., Miyajima, N., Tanaka, A., Sazuka, T., Seki, N., Sato, S., Tabata, S., Ishikawa, K-I., Kawarabayasi, Y., Kotani, H., & Nomura, N. (1995) *DNA Res.* 2, 37–43.
13. Edwards, J. B. D. M., Delort, J., & Mallet, J. (1991) *Nucl. Acid. Res.* 19, 5227–5232.
14. Lusson, J., Vieau, D., Hamelin, J., Day, R., Chrétien, M., & Seidah, N. G. (1993) *Proc Natl Acad Sci USA* 90, 6691–6695.
15. Seidah, N. G., Benjannet, S., Pareek, S., Chrétien, M., & Murphy, R. A. (1996) *FEBS Lett* 379, 247–250.
16. Marcinkiewicz, M., Savaria, D., & Marcinkiewicz, J. (1998) *Mol. Brain Res.* 59, 229–246.
17. Lippincott-Schwartz, J., Youan, L. C., Bonifacino, J. S., & Klausner, R. D. (1989) *Cell* 56, 801–813.
18. Anderson, E. D., Thomas, L., Hayflick, J. S., & Thomas, G. (1993) *J. Biol. Chem.* 268, 24887–24891.
19. Yan, Q., Rosenfeld, R. D., Matheson, C. R., Hawkins, N., Lopez, O. T., Bennett, L., & Welcher, A. A. (1997) *Neuroscience* 78, 431–448.
20. Paquet, L., Bergeron, F., Seidah, N. G., Chrétien, M., Mbikay, M., & Lazure, C. (1994) *J. Biol. Chem.* 269, 19279–19285.
21. Seidah, N. G., Hamelin, J., Mamarbachi, M., Dong, W., Tadros, H., Mbikay, M., Chrétien, M., & Day, R. (1996) *Proc. Natl. Acad. Sci. USA* 93, 3388–3393.
22. Siezen, R. J., & Leunissen, J. A. M. (1997) *Protein Sci.* 6, 501–523.
23. Seidah, N. G., Day, R., & Chrétien, M. (1994) *Biochimie* 76, 197–209.

24. de Bie, I., Marcinkiewicz, M., Malide, D., Lazure, C., Nakayama, K., Bendayan, M., & Seidah, N. G. (1996) *J. Cell Biol.* 135, 1261–1275.
25. Reeves, J. P., Decker, R. S., Crie, J. S., & Wildenthal, K. (1981) *Proc. Natl. Acad. Sci. USA* 78, 4426–4429.
26. Benjannet, S., Savaria, D., Laslop, A., Chrétien, M., Marcinkiewicz, M., & Seidah, N. G. (1997) *J. Biol. Chem.* 272, 26210–26218.
27. Maisonpierre, P. C., Le Beau, M. M., Espinosa, R., Ip, N.Y., Belluscio, L., de la Monte, S. M., Squinto, S., Furth, M. E. & Yancoupolos, G. D. (1991) *Genomics* 10, 558–568.

Example2

1. Seidah, N. G. et al.—Mammalian subtilisin/kexin isozyme SKI-1: A widely expressed proprotein convertase with a unique cleavage specificity and cellular localization.—Proceedings of the National Academy of Sciences of the United States of America 1999; 96: 1321–1326.
2. Sakai, J. et al.—Molecular identification of the sterol-regulated luminal protease that cleaves SREBPs and controls lipid composition of animal cells.—Molecular Cell 1998; 2:505–514.
3. Brown, M. S. and Goldstein, J. L. A proteolytic pathway that controls the cholesterol content of membranes, cells, and blood. Proceedings of the National Academy of Sciences of the United States of America 1999; 96: 11041–11048.
4. Wang, X., Sato, R., Brown, M. S., Hua, X., and Goldstein, J. L. SREBP-1, a membrane-bound transcription factor released by sterol-regulated proteolysis [see comments]. Cell 1994; 77: 53–62.
5. Hua, X. et al. SREBP-2, a second basic-helix-loop-helix-leucine zipper protein that stimulates transcription by binding to a sterol regulatory element. Proceedings of the National Academy of Sciences of the United States of America 1993; 90,11603–11607.
6. Sakai, J. et al.—Sterol-regulated release of SREBP-2 from cell membranes requires two sequential cleavages, one within a transmembrane segment.—Cell 1996; 85:1037–1046.
7. Rawson, R. B. et al.—Complementation cloning of S2P, a gene encoding a putative metalloprotease required for intramembrane cleavage of SREBPs. —Molecular Cell 1997; 1:47–57.
8. Anderson, E. D., VanSlyke, J. K., Thulin, C. D., Jean, F., and Thomas, G.—Activation of the furin endoprotease is a multiple-step process: requirements for acidification and internal propeptide cleavage.—EMBO Journal 1997,16: 1508–1518.
9. Power, S. D., Adams, R. M., and Wells, J. A.—Secretion and autoproteolytic maturation of subtilisin.—Proceedings of the National Academy of Sciences of the United States of America 1986 83: 3096–3100.
10. Seidah, N. G., Mbikay, M., Marcinkiewicz, M. and Chrétien, M., The mammalian precursor convertases: paralogs of the subtilisin/kexin family of calcium-dependent serine proteinases. In: Hook, V. Y. H. (Ed.), Proteolytic and Cellular Mechanisms in Prohormone and Proprotein Processing. R.G. Landes Company, Georgetown, Tex., USA, 1998, pp. 49–76.
11. Chiron, M. F., Fryling, C. M., and FitzGerald, D. J.—Cleavage of pseudomonas exotoxin and diphtheria toxin by a furin-like enzyme prepared from beef liver.— Journal of Biological Chemistry 1994; 269: 18167–18176.
12. Volchkov, V. E., Feldmann, H., Volchkova, V. A., and Klenk, H. D.—Processing of the Ebola virus glycoprotein by the proprotein convertase furin.—Proceedings of the National Academy of Sciences of the United States of America 1998; 95: 5762–5767.
13. Hallenberger, S., Moulard, M., Sordel, M., Klenk, H. D., and Garten, W.—The role of eukaryotic subtilisin-like endoproteases for the activation of human immunodeficiency virus glycoproteins in natural host cells.—Journal of Virology 1997;71; 1036–1045.
14. Chrétien, M., Mbikay, M., Gaspar, L. and Seidah, N. G., Proprotein convertases and the pathophysiology of human diseases: prospective considerations. Proc. Assoc. Am. Physicians., 107 (1995) 47–66.
15. Decroly, E., Benjannet, S., Savaria, D., and Seidah, N. G.—Comparative functional role of PC7 and furin in the processing of the HIV envelope glycoprotein gp160.— FEBS Letters 1997; 405: 68–72.
16. Abrami, L. et al.—The pore-forming toxin proaerolysin is activated by furin.—Journal of Biological Chemistry 1998; 273: 32656–32661.
17. Jean, F., Boudreault, A., Basak, A., Seidah, N. G., and Lazure, C.—Fluorescent peptidyl substrates as an aid in studying the substrate specificity of human prohormone convertase PC1 and human furin and designing a potent irreversible inhibitor.—Journal of Biological Chemistry 1995; 270: 19225–19231.
18. Hallenberger, S. et al.—Inhibition of furin-mediated cleavage activation of HIV-1 glycoprotein gp160.—Nature 1992; 360: 358–361.
19. Sakai, J., Duncan, E. A., Rawson, R. B., Hua, X., Brown, M. S. and Goldstein, J. L. Sterol-regulated release of SREBP-2 from cell membranes requires two sequential cleavages, one within a transmembrane segment. Cell 1996; 85:1037–1046.
20. Laufs, U. and Liao, J. K. Post-transcriptional regulation of endothelial nitric oxide synthase mRNA stability by Rho GTPase. Journal of Biological Chemistry 1998; 273: 24266–24271.
21. Endres, M. et al. Stroke protection by 3-hydroxy-3-methylglutaryl (HMG)-CoA reductase inhibitors mediated by endothelial nitric oxide synthase. Proceedings of the National Academy of Sciences of the United States of America 1998; 95: 8880–8885.
22. Laufs, U., La, F. V., Plutzky, J., and Liao, J. K. Upregulation of endothelial nitric oxide synthase by HMG CoA reductase inhibitors. Circulation 1998; 97: 1129–1135.
23. Laufs, U., Fata, V. L., and Liao, J. K. Inhibition of 3-hydroxy-3-methylglutaryl (HMG)-CoA reductase blocks hypoxia-mediated down-regulation of endothelial nitric oxide synthase. Journal of Biological Chemistry 1997; 272: 31725–31729.
24. Raiteri, M. et al. Pharmacological control of the mevalonate pathway: effect on arterial smooth muscle cell proliferation. Journal of Pharmacology & Experimental Therapeutics 1997; 281:1144–1153.
25. Soma, M. R., Corsini, A., and Paoletti, R. Cholesterol and mevalonic acid modulation in cell metabolism and multiplication. Toxicology Letters 1992; 64–65 Spec No, 1–15.
26. Mutoh, T., Kumano, T., Nakagawa, H., and Kuriyama, M.—Role of tyrosine phosphorylation of phospholipase C gamma1 in the signaling pathway of HMG-CoA reductase inhibitor-induced cell death of L6 myoblasts.—FEBS Letters 1999; 446: 91–94.
27. Mutoh, T., Kumano, T., Nakagawa, H., and Kuriyama, M.—Involvement of tyrosine phosphorylation in HMG- CoA reductase inhibitor-induced cell death in L6 myoblasts.—FEBS Letters 1999; 444: 85–89.
28. Bellosta, S. et al.—Direct vascular effects of HMG-CoA reductase inhibitors. Atherosclerosis 1998; 137 Suppl: S101-S109.
29. Shimomura, I., Hammer, R. E., Ikemoto, S., Brown, M. S., and Goldstein, J. L. Leptin reverses insulin resistance and diabetes mellitus in mice with congenital lipodystrophy. Nature 1999; 401:73–76.
30. Shimomura, I. et al.—Insulin resistance and diabetes mellitus in transgenic mice expressing nuclear SREBP-1c in adipose tissue: model for congenital generalized lipodystrophy.—Genes & Development 1998; 12:3182–3194.
31. Kim, J. B. et al.—Nutritional and insulin regulation of fatty acid synthetase and leptin gene expression through ADD1/SREBP1.—Journal of Clinical Investigation 1998; 101: 1–9.
32. Kim, J. B. and Spiegelman, B. M.—ADD1/SREBP1 promotes adipocyte differentiation and gene expression linked to fatty acid metabolism.—Genes & Development 1996; 10: 1096–1107.
33. Kim, J. B., Wright, H. M., Wright, M., and Spiegelman, B. M.—ADD1/SREBP1 activates PPARgamma through the production of endogenous ligand.—Proceedings of the National Academy of Sciences of the United States of America 1998; 95: 4333–4337.
34. Shimomura, I., Bashmakov, Y. and Horton, J. D.—Increased Levels of Nuclear SREBP-1 c Associated with Fatty Livers in Two Mouse Models of Diabetes Mellitus.—Journal of Biological Chemistry 1999; 274:30028–30032.

Example 3

Seidah, N. G., Day, R., Marcinkiewicz, M., and Chrétien, M. (1998) *Ann. NY Acad. Sci.* 839, 9–24

Steiner, D. F. (1998) *Curr. Opin. Chem. Biol.* 2, 31–39

Seidah, N. G., Mbikay, M., Marcinkiewicz, M., and Chrétien, M. (1998) in *Proteolytic and Cellular Mechanisms in Prohormone and Neuropeptide Precursor Processing.* (Hook, V. Y. H, ed) pp. 49–76, R.G. Landes Co., Georgetown, Tex.

Ling, N., Burgus, R., and Guillemin, R. (1976) *Proc. Natl. Acad. Sci. USA* 73, 3942–3946.

Burbach, J. P. H., Seidah, N. G, and Chrétien, M. (1986) *Eur. J. Biochem.* 156, 137–142

Hudson, P., Haley, J., Cronk, M., Shine, J., and Niall, H. (1981) *Nature* 291, 127–131

Gupta, S. K., Hassel, T., and Singh, J. P. (1995) *Proc. Natl. Acad. Sci. USA* 92, 7799–7803

Duncan, E. A., Brown, M. S., Goldstein, J. L., and Sakai, J. (1997) *J. Biol. Chem.* 272, 12778–12785

Siezen, R. J., and Leunissen, J. A. (1997) *Protein Sci.* 6, 501–523

Seidah, N. G., Mowla, S. J., Hamelin, J., Mamarbachi, A. M., Benjannet, S., Toure, B. B., Basak, A., Munzer, J. S., Marcinkiewicz, J., Zhong, M., Barale, J. C., Lazure, C., Murphy, R. A., Chrétien, M., and Marcinkiewicz, M. (1999) *Proc. Natl. Acad. Sci. USA* 96,1321–1326

Sakai, J., Rawson, R. B., Espenshade, P. J., Cheng, D., Seegmiller, A. C., Goldstein, J. L., and Brown, M. S. (1998) *Mol. Cell.* 2, 505–514

Nagase, T., Miyajima, N., Tanaka, A., Sazuka, T., Seki, N., Sato, S., Tabata, S., Ishikawa, K., Kawarabayasi, Y., and Kotani, H. (1995) *DNA Res.* 2, 37–43

Munzer, J. S., Basak, A., Zhong, M., Mamarbachi, A., Hamelin, J., Savaria, D., Lazure, C., Benjannet, S., Chrétien, M., and Seidah, N. G. (1997) *J. Biol. Chem.* 272, 19672–19681

Rovère, C., Luis, J., Lissitzky, J-C., Basak, A., Marvaldi, J., Chrétien, M., and Seidah, N. G. (1999) *J. Biol. Chem.* 274, 12461–12467

Basak, A., Boudreault, A., Chen, A., Chrétien, M., Seidah, N. G., and Lazure, C. (1995) *J. Pept. Sci.* 1, 385–395

Basak, A., Ernst, B., Brewer, D., Seidah, N. G., Munzer, J. S., Lazure, C., and Lajoie, G. A. (1997) *J. Pept. Res.* 49, 596–603

Jean, F., Boudreault, A., Basak, A., Seidah, N. G., and Lazure, C. (1995) *J. Biol. Chem.* 270,19225–19231

Hooper, N. M., Karran, E. H., and Turner, A. J. (1997) *Biochem. J.* 321, 265–279

Lippincott-Schwartz, J., Yuan, L., Tipper, C., Amherdt, M., Orci, L., and Klausner, R. D. (1991) *Cell* 67, 601–616

Gram, H., Ramage, P., Memmert, K., Gamse, R. and Kocher, P. (1994) *Biotechnology* 12, 1017–1023

Rittenhouse, J., and Marcus, F. (1984) *Anal. Biochem.* 138, 442–448

Mizuno, K., Nakamura, T., Ohshima, T., Tanaka, S., and Matsuo, H. (1989) *Biochem. Biophys. Res. Commun.* 159, 305–311

Lei, Y., Xin, X., Morgan, D., Pintar, J. E., and Fricker, L. D. (1999) *DNA Cell Biol.* 18,175–185

Inouye, M. (1991) *Enzyme* 45, 314–321

Gallagher, T., Gilliland, G., Wang, L., and Bryan, P. (1995) *Structure* 3, 907–914

Anderson, E. D., Vanslyke, J. K., Thulin, C. D., Jean, F., and Thomas, G. (1997) *EMBO J.* 16,1508–1518

Malide, D., Seidah, N. G., Chrétien, M., and Bendayan, M. (1995) *J. Histochem. Cytochem.* 43,11–19

Kendall, J. M., Badminton, M. N., Dormer, R. L., and Campbell, A. K. (1994) *Anal. Biochem.* 221, 173–181

Sambrook, J. F. (1990) *Cell* 61, 197–199

Llopis, J, McCaffery, J. M., Miyawaki, A, Farquha,r M. G., and Tsien, R. Y. (1998) *Proc. Natl. Acad. Sci. USA* 95, 6803–6808

Kim, J. H., Johannes, L., Goud, B., Antony, C., Lingwood, C. A., Daneman, R., and Grinstein, S. (1998) *Proc. Natl. Acad. Sci. USA* 95, 2997–3002

Nohturfft A, DeBose-Boyd, R. A., Scheek, S., Goldstein, J. L., and Brown, M. S. (1999) *Proc. Natl. Acad. Sci. USA* 96, 11235–11240

Nohturfft, A, Brown, M. S., and Goldstein, J. L. (1998) *Proc. Natl. Acad. Sci. USA* 95, 12848–12853

Boudreault, A., Gauthier, D., and Lazure, C. (1998) *J. Biol. Chem.* 273, 31574–31580

Zhong, M., Munzer, J. S., Basak, A., Benjannet, S., Mowla, S. J., Decroly, E., Chretien, M. and Seidah, N. G. (1999) *J. Biol. Chem.* 274:33913–33920.

Muller, L., Zhu, X. R., and Lindberg, I. (1997) *J. Cell Biol.* 139, 625–638

Benjannet, S., Mamarbachi, A. M., Hamelin, J., Savaria, D., Munzer, J. S., Chrétien, M., and Seidah, N. G. (1998) *FEBS Letters* 428, 37–42

Espenshade, P. J., Cheng, D., Goldstein, J. L., and Brown, M. S. (1999) *J. Biol. Chem.* 274, 22795–22804

Cheng, D., Espenshade, P. J., Slaughter, C. A., Jaen, J. C., Brown, M. S., and Goldstein J. L. (1999) *J. Biol. Chem.* 274, 22805–22812

What is claimed is:

1. A soluble polypeptide of the subtilisin-kexin isoenzyme SKI-1 set forth in SEQ ID NO: 6, wherein the soluble polypeptide consists of amino acids 187 to 996 of SEQ ID NO: 6.

2. A polypeptide of the subtilisin-kexin isoenzyme SKI-1 set forth in SEQ ID NO: 6, wherein the soluble polypeptide consists of amino acids 17 to 137 of SEQ ID NO: 6, which is capable of binding with amino acids 17 to 1052 of SKI-1.

3. A purified polypeptide, the amino acid sequence of which consists of amino acids 18 to 188 of SEQ ID NO: 6.

4. A purified polypeptide, the amino acid sequence of which consists of amino acids 18 to 196 of SEQ ID NO: 6.

5. A purified polypeptide, the amino acid sequence of which consists of amino acids 18 to 169 of SEQ ID NO: 6.

6. A purified peptide which comprises the sequence as set forth in SEQ ID NO:13.

7. A peptide as defined in claim 6, the amino acid sequence of which consists of the sequence as set forth in SEQ ID NO: 14.

8. A composition comprising the polypeptide as defined in claim 1.

9. A composition comprising the polypeptide as defined in claim 2.

10. A composition comprising the polypeptide of claim 3.

11. A composition comprising the polypeptide of claim 4.

12. A composition comprising the polypeptide of claim 5.

13. A method for cleaving a substrate for a subtilisin-kexin SKI-1 enzyme, which comprises contacting said substrate with a polypeptide consisting of amino acids 187–996 of SEQ ID NO:6 for a time sufficient and in conditions adequate for such cleavage to occur, whereby cleavage of the substrate occurs.

14. A method for producing a protein or a peptide from a precursor which is an enzymatic substrate for a subtilisin-kexin SK1-1 enzyme, which comprises:
   a) contacting said precursor with a polypeptide consisting of amino acids 187–996 of SEQ ID NO:6 for a time sufficient and in conditions adequate for such cleavage to occur; and
   b) recovering said protein or peptide.

15. The method of claim 14, which takes place in a host cell and wherein step a) further comprises the step of transfecting an isolated host cell with a nucleic acid expressing said SKI-1 enzyme.

16. The method of claim 15, wherein said host cell expresses said precursor or is transfected with a nucleic acid expressing said precursor.

17. An isolated nucleic acid consisting of a nucleic acid sequence encoding the polypeptide as defined in claim 1.

18. An isolated nucleic acid consisting of a nucleic acid sequence encoding the polypeptide as defined in claim 1.

19. A composition comprising a nucleic acid as defined in claim 17.

20. A composition comprising a nucleic acid as defined in claim 18.

21. An isolated nucleic acid consisting of a nucleotide sequence encoding the polypeptide of claim 3.

22. An isolated nucleic acid consisting of a nucleotide sequence encoding the polypeptide of claim 4.

23. An isolated nucleic acid consisting of a nucleotide sequence encoding the polypeptide of claim 5.

24. A recombinant expression vector comprising the isolated nucleic acid of claim 17, wherein a soluble subtilisin-kexin SKI-1 enzyme consisting of the amino acids from position 187 to 996 of SEQ ID NO:6 is produced upon expression of said vector in a host cell.

25. The recombinant vector of claim 24, which comprises a promoter expressible in a target cell wherein expression of said nucleic acid is desirable.

26. The recombinant vector of claim 25, which comprises an inducible promoter.

27. A recombinant vector comprising the isolated nucleic acid defined in claim 21, wherein a polypeptide that consists of the amino acids from position 18 to 188 of SEQ ID NO:6 is produced upon expression of the vector in a host cell.

28. A recombinant vector comprising the isolated nucleic acid defined in claim 22, wherein a polypeptide that consists of the amino acids from position 18 to 196 of SEQ ID NO:6 is produced upon expression of the vector in a host cell.

29. A recombinant vector comprising the isolated nucleic acid defined in claim 23, wherein a polypeptide that consists of the amino acids from position 18 to 169 of SEQ ID NO:6 is produced upon expression of the vector in a host cell.

30. A composition comprising a recombinant vector as defined in claim 24.

31. A composition comprising a recombinant vector as defined in claim 25.

32. A composition comprising a recombinant vector as defined in claim 26.

33. An isolated recombinant host cell comprising the recombinant vector as defined in claim 24.

34. A method of producing a soluble subtilisin-kexin SKI-1 enzyme, which comprises the steps of:

culturing a recombinant host cell expressing a recombinant vector as defined in claim 24 in an expression-supportive culture medium; and recovering the soluble subtilisin-kexin SKI-1 enzyme from the culture medium.

\* \* \* \* \*

UNITED STATES PATENT AND TRADEMARK OFFICE
CERTIFICATE OF CORRECTION

| | | |
|---|---|---|
| PATENT NO. | : 7,211,424 B1 | Page 1 of 1 |
| APPLICATION NO. | : 09/830837 | |
| DATED | : May 1, 2007 | |
| INVENTOR(S) | : Nabil G. Seidah et al. | |

It is certified that error appears in the above-identified patent and that said Letters Patent is hereby corrected as shown below:

On the title page item (75), "Inventors" ADD the following two inventors: --Laaksonen, Reijo and Davignon, Jean--.

Signed and Sealed this

Tenth Day of July, 2007

JON W. DUDAS
*Director of the United States Patent and Trademark Office*

SEQUENCE LISTING

<160> NUMBER OF SEQ ID NOS: 108

<210> SEQ ID NO 1
<211> LENGTH: 3895
<212> TYPE: DNA
<213> ORGANISM: Rattus sp.
<220> FEATURE:
<221> NAME/KEY: CDS
<222> LOCATION: (418)..(3573)

<400> SEQUENCE: 1

| | | |
|---|---|---|
| gcgagtaaac atccccgaa tggatacccg aggcgtgttc gcggcggagg ccccgttttc | 60 | |
| ccgggtccgc cgatcccgag cctgaggcga cgcagatcgg ctcagagcgg tggcttgggc | 120 | |
| tcctgctaga tttgggtctg tggtacaaat ggagtttagg actcagtgga ctcggcccta | 180 | |
| atgagagaag cccctgtcc aagatggaga agaagcggag aaagaaatga agcctcttt | 240 | |
| ttgggccaag ctgtgggtga ccatgggact gaggttttct ttacgttgga caagtctgta | 300 | |
| ggatggctga tcagtaaggt tgcagctttt agcgaaaaca gaaatccact tctgatcaag | 360 | |
| gaagagccta gtgcaatttg aatttatgca attttatgac catattccact taggacc | 417 | |

| atg aag ctc gtc aac atc tgg ctt ctt ctg ctg gtg gtt ttg ctc tgt | 465 |
|---|---|
| Met Lys Leu Val Asn Ile Trp Leu Leu Leu Leu Val Val Leu Leu Cys | |
| 1               5                   10                  15 | |

| ggg aaa aag cat ctg ggt gac agg ctg ggg aag aaa gct ttt gaa aag | 513 |
|---|---|
| Gly Lys Lys His Leu Gly Asp Arg Leu Gly Lys Lys Ala Phe Glu Lys | |
|             20                  25                  30 | |

| gcc cca tgc ccc agc tgt tcc cac ctg act ttg aag gtg gaa ttc tcc | 561 |
|---|---|
| Ala Pro Cys Pro Ser Cys Ser His Leu Thr Leu Lys Val Glu Phe Ser | |
|         35                  40                  45 | |

| tca act gtg gtg gaa tat gaa tat att gtg gct ttc aac gga tac ttc | 609 |
|---|---|
| Ser Thr Val Val Glu Tyr Glu Tyr Ile Val Ala Phe Asn Gly Tyr Phe | |
|     50                  55                  60 | |

| aca gcc aaa gct aga aac tca ttt att tca agt gct cta aaa agc agt | 657 |
|---|---|
| Thr Ala Lys Ala Arg Asn Ser Phe Ile Ser Ser Ala Leu Lys Ser Ser | |
| 65                  70                  75                  80 | |

| gaa gtg gac aac tgg aga ata ata cct cgg aac aac cca tct agt gac | 705 |
|---|---|
| Glu Val Asp Asn Trp Arg Ile Ile Pro Arg Asn Asn Pro Ser Ser Asp | |
|                 85                  90                  95 | |

| tac cct agt gat ttt gag gtg att cag ata aaa gag aag cag aag gcg | 753 |
|---|---|
| Tyr Pro Ser Asp Phe Glu Val Ile Gln Ile Lys Glu Lys Gln Lys Ala | |
|             100                 105                 110 | |

| ggg ctg ctc aca ctt gaa gat cac cca aac atc aag cgg gtg aca ccc | 801 |
|---|---|
| Gly Leu Leu Thr Leu Glu Asp His Pro Asn Ile Lys Arg Val Thr Pro | |
|         115                 120                 125 | |

| cag cgg aaa gtc ttt cgt tcc ctg aag ttt gct gaa tcc gac ccc att | 849 |
|---|---|
| Gln Arg Lys Val Phe Arg Ser Leu Lys Phe Ala Glu Ser Asp Pro Ile | |
|     130                 135                 140 | |

| gtg ccc tgt aat gag acc cgg tgg agc cag aag tgg cag tca tca cgt | 897 |
|---|---|
| Val Pro Cys Asn Glu Thr Arg Trp Ser Gln Lys Trp Gln Ser Ser Arg | |
| 145                 150                 155                 160 | |

| ccc ctg aaa aga gcc agt ctc tcc ctg ggc tct gga ttc tgg cat gca | 945 |
|---|---|
| Pro Leu Lys Arg Ala Ser Leu Ser Leu Gly Ser Gly Phe Trp His Ala | |
|                 165                 170                 175 | |

| aca gga agg cat tca agt cga cga ttg ctg aga gcc att cct cgc cag | 993 |
|---|---|
| Thr Gly Arg His Ser Ser Arg Arg Leu Leu Arg Ala Ile Pro Arg Gln | |
|             180                 185                 190 | |

| gtt gcc cag aca ttg cag gca gat gtg ctt tgg cag atg gga tac aca | 1041 |
|---|---|
| Val Ala Gln Thr Leu Gln Ala Asp Val Leu Trp Gln Met Gly Tyr Thr | |

-continued

```
                195                 200                 205
ggt gct aat gtc agg gtt gcc gtt ttt gat act ggg ctc agt gag aag    1089
Gly Ala Asn Val Arg Val Ala Val Phe Asp Thr Gly Leu Ser Glu Lys
    210                 215                 220 cat cca cat ttc aag aat gtg aag gaa aga acc aac tgg acc aat gag    1137
His Pro His Phe Lys Asn Val Lys Glu Arg Thr Asn Trp Thr Asn Glu
225                 230                 235                 240 cgg acc ctg gac gat ggg ctg ggc cat ggc aca ttc gtt gca ggt gtg    1185
Arg Thr Leu Asp Asp Gly Leu Gly His Gly Thr Phe Val Ala Gly Val
                245                 250                 255 att gcc agc atg aga gag tgc caa gga ttt gcc cca gat gca gag ctg    1233
Ile Ala Ser Met Arg Glu Cys Gln Gly Phe Ala Pro Asp Ala Glu Leu
        260                 265                 270 cac atc ttc agg gtc ttt acc aac aat cag gtg tct tac acg tct tgg    1281
His Ile Phe Arg Val Phe Thr Asn Asn Gln Val Ser Tyr Thr Ser Trp
            275                 280                 285 ttt ttg gat gcc ttc aac tat gcc atc cta aag aag atg gac gtt ctg    1329
Phe Leu Asp Ala Phe Asn Tyr Ala Ile Leu Lys Lys Met Asp Val Leu
    290                 295                 300 aac ctt agc atc ggt ggg cct gac ttc atg gat cac ccc ttt gtt gac    1377
Asn Leu Ser Ile Gly Gly Pro Asp Phe Met Asp His Pro Phe Val Asp
305                 310                 315                 320 aag gta tgg gaa tta aca gcg aac aat gta atc atg gtt tct gct att    1425
Lys Val Trp Glu Leu Thr Ala Asn Asn Val Ile Met Val Ser Ala Ile
                325                 330                 335 ggc aat gat gga cct ctc tat ggc act ctg aat aac cct gct gat cag    1473
Gly Asn Asp Gly Pro Leu Tyr Gly Thr Leu Asn Asn Pro Ala Asp Gln
        340                 345                 350 atg gat gtg att gga gtg ggt ggc att gac ttt gaa gac aac atc gcc    1521
Met Asp Val Ile Gly Val Gly Gly Ile Asp Phe Glu Asp Asn Ile Ala
            355                 360                 365 cgc ttc tct tcc agg gga atg act acc tgg gaa cta ccg gga ggc tat    1569
Arg Phe Ser Ser Arg Gly Met Thr Thr Trp Glu Leu Pro Gly Gly Tyr
    370                 375                 380 ggt cgt gtg aag cct gac att gtc acc tat ggt gct gga gtg cgg ggt    1617
Gly Arg Val Lys Pro Asp Ile Val Thr Tyr Gly Ala Gly Val Arg Gly
385                 390                 395                 400 tct ggt gtg aaa ggg ggc tgc cgt gca ctc tca ggg acc agt gtc gcc    1665
Ser Gly Val Lys Gly Gly Cys Arg Ala Leu Ser Gly Thr Ser Val Ala
                405                 410                 415 tcc cca gtg gtt gct ggg gct gtc acc ttg tta gta agc aca gta cag    1713
Ser Pro Val Val Ala Gly Ala Val Thr Leu Leu Val Ser Thr Val Gln
        420                 425                 430 aag cgg gag cta gtg aat cct gcc agt gtg aag caa gct ttg ata gca    1761
Lys Arg Glu Leu Val Asn Pro Ala Ser Val Lys Gln Ala Leu Ile Ala
            435                 440                 445 tca gcc cgg aga ctt cct ggt gtc aac atg ttt gag caa ggc cat ggc    1809
Ser Ala Arg Arg Leu Pro Gly Val Asn Met Phe Glu Gln Gly His Gly
    450                 455                 460 aag ttg gat cta ctg cga gcc tat cag atc ctc agc agc tat aaa ccg    1857
Lys Leu Asp Leu Leu Arg Ala Tyr Gln Ile Leu Ser Ser Tyr Lys Pro
465                 470                 475                 480 cag gcg agc ctg agt cct agc tac atc gac ctg act gag tgt ccc tac    1905
Gln Ala Ser Leu Ser Pro Ser Tyr Ile Asp Leu Thr Glu Cys Pro Tyr
                485                 490                 495 atg tgg ccc tac tgc tcc cag ccc atc tac tat gga gga atg cca aca    1953
Met Trp Pro Tyr Cys Ser Gln Pro Ile Tyr Tyr Gly Gly Met Pro Thr
        500                 505                 510 att gtt aat gtc acc atc ctc aat ggc atg gga gtt aca gga aga att    2001
```

-continued

| | | | | | | | | | | | | | | | |
|---|---|---|---|---|---|---|---|---|---|---|---|---|---|---|---|
| Ile | Val | Asn | Val | Thr | Ile | Leu | Asn | Gly | Met | Gly | Val | Thr | Gly | Arg | Ile |
| | | 515 | | | | 520 | | | | 525 | | | | | | gtg gat aag cct gag tgg cga ccc tat tta cca cag aat gga gac aac  2049
Val Asp Lys Pro Glu Trp Arg Pro Tyr Leu Pro Gln Asn Gly Asp Asn
    530             535             540 att gaa gtg gcc ttc tcc tac tcc tca gtg ttg tgg cct tgg tca ggt  2097
Ile Glu Val Ala Phe Ser Tyr Ser Ser Val Leu Trp Pro Trp Ser Gly
545             550             555             560 tac ctt gcc atc tcc att tct gtg acc aag aag gca gct tcc tgg gaa  2145
Tyr Leu Ala Ile Ser Ile Ser Val Thr Lys Lys Ala Ala Ser Trp Glu
                565             570             575 ggc atc gcg cag ggc cac atc atg atc aca gtg gct tcc cca gca gag  2193
Gly Ile Ala Gln Gly His Ile Met Ile Thr Val Ala Ser Pro Ala Glu
            580             585             590 acg gaa tta aaa aat ggt gcc gag cat act tcc aca gtg aag ctg ccc  2241
Thr Glu Leu Lys Asn Gly Ala Glu His Thr Ser Thr Val Lys Leu Pro
        595             600             605 atc aag gtg aag atc att ccc acc cct cct cgg agc aag aga gtc ctc  2289
Ile Lys Val Lys Ile Ile Pro Thr Pro Pro Arg Ser Lys Arg Val Leu
610             615             620 tgg gac cag tac cac aac ctc cgc tac cca ccc ggc tac ttc ccc agg  2337
Trp Asp Gln Tyr His Asn Leu Arg Tyr Pro Pro Gly Tyr Phe Pro Arg
625             630             635             640 gac aac ttg cgg atg aag aat gat cct tta gac tgg aat ggc gac cac  2385
Asp Asn Leu Arg Met Lys Asn Asp Pro Leu Asp Trp Asn Gly Asp His
                645             650             655 gtc cac acc aac ttc agg gac atg tac cag cat ctg cgc agc atg ggc  2433
Val His Thr Asn Phe Arg Asp Met Tyr Gln His Leu Arg Ser Met Gly
            660             665             670 tac ttt gtg gag gtg ctt ggt gcc cca ttc aca tgc ttt gac gcc acg  2481
Tyr Phe Val Glu Val Leu Gly Ala Pro Phe Thr Cys Phe Asp Ala Thr
        675             680             685 cag tac ggc act ctg ctt atg gtg gac agt gag gaa gag tac ttc cct  2529
Gln Tyr Gly Thr Leu Leu Met Val Asp Ser Glu Glu Glu Tyr Phe Pro
690             695             700 gag gag att gct aag ctg agg agg gac gtg gac aat ggc ctt tcc ctt  2577
Glu Glu Ile Ala Lys Leu Arg Arg Asp Val Asp Asn Gly Leu Ser Leu
705             710             715             720 gtc gtc ttc agt gac tgg tac aac act tct gtt atg aga aaa gtg aag  2625
Val Val Phe Ser Asp Trp Tyr Asn Thr Ser Val Met Arg Lys Val Lys
                725             730             735 ttt tac gat gaa aac aca agg cag tgg tgg atg cca gat act gga gga  2673
Phe Tyr Asp Glu Asn Thr Arg Gln Trp Trp Met Pro Asp Thr Gly Gly
            740             745             750 gcc aac gtc cca gct cta aac gag ctg ctg tct gtg tgg aac atg ggg  2721
Ala Asn Val Pro Ala Leu Asn Glu Leu Leu Ser Val Trp Asn Met Gly
        755             760             765 ttc agt gac ggc ctg tat gaa ggg gag ttt gcc ctg gca aac cac gac  2769
Phe Ser Asp Gly Leu Tyr Glu Gly Glu Phe Ala Leu Ala Asn His Asp
770             775             780 atg tac tat gca tcg ggg tgc agc att gcc agg ttt cca gaa gat ggt  2817
Met Tyr Tyr Ala Ser Gly Cys Ser Ile Ala Arg Phe Pro Glu Asp Gly
785             790             795             800 gtg gtg atc aca cag act ttc aag gac caa gga ttg gaa gtc tta aaa  2865
Val Val Ile Thr Gln Thr Phe Lys Asp Gln Gly Leu Glu Val Leu Lys
                805             810             815 caa gag aca gca gtt gtc gac aat gtc ccc att ctg ggg cta tat cag  2913
Gln Glu Thr Ala Val Val Asp Asn Val Pro Ile Leu Gly Leu Tyr Gln
            820             825             830

-continued

| | |
|---|---|
| att cca gct gaa ggt gga ggc cgg att gtg ctg tat gga gac tcc aac<br>Ile Pro Ala Glu Gly Gly Gly Arg Ile Val Leu Tyr Gly Asp Ser Asn<br>       835                          840                          845 | 2961 |
| tgc ttg gat gac agt cac aga cag aag gac tgc ttt tgg ctt ctg gat<br>Cys Leu Asp Asp Ser His Arg Gln Lys Asp Cys Phe Trp Leu Leu Asp<br>850                         855                        860 | 3009 |
| gca ctc ctt cag tac aca tcc tat ggt gtg acc cct ccc agc ctc agc<br>Ala Leu Leu Gln Tyr Thr Ser Tyr Gly Val Thr Pro Pro Ser Leu Ser<br>865                         870                        875                   880 | 3057 |
| cat tca ggg aac cgg cag cgc cca ccc agc ggg gct ggc ttg gcc cct<br>His Ser Gly Asn Arg Gln Arg Pro Pro Ser Gly Ala Gly Leu Ala Pro<br>                         885                        890                   895 | 3105 |
| cct gaa agg atg gaa gga aac cac ctt cat cgc tac tcc aaa gtt ctt<br>Pro Glu Arg Met Glu Gly Asn His Leu His Arg Tyr Ser Lys Val Leu<br>             900                        905                        910 | 3153 |
| gag gcc cac ttg gga gac ccg aaa cct cgg ccc ctt cca gcc tgt cca<br>Glu Ala His Leu Gly Asp Pro Lys Pro Arg Pro Leu Pro Ala Cys Pro<br>                 915                        920                     925 | 3201 |
| cac ttg tcg tgg gcc aag cca cag cct ttg aat gag acg gca ccc agt<br>His Leu Ser Trp Ala Lys Pro Gln Pro Leu Asn Glu Thr Ala Pro Ser<br>       930                        935                        940 | 3249 |
| aat ctt tgg aaa cac cag aag ctg ctc tcc att gac ctg gac aaa gta<br>Asn Leu Trp Lys His Gln Lys Leu Leu Ser Ile Asp Leu Asp Lys Val<br>945                       950                        955                   960 | 3297 |
| gtg tta ccc aac ttt cgc tca aat cgc cct caa gtg aga cct ttg tcc<br>Val Leu Pro Asn Phe Arg Ser Asn Arg Pro Gln Val Arg Pro Leu Ser<br>                 965                        970                     975 | 3345 |
| cct gga gaa agt ggt gcc tgg gac att cct gga ggg atc atg cct ggc<br>Pro Gly Glu Ser Gly Ala Trp Asp Ile Pro Gly Gly Ile Met Pro Gly<br>       980                        985                        990 | 3393 |
| cgc tac aac cag gaa gta ggc cag acc atc cct gtt ttt gcc ttc ctt<br>Arg Tyr Asn Gln Glu Val Gly Gln Thr Ile Pro Val Phe Ala Phe Leu<br>             995                       1000                   1005 | 3441 |
| gga gcc atg gtg gcc ctg gcc ttc ttc gtg gta cag atc agt aag<br>Gly Ala Met Val Ala Leu Ala Phe Phe Val Val Gln Ile Ser Lys<br>1010                       1015                        1020 | 3486 |
| gcc aag agc cgg ccg aag cgg agg agg ccc agg gca aag cgt cca<br>Ala Lys Ser Arg Pro Lys Arg Arg Arg Pro Arg Ala Lys Arg Pro<br>1025                       1030                        1035 | 3531 |
| caa ctt gca cag cag gcc cac cct gca agg acc ccg tca gtg<br>Gln Leu Ala Gln Gln Ala His Pro Ala Arg Thr Pro Ser Val<br>1040                       1045                        1050 | 3573 |
| tgatcatcac agtggccaga cacagaagct gacaagcttt gaacccctct ggtgccaca | 3633 |
| cagcatcaga gagcatcctg ggaagtgcct gtttccaagg agccctatct ctggattgtg | 3693 |
| gctggcttag tgtgttctgc ccagacgtct atgaggtaca tcctgcagtg cctcactgtg | 3753 |
| tttggctctg gccgaaggtg cccagtagct cagcctccgg tggcatcagg cccagtgaca | 3813 |
| gtgcaccaaa gacacagagc ctggaagggc tgtcgggaca tactttctac ataatgctac | 3873 |
| aaccctgacc aagcgaagac at | 3895 |

<210> SEQ ID NO 2
<211> LENGTH: 1052
<212> TYPE: PRT
<213> ORGANISM: Rattus sp.

<400> SEQUENCE: 2

Met Lys Leu Val Asn Ile Trp Leu Leu Leu Leu Val Val Leu Leu Cys
1                 5                    10                  15

-continued

Gly Lys Lys His Leu Gly Asp Arg Leu Gly Lys Lys Ala Phe Glu Lys
              20                  25                  30

Ala Pro Cys Pro Ser Cys Ser His Leu Thr Leu Lys Val Glu Phe Ser
          35                  40                  45

Ser Thr Val Val Glu Tyr Glu Tyr Ile Val Ala Phe Asn Gly Tyr Phe
50                  55                  60

Thr Ala Lys Ala Arg Asn Ser Phe Ile Ser Ser Ala Leu Lys Ser Ser
65                  70                  75                  80

Glu Val Asp Asn Trp Arg Ile Ile Pro Arg Asn Asn Pro Ser Ser Asp
              85                  90                  95

Tyr Pro Ser Asp Phe Glu Val Ile Gln Ile Lys Glu Lys Gln Lys Ala
              100                 105                 110

Gly Leu Leu Thr Leu Glu Asp His Pro Asn Ile Lys Arg Val Thr Pro
              115                 120                 125

Gln Arg Lys Val Phe Arg Ser Leu Lys Phe Ala Glu Ser Asp Pro Ile
        130                 135                 140

Val Pro Cys Asn Glu Thr Arg Trp Ser Gln Lys Trp Gln Ser Ser Arg
145                 150                 155                 160

Pro Leu Lys Arg Ala Ser Leu Ser Leu Gly Ser Gly Phe Trp His Ala
              165                 170                 175

Thr Gly Arg His Ser Ser Arg Arg Leu Leu Arg Ala Ile Pro Arg Gln
              180                 185                 190

Val Ala Gln Thr Leu Gln Ala Asp Val Leu Trp Gln Met Gly Tyr Thr
        195                 200                 205

Gly Ala Asn Val Arg Val Ala Val Phe Asp Thr Gly Leu Ser Glu Lys
              210                 215                 220

His Pro His Phe Lys Asn Val Lys Glu Arg Thr Asn Trp Thr Asn Glu
225                 230                 235                 240

Arg Thr Leu Asp Asp Gly Leu Gly His Gly Thr Phe Val Ala Gly Val
              245                 250                 255

Ile Ala Ser Met Arg Glu Cys Gln Gly Phe Ala Pro Asp Ala Glu Leu
              260                 265                 270

His Ile Phe Arg Val Phe Thr Asn Asn Gln Val Ser Tyr Thr Ser Trp
        275                 280                 285

Phe Leu Asp Ala Phe Asn Tyr Ala Ile Leu Lys Lys Met Asp Val Leu
290                 295                 300

Asn Leu Ser Ile Gly Gly Pro Asp Phe Met Asp His Pro Phe Val Asp
305                 310                 315                 320

Lys Val Trp Glu Leu Thr Ala Asn Asn Val Ile Met Val Ser Ala Ile
              325                 330                 335

Gly Asn Asp Gly Pro Leu Tyr Gly Thr Leu Asn Asn Pro Ala Asp Gln
              340                 345                 350

Met Asp Val Ile Gly Val Gly Gly Ile Asp Phe Glu Asp Asn Ile Ala
        355                 360                 365

Arg Phe Ser Ser Arg Gly Met Thr Thr Trp Glu Leu Pro Gly Gly Tyr
370                 375                 380

Gly Arg Val Lys Pro Asp Ile Val Thr Tyr Gly Ala Gly Val Arg Gly
385                 390                 395                 400

Ser Gly Val Lys Gly Gly Cys Arg Ala Leu Ser Gly Thr Ser Val Ala
              405                 410                 415

Ser Pro Val Val Ala Gly Ala Val Thr Leu Leu Val Ser Thr Val Gln
              420                 425                 430

Lys Arg Glu Leu Val Asn Pro Ala Ser Val Lys Gln Ala Leu Ile Ala

-continued

```
            435                 440                 445
Ser Ala Arg Arg Leu Pro Gly Val Asn Met Phe Glu Gln Gly His Gly
            450                 455                 460

Lys Leu Asp Leu Leu Arg Ala Tyr Gln Ile Leu Ser Ser Tyr Lys Pro
465                 470                 475                 480

Gln Ala Ser Leu Ser Pro Ser Tyr Ile Asp Leu Thr Glu Cys Pro Tyr
                485                 490                 495

Met Trp Pro Tyr Cys Ser Gln Pro Ile Tyr Tyr Gly Gly Met Pro Thr
                500                 505                 510

Ile Val Asn Val Thr Ile Leu Asn Gly Met Gly Val Thr Gly Arg Ile
                515                 520                 525

Val Asp Lys Pro Glu Trp Arg Pro Tyr Leu Pro Gln Asn Gly Asp Asn
530                 535                 540

Ile Glu Val Ala Phe Ser Tyr Ser Ser Val Leu Trp Pro Trp Ser Gly
545                 550                 555                 560

Tyr Leu Ala Ile Ser Ile Ser Val Thr Lys Lys Ala Ala Ser Trp Glu
                565                 570                 575

Gly Ile Ala Gln Gly His Ile Met Ile Thr Val Ala Ser Pro Ala Glu
                580                 585                 590

Thr Glu Leu Lys Asn Gly Ala Glu His Thr Ser Thr Val Lys Leu Pro
                595                 600                 605

Ile Lys Val Lys Ile Ile Pro Thr Pro Pro Arg Ser Lys Arg Val Leu
                610                 615                 620

Trp Asp Gln Tyr His Asn Leu Arg Tyr Pro Pro Gly Tyr Phe Pro Arg
625                 630                 635                 640

Asp Asn Leu Arg Met Lys Asn Asp Pro Leu Asp Trp Asn Gly Asp His
                645                 650                 655

Val His Thr Asn Phe Arg Asp Met Tyr Gln His Leu Arg Ser Met Gly
                660                 665                 670

Tyr Phe Val Glu Val Leu Gly Ala Pro Phe Thr Cys Phe Asp Ala Thr
                675                 680                 685

Gln Tyr Gly Thr Leu Leu Met Val Asp Ser Glu Glu Tyr Phe Pro
                690                 695                 700

Glu Glu Ile Ala Lys Leu Arg Arg Asp Val Asp Asn Gly Leu Ser Leu
705                 710                 715                 720

Val Val Phe Ser Asp Trp Tyr Asn Thr Ser Val Met Arg Lys Val Lys
                725                 730                 735

Phe Tyr Asp Glu Asn Thr Arg Gln Trp Trp Met Pro Asp Thr Gly Gly
                740                 745                 750

Ala Asn Val Pro Ala Leu Asn Glu Leu Leu Ser Val Trp Asn Met Gly
                755                 760                 765

Phe Ser Asp Gly Leu Tyr Glu Gly Glu Phe Ala Leu Ala Asn His Asp
                770                 775                 780

Met Tyr Tyr Ala Ser Gly Cys Ser Ile Ala Arg Phe Pro Glu Asp Gly
785                 790                 795                 800

Val Val Ile Thr Gln Thr Phe Lys Asp Gln Gly Leu Glu Val Leu Lys
                805                 810                 815

Gln Glu Thr Ala Val Val Asp Asn Val Pro Ile Leu Gly Leu Tyr Gln
                820                 825                 830

Ile Pro Ala Glu Gly Gly Gly Arg Ile Val Leu Tyr Gly Asp Ser Asn
                835                 840                 845

Cys Leu Asp Asp Ser His Arg Gln Lys Asp Cys Phe Trp Leu Leu Asp
850                 855                 860
```

```
Ala Leu Leu Gln Tyr Thr Ser Tyr Gly Val Thr Pro Pro Ser Leu Ser
865                 870                 875                 880

His Ser Gly Asn Arg Gln Arg Pro Pro Ser Gly Ala Gly Leu Ala Pro
                885                 890                 895

Pro Glu Arg Met Glu Gly Asn His Leu His Arg Tyr Ser Lys Val Leu
            900                 905                 910

Glu Ala His Leu Gly Asp Pro Lys Pro Arg Pro Leu Pro Ala Cys Pro
        915                 920                 925

His Leu Ser Trp Ala Lys Pro Gln Pro Leu Asn Glu Thr Ala Pro Ser
    930                 935                 940

Asn Leu Trp Lys His Gln Lys Leu Leu Ser Ile Asp Leu Asp Lys Val
945                 950                 955                 960

Val Leu Pro Asn Phe Arg Ser Asn Arg Pro Gln Val Arg Pro Leu Ser
                965                 970                 975

Pro Gly Glu Ser Gly Ala Trp Asp Ile Pro Gly Gly Ile Met Pro Gly
            980                 985                 990

Arg Tyr Asn Gln Glu Val Gly Gln  Thr Ile Pro Val Phe  Ala Phe Leu
        995                 1000                 1005

Gly Ala  Met Val Ala Leu Ala  Phe Phe Val Val Gln  Ile Ser Lys
    1010                 1015                 1020

Ala Lys  Ser Arg Pro Lys Arg  Arg Arg Pro Arg Ala  Lys Arg Pro
    1025                 1030                 1035

Gln Leu  Ala Gln Gln Ala His  Pro Ala Arg Thr Pro  Ser Val
    1040                 1045                 1050

<210> SEQ ID NO 3
<211> LENGTH: 3788
<212> TYPE: DNA
<213> ORGANISM: Mus sp.
<220> FEATURE:
<221> NAME/KEY: CDS
<222> LOCATION: (8)..(3163)

<400> SEQUENCE: 3 gcattcc atg aag ctc gtc agc acc tgg ctt ctt gtg ctg gtg gtt ttg        49
        Met Lys Leu Val Ser Thr Trp Leu Leu Val Leu Val Val Leu
        1               5                   10 ctc tgt ggg aaa cgg cac ctg ggc gac agg ctg ggg acg aga gct ttg        97
Leu Cys Gly Lys Arg His Leu Gly Asp Arg Leu Gly Thr Arg Ala Leu
15              20                  25                  30 gaa aag gcc ccg tgc ccc agc tgc tcc cac ctg act ttg aag gtg gaa       145
Glu Lys Ala Pro Cys Pro Ser Cys Ser His Leu Thr Leu Lys Val Glu
                35                  40                  45 ttc tct tca act gtg gtg gag tac gaa tat att gtg gct ttc aac gga       193
Phe Ser Ser Thr Val Val Glu Tyr Glu Tyr Ile Val Ala Phe Asn Gly
            50                  55                  60 tac ttc aca gcc aaa gct aga aac tca ttt att tca agt gcg ctg aaa       241
Tyr Phe Thr Ala Lys Ala Arg Asn Ser Phe Ile Ser Ser Ala Leu Lys
        65                  70                  75 agc agt gaa gtg gaa aac tgg aga ata ata cct cgg aac aac cca tcc       289
Ser Ser Glu Val Glu Asn Trp Arg Ile Ile Pro Arg Asn Asn Pro Ser
    80                  85                  90 agt gac tac cct agt gat ttt gag gtg att cag ata aaa gag aag cag       337
Ser Asp Tyr Pro Ser Asp Phe Glu Val Ile Gln Ile Lys Glu Lys Gln
95                  100                 105                 110 aag gcg ggg ctg ctc aca ctt gaa gat cac ccc aac atc aag cgg gtg       385
Lys Ala Gly Leu Leu Thr Leu Glu Asp His Pro Asn Ile Lys Arg Val
                115                 120                 125
```

```
                                                      -continued aca ccc cag cgg aaa gtc ttt cgt tcc ctc aag ttt gct gaa tcc aac          433
Thr Pro Gln Arg Lys Val Phe Arg Ser Leu Lys Phe Ala Glu Ser Asn
        130                 135                 140 ccc atc gtg ccc tgt aat gaa acc cgg tgg agc cag aag tgg cag tca          481
Pro Ile Val Pro Cys Asn Glu Thr Arg Trp Ser Gln Lys Trp Gln Ser
            145                 150                 155 tca cgt ccc ctg aaa aga gcc agt ctc tcc ctg ggc tct gga ttc tgg          529
Ser Arg Pro Leu Lys Arg Ala Ser Leu Ser Leu Gly Ser Gly Phe Trp
    160                 165                 170 cat gca aca gga aga cat tca agt cgg cga ttg ctg aga gcc att cct          577
His Ala Thr Gly Arg His Ser Ser Arg Arg Leu Leu Arg Ala Ile Pro
175                 180                 185                 190 cgc cag gtc gcc cag aca ctg cag gca gat gtg ctg tgg cag atg gga          625
Arg Gln Val Ala Gln Thr Leu Gln Ala Asp Val Leu Trp Gln Met Gly
                195                 200                 205 tac aca ggt gct aat gtc aga gtt gct gtt ttt gat act ggg ctc agt          673
Tyr Thr Gly Ala Asn Val Arg Val Ala Val Phe Asp Thr Gly Leu Ser
            210                 215                 220 gag aag cat ccg cat ttt aag aat gtg aag gag aga acc aac tgg acc          721
Glu Lys His Pro His Phe Lys Asn Val Lys Glu Arg Thr Asn Trp Thr
    225                 230                 235 aat gag cgg acc ctg gat gat ggg cta ggc cat ggc aca ttc gtt gca          769
Asn Glu Arg Thr Leu Asp Asp Gly Leu Gly His Gly Thr Phe Val Ala
240                 245                 250 ggt gtg att gcc agc atg agg gag tgc caa gga ttt gct cca gat gca          817
Gly Val Ile Ala Ser Met Arg Glu Cys Gln Gly Phe Ala Pro Asp Ala
255                 260                 265                 270 gag ctg cac atc ttc agg gtc ttt acc aac aat cag gtg tct tac aca          865
Glu Leu His Ile Phe Arg Val Phe Thr Asn Asn Gln Val Ser Tyr Thr
                275                 280                 285 tct tgg ttt ctg gat gcc ttc aac tat gcc atc cta aag aag atg gac          913
Ser Trp Phe Leu Asp Ala Phe Asn Tyr Ala Ile Leu Lys Lys Met Asp
            290                 295                 300 gtt ctc aac ctt agc atc ggt ggg ccc gac ttc atg gat cat ccg ttt          961
Val Leu Asn Leu Ser Ile Gly Gly Pro Asp Phe Met Asp His Pro Phe
    305                 310                 315 gtt gac aag gtg tgg gaa tta aca gct aac aat gta att atg gtt tct         1009
Val Asp Lys Val Trp Glu Leu Thr Ala Asn Asn Val Ile Met Val Ser
320                 325                 330 gct att ggc aat gat gga cct ctc tat ggc act ctg aat aac cct gct         1057
Ala Ile Gly Asn Asp Gly Pro Leu Tyr Gly Thr Leu Asn Asn Pro Ala
335                 340                 345                 350 gat cag atg gat gtg att gga gtg ggt ggc att gac ttt gaa gat aac         1105
Asp Gln Met Asp Val Ile Gly Val Gly Gly Ile Asp Phe Glu Asp Asn
                355                 360                 365 atc gct cgc ttt tct tcc agg gga atg act acc tgg gaa tta cca gga         1153
Ile Ala Arg Phe Ser Ser Arg Gly Met Thr Thr Trp Glu Leu Pro Gly
            370                 375                 380 ggc tat ggt cgt gtg aag cct gac att gtc acc tat ggt gct gga gtg         1201
Gly Tyr Gly Arg Val Lys Pro Asp Ile Val Thr Tyr Gly Ala Gly Val
    385                 390                 395 cgg ggt tcc ggt gtg aaa ggg ggc tgc cgt gca ctc tca ggg acc agt         1249
Arg Gly Ser Gly Val Lys Gly Gly Cys Arg Ala Leu Ser Gly Thr Ser
400                 405                 410 gtc gct tcc cca gtg gtc gct ggg gcc gtc acc ttg tta gta agc aca         1297
Val Ala Ser Pro Val Val Ala Gly Ala Val Thr Leu Leu Val Ser Thr
415                 420                 425                 430 gta cag aag cgg gag ctg gtg aat cct gcc agt gtg aag caa gct ttg         1345
Val Gln Lys Arg Glu Leu Val Asn Pro Ala Ser Val Lys Gln Ala Leu
```

-continued

|  | 435 |  |  |  | 440 |  |  |  | 445 |  |  |  |
|---|---|---|---|---|---|---|---|---|---|---|---|---|
| ata | gcg | tca | gcc | cgg | aga | ctt | cct | ggg | gtc | aac | atg | ttc | gag | caa | ggt | 1393 |
| Ile | Ala | Ser | Ala | Arg | Arg | Leu | Pro | Gly | Val | Asn | Met | Phe | Glu | Gln | Gly | |
|  |  | 450 |  |  |  | 455 |  |  |  | 460 |  |  |

```
ata gcg tca gcc cgg aga ctt cct ggg gtc aac atg ttc gag caa ggt    1393
Ile Ala Ser Ala Arg Arg Leu Pro Gly Val Asn Met Phe Glu Gln Gly
        450             455             460 cat ggc aag ttg gat ctg ctg cga gct tat cag atc ctc agc agc tat    1441
His Gly Lys Leu Asp Leu Leu Arg Ala Tyr Gln Ile Leu Ser Ser Tyr
        465             470             475 aaa ccg cag gca agc ctg agt cct agc tac atc gac ctg act gag tgt    1489
Lys Pro Gln Ala Ser Leu Ser Pro Ser Tyr Ile Asp Leu Thr Glu Cys
        480             485             490 ccc tac atg tgg ccc tac tgc tcc cag cct atc tac tat gga gga atg    1537
Pro Tyr Met Trp Pro Tyr Cys Ser Gln Pro Ile Tyr Tyr Gly Gly Met
495             500             505             510 cca aca atc gtt aat gtc acc atc ctc aat ggc atg ggc gtc aca gga    1585
Pro Thr Ile Val Asn Val Thr Ile Leu Asn Gly Met Gly Val Thr Gly
            515             520             525 aga att gtg gat aag cct gag tgg cga ccc tat tta cca cag aat gga    1633
Arg Ile Val Asp Lys Pro Glu Trp Arg Pro Tyr Leu Pro Gln Asn Gly
        530             535             540 gac aac att gaa gtg gcc ttc tcc tac tcc tca gtg ttg tgg ccc tgg    1681
Asp Asn Ile Glu Val Ala Phe Ser Tyr Ser Ser Val Leu Trp Pro Trp
        545             550             555 tca ggt tac ctt gcc atc tcc att tct gtg acc aag aag gca gct tcc    1729
Ser Gly Tyr Leu Ala Ile Ser Ile Ser Val Thr Lys Lys Ala Ala Ser
        560             565             570 tgg gaa ggc atc gct cag ggc cac atc atg atc aca gtg gcg tcc cca    1777
Trp Glu Gly Ile Ala Gln Gly His Ile Met Ile Thr Val Ala Ser Pro
575             580             585             590 gca gag aca gag tta cac agt ggt gcg gag cac act tcc acc gtg aag    1825
Ala Glu Thr Glu Leu His Ser Gly Ala Glu His Thr Ser Thr Val Lys
            595             600             605 ctg ccc atc aag gtg aag atc att ccc acc cct cct cgg agc aag aga    1873
Leu Pro Ile Lys Val Lys Ile Ile Pro Thr Pro Pro Arg Ser Lys Arg
        610             615             620 gtc ctc tgg gac cag tac cac aac ctc cgc tac cca cct ggc tac ttc    1921
Val Leu Trp Asp Gln Tyr His Asn Leu Arg Tyr Pro Pro Gly Tyr Phe
        625             630             635 ccc agg gac aac ttg cgg atg aag aat gac cct tta gac tgg aat ggc    1969
Pro Arg Asp Asn Leu Arg Met Lys Asn Asp Pro Leu Asp Trp Asn Gly
640             645             650 gac cac gtc cac acc aac ttc agg gac atg tac cag cat ctg cgc agc    2017
Asp His Val His Thr Asn Phe Arg Asp Met Tyr Gln His Leu Arg Ser
655             660             665             670 atg ggc tac ttc gtg gag gtg ctc ggc gcc cca ttc aca tgt ttt gac    2065
Met Gly Tyr Phe Val Glu Val Leu Gly Ala Pro Phe Thr Cys Phe Asp
            675             680             685 gcc aca cag tat ggc act ttg ctg ctg gtg gac agt gag gaa gag tac    2113
Ala Thr Gln Tyr Gly Thr Leu Leu Leu Val Asp Ser Glu Glu Glu Tyr
        690             695             700 ttc cct gag gag att gct aag ctg agg agg gat gtg gac aat ggc ctt    2161
Phe Pro Glu Glu Ile Ala Lys Leu Arg Arg Asp Val Asp Asn Gly Leu
705             710             715 tcc ctc gtc atc ttc agt gac tgg tac aac act tct gtt atg aga aaa    2209
Ser Leu Val Ile Phe Ser Asp Trp Tyr Asn Thr Ser Val Met Arg Lys
720             725             730 gtg aag ttt tat gat gaa aac acc agg cag tgg tgg atg cca gac acc    2257
Val Lys Phe Tyr Asp Glu Asn Thr Arg Gln Trp Trp Met Pro Asp Thr
735             740             745             750 gga gga gcg aac atc cca gct ctg aat gag ctg ctg tct gtg tgg aac    2305
Gly Gly Ala Asn Ile Pro Ala Leu Asn Glu Leu Leu Ser Val Trp Asn
```

-continued

| | | |
|---|---|---|
| Gly Gly Ala Asn Ile Pro Ala Leu Asn Glu Leu Leu Ser Val Trp Asn<br>755     760     765 | | |
| atg ggg ttc agt gac ggc cta tat gaa ggg gag ttt gtc ctg gca aac<br>Met Gly Phe Ser Asp Gly Leu Tyr Glu Gly Glu Phe Val Leu Ala Asn<br>770     775     780 | | 2353 |
| cat gac atg tac tat gcg tcg ggg tgc agc atc gcc aag ttt cca gaa<br>His Asp Met Tyr Tyr Ala Ser Gly Cys Ser Ile Ala Lys Phe Pro Glu<br>785     790     795 | | 2401 |
| gat ggc gtc gtg atc aca cag act ttc aag gac caa gga ttg gag gtc<br>Asp Gly Val Val Ile Thr Gln Thr Phe Lys Asp Gln Gly Leu Glu Val<br>800     805     810 | | 2449 |
| tta aaa caa gag aca gca gtt gtg gaa aat gtt ccc att ttg ggg ctt<br>Leu Lys Gln Glu Thr Ala Val Val Glu Asn Val Pro Ile Leu Gly Leu<br>815     820     825     830 | | 2497 |
| tat cag att cca tct gaa ggt gga ggc cgg atc gtg ctg tat gga gac<br>Tyr Gln Ile Pro Ser Glu Gly Gly Gly Arg Ile Val Leu Tyr Gly Asp<br>835     840     845 | | 2545 |
| tcc aac tgc ttg gat gac agt cac aga cag aag gac tgc ttt tgg ctt<br>Ser Asn Cys Leu Asp Asp Ser His Arg Gln Lys Asp Cys Phe Trp Leu<br>850     855     860 | | 2593 |
| ctg gat gcg ctc ctt cag tac aca tcc tat ggc gtg acc cct ccc agc<br>Leu Asp Ala Leu Leu Gln Tyr Thr Ser Tyr Gly Val Thr Pro Pro Ser<br>865     870     875 | | 2641 |
| ctc agc cat tca ggg aac cgg cag cgc cca cct agc gga gcc ggc ttg<br>Leu Ser His Ser Gly Asn Arg Gln Arg Pro Pro Ser Gly Ala Gly Leu<br>880     885     890 | | 2689 |
| gcc cct cct gaa agg atg gaa gga aac cac ctc cat cgg tac tcc aaa<br>Ala Pro Pro Glu Arg Met Glu Gly Asn His Leu His Arg Tyr Ser Lys<br>895     900     905     910 | | 2737 |
| gtt ctt gaa gcc cac ttg gga gac ccg aaa cct cgg ccc ctg cca gcc<br>Val Leu Glu Ala His Leu Gly Asp Pro Lys Pro Arg Pro Leu Pro Ala<br>915     920     925 | | 2785 |
| tgt cca cat ttg tca tgg gcc aag cca cag cct ttg aat gag acg gca<br>Cys Pro His Leu Ser Trp Ala Lys Pro Gln Pro Leu Asn Glu Thr Ala<br>930     935     940 | | 2833 |
| ccc agt aat ctt tgg aaa cat cag aag ctg ctc tcc att gac ctg gac<br>Pro Ser Asn Leu Trp Lys His Gln Lys Leu Leu Ser Ile Asp Leu Asp<br>945     950     955 | | 2881 |
| aaa gta gtg tta ccc aac ttt cga tcc aat cgc cct caa gtg aga cct<br>Lys Val Val Leu Pro Asn Phe Arg Ser Asn Arg Pro Gln Val Arg Pro<br>960     965     970 | | 2929 |
| ttg tcc cct gga gag agt ggt gcc tgg gac att cct gga ggg atc atg<br>Leu Ser Pro Gly Glu Ser Gly Ala Trp Asp Ile Pro Gly Gly Ile Met<br>975     980     985     990 | | 2977 |
| cct ggc cgc tac aac cag gag gtg gga cag acc atc ccc gtc ttc gcc<br>Pro Gly Arg Tyr Asn Gln Glu Val Gly Gln Thr Ile Pro Val Phe Ala<br>995     1000     1005 | | 3025 |
| ttc ctc gga gcc atg gtg gcc ctg gcc ttc ttt gtg gta cag atc<br>Phe Leu Gly Ala Met Val Ala Leu Ala Phe Phe Val Val Gln Ile<br>1010     1015     1020 | | 3070 |
| agc aag gcc aag agc cgg ccg aag cgg agg agg ccc agg gca aag<br>Ser Lys Ala Lys Ser Arg Pro Lys Arg Arg Arg Pro Arg Ala Lys<br>1025     1030     1035 | | 3115 |
| cgt cca caa ctt gca cag cag gcc cac cct gca agg acc cca tca<br>Arg Pro Gln Leu Ala Gln Gln Ala His Pro Ala Arg Thr Pro Ser<br>1040     1045     1050 | | 3160 |
| gtg tgagcatcgc agtagccagc cacagaagct aacaagcctt gaaccactct<br>Val | | 3213 |
| ggtggccaca cagcgcctca gagagcattc tgggaagtgc ctgtttccga ggaccctgtc | | 3273 |

-continued

```
tccagcttgt ggctatctta ctgtgttctg cccaggcacc tgatgaggta catcctgcag    3333
tgcctctctg tgcttggctc tggcagaagg cacccagtga catcaggcat caggcccagt    3393
gacagtgcac caaagacaca gagcctggaa gggctgtcgg acatacttt  ctacataacg    3453 ctacaaccct gaccaagcaa agacatgctt gttacaggct attttctata tttattgtgg    3513
gagagtcact ttaaagactg tgctagttgg aaacagagct gttgctgttg tcagtcgagt    3573
gcagttttct gcagcgatgt cataaggagt cagattccgt gacctcctct ttgatggagg    3633
acacactgaa ctgaagggga cttgcgcgga tgtgggagat gcaagccttc gctttatttt    3693
tttataacta tcaactgcca tcatgttttg taatttgggg atcttgattt caccgttgtt    3753
ggtgaaggaa attttcaata aatatgcata acctt                               3788
```

<210> SEQ ID NO 4
<211> LENGTH: 1052
<212> TYPE: PRT
<213> ORGANISM: Mus sp.

<400> SEQUENCE: 4

```
Met Lys Leu Val Ser Thr Trp Leu Leu Val Leu Val Leu Leu Cys
 1               5                  10                  15

Gly Lys Arg His Leu Gly Asp Arg Leu Gly Thr Arg Ala Leu Glu Lys
            20                  25                  30

Ala Pro Cys Pro Ser Cys Ser His Leu Thr Leu Lys Val Glu Phe Ser
        35                  40                  45

Ser Thr Val Val Glu Tyr Glu Tyr Ile Val Ala Phe Asn Gly Tyr Phe
    50                  55                  60

Thr Ala Lys Ala Arg Asn Ser Phe Ile Ser Ser Ala Leu Lys Ser Ser
65                  70                  75                  80

Glu Val Glu Asn Trp Arg Ile Ile Pro Arg Asn Asn Pro Ser Ser Asp
                85                  90                  95

Tyr Pro Ser Asp Phe Glu Val Ile Gln Ile Lys Glu Lys Gln Lys Ala
            100                 105                 110

Gly Leu Leu Thr Leu Glu Asp His Pro Asn Ile Lys Arg Val Thr Pro
        115                 120                 125

Gln Arg Lys Val Phe Arg Ser Leu Lys Phe Ala Glu Ser Asn Pro Ile
    130                 135                 140

Val Pro Cys Asn Glu Thr Arg Trp Ser Gln Lys Trp Gln Ser Ser Arg
145                 150                 155                 160

Pro Leu Lys Arg Ala Ser Leu Ser Leu Gly Ser Gly Phe Trp His Ala
                165                 170                 175

Thr Gly Arg His Ser Ser Arg Arg Leu Leu Arg Ala Ile Pro Arg Gln
            180                 185                 190

Val Ala Gln Thr Leu Gln Ala Asp Val Leu Trp Gln Met Gly Tyr Thr
        195                 200                 205

Gly Ala Asn Val Arg Val Ala Val Phe Asp Thr Gly Leu Ser Glu Lys
    210                 215                 220

His Pro His Phe Lys Asn Val Lys Glu Arg Thr Asn Trp Thr Asn Glu
225                 230                 235                 240

Arg Thr Leu Asp Asp Gly Leu Gly His Gly Thr Phe Val Ala Gly Val
                245                 250                 255

Ile Ala Ser Met Arg Glu Cys Gln Gly Phe Ala Pro Asp Ala Glu Leu
            260                 265                 270

His Ile Phe Arg Val Phe Thr Asn Asn Gln Val Ser Tyr Thr Ser Trp
```

-continued

```
                275                 280                 285
Phe Leu Asp Ala Phe Asn Tyr Ala Ile Leu Lys Lys Met Asp Val Leu
            290                 295                 300
Asn Leu Ser Ile Gly Gly Pro Asp Phe Met Asp His Pro Phe Val Asp
305                 310                 315                 320
Lys Val Trp Glu Leu Thr Ala Asn Asn Val Ile Met Val Ser Ala Ile
                325                 330                 335
Gly Asn Asp Gly Pro Leu Tyr Gly Thr Leu Asn Asn Pro Ala Asp Gln
            340                 345                 350
Met Asp Val Ile Gly Val Gly Gly Ile Asp Phe Glu Asp Asn Ile Ala
                355                 360                 365
Arg Phe Ser Ser Arg Gly Met Thr Thr Trp Glu Leu Pro Gly Gly Tyr
            370                 375                 380
Gly Arg Val Lys Pro Asp Ile Val Thr Tyr Gly Ala Gly Val Arg Gly
385                 390                 395                 400
Ser Gly Val Lys Gly Gly Cys Arg Ala Leu Ser Gly Thr Ser Val Ala
                405                 410                 415
Ser Pro Val Val Ala Gly Ala Val Thr Leu Leu Val Ser Thr Val Gln
            420                 425                 430
Lys Arg Glu Leu Val Asn Pro Ala Ser Val Lys Gln Ala Leu Ile Ala
            435                 440                 445
Ser Ala Arg Arg Leu Pro Gly Val Asn Met Phe Glu Gln Gly His Gly
            450                 455                 460
Lys Leu Asp Leu Leu Arg Ala Tyr Gln Ile Leu Ser Ser Tyr Lys Pro
465                 470                 475                 480
Gln Ala Ser Leu Ser Pro Ser Tyr Ile Asp Leu Thr Glu Cys Pro Tyr
                485                 490                 495
Met Trp Pro Tyr Cys Ser Gln Pro Ile Tyr Tyr Gly Gly Met Pro Thr
                500                 505                 510
Ile Val Asn Val Thr Ile Leu Asn Gly Met Gly Val Thr Gly Arg Ile
                515                 520                 525
Val Asp Lys Pro Glu Trp Arg Pro Tyr Leu Pro Gln Asn Gly Asp Asn
            530                 535                 540
Ile Glu Val Ala Phe Ser Tyr Ser Ser Val Leu Trp Pro Trp Ser Gly
545                 550                 555                 560
Tyr Leu Ala Ile Ser Ile Ser Val Thr Lys Lys Ala Ala Ser Trp Glu
                565                 570                 575
Gly Ile Ala Gln Gly His Ile Met Ile Thr Val Ala Ser Pro Ala Glu
                580                 585                 590
Thr Glu Leu His Ser Gly Ala Glu His Thr Ser Thr Val Lys Leu Pro
                595                 600                 605
Ile Lys Val Lys Ile Ile Pro Thr Pro Arg Ser Lys Arg Val Leu
            610                 615                 620
Trp Asp Gln Tyr His Asn Leu Arg Tyr Pro Pro Gly Tyr Phe Pro Arg
625                 630                 635                 640
Asp Asn Leu Arg Met Lys Asn Asp Pro Leu Asp Trp Asn Gly Asp His
                645                 650                 655
Val His Thr Asn Phe Arg Asp Met Tyr Gln His Leu Arg Ser Met Gly
                660                 665                 670
Tyr Phe Val Glu Val Leu Gly Ala Pro Phe Thr Cys Phe Asp Ala Thr
            675                 680                 685
Gln Tyr Gly Thr Leu Leu Leu Val Asp Ser Glu Glu Tyr Phe Pro
            690                 695                 700
```

```
Glu Glu Ile Ala Lys Leu Arg Arg Asp Val Asp Asn Gly Leu Ser Leu
705                 710                 715                 720

Val Ile Phe Ser Asp Trp Tyr Asn Thr Ser Val Met Arg Lys Val Lys
                725                 730                 735

Phe Tyr Asp Glu Asn Thr Arg Gln Trp Trp Met Pro Asp Thr Gly Gly
            740                 745                 750

Ala Asn Ile Pro Ala Leu Asn Glu Leu Leu Ser Val Trp Asn Met Gly
        755                 760                 765

Phe Ser Asp Gly Leu Tyr Glu Gly Glu Phe Val Leu Ala Asn His Asp
770                 775                 780

Met Tyr Tyr Ala Ser Gly Cys Ser Ile Ala Lys Phe Pro Glu Asp Gly
785                 790                 795                 800

Val Val Ile Thr Gln Thr Phe Lys Asp Gln Gly Leu Glu Val Leu Lys
                805                 810                 815

Gln Glu Thr Ala Val Val Glu Asn Val Pro Ile Leu Gly Leu Tyr Gln
            820                 825                 830

Ile Pro Ser Glu Gly Gly Gly Arg Ile Val Leu Tyr Gly Asp Ser Asn
        835                 840                 845

Cys Leu Asp Asp Ser His Arg Gln Lys Asp Cys Phe Trp Leu Leu Asp
850                 855                 860

Ala Leu Leu Gln Tyr Thr Ser Tyr Gly Val Thr Pro Pro Ser Leu Ser
865                 870                 875                 880

His Ser Gly Asn Arg Gln Arg Pro Pro Ser Gly Ala Gly Leu Ala Pro
                885                 890                 895

Pro Glu Arg Met Glu Gly Asn His Leu His Arg Tyr Ser Lys Val Leu
            900                 905                 910

Glu Ala His Leu Gly Asp Pro Lys Pro Arg Pro Leu Pro Ala Cys Pro
        915                 920                 925

His Leu Ser Trp Ala Lys Pro Gln Pro Leu Asn Glu Thr Ala Pro Ser
930                 935                 940

Asn Leu Trp Lys His Gln Lys Leu Leu Ser Ile Asp Leu Asp Lys Val
945                 950                 955                 960

Val Leu Pro Asn Phe Arg Ser Asn Arg Pro Gln Val Arg Pro Leu Ser
                965                 970                 975

Pro Gly Glu Ser Gly Ala Trp Asp Ile Pro Gly Gly Ile Met Pro Gly
            980                 985                 990

Arg Tyr Asn Gln Glu Val Gly Gln Thr Ile Pro Val Phe Ala Phe Leu
        995                 1000                1005

Gly Ala Met Val Ala Leu Ala Phe Phe Val Val Gln Ile Ser Lys
        1010                1015                1020

Ala Lys Ser Arg Pro Lys Arg Arg Arg Pro Arg Ala Lys Arg Pro
        1025                1030                1035

Gln Leu Ala Gln Gln Ala His Pro Ala Arg Thr Pro Ser Val
        1040                1045                1050

<210> SEQ ID NO 5
<211> LENGTH: 4338
<212> TYPE: DNA
<213> ORGANISM: Homo sapiens
<220> FEATURE:
<221> NAME/KEY: CDS
<222> LOCATION: (497)..(3652)

<400> SEQUENCE: 5
cagggcacgc tgggtcggcg gagctgaggc tcccagctgt gggcctcgct ggcccggtcg    60
```

```
                                                             -continued cccagtctcg cgagagttgg gagtaaacag ccccgaatgg agtgcccagg cgtgttcgcc    120
gcggaggcgc cgttatcccg ggcccgccgg ccctgagctc ccggcggcgc agattggctc    180
acagtggttg attgatcaac cccattggac gttggttctg tggtacaaat ggagtacagg    240
actcagtcgt cacggcctga gtgagagaag ccttatttcc aagatggaga agaagcggag    300
aaagaaatga aagcctctct tcaggctgaa ccacaaaagg ccatgggatt taacttttat    360
ttatgttggg caagactgta agatggctga tcagtaatgt tgcagctttt agctgaaaca    420
aaaattcact tttaatcaag aagaaaaaag tgtgatttga atatatgcaa ttttatgatc    480
atattcgctt gtgacc atg aag ctt gtc aac atc tgg ctg ctt ctg ctc gtg    532
               Met Lys Leu Val Asn Ile Trp Leu Leu Leu Leu Val
                 1               5                  10 gtt ttg ctc tgt ggg aag aaa cat ctg ggc gac aga ctg gaa aag aaa     580
Val Leu Leu Cys Gly Lys Lys His Leu Gly Asp Arg Leu Glu Lys Lys
         15                  20                  25 tct ttt gaa aag gcc cca tgc cct ggc tgt tcc cac ctg act ttg aag     628
Ser Phe Glu Lys Ala Pro Cys Pro Gly Cys Ser His Leu Thr Leu Lys
     30                  35                  40 gtg gaa ttc tca tca aca gtt gtg gaa tat gaa tat att gtg gct ttc     676
Val Glu Phe Ser Ser Thr Val Val Glu Tyr Glu Tyr Ile Val Ala Phe
45                  50                  55                  60 aat gga tac ttt aca gcc aaa gct aga aat tca ttt att tca agt gcc     724
Asn Gly Tyr Phe Thr Ala Lys Ala Arg Asn Ser Phe Ile Ser Ser Ala
             65                  70                  75 ctg aag agc agt gaa gta gac aat tgg aga att ata cct cga aac aat     772
Leu Lys Ser Ser Glu Val Asp Asn Trp Arg Ile Ile Pro Arg Asn Asn
         80                  85                  90 cca tcc agt gac tac cct agt gat ttt gag gtg att cag ata aaa gaa     820
Pro Ser Ser Asp Tyr Pro Ser Asp Phe Glu Val Ile Gln Ile Lys Glu
     95                  100                 105 aaa cag aaa gcg ggg ctg cta aca ctt gaa gat cat cca aac atc aaa     868
Lys Gln Lys Ala Gly Leu Leu Thr Leu Glu Asp His Pro Asn Ile Lys
110                 115                 120 cgg gtc acg ccc caa cga aaa gtc ttt cgt tcc ctc aag tat gct gaa     916
Arg Val Thr Pro Gln Arg Lys Val Phe Arg Ser Leu Lys Tyr Ala Glu
125                 130                 135                 140 tct gac ccc aca gta ccc tgc aat gaa acc cgg tgg agc cag aag tgg     964
Ser Asp Pro Thr Val Pro Cys Asn Glu Thr Arg Trp Ser Gln Lys Trp
             145                 150                 155 caa tca tca cgt ccc ctg cga aga gcc agc ctc tcc ctg ggc tct ggc    1012
Gln Ser Ser Arg Pro Leu Arg Arg Ala Ser Leu Ser Leu Gly Ser Gly
         160                 165                 170 ttc tgg cat gct acg gga agg cat tcg agc aga cgg ctg ctg aga gcc    1060
Phe Trp His Ala Thr Gly Arg His Ser Ser Arg Arg Leu Leu Arg Ala
     175                 180                 185 atc ccg cgc cag gtt gcc cag aca ctg cag gca gat gtg ctc tgg cag    1108
Ile Pro Arg Gln Val Ala Gln Thr Leu Gln Ala Asp Val Leu Trp Gln
190                 195                 200 atg gga tat aca ggt gct aat gta aga gtt gct gtt ttt gac act ggg    1156
Met Gly Tyr Thr Gly Ala Asn Val Arg Val Ala Val Phe Asp Thr Gly
205                 210                 215                 220 ctg agc gag aag cat ccc cac ttc aaa aat gtg aag gag aga acc aac    1204
Leu Ser Glu Lys His Pro His Phe Lys Asn Val Lys Glu Arg Thr Asn
             225                 230                 235 tgg acc aac gag cga acg ctg gac gat ggg ttg ggc cat ggc aca ttc    1252
Trp Thr Asn Glu Arg Thr Leu Asp Asp Gly Leu Gly His Gly Thr Phe
         240                 245                 250
```

```
gtg gca ggt gtg ata gcc agc atg agg gag tgc caa gga ttt gct cca      1300
Val Ala Gly Val Ile Ala Ser Met Arg Glu Cys Gln Gly Phe Ala Pro
        255                 260                 265 gat gca gaa ctt cac att ttc agg gtc ttt acc aat aat cag gta tct      1348
Asp Ala Glu Leu His Ile Phe Arg Val Phe Thr Asn Asn Gln Val Ser
    270                 275                 280 tac aca tct tgg ttt ttg gac gcc ttc aac tat gcc att tta aag aag      1396
Tyr Thr Ser Trp Phe Leu Asp Ala Phe Asn Tyr Ala Ile Leu Lys Lys
285                 290                 295                 300 atc gac gtg tta aac ctc agc atc ggc ggc ccg gac ttc atg gat cat      1444
Ile Asp Val Leu Asn Leu Ser Ile Gly Gly Pro Asp Phe Met Asp His
                305                 310                 315 ccg ttt gtt gac aag gtg tgg gaa tta aca gct aac aat gta atc atg      1492
Pro Phe Val Asp Lys Val Trp Glu Leu Thr Ala Asn Asn Val Ile Met
            320                 325                 330 gtt tct gct att ggc aat gac gga cct ctt tat ggc act ctg aat aac      1540
Val Ser Ala Ile Gly Asn Asp Gly Pro Leu Tyr Gly Thr Leu Asn Asn
        335                 340                 345 cct gct gat caa atg gat gtg att gga gta ggc ggc att gac ttt gaa      1588
Pro Ala Asp Gln Met Asp Val Ile Gly Val Gly Gly Ile Asp Phe Glu
    350                 355                 360 gat aac atc gcc cgc ttt tct tca agg gga atg act acc tgg gag cta      1636
Asp Asn Ile Ala Arg Phe Ser Ser Arg Gly Met Thr Thr Trp Glu Leu
365                 370                 375                 380 cca gga ggc tac ggt cgc atg aaa cct gac att gtc acc tat ggt gct      1684
Pro Gly Gly Tyr Gly Arg Met Lys Pro Asp Ile Val Thr Tyr Gly Ala
                385                 390                 395 ggc gtg cgg ggt tct ggc gtg aaa ggg ggg tgc cgg gcc ctc tca ggg      1732
Gly Val Arg Gly Ser Gly Val Lys Gly Gly Cys Arg Ala Leu Ser Gly
            400                 405                 410 acc agt gtt gct tct cca gtg gtt gca ggt gct gtc acc ttg tta gtg      1780
Thr Ser Val Ala Ser Pro Val Val Ala Gly Ala Val Thr Leu Leu Val
        415                 420                 425 agc aca gtc cag aag cgt gag ctg gtg aat ccc gcc agt atg aag cag      1828
Ser Thr Val Gln Lys Arg Glu Leu Val Asn Pro Ala Ser Met Lys Gln
    430                 435                 440 gcc ctg atc gcg tca gcc cgg agg ctc ccc ggg gtc aac atg ttt gag      1876
Ala Leu Ile Ala Ser Ala Arg Arg Leu Pro Gly Val Asn Met Phe Glu
445                 450                 455                 460 caa ggc cac ggc aag ctc gat ctg ctc aga gcc tat cag atc ctc aac      1924
Gln Gly His Gly Lys Leu Asp Leu Leu Arg Ala Tyr Gln Ile Leu Asn
                465                 470                 475 agc tac aag cca cag gca agt ttg agc ccc agc tac ata gat ctg act      1972
Ser Tyr Lys Pro Gln Ala Ser Leu Ser Pro Ser Tyr Ile Asp Leu Thr
            480                 485                 490 gag tgt ccc tac atg tgg ccc tac tgc tcc cag ccc atc tac tat gga      2020
Glu Cys Pro Tyr Met Trp Pro Tyr Cys Ser Gln Pro Ile Tyr Tyr Gly
        495                 500                 505 gga atg ccg aca gtt gtt aat gtc acc atc ctc aac ggc atg gga gtc      2068
Gly Met Pro Thr Val Val Asn Val Thr Ile Leu Asn Gly Met Gly Val
    510                 515                 520 aca gga aga att gta gat aag cct gac tgg cag ccc tat ttg cca cag      2116
Thr Gly Arg Ile Val Asp Lys Pro Asp Trp Gln Pro Tyr Leu Pro Gln
525                 530                 535                 540 aac gga gac aac att gaa gtt gcc ttc tcc tac tcc tcg gtc tta tgg      2164
Asn Gly Asp Asn Ile Glu Val Ala Phe Ser Tyr Ser Ser Val Leu Trp
                545                 550                 555 cct tgg tcg ggc tac ctg gcc atc tcc att tct gtg acc aag aaa gcg      2212
Pro Trp Ser Gly Tyr Leu Ala Ile Ser Ile Ser Val Thr Lys Lys Ala
            560                 565                 570
```

```
gct tcc tgg gaa ggc att gct cag ggc cat gtc atg atc act gtg gct      2260
Ala Ser Trp Glu Gly Ile Ala Gln Gly His Val Met Ile Thr Val Ala
    575                 580                 585 tcc cca gca gag aca gag tca aaa aat ggt gca gaa cag act tca aca      2308
Ser Pro Ala Glu Thr Glu Ser Lys Asn Gly Ala Glu Gln Thr Ser Thr
590                 595                 600 gta aag ctc ccc att aag gtg aag ata att cct act ccc ccg cga agc      2356
Val Lys Leu Pro Ile Lys Val Lys Ile Ile Pro Thr Pro Pro Arg Ser
605                 610                 615                 620 aag aga gtt ctc tgg gat cag tac cac aac ctc cgc tat cca cct ggc      2404
Lys Arg Val Leu Trp Asp Gln Tyr His Asn Leu Arg Tyr Pro Pro Gly
            625                 630                 635 tat ttc ccc agg gat aat tta agg atg aag aat gac cct tta gac tgg      2452
Tyr Phe Pro Arg Asp Asn Leu Arg Met Lys Asn Asp Pro Leu Asp Trp
        640                 645                 650 aat ggt gat cac atc cac acc aat ttc agg gat atg tac cag cat ctg      2500
Asn Gly Asp His Ile His Thr Asn Phe Arg Asp Met Tyr Gln His Leu
    655                 660                 665 aga agc atg ggc tac ttt gta gag gtc ctc ggg gcc ccc ttc acg tgt      2548
Arg Ser Met Gly Tyr Phe Val Glu Val Leu Gly Ala Pro Phe Thr Cys
670                 675                 680 ttt gat gcc agt cag tat ggc act ttg ctg atg gtg gac agt gag gag      2596
Phe Asp Ala Ser Gln Tyr Gly Thr Leu Leu Met Val Asp Ser Glu Glu
685                 690                 695                 700 gag tac ttc cct gaa gag atc gcc aag ctc cgg agg gac gtg gac aac      2644
Glu Tyr Phe Pro Glu Glu Ile Ala Lys Leu Arg Arg Asp Val Asp Asn
            705                 710                 715 ggc ctc tcg ctc gtc atc ttc agt gac tgg tac aac act tct gtt atg      2692
Gly Leu Ser Leu Val Ile Phe Ser Asp Trp Tyr Asn Thr Ser Val Met
        720                 725                 730 aga aaa gtg aag ttt tat gat gaa aac aca agg cag tgg tgg atg ccg      2740
Arg Lys Val Lys Phe Tyr Asp Glu Asn Thr Arg Gln Trp Trp Met Pro
    735                 740                 745 gat acc gga gga gct aac atc cca gct ctg aat gag ctg ctg tct gtg      2788
Asp Thr Gly Gly Ala Asn Ile Pro Ala Leu Asn Glu Leu Leu Ser Val
750                 755                 760 tgg aac atg ggg ttc agc gat ggc ctg tat gaa ggg gag ttc acc ctg      2836
Trp Asn Met Gly Phe Ser Asp Gly Leu Tyr Glu Gly Glu Phe Thr Leu
765                 770                 775                 780 gcc aac cat gac atg tat tat gcg tca ggg tgc agc atc gcg aag ttt      2884
Ala Asn His Asp Met Tyr Tyr Ala Ser Gly Cys Ser Ile Ala Lys Phe
            785                 790                 795 cca gaa gat ggc gtc gtg ata aca cag act ttc aag gac caa gga ttg      2932
Pro Glu Asp Gly Val Val Ile Thr Gln Thr Phe Lys Asp Gln Gly Leu
        800                 805                 810 gag gtt tta aag cag gaa aca gca gtt gtt gaa aac gtc ccc att ttg      2980
Glu Val Leu Lys Gln Glu Thr Ala Val Val Glu Asn Val Pro Ile Leu
    815                 820                 825 gga ctt tat cag att cca gct gag ggt gga ggc cgg att gta ctg tat      3028
Gly Leu Tyr Gln Ile Pro Ala Glu Gly Gly Gly Arg Ile Val Leu Tyr
830                 835                 840 ggg gac tcc aat tgc ttg gat gac agt cac cga cag aag gac tgc ttt      3076
Gly Asp Ser Asn Cys Leu Asp Asp Ser His Arg Gln Lys Asp Cys Phe
845                 850                 855                 860 tgg ctt ctg gat gcc ctc ctc cag tac aca tcg tat ggg gtg aca ccg      3124
Trp Leu Leu Asp Ala Leu Leu Gln Tyr Thr Ser Tyr Gly Val Thr Pro
            865                 870                 875 cct agc ctc agt cac tct ggg aac cgc cag cgc cct ccc agt gga gca      3172
Pro Ser Leu Ser His Ser Gly Asn Arg Gln Arg Pro Pro Ser Gly Ala
```

-continued

| | | |
|---|---|---|
| ggc tca gtc act cca gag agg atg gaa gga aac cat ctt cat cgg tac<br>Gly Ser Val Thr Pro Glu Arg Met Glu Gly Asn His Leu His Arg Tyr<br>        895                      900                   905 | 3220 | |
| tcc aag gtt ctg gag gcc cat ttg gga gac cca aaa cct cgg cct cta<br>Ser Lys Val Leu Glu Ala His Leu Gly Asp Pro Lys Pro Arg Pro Leu<br>    910                      915                     920 | 3268 | |
| cca gcc tgt cca cgc ttg tct tgg gcc aag cca cag cct tta aac gag<br>Pro Ala Cys Pro Arg Leu Ser Trp Ala Lys Pro Gln Pro Leu Asn Glu<br>925                  930                  935              940 | 3316 | |
| acg gcg ccc agt aac ctt tgg aaa cat cag aag cta ctc tcc att gac<br>Thr Ala Pro Ser Asn Leu Trp Lys His Gln Lys Leu Leu Ser Ile Asp<br>                  945                  950              955 | 3364 | |
| ctg gac aag gtg gtg tta ccc aac ttt cga tcg aat cgc cct caa gtg<br>Leu Asp Lys Val Val Leu Pro Asn Phe Arg Ser Asn Arg Pro Gln Val<br>            960                  965                  970 | 3412 | |
| agg ccc ttg tcc cct gga gag agc ggc gcc tgg gac att cct gga ggg<br>Arg Pro Leu Ser Pro Gly Glu Ser Gly Ala Trp Asp Ile Pro Gly Gly<br>                975                  980              985 | 3460 | |
| atc atg cct ggc cgc tac aac cag gag gtg ggc cag acc att cct gtc<br>Ile Met Pro Gly Arg Tyr Asn Gln Glu Val Gly Gln Thr Ile Pro Val<br>    990                      995                 1000 | 3508 | |
| ttt gcc ttc ctg gga gcc atg gtg gtc ctg gcc ttc ttt gtg gta<br>Phe Ala Phe Leu Gly Ala Met Val Val Leu Ala Phe Phe Val Val<br>1005                  1010                1015 | 3553 | |
| caa atc aac aag gcc aag agc agg ccg aag cgg agg aag ccc agg<br>Gln Ile Asn Lys Ala Lys Ser Arg Pro Lys Arg Arg Lys Pro Arg<br>1020                  1025                1030 | 3598 | |
| gtg aag cgc ccg cag ctc atg cag cag gtt cac ccg cca aag acc<br>Val Lys Arg Pro Gln Leu Met Gln Gln Val His Pro Pro Lys Thr<br>1035                  1040                1045 | 3643 | |
| cct tcg gtg tgaccggcag cctggctgac cgtgagggcc agagagagcc<br>Pro Ser Val<br>1050 | 3692 | |
| ttcacggacg gcgctggtgg gtgagccgag ctgtggtggc ggctggttta aaagggatcc | 3752 | |
| agtttccagc tgcaggtttg ttagagtctg ttctacatgg gcctgccctc ctgtgatggg | 3812 | |
| cagaggctcc tggtacatcg agaagattcc tgtggatccc gtcaggaggg acttagtggc | 3872 | |
| tctgccgcca gtgagacttc ccgccggcag ctgtgcgcac caaagactcg ggagaactgg | 3932 | |
| aaaggctgtc tggggtcttc tgactgcagg ggaaggatgt actttccaaa caaatgatac | 3992 | |
| aaccctgacc aagctaaaag acgcttgtta aaggctattt tctatattta ttgttgggaa | 4052 | |
| aagtcacttt aaagacttgt gctatttgga agcaaagcta ttttttttgt cagtggaatg | 4112 | |
| cagttttttt actattccat catgaggaac aacatagatt ccatgatctt tttaatgaca | 4172 | |
| gtacagactg agatttgaag gaaacatgca caaatctgta aaacatagac cttcgcttta | 4232 | |
| ttttgtaag tatcacctgc caccatgttt tgtaatttga ggtcttgatt tcaccattgt | 4292 | |
| cggtgaagaa aattttcaat aaatatgtat tacccgtctg aagctt | 4338 | |

<210> SEQ ID NO 6
<211> LENGTH: 1052
<212> TYPE: PRT
<213> ORGANISM: Homo sapiens
<400> SEQUENCE: 6

Met Lys Leu Val Asn Ile Trp Leu Leu Leu Val Val Leu Leu Cys
1               5                   10                 15

```
Gly Lys Lys His Leu Gly Asp Arg Leu Glu Lys Lys Ser Phe Glu Lys
         20                  25                  30

Ala Pro Cys Pro Gly Cys Ser His Leu Thr Leu Lys Val Glu Phe Ser
             35                  40                  45

Ser Thr Val Val Glu Tyr Glu Tyr Ile Val Ala Phe Asn Gly Tyr Phe
 50                  55                  60

Thr Ala Lys Ala Arg Asn Ser Phe Ile Ser Ser Ala Leu Lys Ser Ser
 65                  70                  75                  80

Glu Val Asp Asn Trp Arg Ile Ile Pro Arg Asn Asn Pro Ser Ser Asp
                 85                  90                  95

Tyr Pro Ser Asp Phe Glu Val Ile Gln Ile Lys Glu Lys Gln Lys Ala
             100                 105                 110

Gly Leu Leu Thr Leu Glu Asp His Pro Asn Ile Lys Arg Val Thr Pro
             115                 120                 125

Gln Arg Lys Val Phe Arg Ser Leu Lys Tyr Ala Glu Ser Asp Pro Thr
 130                 135                 140

Val Pro Cys Asn Glu Thr Arg Trp Ser Gln Lys Trp Gln Ser Ser Arg
145                 150                 155                 160

Pro Leu Arg Arg Ala Ser Leu Ser Leu Gly Ser Gly Phe Trp His Ala
             165                 170                 175

Thr Gly Arg His Ser Ser Arg Arg Leu Leu Arg Ala Ile Pro Arg Gln
             180                 185                 190

Val Ala Gln Thr Leu Gln Ala Asp Val Leu Trp Gln Met Gly Tyr Thr
 195                 200                 205

Gly Ala Asn Val Arg Val Ala Val Phe Asp Thr Gly Leu Ser Glu Lys
 210                 215                 220

His Pro His Phe Lys Asn Val Lys Glu Arg Thr Asn Trp Thr Asn Glu
225                 230                 235                 240

Arg Thr Leu Asp Asp Gly Leu Gly His Gly Thr Phe Val Ala Gly Val
             245                 250                 255

Ile Ala Ser Met Arg Glu Cys Gln Gly Phe Ala Pro Asp Ala Glu Leu
             260                 265                 270

His Ile Phe Arg Val Phe Thr Asn Asn Gln Val Ser Tyr Thr Ser Trp
             275                 280                 285

Phe Leu Asp Ala Phe Asn Tyr Ala Ile Leu Lys Lys Ile Asp Val Leu
 290                 295                 300

Asn Leu Ser Ile Gly Gly Pro Asp Phe Met Asp His Pro Phe Val Asp
305                 310                 315                 320

Lys Val Trp Glu Leu Thr Ala Asn Asn Val Ile Met Val Ser Ala Ile
             325                 330                 335

Gly Asn Asp Gly Pro Leu Tyr Gly Thr Leu Asn Asn Pro Ala Asp Gln
             340                 345                 350

Met Asp Val Ile Gly Val Gly Gly Ile Asp Phe Glu Asp Asn Ile Ala
             355                 360                 365

Arg Phe Ser Ser Arg Gly Met Thr Thr Trp Glu Leu Pro Gly Gly Tyr
 370                 375                 380

Gly Arg Met Lys Pro Asp Ile Val Thr Tyr Gly Ala Gly Val Arg Gly
385                 390                 395                 400

Ser Gly Val Lys Gly Gly Cys Arg Ala Leu Ser Gly Thr Ser Val Ala
             405                 410                 415

Ser Pro Val Val Ala Gly Ala Val Thr Leu Leu Val Ser Thr Val Gln
             420                 425                 430

Lys Arg Glu Leu Val Asn Pro Ala Ser Met Lys Gln Ala Leu Ile Ala
```

-continued

```
            435                 440                 445
Ser Ala Arg Arg Leu Pro Gly Val Asn Met Phe Glu Gln Gly His Gly
450                 455                 460

Lys Leu Asp Leu Leu Arg Ala Tyr Gln Ile Leu Asn Ser Tyr Lys Pro
465                 470                 475                 480

Gln Ala Ser Leu Ser Pro Ser Tyr Ile Asp Leu Thr Glu Cys Pro Tyr
                485                 490                 495

Met Trp Pro Tyr Cys Ser Gln Pro Ile Tyr Tyr Gly Gly Met Pro Thr
                500                 505                 510

Val Val Asn Val Thr Ile Leu Asn Gly Met Gly Val Thr Gly Arg Ile
                515                 520                 525

Val Asp Lys Pro Asp Trp Gln Pro Tyr Leu Pro Gln Asn Gly Asp Asn
530                 535                 540

Ile Glu Val Ala Phe Ser Tyr Ser Ser Val Leu Trp Pro Trp Ser Gly
545                 550                 555                 560

Tyr Leu Ala Ile Ser Ile Ser Val Thr Lys Lys Ala Ala Ser Trp Glu
                565                 570                 575

Gly Ile Ala Gln Gly His Val Met Ile Thr Val Ala Ser Pro Ala Glu
                580                 585                 590

Thr Glu Ser Lys Asn Gly Ala Glu Gln Thr Ser Thr Val Lys Leu Pro
                595                 600                 605

Ile Lys Val Lys Ile Ile Pro Thr Pro Pro Arg Ser Lys Arg Val Leu
610                 615                 620

Trp Asp Gln Tyr His Asn Leu Arg Tyr Pro Pro Gly Tyr Phe Pro Arg
625                 630                 635                 640

Asp Asn Leu Arg Met Lys Asn Asp Pro Leu Asp Trp Asn Gly Asp His
                645                 650                 655

Ile His Thr Asn Phe Arg Asp Met Tyr Gln His Leu Arg Ser Met Gly
                660                 665                 670

Tyr Phe Val Glu Val Leu Gly Ala Pro Phe Thr Cys Phe Asp Ala Ser
                675                 680                 685

Gln Tyr Gly Thr Leu Leu Met Val Asp Ser Glu Glu Tyr Phe Pro
690                 695                 700

Glu Glu Ile Ala Lys Leu Arg Arg Asp Val Asp Asn Gly Leu Ser Leu
705                 710                 715                 720

Val Ile Phe Ser Asp Trp Tyr Asn Thr Ser Val Met Arg Lys Val Lys
                725                 730                 735

Phe Tyr Asp Glu Asn Thr Arg Gln Trp Trp Met Pro Asp Thr Gly Gly
                740                 745                 750

Ala Asn Ile Pro Ala Leu Asn Glu Leu Leu Ser Val Trp Asn Met Gly
                755                 760                 765

Phe Ser Asp Gly Leu Tyr Glu Gly Glu Phe Thr Leu Ala Asn His Asp
770                 775                 780

Met Tyr Tyr Ala Ser Gly Cys Ser Ile Ala Lys Phe Pro Glu Asp Gly
785                 790                 795                 800

Val Val Ile Thr Gln Thr Phe Lys Asp Gln Gly Leu Glu Val Leu Lys
                805                 810                 815

Gln Glu Thr Ala Val Val Glu Asn Val Pro Ile Leu Gly Leu Tyr Gln
                820                 825                 830

Ile Pro Ala Glu Gly Gly Gly Arg Ile Val Leu Tyr Gly Asp Ser Asn
                835                 840                 845

Cys Leu Asp Asp Ser His Arg Gln Lys Asp Cys Phe Trp Leu Leu Asp
850                 855                 860
```

```
Ala Leu Leu Gln Tyr Thr Ser Tyr Gly Val Thr Pro Pro Ser Leu Ser
865                 870                 875                 880

His Ser Gly Asn Arg Gln Arg Pro Pro Ser Gly Ala Gly Ser Val Thr
                885                 890                 895

Pro Glu Arg Met Glu Gly Asn His Leu His Arg Tyr Ser Lys Val Leu
            900                 905                 910

Glu Ala His Leu Gly Asp Pro Lys Pro Arg Pro Leu Pro Ala Cys Pro
            915                 920                 925

Arg Leu Ser Trp Ala Lys Pro Gln Pro Leu Asn Glu Thr Ala Pro Ser
        930                 935                 940

Asn Leu Trp Lys His Gln Lys Leu Leu Ser Ile Asp Leu Asp Lys Val
945                 950                 955                 960

Val Leu Pro Asn Phe Arg Ser Asn Arg Pro Gln Val Arg Pro Leu Ser
                965                 970                 975

Pro Gly Glu Ser Gly Ala Trp Asp Ile Pro Gly Gly Ile Met Pro Gly
            980                 985                 990

Arg Tyr Asn Gln Glu Val Gly Gln  Thr Ile Pro Val Phe  Ala Phe Leu
        995                 1000                 1005

Gly Ala  Met Val Val Leu Ala  Phe Phe Val Val Gln  Ile Asn Lys
    1010                 1015                 1020

Ala Lys  Ser Arg Pro Lys Arg  Arg Lys Pro Arg Val  Lys Arg Pro
    1025                 1030                 1035

Gln Leu  Met Gln Gln Val His  Pro Pro Lys Thr Pro  Ser Val
    1040                 1045                 1050

<210> SEQ ID NO 7
<211> LENGTH: 7
<212> TYPE: PRT
<213> ORGANISM: Artificial Sequence
<220> FEATURE:
<223> OTHER INFORMATION: Peptide substrate
<220> FEATURE:
<221> NAME/KEY: VARIANT
<222> LOCATION: (2)..(2)
<223> OTHER INFORMATION: Xaa represents any amino acid
<220> FEATURE:
<221> NAME/KEY: VARIANT
<222> LOCATION: (3)..(3)
<223> OTHER INFORMATION: Xaa represents an alkyl or an aromatic
     hydrophobic amino acid
<220> FEATURE:
<221> NAME/KEY: VARIANT
<222> LOCATION: (4)..(6)
<220> FEATURE:
<221> NAME/KEY: VARIANT
<222> LOCATION: (4)..(6)
<223> OTHER INFORMATION: Xaa represents any amino acid
<220> FEATURE:
<221> NAME/KEY: VARIANT
<222> LOCATION: (7)..(7)
<223> OTHER INFORMATION: Xaa represents an acidic amino acid

<400> SEQUENCE: 7

Arg Xaa Xaa Xaa Xaa Xaa Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Peptide substrate
<220> FEATURE:
<221> NAME/KEY: VARIANT
```

```
<222> LOCATION: (2)..(2)
<223> OTHER INFORMATION: Xaa represents any amino acid
<220> FEATURE:
<221> NAME/KEY: VARIANT
<222> LOCATION: (3)..(3)
<223> OTHER INFORMATION: Xaa represents an alkyl or aromatic hydrophobic
      amino acid
<220> FEATURE:
<221> NAME/KEY: VARIANT
<222> LOCATION: (4)..(4)
<223> OTHER INFORMATION: Xaa represents Lys, Leu, Phe or Thr
<220> FEATURE:
<221> NAME/KEY: VARIANT
<222> LOCATION: (5)..(6)
<223> OTHER INFORMATION: Xaa represents any amino acid
<220> FEATURE:
<221> NAME/KEY: VARIANT
<222> LOCATION: (7)..(7)
<223> OTHER INFORMATION: Xaa represents an acidic amino acid

<400> SEQUENCE: 8

Arg Xaa Xaa Xaa Xaa Xaa Xaa
1               5

<210> SEQ ID NO 9
<211> LENGTH: 8
<212> TYPE: PRT
<213> ORGANISM: Artificial Sequence
<220> FEATURE:
<223> OTHER INFORMATION: Peptide substrate
<220> FEATURE:
<221> NAME/KEY: VARIANT
<222> LOCATION: (2)..(2)
<223> OTHER INFORMATION: Xaa represents any amino acid
<220> FEATURE:
<221> NAME/KEY: VARIANT
<222> LOCATION: (3)..(3)
<223> OTHER INFORMATION: Xaa represents and alkyl or aromatic
      hydrophobic amino acid
<220> FEATURE:
<221> NAME/KEY: VARIANT
<222> LOCATION: (4)..(7)
<223> OTHER INFORMATION: Xaa represents any amino acid
<220> FEATURE:
<221> NAME/KEY: VARIANT
<222> LOCATION: (8)..(8)
<223> OTHER INFORMATION: Xaa represents an acidic amino acid

<400> SEQUENCE: 9

Arg Xaa Xaa Xaa Xaa Xaa Xaa Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: Peptide substrate
<220> FEATURE:
<221> NAME/KEY: VARIANT
<222> LOCATION: (2)..(2)
<223> OTHER INFORMATION: Xaa represents any amino acid
<220> FEATURE:
<221> NAME/KEY: VARIANT
<222> LOCATION: (3)..(3)
<223> OTHER INFORMATION: Xaa represents an alkyl or aromatic hydrophobic
      amino acid
<220> FEATURE:
<221> NAME/KEY: VARIANT
<222> LOCATION: (4)..(4)
<223> OTHER INFORMATION: Xaa represents Lys, Leu, Phe or Thr
<220> FEATURE:
<221> NAME/KEY: VARIANT
<222> LOCATION: (5)..(7)
<223> OTHER INFORMATION: Xaa represents any amino acid
```

```
<220> FEATURE:
<221> NAME/KEY: VARIANT
<222> LOCATION: (8)..(8)
<223> OTHER INFORMATION: Xaa represents an acidic amino acid

<400> SEQUENCE: 10

Arg Xaa Xaa Xaa Xaa Xaa Xaa Xaa
1               5

<210> SEQ ID NO 11
<211> LENGTH: 9
<212> TYPE: PRT
<213> ORGANISM: Artificial Sequence
<220> FEATURE:
<223> OTHER INFORMATION: Peptide substrate
<220> FEATURE:
<221> NAME/KEY: VARIANT
<222> LOCATION: (2)..(2)
<223> OTHER INFORMATION: Xaa represents any amino acid
<220> FEATURE:
<221> NAME/KEY: VARIANT
<222> LOCATION: (3)..(3)
<223> OTHER INFORMATION: Xaa represents an alkyl or an aromatic
      hydrophobic amino acid
<220> FEATURE:
<221> NAME/KEY: VARIANT
<222> LOCATION: (4)..(8)
<223> OTHER INFORMATION: Xaa represents any amino acid
<220> FEATURE:
<221> NAME/KEY: VARIANT
<222> LOCATION: (9)..(9)
<223> OTHER INFORMATION: Xaa represents an acidic amino acid

<400> SEQUENCE: 11

Arg Xaa Xaa Xaa Xaa Xaa Xaa Xaa Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Peptide substrate
<220> FEATURE:
<221> NAME/KEY: VARIANT
<222> LOCATION: (2)..(2)
<223> OTHER INFORMATION: Xaa represents any amino acid
<220> FEATURE:
<221> NAME/KEY: VARIANT
<222> LOCATION: (3)..(3)
<223> OTHER INFORMATION: Xaa represents an alkyl or aromatic hydrophobic
      amino acid
<220> FEATURE:
<221> NAME/KEY: VARIANT
<222> LOCATION: (4)..(4)
<223> OTHER INFORMATION: Xaa represents Lys, Leu, Phe or Thr
<220> FEATURE:
<221> NAME/KEY: VARIANT
<222> LOCATION: (5)..(8)
<223> OTHER INFORMATION: Xaa represents any amino acid
<220> FEATURE:
<221> NAME/KEY: VARIANT
<222> LOCATION: (9)..(9)
<223> OTHER INFORMATION: Xaa represents an acidic amino acid

<400> SEQUENCE: 12

Arg Xaa Xaa Xaa Xaa Xaa Xaa Xaa Xaa
1               5

<210> SEQ ID NO 13
<211> LENGTH: 11
<212> TYPE: PRT
<213> ORGANISM: Artificial Sequence
```

-continued

```
<220> FEATURE:
<223> OTHER INFORMATION: Peptide substrate

<400> SEQUENCE: 13

Val Phe Arg Ser Leu Lys Tyr Ala Glu Ser Asp
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Peptide substrate
<220> FEATURE:
<221> NAME/KEY: Modified_res
<222> LOCATION: (1)..(1)
<223> OTHER INFORMATION: Xaa represents orthoaminobenzoic acid
<220> FEATURE:
<221> NAME/KEY: Modified_res
<222> LOCATION: (13)..(13)
<223> OTHER INFORMATION: Xaa represents3-nitrotyrosine

<400> SEQUENCE: 14

Xaa Val Phe Arg Ser Leu Lys Tyr Ala Glu Ser Asp Xaa
1               5                   10

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide
<220> FEATURE:
<221> NAME/KEY: variation
<222> LOCATION: (3)..(3)
<223> OTHER INFORMATION: i
<220> FEATURE:
<221> NAME/KEY: variation
<222> LOCATION: (9)..(9)
<223> OTHER INFORMATION: i
<220> FEATURE:
<221> NAME/KEY: variation
<222> LOCATION: (12)..(12)
<223> OTHER INFORMATION: i
<220> FEATURE:
<221> NAME/KEY: variation
<222> LOCATION: (18)..(18)
<223> OTHER INFORMATION: i
<220> FEATURE:
<221> NAME/KEY: variation
<222> LOCATION: (21)..(21)
<223> OTHER INFORMATION: i

<400> SEQUENCE: 15
ggncayggna cnywykkngc ngg                                              23

<210> SEQ ID NO 16
<211> LENGTH: 31
<212> TYPE: DNA
<213> ORGANISM: Artificial Sequence
<220> FEATURE:
<223> OTHER INFORMATION: Oligonucleotide
<220> FEATURE:
<221> NAME/KEY: variation
<222> LOCATION: (3)..(3)
<223> OTHER INFORMATION: i
<220> FEATURE:
<221> NAME/KEY: variation
<222> LOCATION: (6)..(6)
<223> OTHER INFORMATION: i
<220> FEATURE:
<221> NAME/KEY: variation
<222> LOCATION: (9)..(9)
```

<223> OTHER INFORMATION: i
<220> FEATURE:
<221> NAME/KEY: variation
<222> LOCATION: (12)..(12)
<223> OTHER INFORMATION: i
<220> FEATURE:
<221> NAME/KEY: variation
<222> LOCATION: (15)..(15)
<223> OTHER INFORMATION: i
<220> FEATURE:
<221> NAME/KEY: variation
<222> LOCATION: (18)..(18)
<223> OTHER INFORMATION: i
<220> FEATURE:
<221> NAME/KEY: variation
<222> LOCATION: (21)..(21)
<223> OTHER INFORMATION: i
<220> FEATURE:
<221> NAME/KEY: variation
<222> LOCATION: (24)..(24)
<223> OTHER INFORMATION: i
<220> FEATURE:
<221> NAME/KEY: variation
<222> LOCATION: (29)..(29)
<223> OTHER INFORMATION: i

<400> SEQUENCE: 16
ccngynacnw snggnswngc nacnswgtnc c 31

<210> SEQ ID NO 17
<211> LENGTH: 8
<212> TYPE: PRT
<213> ORGANISM: Artificial Sequence
<220> FEATURE:
<223> OTHER INFORMATION: Peptide substrate
<220> FEATURE:
<221> NAME/KEY: VARIANT
<222> LOCATION: (5)..(5)
<223> OTHER INFORMATION: Xaa respresent histidine or phenylalanine
<220> FEATURE:
<221> NAME/KEY: VARIANT
<222> LOCATION: (6)..(6)
<223> OTHER INFORMATION: Xaa represents valine or cysteine

<400> SEQUENCE: 17

Gly His Gly Thr Xaa Xaa Ala Gly
1 5

<210> SEQ ID NO 18
<211> LENGTH: 11
<212> TYPE: PRT
<213> ORGANISM: Artificial Sequence
<220> FEATURE:
<223> OTHER INFORMATION: Peptide substrate
<220> FEATURE:
<221> NAME/KEY: VARIANT
<222> LOCATION: (4)..(4)
<223> OTHER INFORMATION: Xaa represents valine or methionine
<220> FEATURE:
<221> NAME/KEY: VARIANT
<222> LOCATION: (6)..(6)
<223> OTHER INFORMATION: Xaa represents threonine or serine
<220> FEATURE:
<221> NAME/KEY: VARIANT
<222> LOCATION: (8)..(8)
<223> OTHER INFORMATION: Xaa represents histidine or valine
<220> FEATURE:
<221> NAME/KEY: VARIANT
<222> LOCATION: (10)..(10)
<223> OTHER INFORMATION: Xaa represents alanine or threonine

<400> SEQUENCE: 18

Gly Thr Ser Xaa Ala Xaa Pro Xaa Val Xaa Gly
1 5 10

-continued

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
ggatccgaag aaacatctgg gcgacaga                               28

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
ctcgagggct ctcagccgtg tgct                                   24

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gaggaagaga cagggataaa c                                      21

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gggatatgct tagcattgac                                        20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
agccctatta cctgaacctg                                        20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gaatctgaaa gaactccccc                                        20

<210> SEQ ID NO 25
<211> LENGTH: 20
<212> TYPE: DNA
<213> ORGANISM: Artificial Sequence
<220> FEATURE:

```
<223> OTHER INFORMATION: Primer

<400> SEQUENCE: 25
ttccgagatt ccatcctacg                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tgcagctcag caggtctatg                                               20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tctcctccaa cctcaaccac                                               20

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
ccagcctgtc atcctcaata tc                                            22

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ggagccatgg attgcacttt c                                             21

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
aggagctcaa tgtggcagga                                               20

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
gtgaccatga agcttgtcaa catctgg                                       27
```

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
acactggtcc ctgagagggc ccggca                                   26

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
attgacctgg acaaggtggt g                                        21

<210> SEQ ID NO 34
<211> LENGTH: 57
<212> TYPE: DNA
<213> ORGANISM: Artificial Sequence
<220> FEATURE:
<223> OTHER INFORMATION: Primer

<400> SEQUENCE: 34
ggatcctcta gatcagtggt ggtggtggtg gtggtgctcc tggttgtagc ggccagg  57

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
ctcgagggag aggctggctc ttcg                                     24

<210> SEQ ID NO 36
<211> LENGTH: 28
<212> TYPE: DNA
<213> ORGANISM: Artificial Sequence
<220> FEATURE:
<223> OTHER INFORMATION: Primer

<400> SEQUENCE: 36
ctcgagtgtc tgggcaacct ggcgcggg                                 28

<210> SEQ ID NO 37
<211> LENGTH: 14
<212> TYPE: PRT
<213> ORGANISM: Homo sapiens

<400> SEQUENCE: 37

Lys Ala Gly Ser Arg Gly Leu Thr Ser Leu Ala Asp Thr Phe
 1               5                  10

<210> SEQ ID NO 38
<211> LENGTH: 27
<212> TYPE: PRT
<213> ORGANISM: Artificial Sequence
<220> FEATURE:
<223> OTHER INFORMATION: Peptide Substrate

<400> SEQUENCE: 38

```
Gly Gly Ala His Asp Ser Asp Gln His Pro His Ser Gly Ser Gly Arg
1               5                   10                  15

Ser Val Leu Ser Phe Glu Ser Gly Ser Gly Gly
                20                  25
```

<210> SEQ ID NO 39
<211> LENGTH: 18
<212> TYPE: PRT
<213> ORGANISM: Artificial Sequence
<220> FEATURE:
<223> OTHER INFORMATION: Peptide Substrate

<400> SEQUENCE: 39

```
Trp His Ala Thr Gly Arg His Ser Ser Arg Arg Leu Leu Arg Ala Ile
1               5                   10                  15

Pro Arg
```

<210> SEQ ID NO 40
<211> LENGTH: 17
<212> TYPE: PRT
<213> ORGANISM: Artificial Sequence
<220> FEATURE:
<223> OTHER INFORMATION: Peptide Substrate

<400> SEQUENCE: 40

```
Trp His Ala Thr Gly Arg His Ser Ser Arg Arg Leu Leu Arg Ala Leu
1               5                   10                  15

Glu
```

<210> SEQ ID NO 41
<211> LENGTH: 9
<212> TYPE: PRT
<213> ORGANISM: Artificial Sequence
<220> FEATURE:
<223> OTHER INFORMATION: Peptide Substrate

<400> SEQUENCE: 41

```
Ser Arg Arg Leu Leu Arg Ala Leu Glu
1               5
```

<210> SEQ ID NO 42
<211> LENGTH: 17
<212> TYPE: PRT
<213> ORGANISM: Artificial Sequence
<220> FEATURE:
<223> OTHER INFORMATION: Peptide Substrate

<400> SEQUENCE: 42

```
Trp Gln Ser Ser Arg Pro Leu Arg Arg Ala Ser Leu Ser Leu Gly Ser
1               5                   10                  15

Gly
```

<210> SEQ ID NO 43
<211> LENGTH: 15
<212> TYPE: PRT
<213> ORGANISM: Artificial Sequence
<220> FEATURE:
<223> OTHER INFORMATION: Peptide Substrate

<400> SEQUENCE: 43

```
Arg Ala Ile Pro Arg Gln Val Ala Gln Thr Leu Gln Ala Asp Val
1               5                   10                  15
```

```
<210> SEQ ID NO 44
<211> LENGTH: 9
<212> TYPE: PRT
<213> ORGANISM: Artificial Sequence
<220> FEATURE:
<223> OTHER INFORMATION: Peptide Substrate

<400> SEQUENCE: 44

Pro Gln Arg Lys Val Phe Arg Ser Leu
1               5

<210> SEQ ID NO 45
<211> LENGTH: 15
<212> TYPE: PRT
<213> ORGANISM: Artificial Sequence
<220> FEATURE:
<223> OTHER INFORMATION: Peptide Substrate

<400> SEQUENCE: 45

Pro Gln Arg Lys Val Phe Arg Ser Leu Lys Tyr Ala Glu Ser Asp
1               5                   10                  15

<210> SEQ ID NO 46
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: Xaa represents orthoaminobenzoic acid
<220> FEATURE:
<221> NAME/KEY: MOD_RES
<222> LOCATION: (13)..(13)
<223> OTHER INFORMATION: Xaa represents 3-nitrotyrosine

<400> SEQUENCE: 46

Xaa Val Phe Arg Ser Leu Lys Tyr Ala Glu Ser Asp Xaa Ala
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: Xaa represents orthoaminobenzoic acid
<220> FEATURE:
<221> NAME/KEY: MOD_RES
<222> LOCATION: (11)..(11)
<223> OTHER INFORMATION: Xaa represents 3-nitrotyrosine

<400> SEQUENCE: 47

Xaa Arg Ser Leu Lys Tyr Ala Glu Ser Asp Xaa Ala
1               5                   10

<210> SEQ ID NO 48
<211> LENGTH: 16
<212> TYPE: PRT
<213> ORGANISM: Homo sapiens

<400> SEQUENCE: 48

Lys Ala Gly Ser Arg Gly Leu Thr Ser Leu Ala Asp Thr Phe Glu His
1               5                   10                  15
```

```
<210> SEQ ID NO 49
<211> LENGTH: 16
<212> TYPE: PRT
<213> ORGANISM: Rattus sp.

<400> SEQUENCE: 49

Lys Ala Gly Ser Arg Gly Leu Thr Thr Thr Ser Leu Ala Asp Thr Phe
1               5                   10                  15

<210> SEQ ID NO 50
<211> LENGTH: 16
<212> TYPE: PRT
<213> ORGANISM: Homo sapiens

<400> SEQUENCE: 50

Arg His Ser Ser Arg Arg Leu Leu Arg Ala Ile Pro Arg Gln Val Ala
1               5                   10                  15

<210> SEQ ID NO 51
<211> LENGTH: 16
<212> TYPE: PRT
<213> ORGANISM: Homo sapiens

<400> SEQUENCE: 51

Arg Lys Val Phe Arg Ser Leu Lys Tyr Ala Glu Ser Asp Pro Thr Val
1               5                   10                  15

<210> SEQ ID NO 52
<211> LENGTH: 16
<212> TYPE: PRT
<213> ORGANISM: Homo sapiens

<400> SEQUENCE: 52

Thr Pro Gln Arg Lys Val Phe Arg Ser Leu Lys Tyr Ala Glu Ser Asp
1               5                   10                  15

<210> SEQ ID NO 53
<211> LENGTH: 16
<212> TYPE: PRT
<213> ORGANISM: Homo sapiens

<400> SEQUENCE: 53

Val Thr Pro Gln Arg Lys Val Phe Arg Ser Leu Lys Lys Tyr Ala Glu
1               5                   10                  15

<210> SEQ ID NO 54
<211> LENGTH: 16
<212> TYPE: PRT
<213> ORGANISM: Homo sapiens

<400> SEQUENCE: 54

Ser Gly Ser Gly Arg Ser Val Leu Ser Phe Glu Ser Gly Ser Gly Gly
1               5                   10                  15

<210> SEQ ID NO 55
<211> LENGTH: 16
<212> TYPE: PRT
<213> ORGANISM: Homo sapiens

<400> SEQUENCE: 55

His Ser Pro Gly Arg Asn Val Leu Gly Thr Glu Ser Arg Asp Gly Pro
1               5                   10                  15

<210> SEQ ID NO 56
<211> LENGTH: 16
```

```
<212> TYPE: PRT
<213> ORGANISM: Rattus sp.

<400> SEQUENCE: 56

Ala Ser Val Gly Arg Leu Ala Leu Ser Gln Glu Glu Pro Ala Pro Leu
1               5                   10                  15

<210> SEQ ID NO 57
<211> LENGTH: 16
<212> TYPE: PRT
<213> ORGANISM: Homo sapiens

<400> SEQUENCE: 57

Arg Ile Ser Asp Arg Asp Tyr Met Gly Trp Met Asp Phe Gly Arg Arg
1               5                   10                  15

<210> SEQ ID NO 58
<211> LENGTH: 16
<212> TYPE: PRT
<213> ORGANISM: Rattus sp.

<400> SEQUENCE: 58

Asp Pro Arg Leu Arg Gln Phe Leu Gln Lys Ser Leu Ala Ala Ala Thr
1               5                   10                  15

<210> SEQ ID NO 59
<211> LENGTH: 16
<212> TYPE: PRT
<213> ORGANISM: Bovis sp.

<400> SEQUENCE: 59

Leu Leu Lys Glu Leu Gln Asp Leu Ala Leu Gln Gly Ala Lys Glu Arg
1               5                   10                  15

<210> SEQ ID NO 60
<211> LENGTH: 16
<212> TYPE: PRT
<213> ORGANISM: Bovis sp.

<400> SEQUENCE: 60

Met Ala Arg Ala Pro Gln Val Leu Phe Arg Gly Gly Lys Ser Gly Glu
1               5                   10                  15

<210> SEQ ID NO 61
<211> LENGTH: 16
<212> TYPE: PRT
<213> ORGANISM: Bovis sp.

<400> SEQUENCE: 61

Glu Leu Glu Asn Leu Ala Ala Met Asp Leu Glu Leu Gln Lys Ile Ala
1               5                   10                  15

<210> SEQ ID NO 62
<211> LENGTH: 16
<212> TYPE: PRT
<213> ORGANISM: Bovis sp.

<400> SEQUENCE: 62

Ala Ala Met Asp Leu Glu Leu Gln Lys Ile Ala Glu Lys Phe Ser Gly
1               5                   10                  15

<210> SEQ ID NO 63
<211> LENGTH: 16
<212> TYPE: PRT
<213> ORGANISM: Rattus sp.
```

-continued

<400> SEQUENCE: 63

Lys Ser Ser Phe Thr Asn Val Thr Ser Pro Val Val Leu Thr Asn Tyr
1               5                   10                  15

<210> SEQ ID NO 64
<211> LENGTH: 16
<212> TYPE: PRT
<213> ORGANISM: Rattus sp.

<400> SEQUENCE: 64

Lys Ser Gln Thr Pro Leu Val Thr Leu Phe Lys Asn Ala Ile Ile Lys
1               5                   10                  15

<210> SEQ ID NO 65
<211> LENGTH: 16
<212> TYPE: PRT
<213> ORGANISM: Rattus sp.

<400> SEQUENCE: 65

Ser Gln Thr Pro Leu Val Thr Leu Phe Lys Asn Ala Ile Ile Lys Asn
1               5                   10                  15

<210> SEQ ID NO 66
<211> LENGTH: 16
<212> TYPE: PRT
<213> ORGANISM: Rattus sp.

<400> SEQUENCE: 66

Gly Pro Ala Arg Glu Leu Leu Leu Arg Leu Val Gln Leu Ala Gly Thr
1               5                   10                  15

<210> SEQ ID NO 67
<211> LENGTH: 16
<212> TYPE: PRT
<213> ORGANISM: Homo sapiens

<400> SEQUENCE: 67

Leu Leu Arg Lys Lys Arg Thr Thr Ser Ala Glu Lys Asn Thr Cys Gln
1               5                   10                  15

<210> SEQ ID NO 68
<211> LENGTH: 16
<212> TYPE: PRT
<213> ORGANISM: Homo sapiens

<400> SEQUENCE: 68

Glu Glu Ile Ser Glu Val Lys Met Asp Ala Glu Phe Arg His Asp Ser
1               5                   10                  15

<210> SEQ ID NO 69
<211> LENGTH: 16
<212> TYPE: PRT
<213> ORGANISM: Homo sapiens

<400> SEQUENCE: 69

Glu Glu Ile Ser Glu Val Asn Leu Asp Ala Glu Phe Arg His Asp Ser
1               5                   10                  15

<210> SEQ ID NO 70
<211> LENGTH: 16
<212> TYPE: PRT
<213> ORGANISM: Homo sapiens

<400> SEQUENCE: 70

-continued

```
Ile Ser Glu Val Lys Met Asp Ala Glu Phe Arg His Asp Ser Gly Tyr
1               5                   10                  15

<210> SEQ ID NO 71
<211> LENGTH: 16
<212> TYPE: PRT
<213> ORGANISM: Homo sapiens

<400> SEQUENCE: 71

Glu Phe Arg His Asp Ser Gly Tyr Glu Val His His Gln Lys Leu Val
1               5                   10                  15

<210> SEQ ID NO 72
<211> LENGTH: 10
<212> TYPE: PRT
<213> ORGANISM: Artificial Sequence
<220> FEATURE:
<223> OTHER INFORMATION: Peptide substrate

<400> SEQUENCE: 72

Ser Ser Arg Arg Leu Leu Arg Ala Ile Glu
1               5                   10

<210> SEQ ID NO 73
<211> LENGTH: 12
<212> TYPE: PRT
<213> ORGANISM: Artificial sequence
<220> FEATURE:
<223> OTHER INFORMATION: Peptide Substrate

<400> SEQUENCE: 73

Ser Gly Ser Gly Arg Ser Val Leu Ser Phe Glu Ser
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Peptide Substrate
<220> FEATURE:
<221> NAME/KEY: MOD_RES
<222> LOCATION: (1)..(1)
<223> OTHER INFORMATION: Xaa represents orthoaminobenzoic acid
<220> FEATURE:
<221> NAME/KEY: MOD_RES
<222> LOCATION: (13)..(13)
<223> OTHER INFORMATION: Xaa represents 3-nitrotyrosine

<400> SEQUENCE: 74

Xaa Arg His Ser Ser Arg Arg Leu Leu Arg Ala Ile Xaa Ala
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Peptide Substrate
<220> FEATURE:
<221> NAME/KEY: MOD_RES
<222> LOCATION: (1)..(1)
<223> OTHER INFORMATION: Xaa represents orthoaminobenzoic acid
<220> FEATURE:
<221> NAME/KEY: MOD_RES
<222> LOCATION: (11)..(11)
<223> OTHER INFORMATION: Xaa represents 3-nitrotyrosine

<400> SEQUENCE: 75
```

Xaa Ser Arg Arg Leu Leu Arg Ala Leu Glu Xaa Ala
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Peptide Substrate
<220> FEATURE:
<221> NAME/KEY: MOD_RES
<222> LOCATION: (1)..(1)
<223> OTHER INFORMATION: Xaa represents orthoaminobenzoic acid
<220> FEATURE:
<221> NAME/KEY: MOD_RES
<222> LOCATION: (14)..(14)
<223> OTHER INFORMATION: Xaa represents 3-nitrotyrosine

<400> SEQUENCE: 76

Xaa Asn Gly Pro Lys Ala Gly Ser Arg Gly Leu Thr Ser Xaa Ala
1               5                   10                  15

<210> SEQ ID NO 77
<211> LENGTH: 13
<212> TYPE: PRT
<213> ORGANISM: Artificial Sequence
<220> FEATURE:
<223> OTHER INFORMATION: Consensus sequence for growth factors

<400> SEQUENCE: 77

Cys Leu Asp Asp Ser His Arg Gln Lys Asp Cys Phe Trp
1               5                   10

<210> SEQ ID NO 78
<211> LENGTH: 9
<212> TYPE: PRT
<213> ORGANISM: Homo sapiens

<400> SEQUENCE: 78

Gly Cys Met Leu Ala Ala Pro Met Lys
1               5

<210> SEQ ID NO 79
<211> LENGTH: 18
<212> TYPE: PRT
<213> ORGANISM: Homo sapiens

<400> SEQUENCE: 79

Arg Gly Leu Thr Ser Leu Ala Asp Thr Phe Glu His Val Ile Glu Glu
1               5                   10                  15

Leu Leu

<210> SEQ ID NO 80
<211> LENGTH: 10
<212> TYPE: PRT
<213> ORGANISM: Homo sapiens

<400> SEQUENCE: 80

Lys Ala Gly Ser Arg Gly Leu Thr Ser Leu
1               5                   10

<210> SEQ ID NO 81
<211> LENGTH: 10
<212> TYPE: PRT
<213> ORGANISM: Homo sapiens

```
<400> SEQUENCE: 81

Gln Cys Leu Cys Val Lys Thr Thr Ser Gln
1               5                  10

<210> SEQ ID NO 82
<211> LENGTH: 10
<212> TYPE: PRT
<213> ORGANISM: Homo sapiens

<400> SEQUENCE: 82

Lys Gly Pro Trp Cys Phe Thr Thr Asp Pro
1               5                  10

<210> SEQ ID NO 83
<211> LENGTH: 10
<212> TYPE: PRT
<213> ORGANISM: Homo sapiens

<400> SEQUENCE: 83

Lys Ser Gln Thr Pro Leu Val Thr Leu Phe
1               5                  10

<210> SEQ ID NO 84
<211> LENGTH: 10
<212> TYPE: PRT
<213> ORGANISM: Homo sapiens

<400> SEQUENCE: 84

Leu Leu Arg Lys Lys Arg Thr Thr Ser Ala
1               5                  10

<210> SEQ ID NO 85
<211> LENGTH: 10
<212> TYPE: PRT
<213> ORGANISM: Homo sapiens

<400> SEQUENCE: 85

Val Gly Gly Val Val Ile Ala Thr Val Ile
1               5                  10

<210> SEQ ID NO 86
<211> LENGTH: 8
<212> TYPE: PRT
<213> ORGANISM: Mus sp.

<400> SEQUENCE: 86

Arg Gly Leu Thr Thr Thr Ser Leu
1               5

<210> SEQ ID NO 87
<211> LENGTH: 11
<212> TYPE: PRT
<213> ORGANISM: Sus sp.

<400> SEQUENCE: 87

Arg Gly Leu Thr Ser Ser Ser Ser Ser Ser Leu
1               5                  10

<210> SEQ ID NO 88
<211> LENGTH: 10
<212> TYPE: PRT
<213> ORGANISM: Homo sapiens

<400> SEQUENCE: 88
```

```
Arg Asn Asn Pro Ser Ser Asp Tyr Pro Ser
1               5                   10
```

<210> SEQ ID NO 89
<211> LENGTH: 8
<212> TYPE: PRT
<213> ORGANISM: Homo sapiens

<400> SEQUENCE: 89

```
Arg His Ser Ser Arg Arg Leu Leu
1               5
```

<210> SEQ ID NO 90
<211> LENGTH: 4
<212> TYPE: PRT
<213> ORGANISM: Homo sapiens

<400> SEQUENCE: 90

```
Arg Arg Leu Leu
1
```

<210> SEQ ID NO 91
<211> LENGTH: 13
<212> TYPE: PRT
<213> ORGANISM: Artificial sequence
<220> FEATURE:
<223> OTHER INFORMATION: Fragment resulting from cloning

<400> SEQUENCE: 91

```
Pro Gly Arg Tyr Asn Gln Glu His His His His His
1               5                   10
```

<210> SEQ ID NO 92
<211> LENGTH: 12
<212> TYPE: PRT
<213> ORGANISM: Homo sapiens

<400> SEQUENCE: 92

```
Leu Val Val Leu Leu Cys Gly Lys Lys His Leu Gly
1               5                   10
```

<210> SEQ ID NO 93
<211> LENGTH: 19
<212> TYPE: PRT
<213> ORGANISM: Homo sapiens

<400> SEQUENCE: 93

```
Lys Tyr Ala Glu Ser Asp Pro Thr Val Pro Cys Asn Glu Thr Arg Trp
1               5                   10                  15

Ser Gln Lys
```

<210> SEQ ID NO 94
<211> LENGTH: 8
<212> TYPE: PRT
<213> ORGANISM: Homo sapiens

<400> SEQUENCE: 94

```
Arg Lys Val Phe Arg Ser Leu Lys
1               5
```

<210> SEQ ID NO 95
<211> LENGTH: 7
<212> TYPE: PRT
<213> ORGANISM: Homo sapiens

```
<400> SEQUENCE: 95

Gly Lys Lys Arg Lys Val Phe
1               5

<210> SEQ ID NO 96
<211> LENGTH: 8
<212> TYPE: PRT
<213> ORGANISM: Homo sapiens

<400> SEQUENCE: 96

Gly Lys Lys Arg Lys Val Phe Arg
1               5

<210> SEQ ID NO 97
<211> LENGTH: 10
<212> TYPE: PRT
<213> ORGANISM: Homo sapiens

<400> SEQUENCE: 97

Gly Lys Lys Arg Lys Val Phe Arg Ser Leu
1               5                   10

<210> SEQ ID NO 98
<211> LENGTH: 11
<212> TYPE: PRT
<213> ORGANISM: Homo sapiens

<400> SEQUENCE: 98

Gly Lys Lys Arg Lys Val Phe Arg Ser Leu Lys
1               5                   10

<210> SEQ ID NO 99
<211> LENGTH: 6
<212> TYPE: PRT
<213> ORGANISM: Homo sapiens

<400> SEQUENCE: 99

Arg Gly Leu Thr Ser Leu
1               5

<210> SEQ ID NO 100
<211> LENGTH: 4
<212> TYPE: PRT
<213> ORGANISM: Homo sapiens

<400> SEQUENCE: 100

Arg Ser Leu Lys
1

<210> SEQ ID NO 101
<211> LENGTH: 7
<212> TYPE: PRT
<213> ORGANISM: Artificial Sequence
<220> FEATURE:
<223> OTHER INFORMATION: Fluorescent candidate substrate
<220> FEATURE:
<221> NAME/KEY: VARIANT
<222> LOCATION: (1)..(1)
<223> OTHER INFORMATION: Xaa represents Abz

<400> SEQUENCE: 101

Xaa Val Phe Arg Ser Leu Lys
1               5

<210> SEQ ID NO 102
```

```
<211> LENGTH: 5
<212> TYPE: PRT
<213> ORGANISM: Artificial sequence
<220> FEATURE:
<223> OTHER INFORMATION: Fluorescent candidate substrate
<220> FEATURE:
<221> NAME/KEY: VARIANT
<222> LOCATION: (1)..(1)
<223> OTHER INFORMATION: Xaa represents Abz

<400> SEQUENCE: 102

Xaa Arg Ser Leu Lys
1               5

<210> SEQ ID NO 103
<211> LENGTH: 7
<212> TYPE: PRT
<213> ORGANISM: Artificial sequence
<220> FEATURE:
<223> OTHER INFORMATION: Non fluorescent candidate substrate
<220> FEATURE:
<221> NAME/KEY: VARIANT
<222> LOCATION: (6)..(6)
<223> OTHER INFORMATION: Xaa represents Y(NO2)

<400> SEQUENCE: 103

Tyr Ala Glu Ser Asp Xaa Ala
1               5

<210> SEQ ID NO 104
<211> LENGTH: 8
<212> TYPE: PRT
<213> ORGANISM: Homo sapiens

<400> SEQUENCE: 104

Arg Arg Leu Leu Arg Ala Ile Pro
1               5

<210> SEQ ID NO 105
<211> LENGTH: 8
<212> TYPE: PRT
<213> ORGANISM: Homo sapiens

<400> SEQUENCE: 105

Arg Ser Leu Lys Tyr Ala Glu Ser
1               5

<210> SEQ ID NO 106
<211> LENGTH: 6
<212> TYPE: PRT
<213> ORGANISM: Homo sapiens

<400> SEQUENCE: 106

Arg Arg Leu Leu Arg Ala
1               5

<210> SEQ ID NO 107
<211> LENGTH: 11
<212> TYPE: PRT
<213> ORGANISM: Artificial Sequence
<220> FEATURE:
<223> OTHER INFORMATION: Fluorogenic substrate
<220> FEATURE:
<221> NAME/KEY: VARIANT
<222> LOCATION: (1)..(1)
<223> OTHER INFORMATION: Xaa represents Abz
<220> FEATURE:
<221> NAME/KEY: VARIANT
<222> LOCATION: (11)..(11)
```

```
-continued

<223> OTHER INFORMATION: Xaa represents Y(NO2)

<400> SEQUENCE: 107

Xaa Arg Ser Leu Lys Tyr Ala Glu Ser Asp Xaa
1               5                   10

<210> SEQ ID NO 108
<211> LENGTH: 12
<212> TYPE: PRT
<213> ORGANISM: Homo sapiens

<400> SEQUENCE: 108

Gln Arg Lys Val Phe Arg Ser Leu Lys Tyr Ala Glu
1               5                   10
```